(12) United States Patent
Foster et al.

(10) Patent No.: US 7,658,933 B2
(45) Date of Patent: *Feb. 9, 2010

(54) NON-CYTOTOXIC PROTEIN CONJUGATES

(75) Inventors: Keith Foster, Salisbury (GB); John Chaddock, Salisbury (GB); Charles Penn, Salisbury (GB); Kei Roger Aoki, Irvine, CA (US); Joseph Francis, Irvine, CA (US); Lance Steward, Irvine, CA (US)

(73) Assignees: Syntaxin, Ltd., Abingdon (GB); Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/829,118

(22) Filed: Jul. 27, 2007

(65) Prior Publication Data
US 2008/0187960 A1 Aug. 7, 2008

Related U.S. Application Data

(63) Continuation of application No. 11/791,979, filed as application No. PCT/GB2005/004598 on Dec. 1, 2005.

(30) Foreign Application Priority Data

| Dec. 1, 2004 | (GB) | ................................. 0426394.3 |
| Mar. 10, 2005 | (GB) | ................................. 0504964.8 |
| Mar. 10, 2005 | (GB) | ................................. 0504966.3 |

(51) Int. Cl.
  *A61K 39/08* (2006.01)
  *C07K 14/00* (2006.01)
  *C07H 21/04* (2006.01)

(52) U.S. Cl. ................ 424/239.1; 424/236.1; 435/69.1; 435/69.7; 435/320.1; 530/350; 514/2; 514/12; 536/23.7

(58) Field of Classification Search .............. 424/239.1, 424/236.1; 435/69.1, 325, 320.1, 69.7; 530/350; 514/2, 12; 536/23.7
See application file for complete search history.

(56) References Cited

U.S. PATENT DOCUMENTS

| 5,668,255 | A | 9/1997 | Murphy |
| 5,989,545 | A | 11/1999 | Foster |
| 6,395,513 | B1 | 5/2002 | Foster |
| 6,461,617 | B1 | 10/2002 | Shone |
| 6,632,440 | B1 | 10/2003 | Quinn |
| 6,843,998 | B1 | 1/2005 | Steward |
| 6,962,703 | B2 | 11/2005 | Foster |
| 7,052,702 | B1 | 5/2006 | Duggan |
| 7,056,729 | B2 | 6/2006 | Donovan |
| 7,132,259 | B1 | 11/2006 | Dolly |
| 7,192,596 | B2 | 3/2007 | Shone |
| 7,208,466 | B1 | 4/2007 | Foster |
| 7,244,436 | B2 | 7/2007 | Donovan |
| 7,244,437 | B2 * | 7/2007 | Donovan ................. 424/239.1 |
| 7,262,291 | B2 | 8/2007 | Donovan |
| 7,452,543 | B2 | 11/2008 | Chaddock |
| 2003/0049264 | A1 | 3/2003 | Foster et al. |
| 2003/0180289 | A1 | 9/2003 | Foster |
| 2004/0071736 | A1 | 4/2004 | Quinn |
| 2005/0244435 | A1 | 11/2005 | Shone |
| 2006/0051356 | A1 | 3/2006 | Foster |
| 2006/0110410 | A1 | 5/2006 | Shone |
| 2006/0216283 | A1 | 9/2006 | Foster |
| 2007/0010447 | A1 | 1/2007 | Quinn |
| 2007/0184048 | A1 | 8/2007 | Foster |
| 2007/0184070 | A1 | 8/2007 | Shone |
| 2007/0248626 | A1 | 10/2007 | Shone |
| 2008/0032928 | A1 | 2/2008 | Quinn |
| 2008/0038274 | A1 | 2/2008 | Foster |
| 2008/0070278 | A1 | 3/2008 | North |

FOREIGN PATENT DOCUMENTS

| EP | 1 422 240 A2 | 5/2004 |
| WO | WO 96/33273 | 10/1996 |
| WO | WO 98/07864 | 2/1998 |
| WO | WO 99/17806 | 4/1999 |
| WO | WO 2000/057897 | 10/2000 |
| WO | WO 01/14570 A1 | 3/2001 |

(Continued)

OTHER PUBLICATIONS

Okada et al., Biochem. Biophys. Res. Comm. 278, 493-498 (2000).*
J. A. Chaddock, et al., "Retargeted Clostridial Endopeptidases: Inhibition of Nociceptive Neurotransmitter Release In Vitro, and Antinociceptive Activity in In Vivo Models of Pain," Movement Disorders, vol. 19, pp. S42-S47; Sep. 8, 2004.
Okada et al., Biochem. Biophys. Res. Comm. 278 :493-498 (2000).
U.S. Appl. No. 11/798,610, Quinn.
U.S. Appl. No. 08/513,878, filed Dec. 1, 1995, North.
U.S. Appl. No. 09/572,431, filed May 17, 2000, North.
U.S. Appl. No. 11/819,648, filed Jun. 28, 2007, Foster.

*Primary Examiner*—Chih-Min Kam

(57) ABSTRACT

The present invention is directed to non-cytotoxic protein conjugates for inhibition or reduction of exocytic fusion in a nociceptive sensory afferent cell. The protein conjugates comprise: (i) a Targeting Moiety (TM), wherein the TM is an agonist of a receptor present on a nociceptive sensory afferent cell, and wherein the receptor undergoes endocytosis to be incorporated into an endosome within the nociceptive sensory afferent cell; (ii) a non-cytotoxic protease or a fragment thereof, wherein the protease or protease fragment is capable of cleaving a protein of the exocytic fusion apparatus of the nociceptive sensory afferent cell; and (iii) a Translocation Domain, wherein the Translocation Domain translocates the protease or protease fragment from within the endosome, across the endosomal membrane, and into the cytosol of the nociceptive sensory afferent cell. Nucleic acid sequences encoding the protein conjugates, methods of preparing same and uses thereof are also described.

4 Claims, 32 Drawing Sheets

FOREIGN PATENT DOCUMENTS

Figure 1:
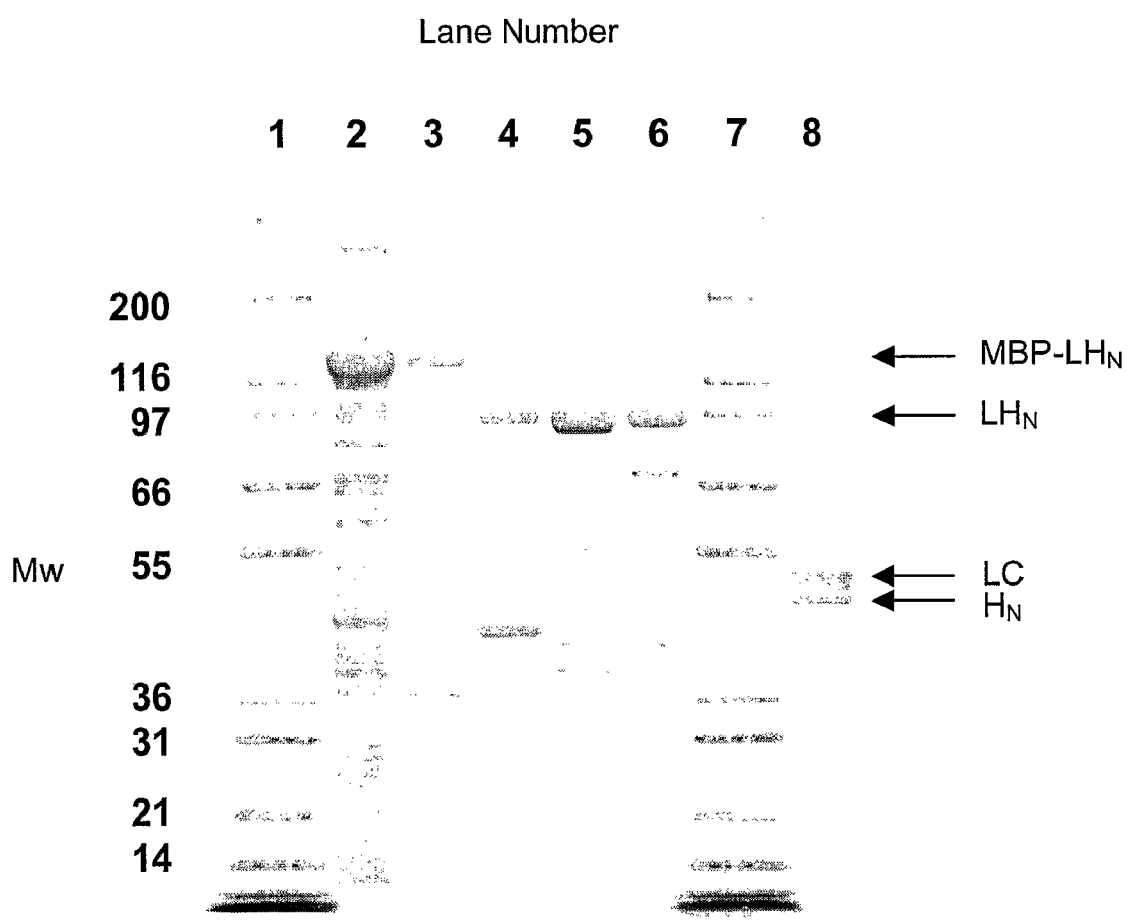

| | | |
|---|---|---|
| WO | WO 02/007759 A3 | 1/2002 |
| WO | WO 2004/024909 A2 | 3/2004 |
| WO | WO 2005/023309 A2 | 3/2005 |
| WO | WO 2006/059113 | 6/2006 |

\* cited by examiner

Figure 11

Competition Assay: CPN fusions vs 1nM [3H] - Nociceptin
on eDRGs for 1 hour at 4°C

- Tocris
- CPN-LH$_N$/A
- CPNv-LH$_N$/A
- Controls

CPN-A (GS10)

CPN-A (GS15)

CPN-A (GS25)

CPN-A (GS30)

CPN-A (HX27)

CPN-A on eDRG for 1 Day

Duration of action following eDRG exposure for 1 Day

Figure 15

1 2 3 4 5

NON-CYTOTOXIC PROTEIN CONJUGATES

CROSS REFERENCE TO RELATED APPLICATIONS

This application is a continuation of U.S. patent application Ser. No. 11/791,979, filed Jun. 23, 2008, pending, which is a national stage application of PCT/GB2005/004598, filed Dec. 1, 2005. Each of the above-mentioned applications is hereby incorporated by reference in its entirety.

This invention relates to a non-cytotoxic protein conjugate, and to the use of said conjugate for treating pain.

Toxins may be generally divided into two groups according to the type of effect that they have on a target cell. In more detail, the first group of toxins kill their natural target cells, and are therefore known as cytotoxic toxin molecules. This group of toxins is exemplified inter alia by plant toxins such as ricin, and abrin, and by bacterial toxins such as diphtheria toxin, and *Pseudomonas* exotoxin A. Cytotoxic toxins typically kill their target cells by inhibiting the cellular process of protein synthesis.

In contrast, the second group of toxins, which are known as non-cytotoxic toxins, do not (as their name confirms) kill their natural target cells. Non-cytotoxic toxins have attracted much less commercial interest than have their cytotoxic counterparts, and exert their effects on a target cell by inhibiting cellular processes other than protein synthesis. As with their cytotoxic counterparts, non-cytotoxic toxins are produced from a variety of sources such as plants, and bacteria. Bacterial non-cytotoxic toxins are now described in more detail.

Clostridial neurotoxins are proteins that typically have a molecular mass of the order of 150 kDa. They are produced by various species of bacteria, especially of the genus *Clostridium*, most importantly *C. tetani* and several strains of *C. botulinum*, *C. butyricum* and *C. argentinense*. There are at present eight different classes of the clostridial neurotoxin, namely: tetanus toxin, and botulinum neurotoxin in its serotypes A, B, $C_1$, D, E, F and G, and they all share similar structures and modes of action.

Clostridial neurotoxins represent a major group of non-cytotoxic toxin molecules, and are synthesised by the host bacterium as single polypeptides that are modified post-translationally by a proteolytic cleavage event to form two polypeptide chains joined together by a disulphide bond. The two chains are termed the heavy chain (H-chain), which has a molecular mass of approximately 100 kDa, and the light chain (L-chain), which has a molecular mass of approximately 50 kDa.

L-chains possess a protease function (zinc-dependent endopeptidase activity) and exhibit high substrate specificity for vesicle and/or plasma membrane associated proteins involved in the exocytic process. L-chains from different clostridial species or serotypes may hydrolyse different but specific peptide bonds in one of three substrate proteins, namely synaptobrevin, syntaxin or SNAP-25. These substrates are important components of the neurosecretory machinery.

Non-cytotoxic toxins are also produced by other bacteria, such as from the genus *Neisseria*, most importantly from the species *N. gonorrhoeae*. For example, *Neisseria* sp. produces the non-cytotoxic toxin IgA protease (see WO99/58571).

It has been well documented in the art that toxin molecules may be re-targeted to a cell that is not the toxin's natural target cell. When so re-targeted, the modified toxin is capable of binding to a desired target cell and, following subsequent translocation into the cytosol, is capable of exerting its effect on the target cell. Said re-targeting is achieved by replacing the natural Targeting Moiety (TM) of the toxin with a different TM. In this regard, the TM is selected so that it will bind to a desired target cell, and allow subsequent passage of the modified toxin into an endosome within the target cell. The modified toxin also comprises a translocation domain to enable entry of the non-cytotoxic protease into the cell cytosol. The translocation domain can be the natural translocation domain of the toxin or it can be a different translocation domain obtained from a microbial protein with translocation activity.

For example, in the context of non-cytotoxic toxin molecules, it has been well documented that a clostridial neurotoxin may be re-targeted by incorporation of a Targeting Moiety (TM), which is not the natural TM of a clostridial neurotoxin. The described chemical conjugation and recombinant methodologies are now regarded as conventional, and reference is made to Hermanson, G. T. (1996), Bioconjugate techniques, Academic Press, and to Wong, S. S. (1991), Chemistry of protein conjugation and cross-linking, CRC Press.

For example, WO94/21300 describes modified clostridial neurotoxin molecules that are capable of regulating Integral Membrane Protein (IMP) density present at the cell surface of the target cell. The modified neurotoxin molecules are thus capable of controlling cell activity (e.g. glucose uptake) of the target cell. WO96/33273 and WO99/17806 describe modified clostridial neurotoxin molecules that target peripheral sensory afferents. The modified neurotoxin molecules are thus capable of demonstrating an analgesic effect. WO00/10598 describes the preparation of modified clostridial neurotoxin molecules that target mucus hypersecreting cells (or neuronal cells controlling said mucus hypersecreting cells), which modified neurotoxins are capable of inhibiting hypersecretion from said cells. WO01/21213 describes modified clostridial neurotoxin molecules that target a wide range of different types of non-neuronal target cells. The modified molecules are thus capable of preventing secretion from the target cells. Additional publications in the technical field of re-targeted toxin molecules include: WO00162814; WO00/04926; U.S. Pat. No. 5,773,586; WO93/15766; WO00/61192; and WO99/58571.

Thus, from the above-described publications, it will be appreciated that the basic concept of re-targeting a non-cytotoxic protease to a desired target cell, by selecting a TM that has a corresponding receptor present on the target cell, has been well documented.

However, different receptors present on a target cell of interest demonstrate different binding affinities for different TMs. This may be a particular problem with pain-sensing cells, which possess a wide range of receptor types having different binding affinities for different TMs. Thus, a re-targeted conjugate comprising a particular TM (that binds to a receptor on a pain-sensing cell) may demonstrate a low binding affinity for a pain-sensing target cell, which is undesirable.

There is therefore a need to develop modified non-cytotoxic conjugates that address one or more of the above problems. Of particular interest is the development of an improved conjugate for use in treating-pain.

The present invention seeks to address one or more of the above problems by using as the conjugate's Targeting Moiety (TM) an "agonist" of a receptor that is present on the pain-sensing target cell of interest. In preferred embodiments, the pain-sensing target cell is a nociceptive sensory afferent, more preferably a primary nociceptive sensory afferent. In particularly preferred embodiments, the TM is an agonist of the opioid-like receptor-1 ($ORL_1$) receptor.

Accordingly, in a first aspect, the present invention provides a non-cytotoxic conjugate for inhibition or reduction of exocytic fusion in a nociceptive sensory afferent cell, comprising:

(i) a Targeting Moiety (TM),
   wherein said TM is an agonist of a receptor present on said nociceptive sensory afferent cell, and wherein said receptor undergoes endocytosis to be incorporated into an endosome within the nociceptive sensory afferent cell;

(ii) a non-cytotoxic protease or a fragment thereof,
   wherein the protease or protease fragment is capable of cleaving a protein of the exocytic fusion apparatus of said nociceptive sensory afferent cell; and (iii) a Translocation Domain,
   wherein the Translocation Domain translocates the protease or protease fragment from within the endosome, across the endosomal membrane, and into the cytosol of the nociceptive sensory afferent cell.

The use of an "agonist", which would normally stimulate a biological process, particularly exocytosis (for example, an increase in cellular secretion, or an up-regulation in membrane protein expression), is an exciting development in the technical field of re-targeted toxins. Furthermore, it is particularly surprising that an agonist may be employed in a therapeutic composition to achieve a reduction or inhibition of a biological process that the agonist would normally stimulate.

The agonist-containing conjugates of the present invention represent a distinct sub-set of toxin conjugates. In more detail, the conjugates of the present invention comprise TMs that have been selected on the basis of specific agonist properties rather than on the simple basis that they have a corresponding receptor on a pain-sensing target cell of interest.

Conventionally, an agonist has been considered any molecule that can either increase or decrease activities within a cell, namely any molecule that simply causes an alteration of cell activity. For example, the conventional meaning of an agonist would include: a chemical substance capable of combining with a receptor on a cell and initiating a reaction or activity, or a drug that induces an active response by activating receptors, whether the response is an increase or decrease in cellular activity.

However, for the purposes of this invention, an agonist is more specifically defined as a molecule that is capable of stimulating the process of exocytic fusion in a pain-sensing target cell, which process is susceptible to inhibition by a protease (or fragment thereof) capable of cleaving a protein of the exocytic fusion apparatus in said target cell.

Accordingly, the particular agonist definition of the present invention would exclude many molecules that would be conventionally considered as agonists. For example, nerve growth factor (NGF) is an agonist in respect of its ability to promote neuronal differentiation via binding to a TrkA receptor. However, NGF is not an agonist when assessed by the above criteria because it is not a principal inducer of exocytic fusion. In addition, the process that NGF stimulates (i.e. cell differentiation) is not susceptible to inhibition by the protease activity of a non-cytotoxic toxin molecule.

In use, an agonist-containing conjugate of the present invention does not deactivate an agonist receptor on a pain-sensing target cell, but rather the protease activity of the conjugate serves to negate the agonist-mediated response.

Furthermore, once delivered to the cytosol of the pain-sensing target cell, the protease component of a conjugate of the present invention inhibits or blocks the action of all subsequent agonists capable of causing the same effect (i.e. increased exocytic fusion) in the same target cell. This is advantageous and means that the conjugates of the present invention have application in situations where multiple agonists may be responsible for causing the sensation of pain. Thus, when designing a conjugate of the present invention, the TM that is selected for delivery need not necessarily be the principal agonist involved in causing the sensation of pain.

Agonist-mediated delivery according to the present invention provides the following significant advantage over previous non-cytotoxic protease-containing therapeutics: use of an agonist may confer preferential binding and/or internalisation properties on the conjugate. This, in turn, may result in more efficient delivery of the protease component to a pain-sensing target cell.

In addition, use of an agonist as a TM is self-limiting with respect to side-effects. In more detail, binding of an agonist to a pain-sensing target cell increases exocytic fusion, which may exacerbate the sensation of pain. However, the exocytic process that is stimulated by agonist binding is subsequently reduced or inhibited by the protease component of the conjugate.

In preferred embodiments of the invention, the TM is an agonist of the $OR_1$ receptor. The $ORL_1$ receptor is present on pain-sensing cells in the body.

The $ORL_1$ receptor is a member of the G-protein-coupled class of receptors, and has a seven transmembrane domain structure. The properties of the $ORL_1$ receptor are discussed in detail in Mogil & Pasternak (2001), *Pharmacological Reviews*, Vol. 53, No. 3, pages 381-415.

Throughout this specification, reference to the "$ORL_1$ receptor" embraces all members of the $ORL_1$ receptor family. Members of the $ORL_1$ receptor family typically have a seven transmembrane domain structure, and are coupled to G-proteins of the $G_i$ and $G_0$ families. A method for determining the G-protein-stimulating activity of ligands of the $ORL_1$ receptor is given in Example 17. A method for measuring reduction in cellular cAMP levels following $ORL_1$-activation is given in Example 16. A further characteristic of members of the $ORL_1$ receptor family is that they are typically able to bind nociceptin (the natural ligand of $ORL_1$). As an example, all alternative splice variants of the $ORL_1$ receptor, are members of the $ORL_1$ receptor family.

The conjugates of the present invention generally demonstrate a reduced binding affinity (in the region of up to 100-fold) for nociceptive sensory afferent target cells when compared with the corresponding 'free' TM. However, despite this observation, the conjugates of the present invention surprisingly demonstrate good efficacy. This can be attributed to two principal features. First, the non-cytotoxic protease component is catalytic—thus, the therapeutic effect of a few such molecules is rapidly amplified. Secondly, the receptors present on the nociceptive sensory afferents need only act as a gateway for entry of the therapeutic, and need not necessarily be stimulated to a level required in order to achieve a ligand-receptor mediated pharmacological response. Accordingly, the conjugates of the present invention may be administered at a dosage that is much lower that would be employed for other types of analgesic molecules such as NSAIDS, morphine, and gabapentin. The latter molecules are typically administered at high microgram to milligram (even up to hundreds of milligram) quantities, whereas the conjugates of the present invention may be administered at much lower dosages, typically at least 10-fold lower, and more typically at 100-fold lower.

In a particularly preferred embodiment of the invention, the TM of the conjugate is nociceptin—the natural ligand for the $ORL_1$ receptor. Nociceptin targets the $ORL_1$ receptor with high affinity.

Examples of other preferred TMs include:

| Code | Sequence | Ref. | SEQ ID No. |
| --- | --- | --- | --- |
| Nociceptin 1-17 | FGGFTGARKSARKLANQ | [1] | 1, 2 |
| Nociceptin 1-11 | FGGFTGARKSA | [1] | 3, 4 |
| Nociceptin [Y10]1-11 | FGGFTGARKYA | [1] | 5, 6 |
| Nociceptin [Y11]1-11 | FGGFTGARKSY | [1] | 7, 8 |
| Nociceptin [Y14]1-17 | FGGFTGARKSARKYANQ | [1] | 9, 10 |
| Nociceptin 1-13 | FGGFTGARKSARK | [2] | 11, 12 |
| Nociceptin [R14K15] 1-17 (also known as "variant" nociceptin) | FGGFTGARKSARKRKNQ | [3, 4] | 13, 14 |
| Nociceptin 1-13-$NH_2$ | FGGFTGARKSARK-$NH_2$ | [5] | 12 |
| Nociceptin Phe (p-$NO_2$) 1-17 | (p$NO_2$)FGGFTGARKSARKLANQ | [5] | 2 |
| Lofentanil | Non-peptide agonists | [5] | — |
| Etorphine | Non-peptide agonists | [5] | — |
| Peptide agonist | Peptide agonists from combinatorial library approach | [6] | — |

[1] Mogil & Pasternak, 2001, Pharmacol. Rev., 53, 381-415
[2] Maile et al., 2003, Neurosci. Lett., 350, 190-192
[3] Rizzi et al., 2002, J. Pharmacol. Exp. Therap., 300, 57-63
[4] Okada et al., 2000, Biochem. Biophys. Res. Commun., 278, 493-498
[5] Zaveri, 2003, Life Sci., 73, 663-678.
[6] Dooley et al., 1997, J Pharmacol Exp Ther. 283(2), 735-41.

The TM preferably comprises a maximum of 50 amino acid residues, more preferably a maximum of 40 amino acid residues, particularly preferably a maximum of 30 amino acid residues, and most preferably a maximum of 20 amino acid residues. For example, nociceptin is a 17 amino acid residue peptide.

The above-identified "variant" TM demonstrates particularly good binding affinity (when compared with natural nociceptin) for nociceptive sensory afferents. Generally speaking, a TM-containing conjugate will demonstrate an approximate 100-fold reduction in binding ability vis-à-vis the TM per se. The above-mentioned "variant" TM per se demonstrates an approximate 3- to 10-fold increase in binding ability for a nociceptive sensory afferent vis-à-vis natural nociceptin. Thus, a "variant" TM-containing fusion might be expected to demonstrate an approximate 10-fold reduction in binding ability for a nociceptive sensory afferent vis-à-vis 'free' nociceptin. However, the present inventors have demonstrated that conjugates comprising said "variant" TM demonstrate a binding ability that (most surprisingly) closely mirrors that of 'free' nociceptin—see FIG. 17.

In the context of the present invention, the term agonist of the $ORL_1$ receptor (such as nociceptin, or any one of the peptides listed in the table above) embraces molecules having at least 70%, preferably at least 80%, more preferably at least 90%, and most preferably at least 95% homology with said agonist. The agonist homologues retain the agonist properties of nociceptin at the $ORL_1$ receptor, which may be tested using the methods provided in Example 10.

The invention also encompasses fragments, variants, and derivatives of any one of the TMs described above. These fragments, variants, and derivatives will substantially retain the properties that are ascribed to said TMs.

The agonist properties of a TM can be confirmed using the methods described in Example 1. These methods are based on previous experiments (see Inoue et al. (1998) Proc. Natl. Acad. Sci., 95, 10949-10953), which confirm that the natural agonist of the $ORL_1$ receptor, nociceptin, causes the induction of substance P release from nociceptive primary afferent neurons. This is supported by the facts that:

the nociceptin-induced responses are abolished by specific NK1 receptor (the substance P receptor) antagonists; and pre-treatment of the cells with capsaicin (which depletes substance P from small diameter primary afferent neurons) attenuates the nociceptin-induced responses.

Similarly, Inoue et al. confirm that an intraplantar injection of botulinum neurotoxin type A abolishes the nociceptin-induced responses. Since it is known that BoNT inhibits the release of substance P from primary afferent neurons (Welch et al., (2000), Toxicon, 38, 245-258), this confirms the link between nociceptin-$ORL_1$ interaction and subsequent release of substance P.

Thus, a TM can be said to have agonist activity at the $ORL_1$ receptor if the TM causes an induction in the release of substance P from a nociceptive sensory afferent neuron (see Example 1).

In another embodiment, opioids represent a preferred group of TMs of the present invention. Within this family of peptides is included enkephalins (met and leu), endomorphins 1 and 2, β-endorphin and dynorphin. Opioid peptides are frequently used in the clinic to modify the activity to nociceptors, and other cells involved in the pain response. As exemplified by the three-step World Health Organisation Analgesic Ladder, opioids have entry points into the pharmacological treatment of chronic cancer and non-cancer pain at all three stages, underlining their importance to the treatment of pain. Reference to opioids embraces fragments, variants and derivatives thereof, which retain the ability to bind to nociceptive sensory afferents. The protease of the present invention embraces all naturally-occurring non-cytotoxic proteases that are capable of cleaving one or more proteins of the exocytic fusion apparatus in eukaryotic cells.

The protease of the present invention is preferably a bacterial protease.

More preferably, the bacterial protease is selected from the genera *Clostridium* or *Neisseria* (e.g. a clostridial L-chain, or a neisserial IgA protease preferably from *N. gonorrhoeae*).

The present invention also embraces modified non-cytotoxic proteases, which include amino acid sequences that do not occur in nature and/or synthetic amino acid residues, so long as the modified proteases still demonstrate the above-mentioned protease activity.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

A Translocation Domain is a molecule that enables translocation of a protease (or fragment thereof) into a pain-sensing target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored (see Shone C. (1987) Eur. J. Biochem; vol. 167(1): pp. 175-180).

A further example is provided by Blaustein R. (1987), which describes a simple in vitro assay employing planar phospholipid bilayer membranes. The membranes are challenged with a test molecule and the requisite translocation function is confirmed by an increase in conductance across said membranes (see Blaustein (1987) FEBS Letts; vol. 226, no. 1: pp. 115-120).

Additional methodology to enable assessment of membrane fusion and thus identification of Translocation Domains suitable for use in the present invention are provided by Methods in Enzymology, Vols. 220 and 221, Membrane Fusion Techniques, Parts A and B, Academic Press 1993.

The Translocation Domain is preferably capable of formation of ion-permeable pores in lipid membranes under conditions of low pH. Preferably, it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, namely the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. Examples of suitable clostridial Translocation Domains include:

| | |
|---|---|
| Botulinum type A neurotoxin | amino acid residues (449-871) |
| Botulinum type B neurotoxin | amino acid residues (441-858) |
| Botulinum type C neurotoxin | amino acid residues (442-866) |
| Botulinum type D neurotoxin | amino acid residues (446-862) |
| Botulinum type E neurotoxin | amino acid residues (423-845) |
| Botulinum type F neurotoxin | amino acid residues (440-864) |
| Botulinum type G neurotoxin | amino acid residues (442-863) |
| Tetanus neurotoxin | amino acid residues (458-879) |

For further details on the genetic basis of toxin production in *Clostridium botulinum* and *C. tetani*, we refer to Henderson et al. (1997) in *The Clostridia: Molecular Biology and Pathogenesis*, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin (see table below). Examples of non-clostridial Translocation Domain origins include, but are not restricted to, the translocation domain of diphtheria toxin [O'Keefe et al., Proc. Natl. Acad. Sci. USA (1992) 89, 6202-6206; Silverman et al., J. Biol. Chem. (1993) 269, 22524-22532; and London, E. (1992) Biochem. Biophys. Acta., 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS*, 89, pp. 7934-7938], and amphiphilic peptides [Murata et al (1992) *Biochem.*, 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus hemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded "spike proteins" have particular application in the context of the present invention, for example, the E1 protein of SFV and the G protein of VSV.

Use of the Translocation Domains (listed below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

Standard text, for example "Receptor-Ligand Interactions. A Practical Approach. Ed. E. C. Hulme, IRL Press, 1992" are available that describe such approaches in detail. In brief, the agonist or putative agonist molecule is labelled (for example, with 125-iodine) and applied to a cell preparation in vitro in the presence of an excess of unlabelled agonist. The purpose of the unlabelled material is to saturate any non-specific binding sites. The agonist is incubated with the cell-preparation for sufficient time to achieve equilibrium, and the amount of label bound to the cells assessed by measuring cell associated radioactivity, for example by scintillation or gamma counting.

| Translocation Domain source | Amino acid residues | References |
|---|---|---|
| Diphtheria toxin | 194-380 | Silverman et al., 1994, J. Biol. Chem. 269, 22524-22532<br>London E., 1992, Biochem. Biophys. Acta., 1113, 25-51 |
| Domain II of pseudomonas exotoxin | 405-613 | Prior et al., 1992, Biochemistry 31, 3555-3559<br>Kihara & Pastan, 1994, Bioconj Chem. 5, 532-538 |
| Influenza virus haemagglutinin | GLFGAIAGFIENGWE GMIDGWYG (SEQ ID NO:101), and Variants thereof | Plank et al., 1994, J. Biol. Chem. 269, 12918-12924<br>Wagner et al., 1992, PNAS, 89, 7934-7938<br>Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

Once a potential receptor agonist (e.g. an ORL1 agonist) has been identified, one or more of the following optional steps may be carried out:

(A) confirming that the putative agonist molecule or agonist is capable of being combined with a non-cytotoxic protease (or a fragment thereof) and optionally a Translocation Domain to form a conjugate of the present invention; and/or (B) confirming that said putative agonist molecule or agonist binds to the receptor on the pain-sensing target cell, which receptor is susceptible to receptor-mediated endocytosis; and/or (C) confirming that said putative agonist molecule or agonist is able to deliver a non-cytotoxic protease (or fragment thereof) into the cytosol of a pain-sensing target cell.

The above steps (A)-(C) may be confirmed by routine tests that would be readily available to a skilled person.

For example, step (A) may be performed by a simple chemical conjugation experiment using conventional conjugation reagents and/or linker molecules, followed by native polyacrylamide gel electrophoresis to confirm that a conjugate of the present invention is formed that has the anticipated molecular weight. The conjugate components are typically linked together (optionally via linker molecules) by covalent bonds.

For example, step (B) may be performed by any one of a range of methodologies for assessment of binding of a ligand.

A further example involves gold-labelling of the agonist (or putative agonist), followed by the use of electron microscopy to monitor the cellular transport progress of the labelled agonist [see the basic methodology described by Rabinowitz S. (1992); J. Cell. Biol. 116(1): pp. 95-112; and that described by van Deurs (1986); J. Cell. Biol. 102: pp. 37-47].

For example, step (C) may be performed by contacting the conjugate prepared in step (A) with a suitable target cell and assessing cleavage of the substrate. This is performed by extraction of the SNARE proteins, followed by Western blotting of SDS-PAGE-separated samples. Cleavage of substrate is indicative of delivery of the protease into the target cell. In this regard, cleavage may be monitored by disappearance of substrate and/or appearance of cleavage product. A particularly useful antibody that selectively binds to the cleaved substrate product is described in WO95/33850.

Preparation of a Conjugate According to the Present Invention is Now Discussed.

It is known in the art that the $H_C$ portion of a neurotoxin molecule can be removed from the other portion of the H-chain, known as $H_N$, such that the $H_N$ fragment remains disulphide linked to the L-chain of the neurotoxin providing a fragment known as $LH_N$. Thus, in one embodiment of the present invention the $LH_N$ fragment of a neurotoxin is covalently linked, using linkages which may include one or more spacer regions, to a TM.

In another embodiment of the invention, the $H_C$ domain of a neurotoxin is mutated, blocked or modified, e.g. by chemical modification, to reduce or preferably incapacitate its ability to bind the neurotoxin to receptors at the neuromuscular junction. This modified neurotoxin is then covalently linked, using linkages which may include one or more spacer regions, to a TM.

In another embodiment of the invention, the H-chain of a neurotoxin, in which the $H_C$ domain is mutated, blocked or modified, e.g. by chemical modification, to reduce or preferably incapacitate its native binding ability, is combined with the L-chain of a different neurotoxin, or another protease capable of cleaving a protein of the exocytic fusion apparatus (e.g. IgA protease of *N. gonorrhoeae*). This hybrid, modified neurotoxin is then covalently linked, using linkages which may include one or more spacer regions, to a TM.

In another embodiment of the invention, the $H_N$ domain of a neurotoxin is combined with the L-chain of a different neurotoxin, or another protease capable of cleaving a protein of the exocytic fusion apparatus (e.g. IgA protease of *N. gonorrhoeae*). This hybrid is then covalently linked, using linkages which may include one or more spacer regions, to a TM.

In another embodiment of the invention, the protease (for example the L-chain component of a neurotoxin) is covalently linked, using linkages that may include one or more spacer regions, to a TM that can also effect the internalisation of the protease into the cytoplasm of the relevant target cell(s).

In another embodiment of the invention, the protease (for example the L-chain component of a neurotoxin) is covalently linked, using linkages which may include one or more spacer regions, to a translocation domain to effect transport of the protease fragment into the cytosol.

In use, the domains of a conjugate according to the present invention are associated with each other. In one embodiment, two or more of the domains may be joined together either directly (e.g. by a covalent linkage), or via a linker molecule.

A variety of different linker/spacer molecules may be employed in any of the fusion proteins of the present invention. Examples of such spacer molecules include those illustrated in FIGS. 31 and 32. Particular mention here is made to GS15, GS20, GS25, and Hx27—see FIGS. 31 and 32.

The present inventors have unexpectedly found that non-cytotoxic protease-TM conjugates (eg. CPNv/A) may demonstrate an improved binding activity for nociceptive sensory afferents when the size of the spacer is selected so that (in use) the TM (preferably the C-terminus thereof) and the translocation domain (preferably the N-terminus thereof) are separated from one another by 40-105 angstroms, preferably by 50-100 angstroms, and more preferably by 50-90 angstroms. In another embodiment, the preferred spacers have an amino acid sequence of 11-29 amino acid residues, preferably 15-27 amino acid residues, and more preferably 20-27 amino acid residues. Suitable spacers may be routinely identified and obtained according to Crasto, C. J. and Feng, J. A. (2000) May, 13(5), pp. 309-312—see also the world wide website having the url ending in: fccc./edu/research/labs/feng/limker.html.

Conjugation techniques suitable for use in the present invention have been well documented and are routine for a person skilled in the art.

The methodology involved in coupling two protein molecules (A and B) together is simple, and is achieved through the use of a cross-linking agent (also known as a chemical coupling agent). For example, molecules A and B are separately contacted with a cross-linking agent, which chemically-modifies a specific surface group on each of molecules A and B thereby forming derivatised molecules A' and B'. The modified surface group on molecule A' is capable of covalently bonding with the modified surface group on molecule B'. Thus, the coupling reaction is completed by mixing together the two protein molecules A' and B'.

Chemical conjugation is illustrated by reference to the following embodiments, where P=non-cytotoxic protease component, T=translocation component, and TM=targeting moiety.

In one embodiment, a single chain P-T is prepared, which is then conjugated to a TM. In another embodiment, a single chain TM-T (or T-TM) is prepared, which is then conjugated to a P. In a further embodiment, a single chain P-TM (or TM-P) is prepared, which is then conjugated to a T. Another particularly preferred conjugate has the structure P-TM-T (with an optional protease cleavage site between P and TM).

Where the T and P components are prepared as a single chain polypeptide, a protease cleavage site is typically included between said components. Any protease cleavage site may be employed in this regard.

In an alternative embodiment, the three components may be simultaneously or sequentially conjugated together. Thus, the conjugation may be a one- or two-step process, and may include one or more different coupling agents.

Chemical coupling agents and cross-linking agents have been commercially available for many years.

Example 5 of the present invention describes in detail the use of one such coupling agent, namely SPDP, to chemically couple two protein molecules (nociceptin, and the $LH_N$ of botulinum neurotoxin). The two molecules are separately contacted with SPDP, and then mixed together to allow covalent conjugation.

The conjugate described in Example 6 confirms that another coupling agent, PDPH/EDAC, or Traut's reagent, may be employed as an alternative coupling agent to SPDP.

SPDP and Traut's reagent are popular and well-documented coupling agents in the technical field of protein conjugation chemistry and are presented here simply as two examples of a well known class of compounds that may be employed to covalently link together the Targeting Moiety component and the clostridial neurotoxin component of the conjugate of the present invention. Other suitable agents include SMPB, SMCC (succinimidyl 4-(N-maleimidomethyl)cyclohexan-1-carboxylate), and LC-SPDP.

In more detail, commercially available members of the well-known coupling agents may be used for conjugation purposes to produce a conjugate of the invention. Details of such agents can be found in the following publications:

Hermanson, G. T. (1996), Bioconjugate techniques, Academic Press;

Wong, S. S. (1991), Chemistry of protein conjugation and cross-linking, CRC Press;

Thorpe et al (1987), Cancer Res, 1987, 47, 5924-31. This paper describes the use of SMBT (sodium S-4-succinimidyloxycarbonyl-alpha-methyl benzyl thiosulfate) and SMPT (4-succinimidyloxycarbonyl-alpha-methyl-alpha (2-pyridyldithio)toluene); and Peeters et al (1989), J Immunol Methods. 1989, 120, 133-43. This paper describes the use of 4 coupling reagents, MHS (succinimidyl 6-(N-maleimido)-n-hexanoate), SMCC (succinimidyl 4-(N-maleimidomethyl)-cyclohexane-1-carboxylate), MBS (succinimidyl m-maleimidobenzoate), and SPDP.

The conjugates according to the present invention may also be prepared recombinantly, as detailed in Examples 9 to 12.

In one embodiment, the preparation of a recombinant conjugate involves arrangement of the coding sequences of a selected TM, a selected non-cytotoxic protease component, and a translocation component (in any order) in a single genetic construct. These coding sequences may be arranged in-frame so that subsequent transcription and translation is continuous through both coding sequences and results in a fusion protein. All constructs would have a 5' ATG codon to encode an N-terminal methionine, and a C-terminal translational stop codon.

Thus, the recombinant preparation method results in the generation of a single chain polypeptide. In order to activate this polypeptide, a protease cleavage site is present between the non-cytotoxic protease component and the translocation component. Cleavage of this site generates a di-chain polypeptide in which the protease and translocation domains are linked together by way of a covalent bond, preferably a disulphide bond. In this regard, any protease cleavage site may be employed.

In the single polypeptide aspect of the present invention, the TM is preferably either N- or C-terminally located with respect to the fusion protein. In other words, it is preferred that the TM is not located between the P and T components of the single polypeptide fusion protein. In a particularly preferred embodiment, the TM is N-terminally located with respect to the fusion protein.

In one embodiment, an L-chain of a clostridial neurotoxin or another protease capable of cleaving a protein of the exocytic fusion apparatus (e.g. an IgA protease), or a fragment/variant thereof, may be expressed recombinantly as a fusion protein with a TM, which TM can also effect the internalisation of the L-chain component into the cytoplasm of the relevant target cell(s) responsible for secretion. Alternatively, the fusion protein may further comprise a Translocation Domain. The expressed fusion protein may include one or more spacer regions.

By way of example, the following information is required to produce, recombinantly, an agent of the present invention:

(I) DNA sequence data relating to a selected TM;
(II) DNA sequence data relating to the protease component;
(III) DNA sequence data relating to the translocation domain; and
(IV) a protocol to permit construction and expression of the construct comprising (I), (II) and (III).

All of the above basic information (I)-(IV) are either readily available, or are readily determinable by conventional methods. For example, both WO98/07864 and WO99/17806 exemplify recombinant technology suitable for use in the present application.

In addition, methods for the construction and expression of the constructs of the present invention may employ information from the following references and others:

Lorberboum-Galski, H., FitzGerald, D., Chaudhary, V., Adhya, S., Pastan, I. (1988), Cytotoxic activity of an interleukin 2-Pseudomonas exotoxin chimeric protein produced in *Escherichia coli*. Proc. Natl. Acad. Sci. USA, 85(6):1922-6;

Murphy, J. R. (1988), Diphtheria-related peptide hormone gene fusions: a molecular genetic approach to chimeric toxin development. Cancer Treat. Res.; 37:123-40;

Williams, D. P., Parker, K., Bacha, P., Bishai, W., Borowski, M., Genbauffe, F., Strom, T. B., Murphy, J. R. (1987), Diphtheria toxin receptor binding domain substitution with interleukin-2: genetic construction and properties of a diphtheria toxin-related interleukin-2-fusion protein. Protein Eng; 1(6):493-8;

Arora, N., Williamson, L. C., Leppla, S. H., Halpern, J. L. (1994), Cytotoxic effects of a chimeric protein consisting of tetanus toxin light chain and anthrax toxin lethal factor in non-neuronal cells J. Biol. Chem., 269(42):26165-71;

Brinkmann, U., Reiter, Y., Jung, S. H., Lee, B., Pastan, I. (1993), A recombinant immunotoxin containing a disulphide-stabilized Fv fragment. Proc. Natl. Acad. Sci. USA, 90(16):7538-42; and O'Hare, M., Brown, A. N., Hussain, K., Gebhardt, A., Watson, G., Roberts, L. M., Vitetta, E. S., Thorpe, P. E., Lord, J. M. (1990), Cytotoxicity of a recombinant ricin-A-chain fusion protein containing a proteolytically-cleavable spacer sequence. FEBS Lett October 29; 273(1-2):200-4.

Suitable clostridial neurotoxin sequence information relating to L- and $LH_N$-chains may be obtained from, for example, Kurazono, H. (1992) *J. Biol. Chem.*, vol. 267, No. 21, pp. 14721-14729; and Popoff, M. R., and Marvaud, J.-C. (1999) *The Comprehensive Sourcebook of Bacterial Protein Toxins*, 2nd edition (ed. Alouf, J. E., and Freer, J. H.), Academic Press, pp. 174-201.

All of the aforementioned publications are hereby incorporated into the present specification by reference thereto.

Similarly, suitable TM sequence data are widely available in the art. Alternatively, any necessary sequence data may be obtained by techniques which are well-known to the skilled person.

For example, DNA encoding the TM component may be cloned from a source organism by screening a cDNA library for the correct coding region (for example by using specific oligonucleotides-based on the known sequence information to probe the library), isolating the TM DNA, sequencing this DNA for confirmation purposes, and then placing the isolated DNA in an appropriate expression vector for expression in the chosen host.

As an alternative to isolation of the sequence from a library, the available sequence information may be employed to prepare specific primers for use in PCR, whereby the coding sequence is then amplified directly from the source material and, by suitable use of primers, may be cloned directly into an expression vector.

Another alternative method for isolation of the coding sequence is to use the existing sequence information and synthesise a copy, possibly incorporating alterations, using DNA synthesis technology. For example, DNA sequence data may be generated from existing protein and/or RNA sequence information. Using DNA synthesis technology to do this (and the alternative described above) enables the codon bias of the coding sequence to be modified to be optimal for the chosen expression host. This may give rise to superior expression levels of the fusion protein.

Optimisation of the codon bias for the expression host may be applied to the DNA sequences encoding the TM and clostridial components of the construct. Optimisation of the codon bias is possible by application of the protein sequence into freely available DNA/protein database software, e.g. programs available from Genetics Computer Group, Inc.

Having prepared a conjugate of the invention, it is a matter of routine to confirm that the various domains have retained their specified function.

Protease function after conjugation may be tested by using, for example, any one of the following routine tests:

SNAP-25 (or synaptobrevin, or syntaxin) may be challenged with a conjugate to be tested, and then analysed by SDS-PAGE peptide separation techniques. Subsequent detection of peptides (e.g. by silver staining) having molecular weights corresponding to the cleaved products of SNAP-25 (or other component of the neurosecretory machinery) would confirm the presence of a functional L-chain.

As a further alternative, the conjugate may be tested by assaying for SNAP-25 (or synaptobrevin, or syntaxin) cleavage products via antibody-specific binding (see WO95/33850). In more detail, a specific antibody is employed for detecting cleavage of SNAP-25. Since the antibody recognises cleaved SNAP-25, but not uncleaved SNAP-25, identification of the cleaved product by the antibody confirms the presence of L-chain proteolytic function. By way of exemplification, such a method is described in Examples 2 and 3 of WO96/33273.

Translocation component function after conjugation may be tested using, for example, any one of the following routine tests:

Suitable methods are, for example, described by Shone et al. (1987) Eur. J. Biochem. 167, pp. 175-180; and by Blaustein et al. (1987) FEBS 226 (1), pp. 115-120.

The Shone et al. method employs artificial liposomes loaded with potassium phosphate buffer (pH 7.2) and radiolabelled NAD. Release of K+ and NAD from the liposomes correlates with a positive result for channel forming activity and hence translocation activity. In this regard, K+ release from liposomes may be measured using an electrode and NAD release calculated by measuring the radioactivity in the supernatant (see page 176, column 1, line 33-column 2, line 17).

The Blaustein et al. method employs planar phospholipid bilayer membranes, which are used to test for channel forming activity. In more detail, salt solutions on either side of the membrane are buffered at a different pH—on the cis side, pH 4.7 or 5.5 and on the trans side, pH 7.4. The "conjugate" to be tested is added to the cis side of the membrane and electrical measurements are made under voltage clamp conditions, in order to monitor the flow of current across the membrane (see paragraph 2.2, pages 116-118). The presence of an active translocation function is confirmed by a steady rate of channel turn-on (i.e. a positive result for channel formation)—see paragraph 3, page 118.

Targeting Moiety (TM) function after conjugation may be tested by assaying for the agonist function inherent to the TM. Suitable methods include those described in Example 1.

The ability of the conjugate of the invention to inhibit substance P release from nociceptive afferent cells can be assessed using the methods described in Example 15.

In Example 15, a nociceptin-$LH_N$/A conjugate according to the first aspect of the invention is assessed for its ability to inhibit the release of substance P from primary nociceptive sensory afferent neurons. As can be seen from Table 1, incubation of the conjugate with cultures of nociceptive afferent neurons results in a significant inhibition of release of substance P (when compared to incubation of the cells with LHN/A alone). The experiment therefore confirms that the conjugate is inhibiting substance P release from these cells.

In use of the present invention, a pain-sensing target cell is selected in which it is desired to reduce or inhibit the process of exocytic fusion, which exocytic process contributes to the symptoms associated with the sensation of pain. For example, the target cell in question may demonstrate an undesirable phenotype (e.g. an undesirable secretion, or the expression of an undesirable concentration of membrane receptor, transporter or membrane channel), which contributes to the symptoms associated with pain. Alternatively, a target cell may be selected in which the process of exocytic fusion contributes to the sensation of pain.

In preferred embodiments of the invention, the target cell is a nociceptive sensory afferent cell, preferably a primary nociceptive afferent cell (e.g. an A-fibre such as an Aδ-fibre or a C-fibre). Thus, the conjugates of the present invention are capable of inhibiting neurotransmitter or neuromodulator (e.g. glutamate, substance P, calcitonin-gene related peptide (CGRP), and/or neuropeptide Y) release from discrete populations of nociceptive sensory afferent neurons. In use, the conjugates reduce or prevent the transmission of sensory afferent signals (e.g. neurotransmitters or neuromodulators) from peripheral to central pain fibres, and therefore have application as therapeutic molecules for the treatment of pain, in particular chronic pain.

It is routine to confirm that a TM binds to a nociceptive sensory afferent. For example, a simple radioactive displacement experiment may be employed in which tissue or cells representative of the nociceptive sensory afferent (for example DRGs) are exposed to labelled (e.g. tritiated) ligand in the presence of an excess of unlabelled ligand. In such an experiment, the relative proportions of non-specific and specific binding may be assessed, thereby allowing confirmation that the ligand binds to the nociceptive sensory afferent target cell. Optionally, the assay may include one or more binding antagonists, and the assay may further comprise observing a loss of ligand binding. Examples of this type of experiment can be found in Hulme, E. C. (1990), Receptor-binding studies, a brief outline, pp 303-311, in Receptor biochemistry, A Practical Approach, Ed. E. C. Hulme, Oxford University Press.

According to a second aspect, the present invention provides a non-cytotoxic conjugate for inhibition or reduction of exocytotic fusion in a nociceptive sensory afferent cell, comprising:

(i) a Targeting Moiety (TM),
  wherein said TM is an agonist of a receptor that is present on said nociceptive sensory afferent cell, and wherein said receptor undergoes endocytosis to be incorporated into an endosome within the nociceptive sensory afferent cell;

(ii) a DNA sequence encoding a non-cytotoxic protease or a fragment thereof,
  wherein the DNA sequence is expressible in the nociceptive sensory afferent cell and when so expressed provides a protease or protease fragment capable of cleaving a protein of the exocytic fusion apparatus of said nociceptive sensory afferent cell; and (iii) a Translocation Domain,
  wherein the Translocation Domain translocates the DNA sequence encoding the protease or protease fragment from within the endosome, across the endosomal membrane, and into the nociceptive sensory afferent cell.

In a preferred embodiment, the receptor is an $ORL_1$ receptor.

DNA encoding a protein of interest can be transfected into eukaryotic cells through receptor-mediated endocytosis of a protein-DNA conjugate, as confirmed by Cotton et al. (Cotton, M., Wagner, E. and Birnstiel, L. (1993) Receptor-mediated transport of DNA into eukaryotic cells. Methods in Enzymol. 217, 619-645). Several methods exist for condensing DNA to a suitable size using polycationic ligands. These include: polylysine, various cationic peptides and cationic liposomes. Of these, polylysine was used in the present study because of its successfully reported use in receptor-mediated transfection studies (Cotton et al., 1993).

The DNA sequence encoding the non-cytotoxic protease component may be expressed under the control of an operably linked promoter present as part of the agent (e.g. as part of the protease DNA sequence upstream of the coding region). Alternatively, expression of the protease component in the target cell may rely on a promoter present in the target cell.

The DNA sequence encoding the protease component may integrate into a DNA sequence of the target cell. One or more integration site(s) may be provided as part of the conjugate (e.g. as part of the protease DNA sequence).

The TM, Translocation Domain and protease components of this second aspect of the invention are as defined for the first aspect of the invention. Examples 13 and 14 describe the preparation of conjugates according to the second aspect of the invention.

According to a third aspect, the present invention provides a pharmaceutical composition comprising a conjugate according to the first and/or second aspect of the present invention.

The pharmaceutical composition may further comprise a pharmaceutically-acceptable carrier, and/or a suitable diluent and/or excipient, although the exact form of the composition may be tailored to the mode of administration. Administration is preferably to a mammal, more preferably to a human.

The components of the composition may, for example, be employed in the form of an aerosol or nebulisable solution for inhalation or a sterile solution for parenteral administration, intra-articular administration or intra-cranial administration.

The composition may also be administered by i.v. injection, which includes the use of pump systems. Spinal injection (e.g. epidural or intrathecal) or indwelling pumps may also be used.

The dosage ranges for administration of the components of the present invention are those to produce the desired therapeutic effect. It will be appreciated that the dosage range required depends on the precise nature of the components, the route of administration, the nature of the formulation, the age of the patient, the nature, extent or severity of the patient's condition, contraindications, if any, and the judgement of the attending physician.

Suitable daily dosages (for each component) are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly.

A particularly preferred dosing regimen is based on 2.5 ng of fusion protein (e.g. CPNv/A) as the 1× dose. In this regard, preferred dosages are in the range 1×-100× (i.e. 2.5-250 ng). This dosage range is significantly lower (i.e. at least 10-fold, typically 100-fold lower) than would be employed with other types of analgesic molecules such as NSAIDS, morphine, and gabapentin. Moreover, the above-mentioned difference is considerably magnified when the same comparison is made on a molar basis—this is because the fusion proteins of the present invention have a considerably greater Mw than do conventional 'small' molecule therapeutics.

Wide variations in the required dosage, however, are to be expected depending on the precise nature of the components, and the differing efficiencies of various routes of administration. For example, oral administration would be expected to require higher dosages than administration by intravenous injection.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile vehicle.

The active ingredients, depending on the vehicle and concentration used, can be either dissolved or suspended in the vehicle.

Solutions may be used for all forms of parenteral administration, and are particularly used for intravenous injection. In preparing solutions the components can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area.

Alternatively the components of the composition may be dissolved in an aqueous vehicle, the solution is sterilized by filtration and distributed into suitable containers using aseptic technique in a sterile area. The product is then freeze-dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

The compositions described in this invention can be used in vivo, either directly or as a pharmaceutically acceptable salt, for the treatment of conditions involving exocytosis (for example secretion, or the delivery of proteins such as receptors, transporters, and membrane channels to the plasma membrane of a cell).

According to a fourth aspect, the present invention provides a DNA construct that encodes a conjugate according to the first or second aspects of the invention.

By expressing the construct in a host cell, conjugates of the invention may be prepared.

According to a fifth aspect, the present invention provides a method of treatment of pain by administration to a patient of a conjugate, composition, or construct according to the first to fourth aspects of the invention, or any combination thereof.

In a preferred embodiment, the invention provides a method of treating chronic pain.

According to a sixth aspect, the present invention provides for the use of a conjugate, composition or construct according to the first to fourth aspects of the invention, for the manufacture of a medicament for treating pain, preferably chronic pain.

DEFINITIONS SECTION

Exocytic fusion is a process by which intracellular molecules are transported from the cytosol of a pain-sensing target cell to the plasma (i.e. cell) membrane thereof. Thereafter, the intracellular molecules may become displayed on the outer surface of the plasma membrane, or may be secreted into the extracellular environment.

In a healthy individual, the rate of exocytic fusion is carefully regulated and allows control of the transport of molecules between the cytosol and the plasma membrane of a pain-sensing cell. For example, regulation of the exocytic cycle allows control of the density of receptors, transporters, or membrane channels present at the cell's surface, and/or allows control of the secretion rate of intracellular components (e.g. neurotransmitters) from the cytosol of the cell.

However, in an unhealthy individual, the regulation of exocytic fusion may be modified. For example, exocytic fusion may cause affected pain-sensing cells to enter a state of hypersecretion. Alternatively, exocytic fusion may result in the display of an increased concentration of receptors, transporters, or membrane channels present on the surface of the pain-sensing, which may expose the cell to undesirable external stimuli. Thus, the process of exocytic fusion may contribute to the progression and/or severity of pain, and therefore provides a target for therapeutic intervention.

It should also be appreciated that otherwise normal rates of cellular exocytic fusion may contribute to the progression and severity of pain in compromised patients. Thus, by targeting exocytic fusion in accordance with the present invention, it is also possible to provide therapy in such patients Targeting Moiety (TM) means any chemical structure associated with a conjugate that functionally interacts with a receptor, e.g. an $ORL_1$ receptor, to cause a physical association between the conjugate and the surface of a pain-sensing target cell. The term TM embraces any molecule (i.e. a naturally occurring molecule, or a chemically/physically modified variant thereof) that is capable of binding to a receptor on the target cell, which receptor is capable of internalisation (e.g. endosome formation)—also referred to as receptor-mediated-endocytosis. The TM may possess an endosomal membrane translocation domain, in which case separate TM and Translocation Domain components need not be present in an agent of the present invention.

The term "fragment" means a peptide having at least thirty-five, preferably at least twenty-five, more preferably at least fifteen, and most preferably at least ten amino acid residues of the TM in question. In one embodiment, the first amino acid residue of the fragment is the N-terminal amino acid residue of the TM from which the fragment has been derived.

An example of a "variant" is a peptide or peptide fragment of a TM that contains one or more analogues of an amino acid (e.g. an unnatural amino acid), or a substituted linkage.

A "derivative" comprises the TM in question, and a further peptide sequence. The further peptide sequence should preferably not interfere with the basic folding and thus conformational structure of the TM. Two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polyketide components may be included.

The term non-cytotoxic means that the protease molecule in question does not kill the pain-sensing target cell to which it has been re-targeted.

The "protease cleavage site" of the present invention allows cleavage (preferably controlled cleavage) of the conjugate at a position between the non-cytotoxic protease component and the TM component. In one embodiment, the conjugate may include more than one proteolytic cleavage site. However, where two or more such sites exist, they are different, thereby substantially preventing the occurrence of multiple cleavage events in the presence of a single protease. In another embodiment, it is preferred that the conjugate has a single protease cleavage site. The protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.).

Whilst any protease cleavage site may be employed, the following are preferred:

| | | |
|---|---|---|
| Enterokinase | (DDDDK↓) | SEQ ID NO:102 |
| Factor Xa | (IEGR↓/IDGP↓) | SEQ ID NO:103 |
| TEV(Tobacco Etch virus) | (ENLYFQ↓G) | SEQ ID NO:104 |
| Thrombin | (LVPR↓GS) | SEQ ID NO:105 |
| PreScission | (LEVLFQ↓GP). | SEQ ID NO:106 |

Also embraced by the term protease cleavage site is an intein, which is a self-cleaving sequence. The self-splicing reaction is controllable, for example by varying the concentration of reducing agent present.

The present invention is now described by reference to the following Examples and Figures, without intended limitation thereto.

Figure 2:
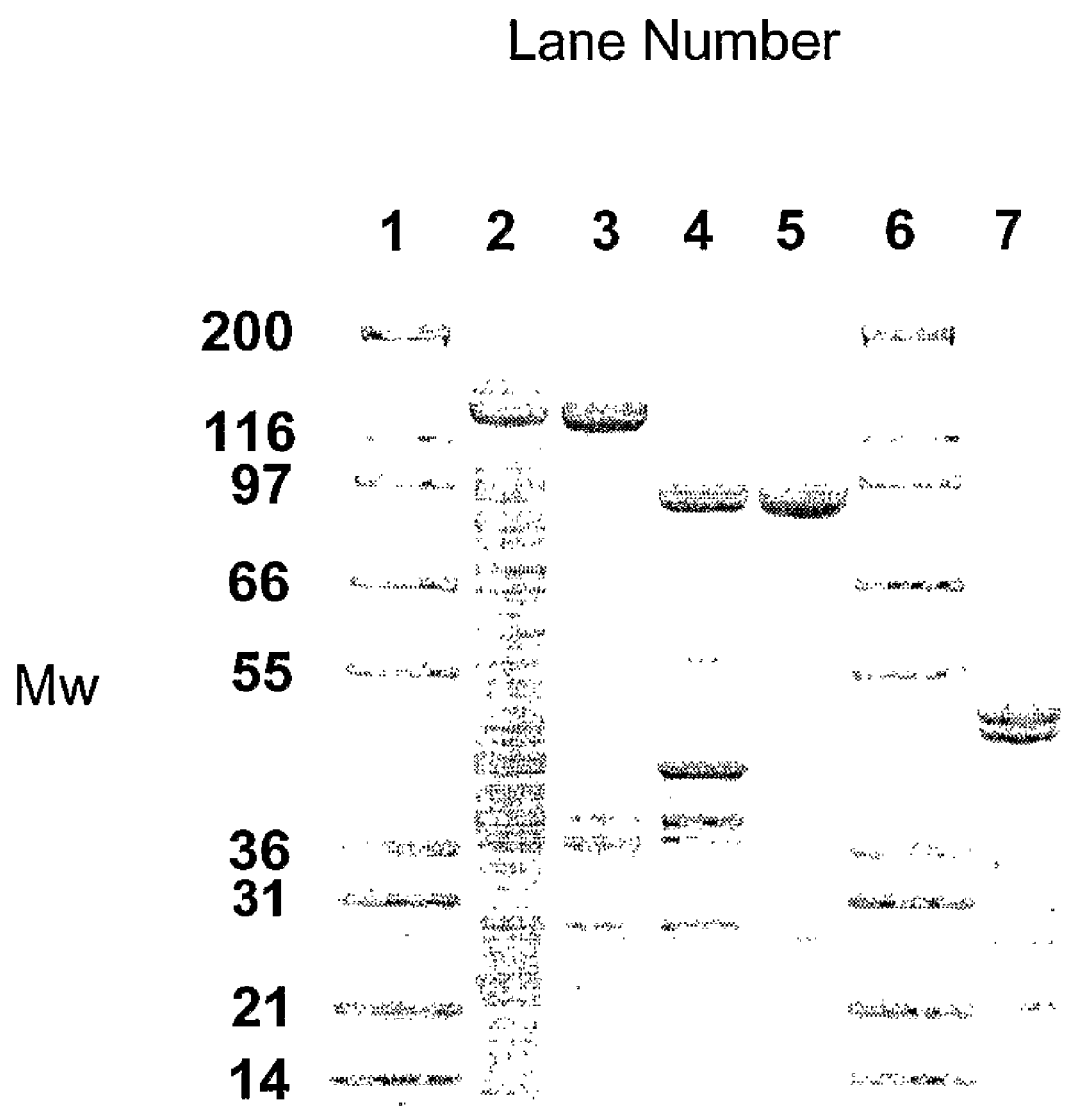
Figure 3:
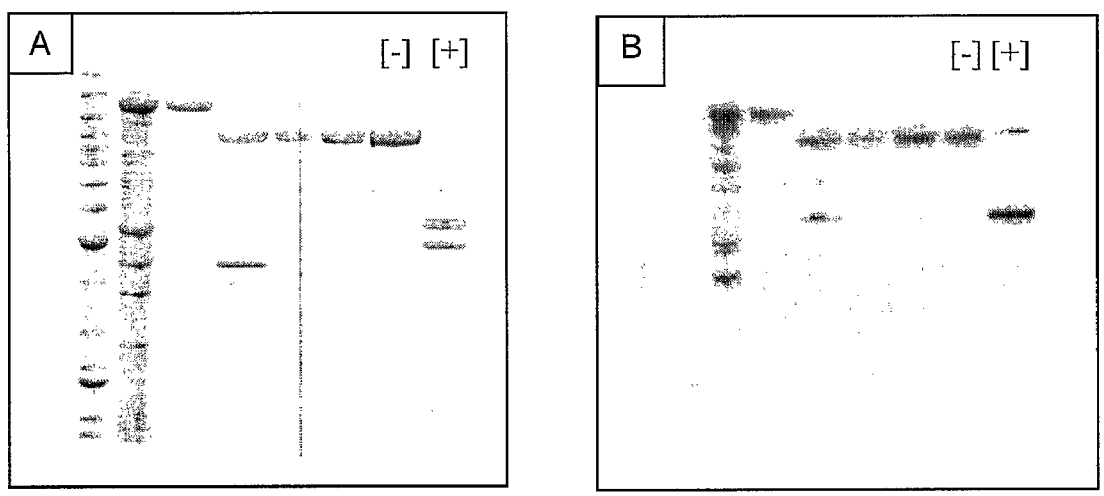
Figure 4:
Figure 4:
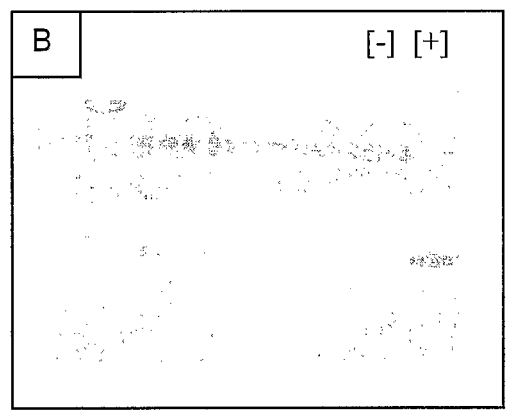
Figure 5:
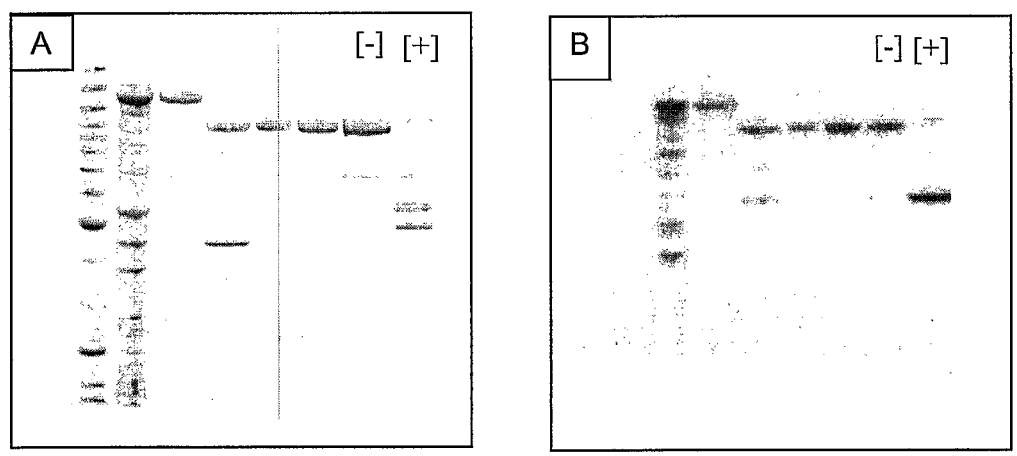
Figure 6:
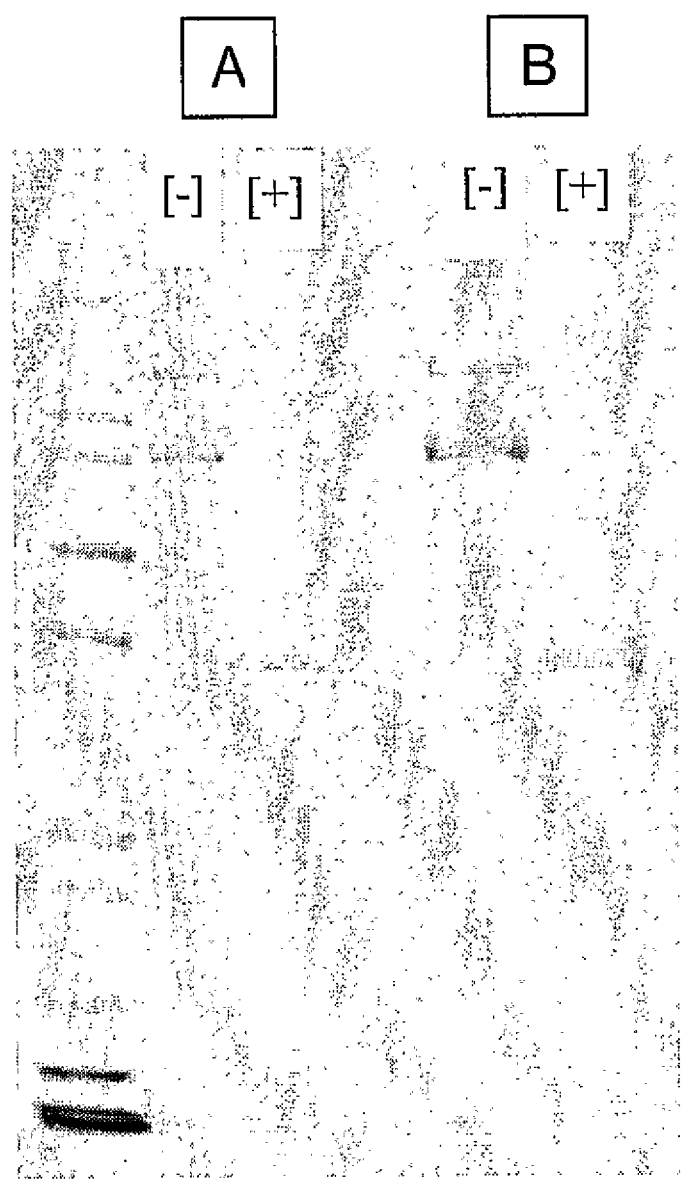
Figure 7:
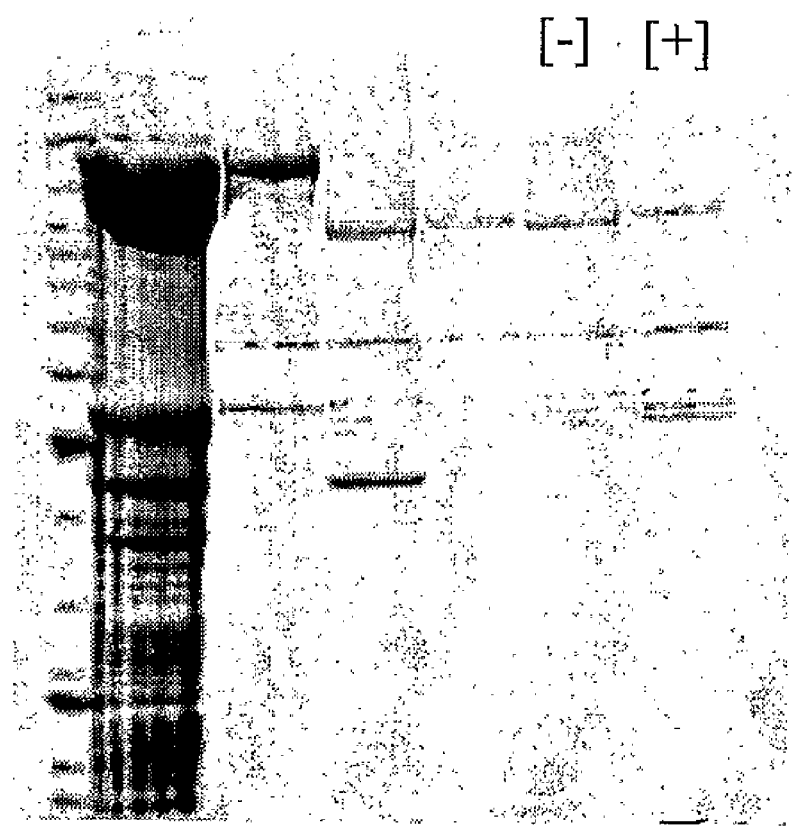
Figure 8:
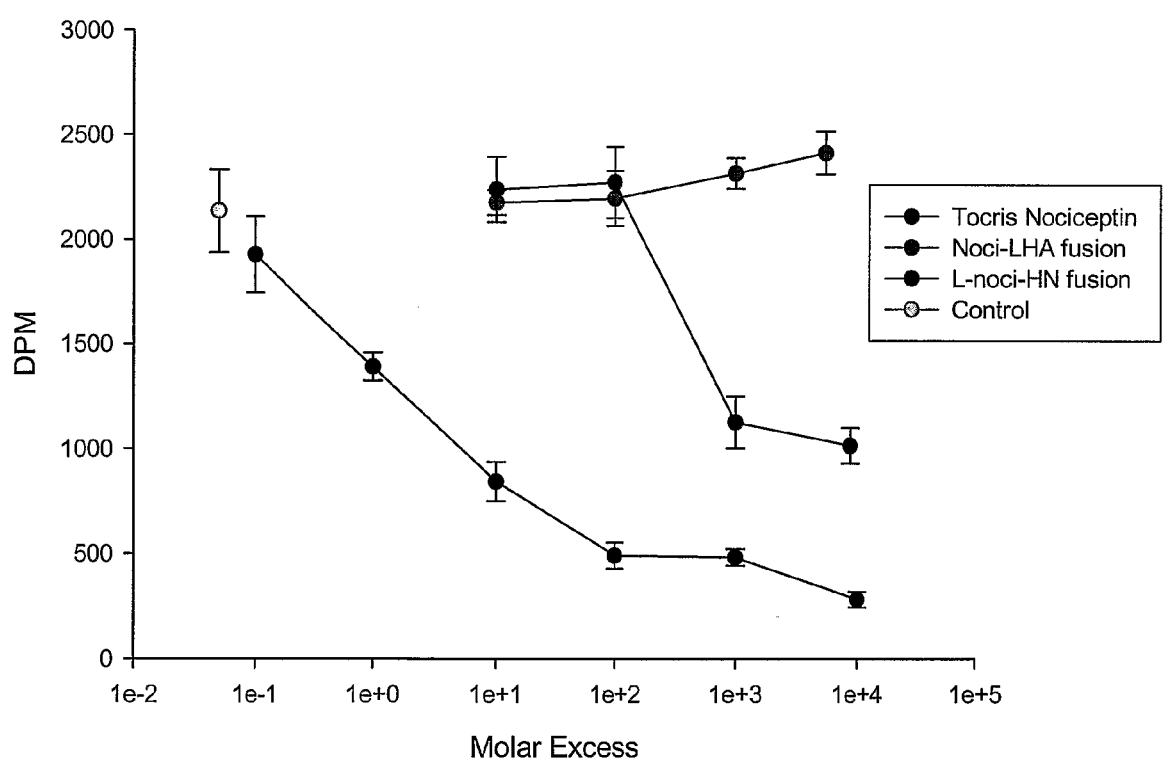
Figure 9:
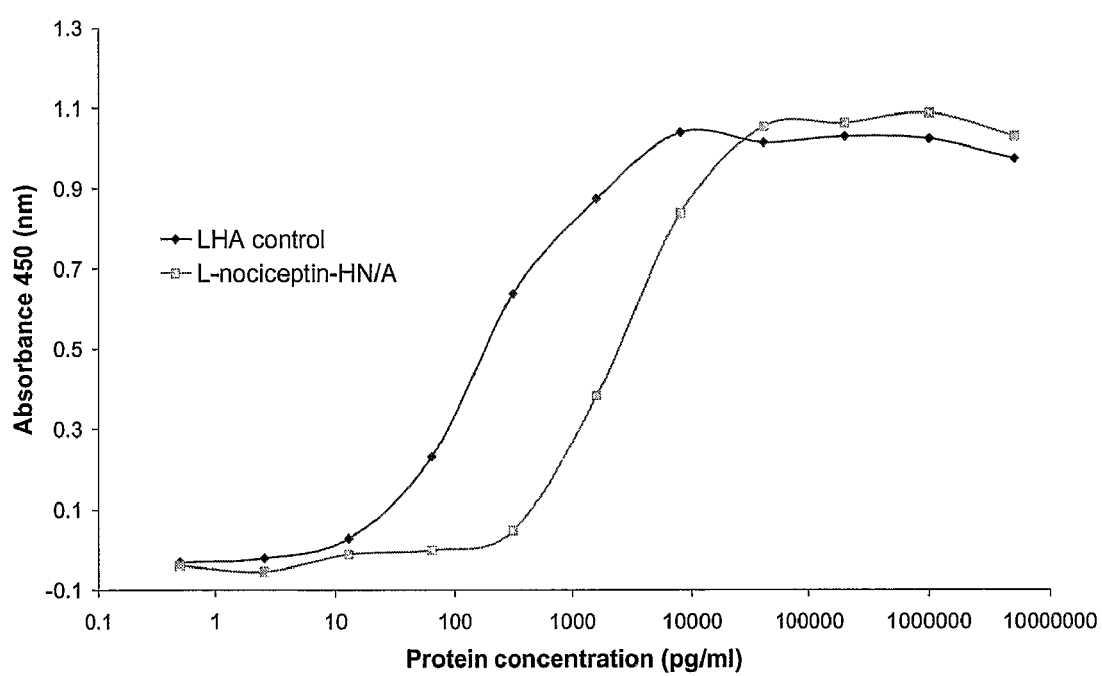
Figure 10:
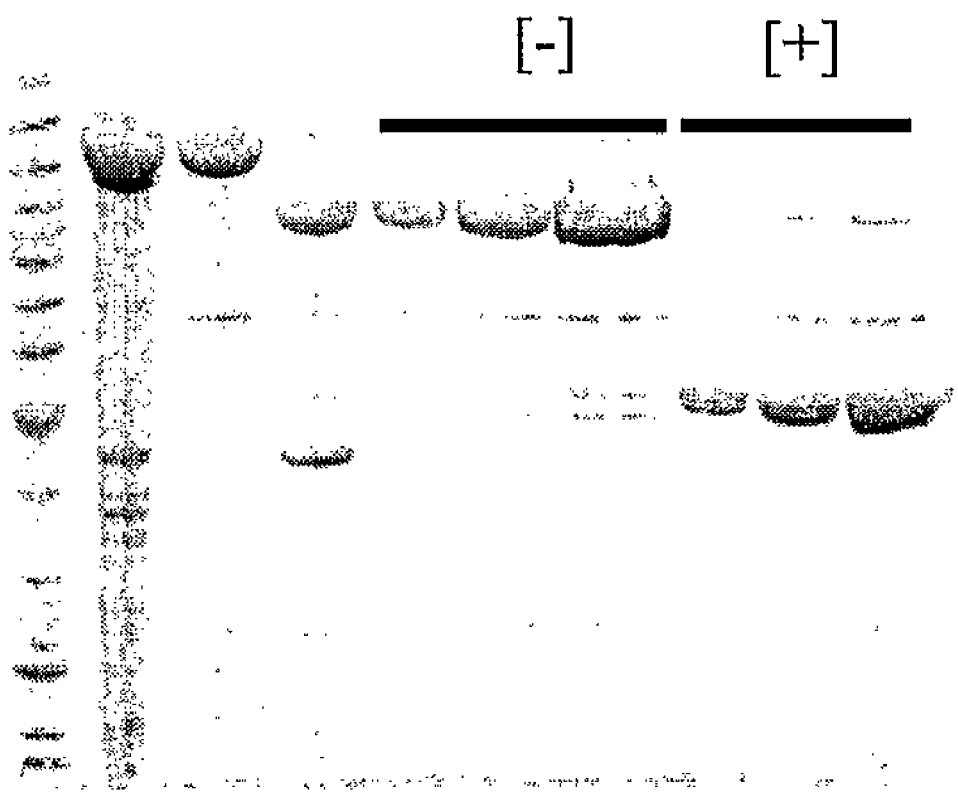
Figure 12:
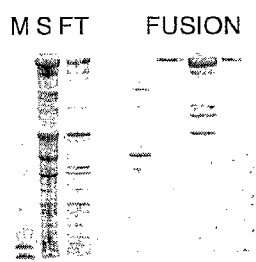
Figure 12:
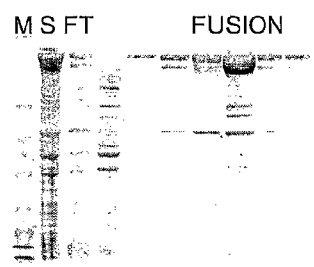
Figure 12:
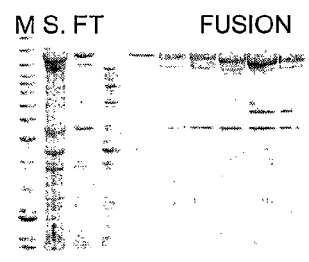
Figure 12:
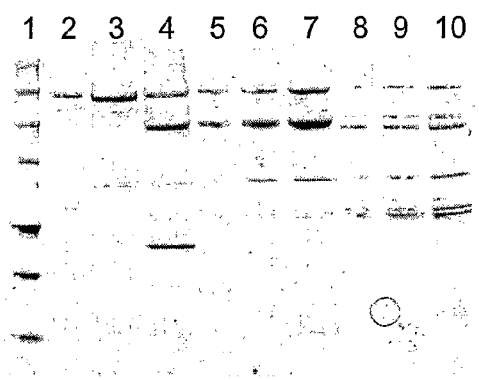
Figure 12:
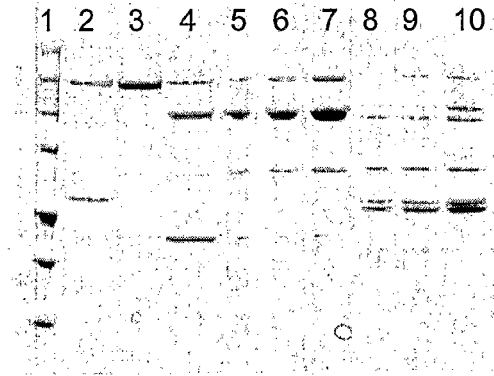
Figure 13:
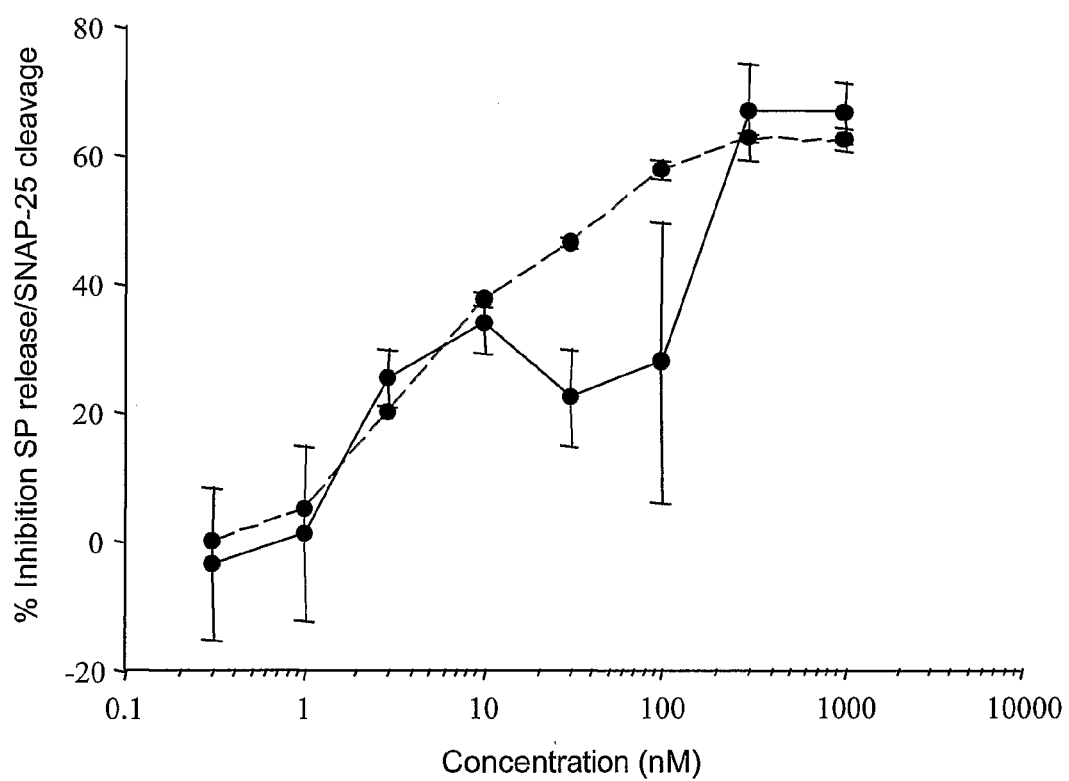
Figure 14:
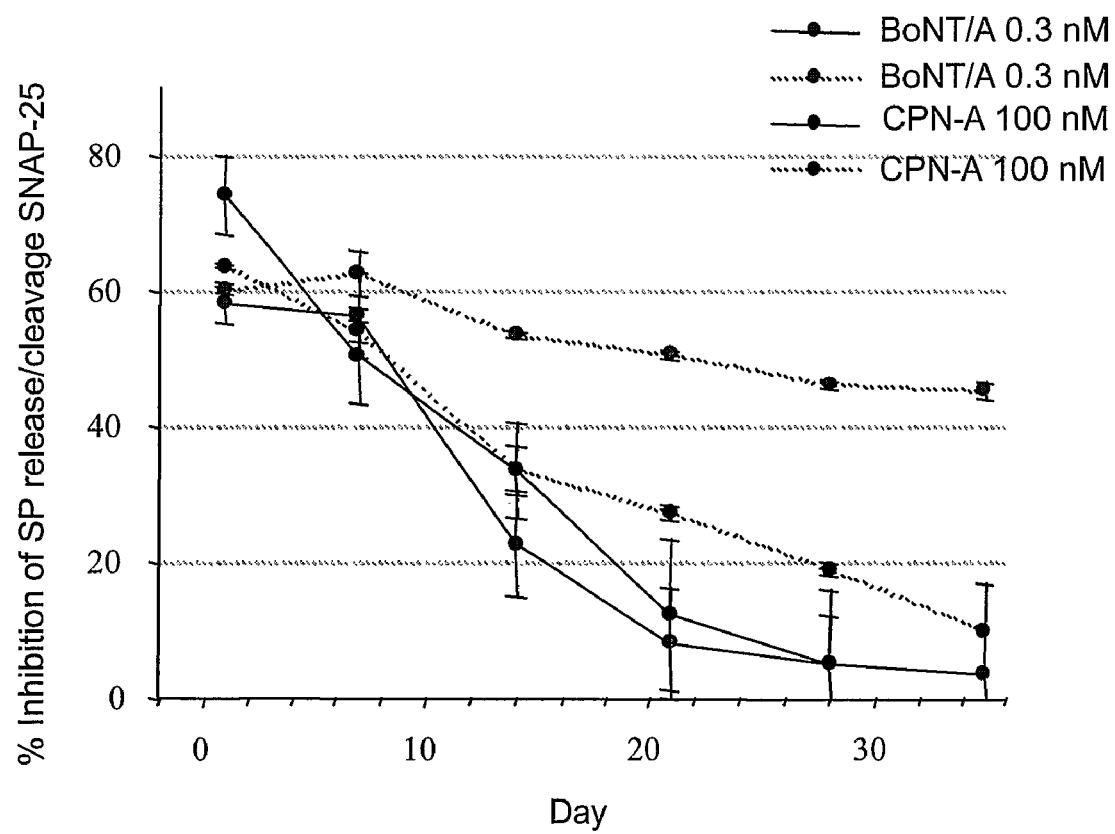
Figure 16:
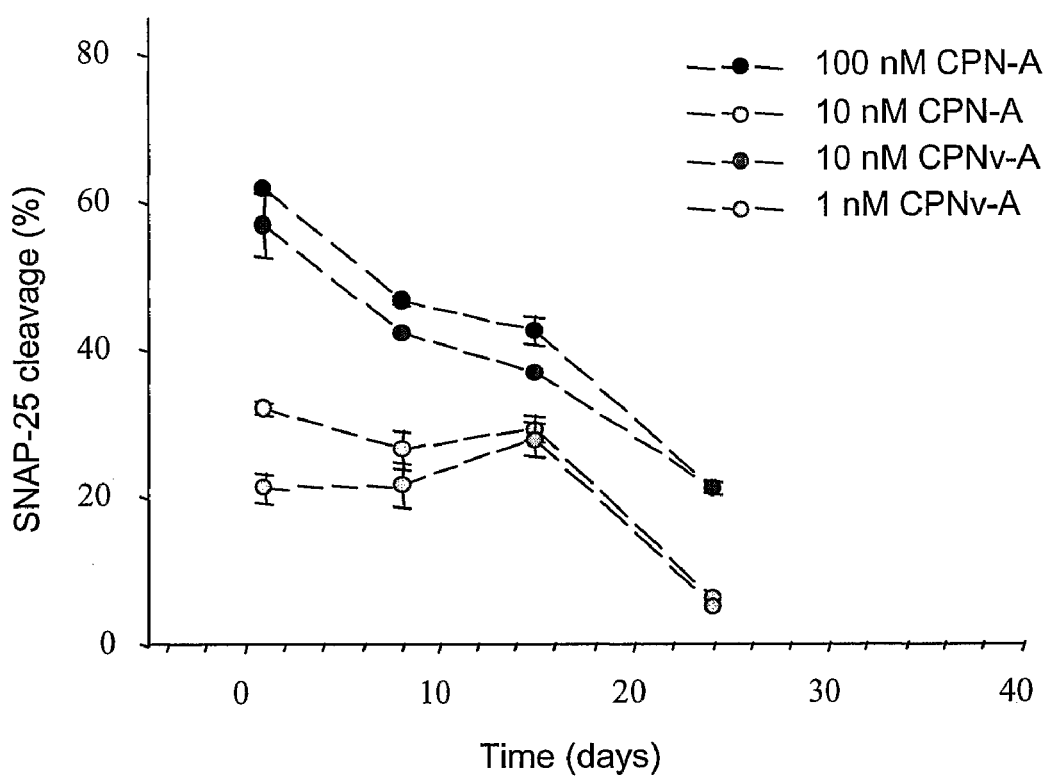
Figure 17:
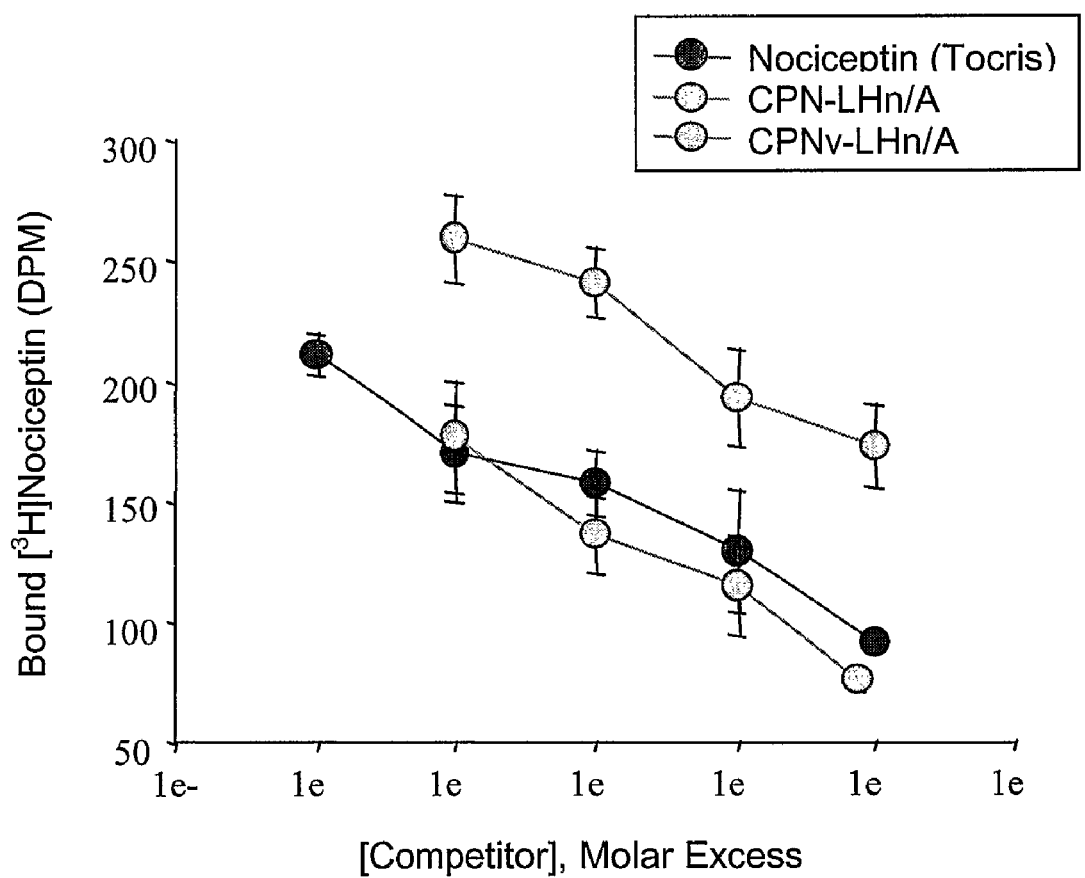
Figure 18:
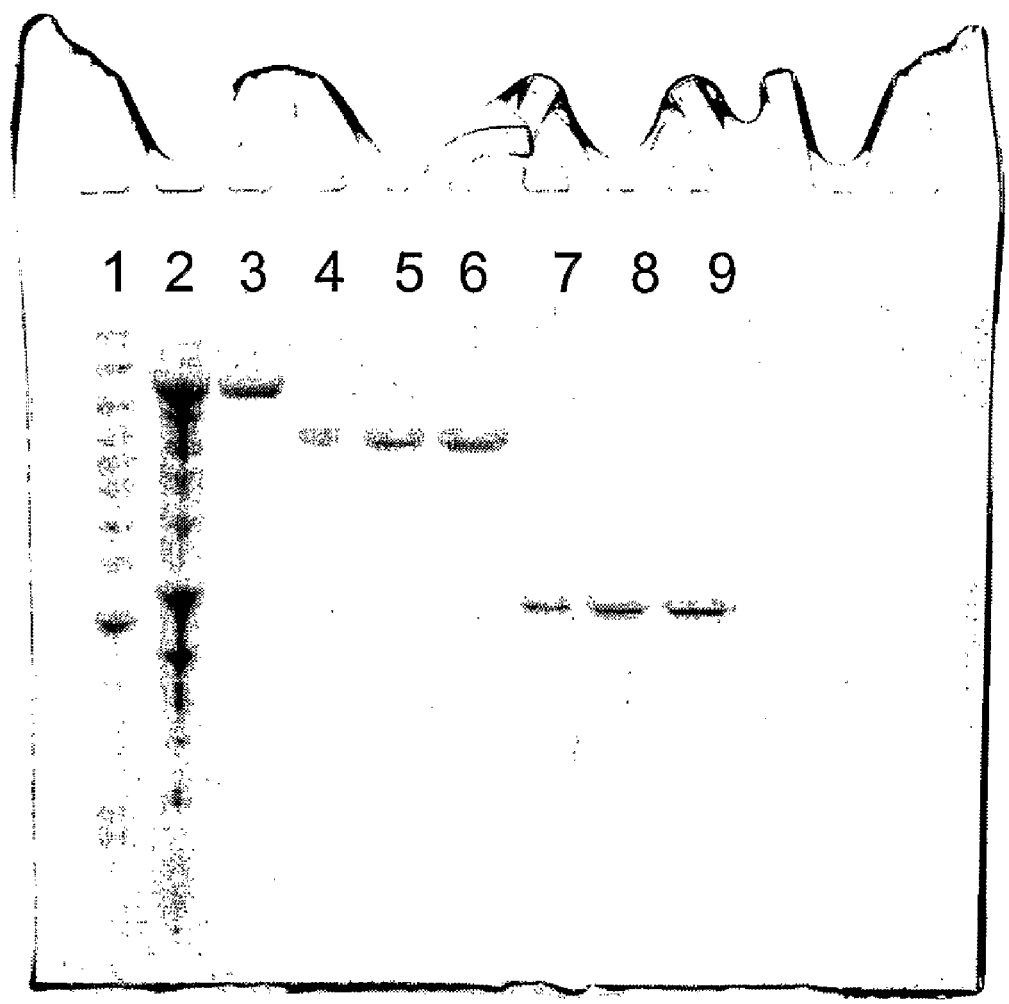
Figure 19:
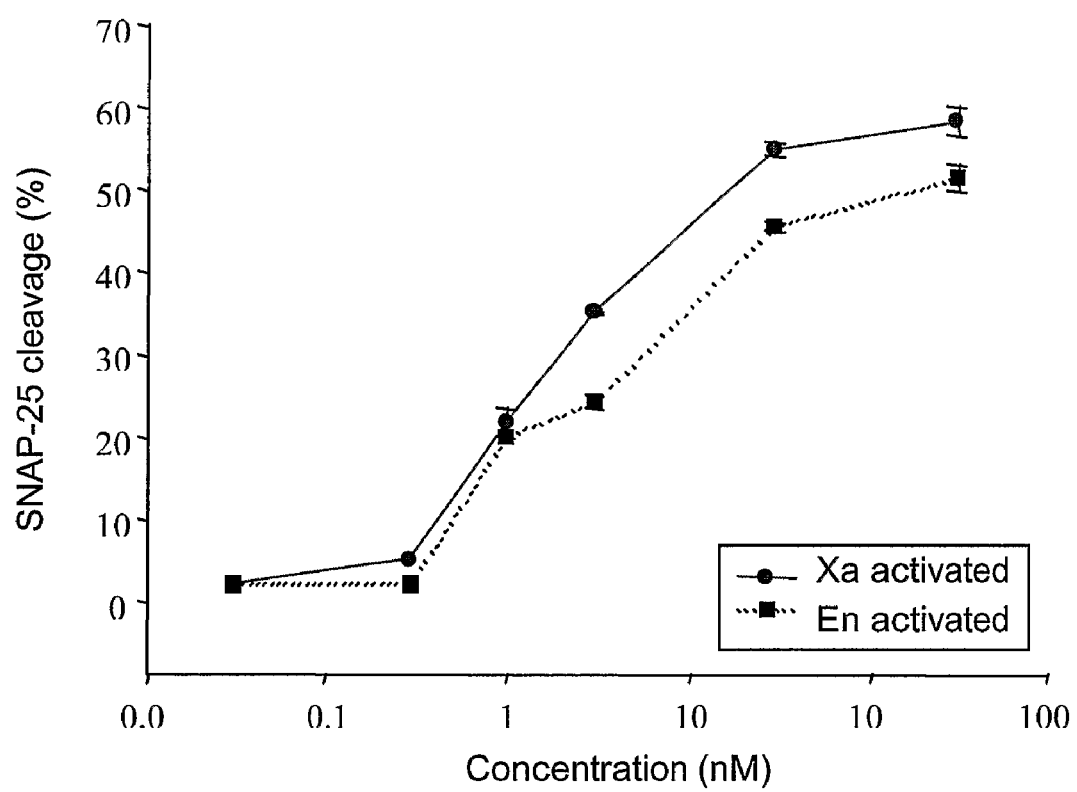
Figure 20:
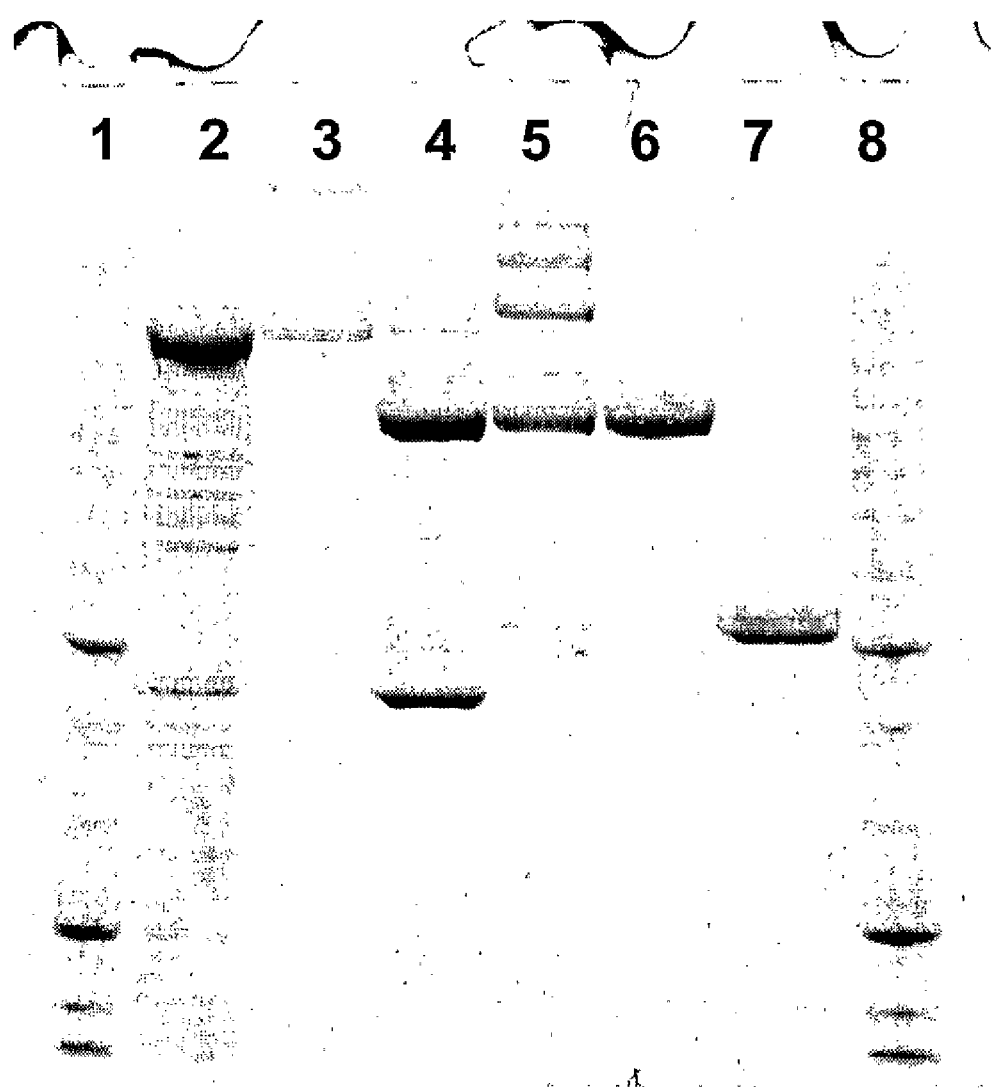

| Figures | |
|---|---|
| FIG. 1 | Expression and purification of recLH$_N$/B fusion protein |
| FIG. 2 | Expression and purification of LH$_N$/C fusion protein |
| FIG. 3 | Expression and purification of N[1-17]-LH$_N$/A fusion protein |
| FIG. 4 | Purification of a LC/A-nociceptin-H$_N$/A fusion protein |
| FIG. 5 | Purification of a nociceptin-LC/A-H$_N$/A fusion protein |
| FIG. 6 | Purification of a LC/C-nociceptin-H$_N$/C fusion protein |
| FIG. 7 | Purification of a LC/A-met enkephalin-H$_N$/A fusion protein |
| FIG. 8 | Comparison of binding efficacy of a LC/A-nociceptin-H$_N$/A fusion protein and a nociceptin-LC/A-H$_N$/A fusion protein |
| FIG. 9 | In vitro catalytic activity of a LC/A-nociceptin-H$_N$/A fusion protein |
| FIG. 10 | Purification of a LC/A-nociceptin variant-H$_N$/A fusion protein |
| FIG. 11 | Comparison of binding efficacy of a LC/A-nociceptin-H$_N$/A fusion protein and a LC/A-nociceptin variant-H$_N$/A fusion protein |
| FIG. 12 | Expressed/purified LC/A-nociceptin-H$_N$/A fusion protein family with variable spacer length product(s) |
| FIG. 13 | Inhibition of SP release and cleavage of SNAP-25 by CPN-A |
| FIG. 14 | Inhibition of SP release and cleavage of SNAP-25 over extended time periods after exposure of DRG to CPN-A |
| FIG. 15 | Cleavage of SNAP-25 by CPNv-A |
| FIG. 16 | Cleavage of SNAP-25 over extended time periods after exposure of DRG to CPNv-A |
| FIG. 17 | CPNv-A fusion-mediated displacement of [3H]-nociceptin binding |
| FIG. 18 | Expressed/purified CPNv(Ek)-A product |
| FIG. 19 | Cleavage of SNAP-25 by CPNv(Ek)-A |
| FIG. 20 | Expressed/purified CPNv-C product |

-continued

Figure 21:
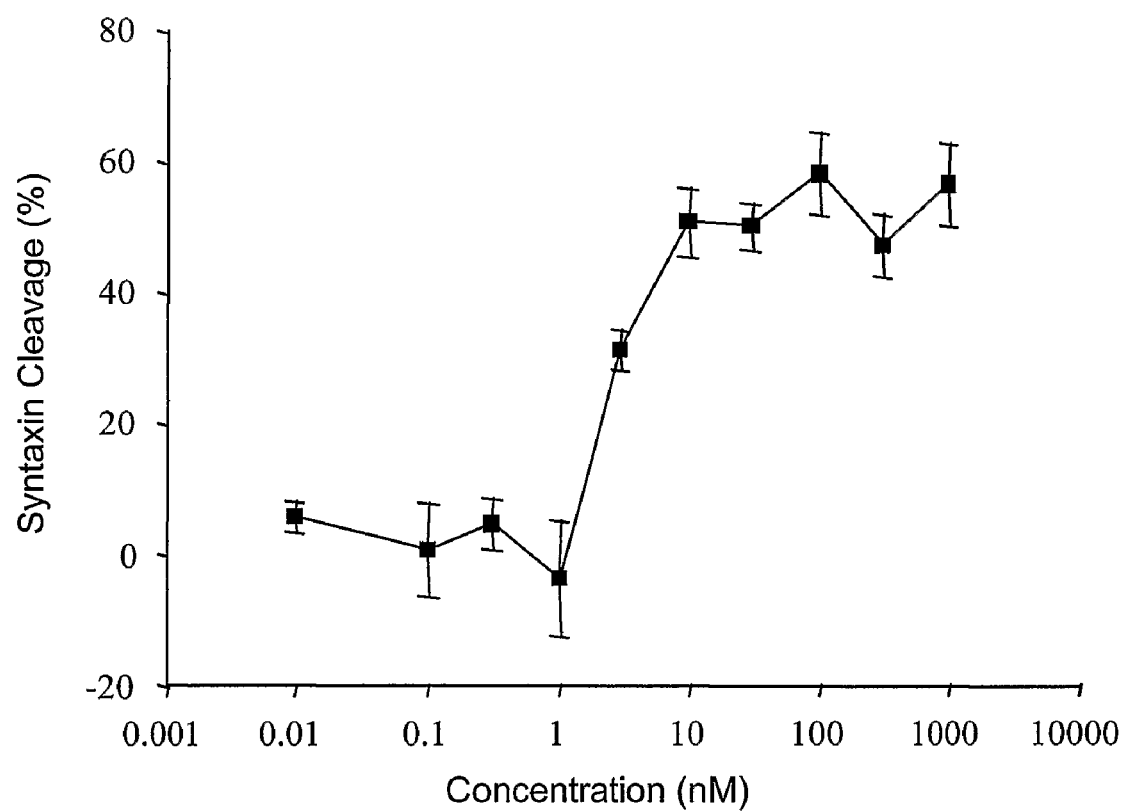
Figure 22:
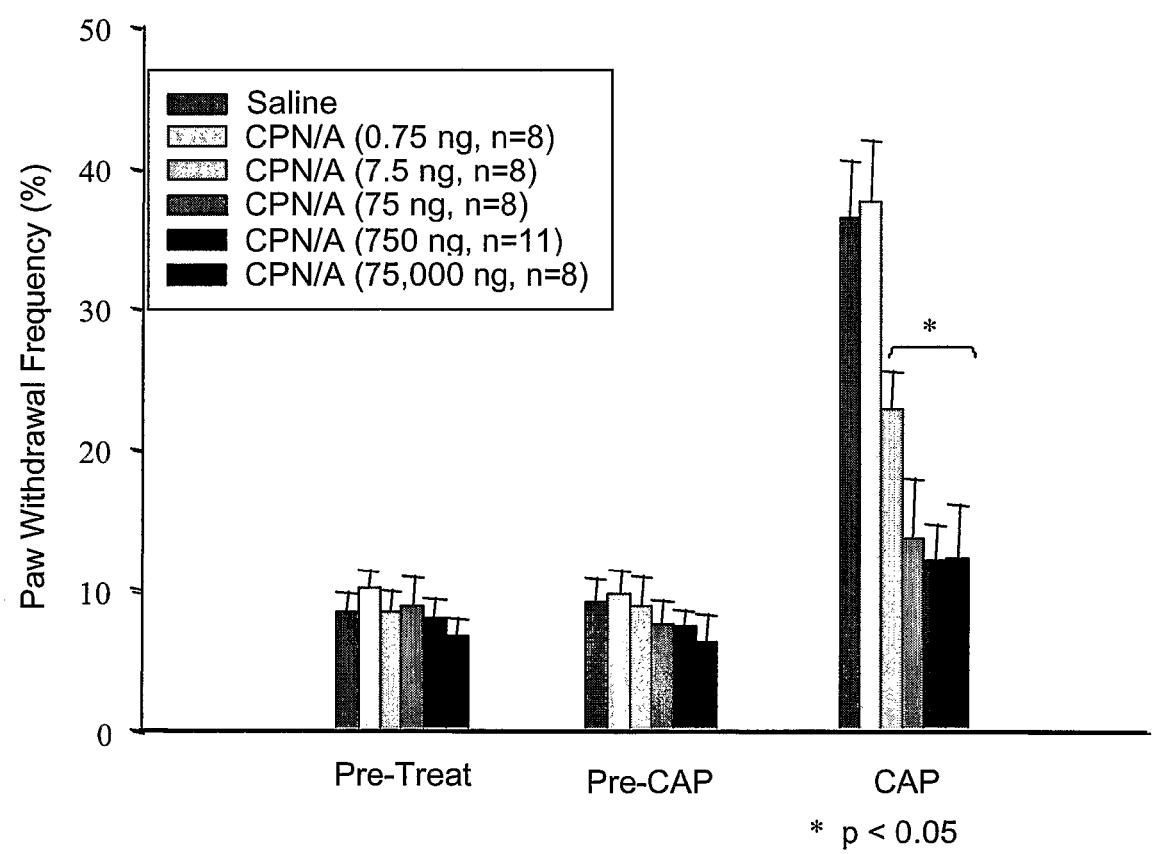
Figure 23:
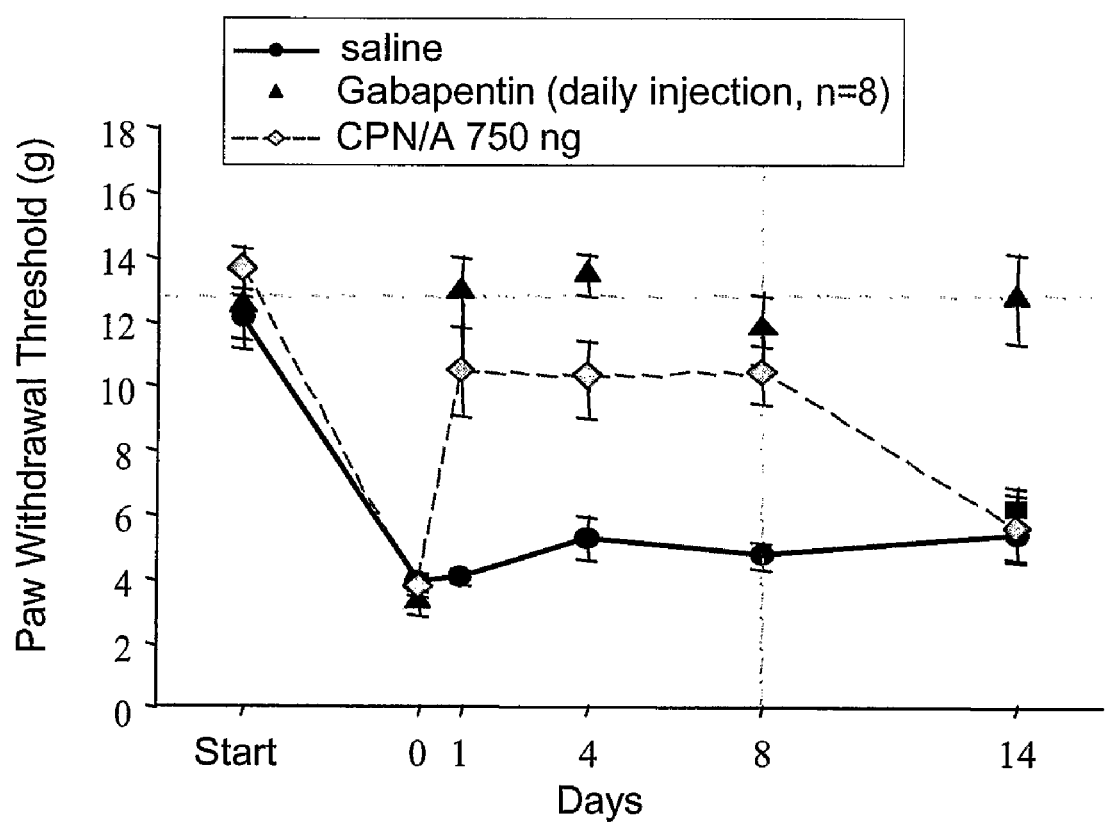
Figure 24:
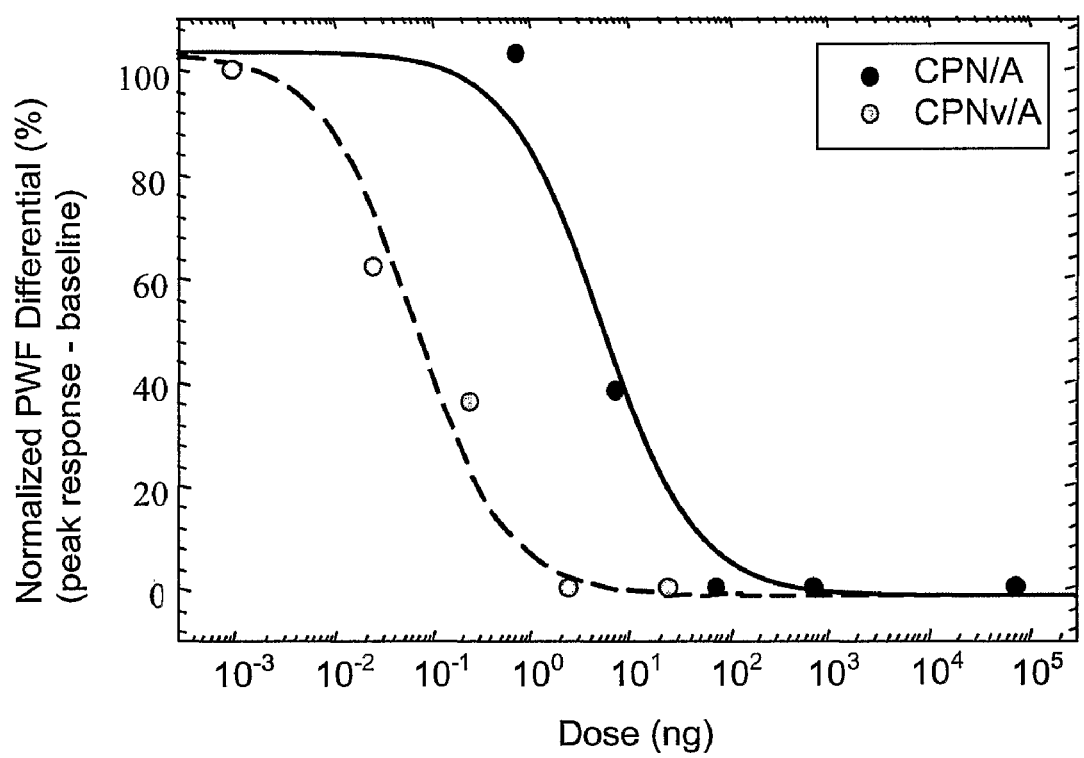
Figure 25:
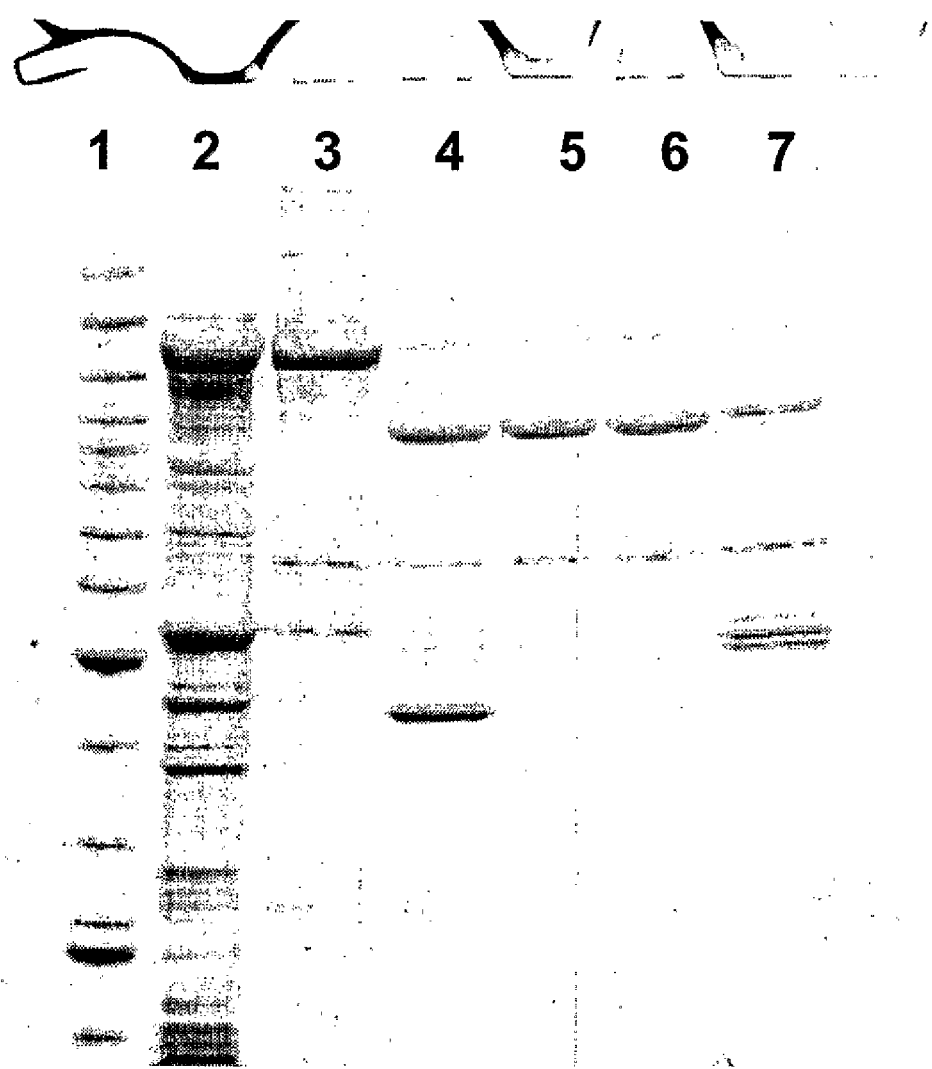
Figure 26:
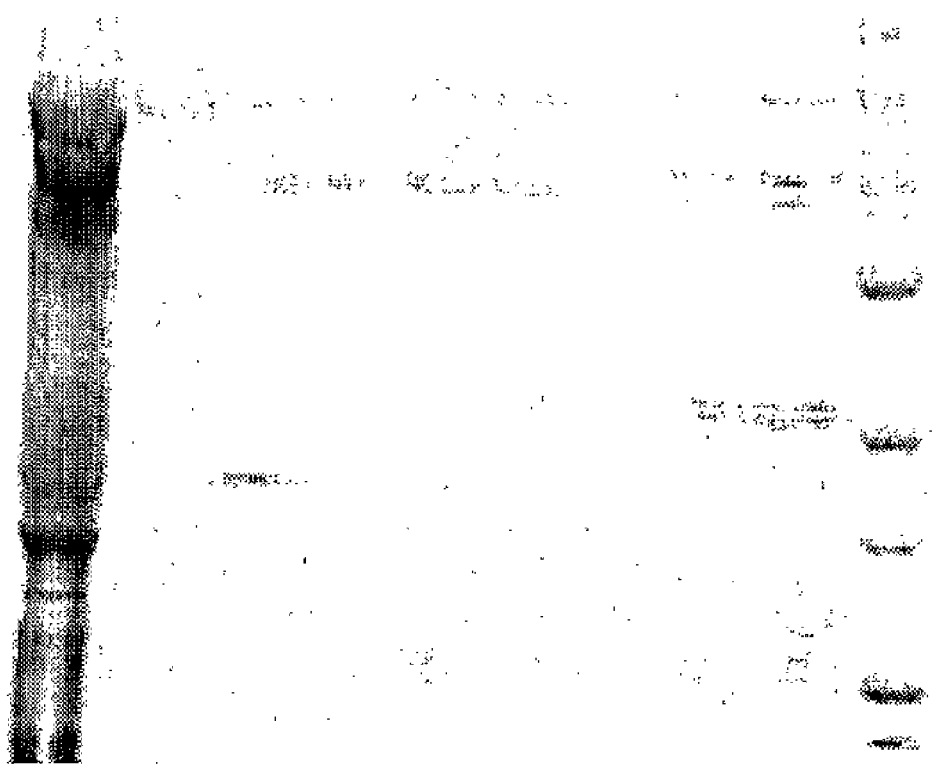
Figure 27:
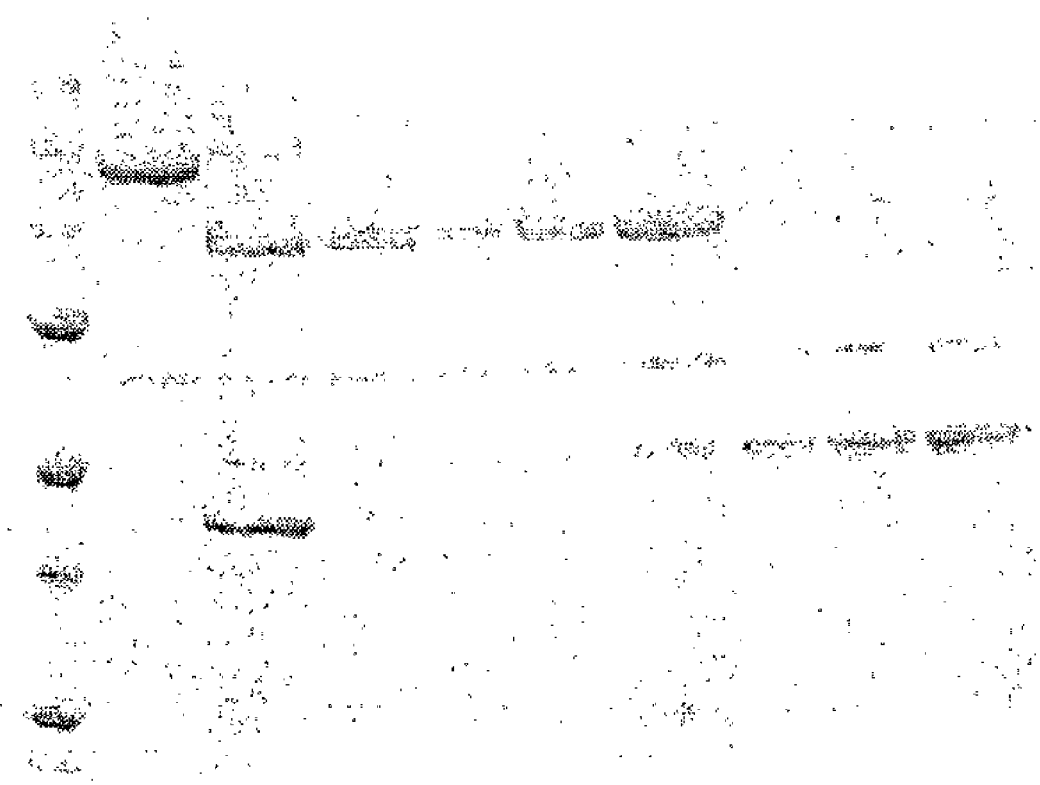
Figure 28:
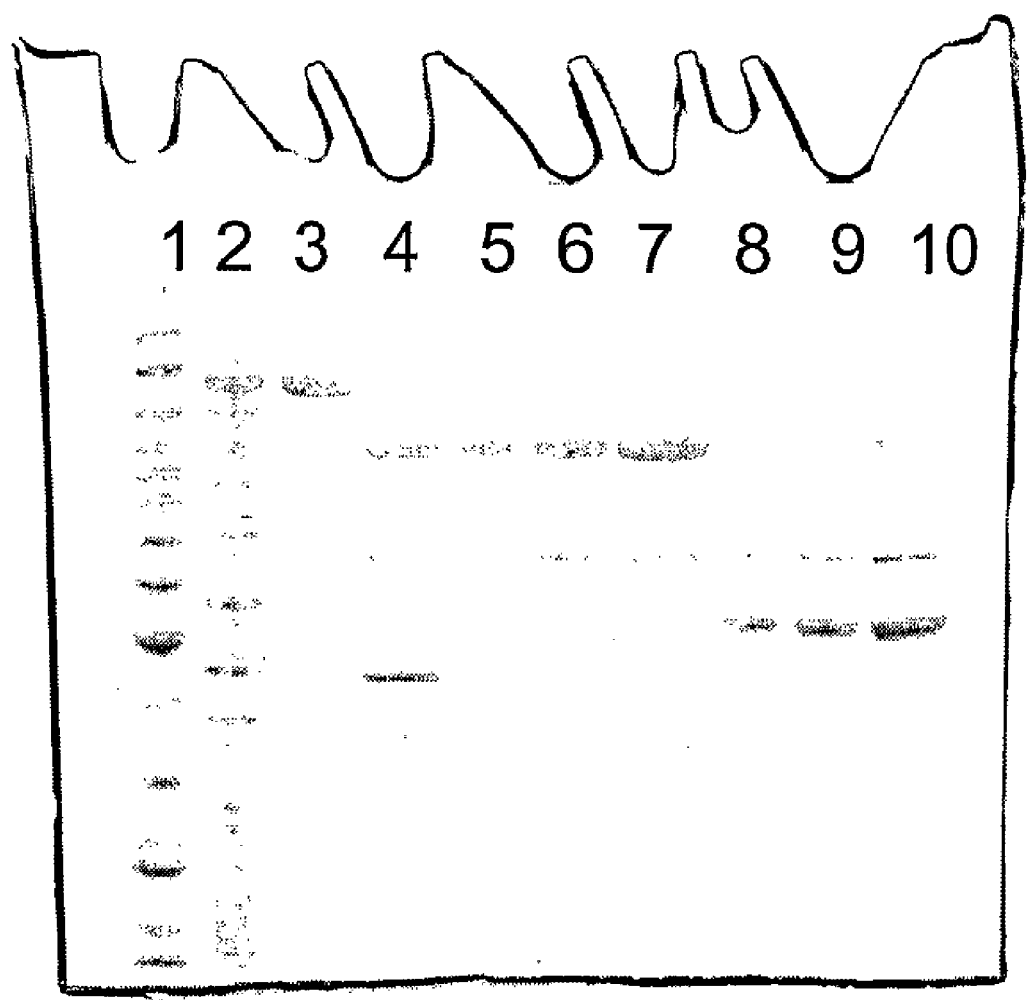
Figure 29:
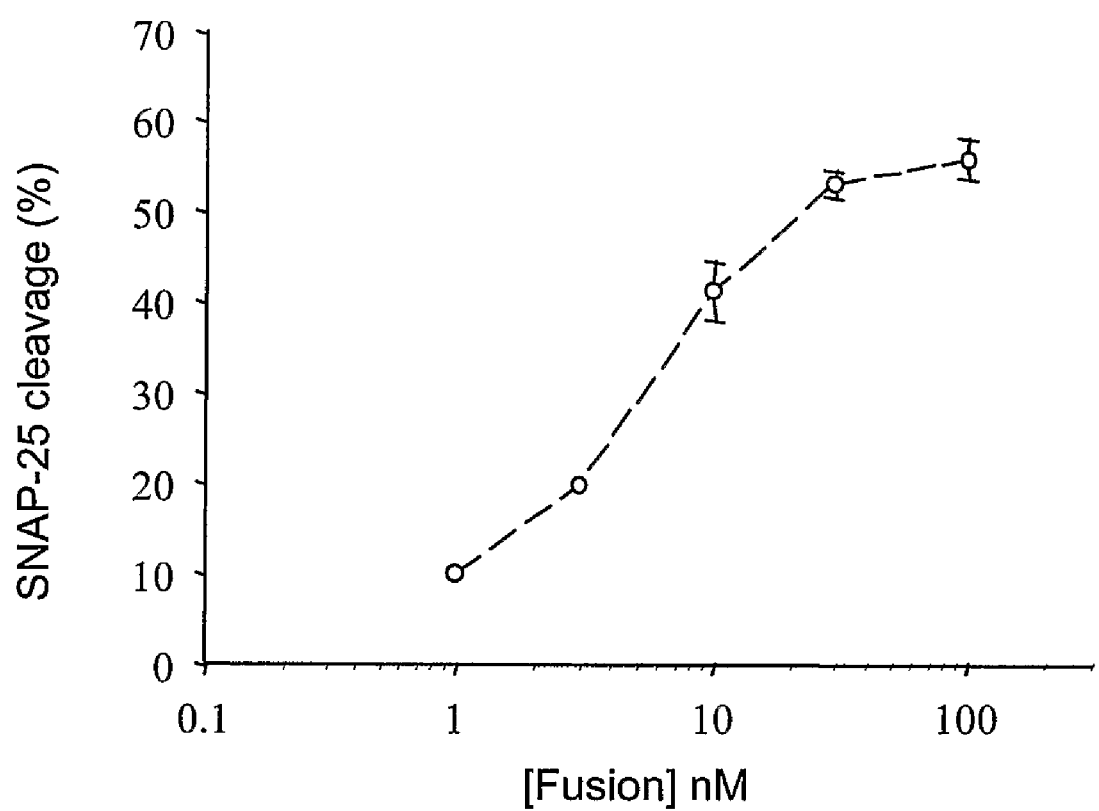
Figure 30:
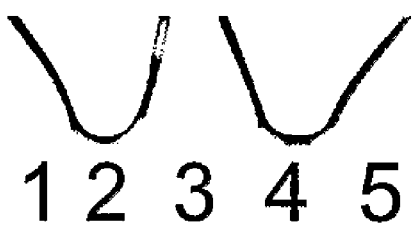
Figure 30:
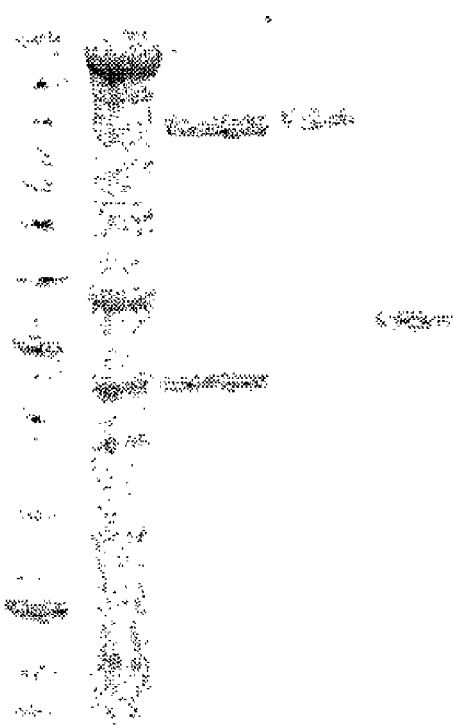
Figure 31:
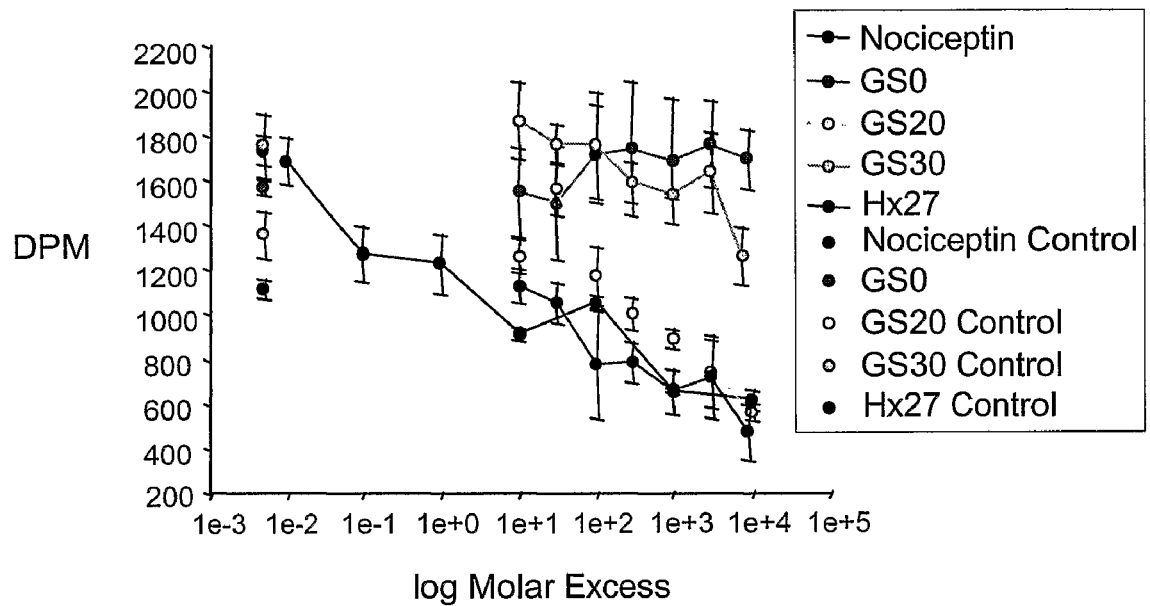
Figure 31:
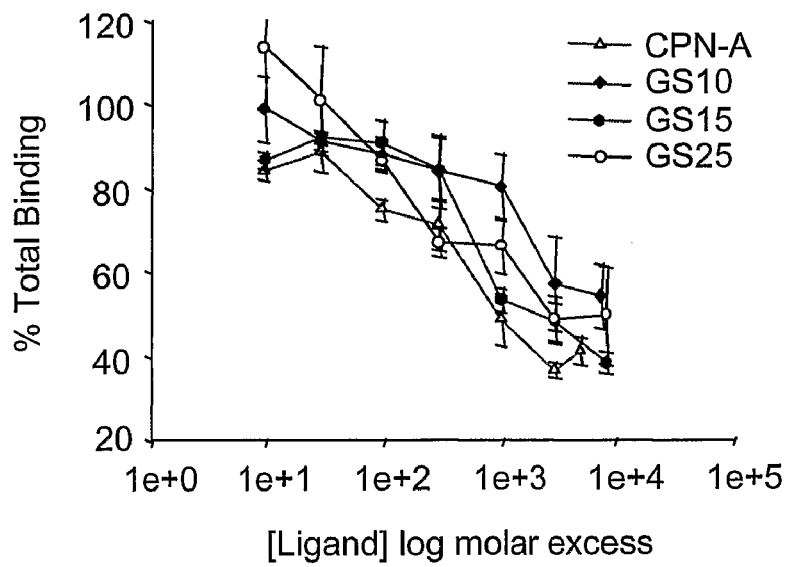
Figure 32:
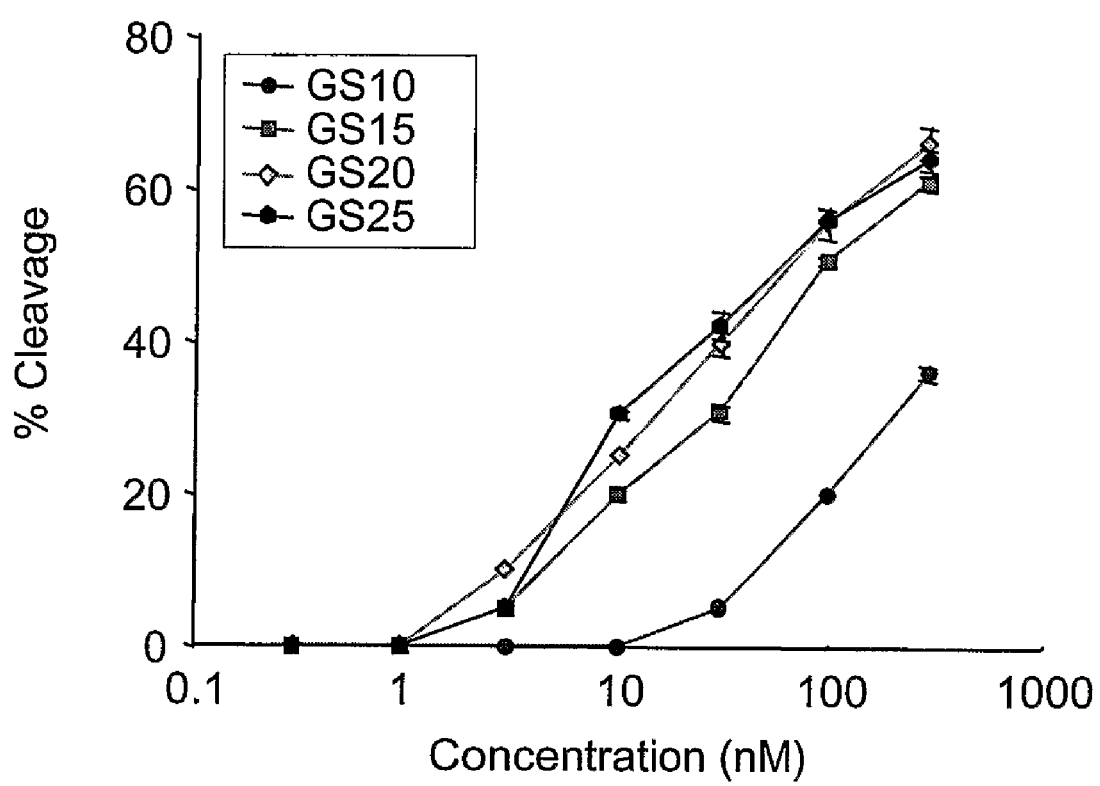

| Figures | |
|---|---|
| FIG. 21 | Cleavage of syntaxin by CPNv-C |
| FIG. 22 | CPN-A efficacy in the Acute Capsaicin-Induced Mechanical Allodynia model |
| FIG. 23 | CPN-A efficacy in the Streptozotocin (STZ)-Induced Peripheral Diabetic Neuropathy (Neuropathic Pain) model |
| FIG. 24 | CPNv-A efficacy in the Acute Capsaicin-Induced Mechanical Allodynia model |
| FIG. 25 | Expressed/purified LC/A-CPLE-$H_N$/A product |
| FIG. 26 | Expressed/purified LC/A-CPBE-$H_N$/A product |
| FIG. 27 | Expressed/purified CPOP-A product |
| FIG. 28 | Expressed/purified CPOPv-A product |
| FIG. 29 | In vitro SNAP-25 cleavage in a DRG cell model |
| FIG. 30 | Expressed/purified CPNv-A-FXa-HT (removable his-tag) |
| FIG. 31 | In vitro efficacy of LC/A-nociceptin-$H_N$/A fusion proteins with variable spacer length, as assessed by ligand competition assay |
| FIG. 32 | In vitro efficacy of LC/A-nociceptin-$H_N$/A fusion proteins with variable spacer length, as assessed by in vitro SNAP-25 cleavage |

The Figures are now described in more detail.

FIG. 1—Expression and Purification of recLH$_N$/B Fusion Protein

SDS-PAGE analysis of expression and purification of recLH$_N$/B from E. coli. In FIG. 1, recLH$_N$/B is purified from cell paste using a three column strategy as described in Example 3. Protein samples are separated by SDS-PAGE and visualised by staining with simply blue safe stain coomassie reagent. Crude, soluble MBP-LH$_N$/B fusion protein contained within the clarified extract (lane 2) is loaded onto Q-Sepharose FF anion-exchange resin. Lane 3 represents recombinant MBP-LH$_N$/B fusion eluted from column at 150-200 mM salt. This sample is treated with factor Xa protease to remove MBP affinity tag (lane 4), and cleaved mixture diluted to lower salt concentration prior to loading onto a Q-Sepharose FF anion-exchange column. Material eluted between 120-170 mM salt was rich in LH$_N$/B (lane 5). Protein in lanes 6 and 8 represents LH$_N$/B harvested after treatment with enterokinase and final purification using Benzamidine Sepharose, under non-reducing and reducing conditions respectively. Lanes 1 and 7 represent molecular mass markers [Mark 12 (Invitrogen)].

FIG. 2—Expression and Purification of LH$_N$/C Fusion Protein

SDS-PAGE analysis of expression and purification of LH$_N$/C from E. coli. In FIG. 2, recLH$_N$/C is purified from E. coli cell paste using a two-step strategy described in Example 4. Protein samples are separated by SDS-PAGE and visualised by staining with coomassie blue. Clarified Crude cell lysate (lane 2) is loaded onto Q-Sepharose FF anion-exchange resin. Fusion protein, MBP-LH$_N$/C is eluted with 0.1 M NaCl (lane 3). Eluted material incubated at 22° C. for 16 h with factor Xa protease (New England Biolabs) to cleave fusion tag MBP and nick recLH$_N$/C at the linker site. The protein of interest is further purified from cleaved-fusion products (lane 4) using Q-Sepharose FF. Lanes 5 and 7 show purified recLH$_N$/C under non-reducing conditions and reduced with 10 mM DTT respectively, to illustrate disulphide bonding at the linker region between LC and H$_N$ domains after nicking with factor Xa. Lanes 1 and 6 represent molecular mass markers (shown in KDa); Mark 12 (Invitrogen).

FIG. 3—Expression and Purification of N[1-17]-LH$_N$/A Fusion Protein

SDS-PAGE analysis of expression and purification of N[1-1,7]-LH$_N$/A from E. coli. In FIG. 3, N[1-17]-LH$_N$/A is purified from E. coli BL21 cell paste using the methodology outlined in Example 9. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

FIG. 4—Purification of a LC/A-Nociceptin-H$_N$/A Fusion Protein

Using the methodology outlined in Example 26, a LC/A-nociceptin-H$_N$/A fusion protein was purified from E. coli BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

FIG. 5—Purification of a Nociceptin-LC/A-H$_N$/A Fusion Protein

Using the methodology outlined in Example 26, a nociceptin-LC/A-H$_N$/A fusion protein was purified from E. coli BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

FIG. 6—Purification of a LC/C-Nociceptin-H$_N$/C Fusion Protein

Using the methodology outlined in Example 26, an LC/C-nociceptin-H$_N$/C fusion protein was purified from E. coli BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

FIG. 7—Purification of a LC/A-met Enkephalin-H$_N$/A Fusion Protein

Using the methodology outlined in-Example 26, an LC/A-met enkephalin-H$_N$/A fusion protein was purified from E. coli BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

FIG. 8—Comparison of Binding Efficacy of a LC/A-Nociceptin-$H_N$/A Fusion Protein and a Nociceptin-LC/A-$H_N$/A Fusion Protein The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin-$H_N$/A fusion is far superior to the nociceptin-LC/A-$H_N$/A fusion at interacting with the $ORL_1$ receptor.

FIG. 9—In Vitro Catalytic Activity of a LC/A-Nociceptin-$H_N$/A Fusion Protein

The in vitro endopeptidase activity of the purified LC/A-nociceptin-$H_N$/A fusion protein was determined essentially as described in Chaddock et al 2002, Prot. Express Purif. 25, 219-228. Briefly, SNAP-25 peptide immobilised to an ELISA plate was exposed to varying concentrations of fusion protein for 1 hour at 37° C. Following a series of washes, the amount of cleaved SNAP-25 peptide was quantified by reactivity with a specific antisera.

FIG. 10—Purification of a LC/A-Nociceptin Variant-$H_N$/A Fusion Protein

Using the methodology outlined in Example 26, an LC/A-nociceptin variant-$H_N$/A fusion protein was purified from E. coli BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

FIG. 11—Comparison of Binding Efficacy of a LC/A-Nociceptin-$H_N$/A Fusion Protein and a LC/A-Nociceptin Variant-$H_N$/A Fusion Protein The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (CPNv-LHA) is superior to the LC/A-nociceptin variant-$H_N$/A fusion (CPN-LHA) at interacting with the $ORL_1$ receptor.

FIG. 12—Expressed/Purified LC/A-Nociceptin-$H_N$/A Fusion Protein Family with Variable Spacer Length Product(s)

Using the methodology outlined in Example 26, variants of the LC/A-CPN-$H_N$/A fusion consisting of GS10, GS30 and HX27 are purified from E. coli cell paste. Samples from the purification of LC/A-CPN(GS10)-$H_N$/A, LC/A-CPN(GS15)-$H_N$/A, LC/A-CPN(GS25)-$H_N$/A, LC/A-CPN(GS30)-$H_N$/A and LC/A-CPN(HX27)-$H_N$/A were assessed by SDS-PAGE prior to staining with Coomassie Blue. The electrophoresis profile indicates purification of a disulphide-bonded di-chain species of the expected molecular mass of CPBE-A. Top panel: M=benchmark molecular mass markers; S=total E. coli protein soluble fraction; FT=proteins that did not bind to the $Ni^{2+}$-charged Sepharose column; FUSION=fusion protein eluted by the addition of imidazole. Bottom panel: Lane 1=benchmark molecular mass markers; Lane 2=total E. coli protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 μl); Lane 8=purified final material post activation with Factor Xa+DTT (5 μl); Lane 9=purified final-material post activation with Factor Xa+DTT (10 μl); Lane 10=purified final material post activation with Factor Xa+DTT (20 μl).

FIG. 13—Inhibition of SP Release and Cleavage of SNAP-25 by CPN-A

Briefly, primary cultures of dorsal root ganglia (DRG) were exposed to varying concentrations of CPN-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and plotted against fusion concentration (dashed line). Material was also recovered for an analysis of substance P content using a specific EIA kit. Inhibition of substance P release is illustrated by the solid line. The fusion concentration required to achieve 50% maximal SNAP-25 cleavage is estimated to be 6.30±2.48 nM.

FIG. 14—Inhibition of SP Release and Cleavage of SNAP-25 Over Extended Time Periods after Exposure of DRG to CPN-A Primary cultures of dorsal root ganglia (DRG) were exposed to varying concentrations of CPN-A for 24 hours. Botulinum neurotoxin (BoNT/A) was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and illustrated by the dotted lines. Material was also recovered for an analysis of substance P content using a specific EIA kit. Inhibition of substance P release is illustrated by the solid lines.

FIG. 15—Cleavage of SNAP-25 by CPNv-A

Primary cultures of dorsal root ganglia (DRG) were exposed to varying concentrations of CPNv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The fusion concentration required to achieve 50% maximal SNAP-25 cleavage is estimated to be 1.38±0.36 nM.

FIG. 16—Cleavage of SNAP-25 Over Extended Time Periods after Exposure of DRG to CPNv-A Primary cultures of dorsal root ganglia (DRG) were exposed to varying concentrations of CPNv-A for 24 hours. CPN-A was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

FIG. 17—CPNv-A Fusion-Mediated Displacement of [3H]-Nociceptin Binding.

The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (labelled as CPNv-LHnA) is superior to the LC/A-nociceptin-$H_N$/A fusion (labelled as CPN-LHnA) at interacting with the $ORL_1$ receptor.

FIG. 18—Expressed/Purified CPNv(Ek)-A Product

Proteins were subjected to SDS-PAGE prior to staining with Coomassie Blue. The electrophoresis profile indicates purification of a disulphide-bonded di-chain species of the expected molecular mass of CPNv(Ek)-A. Lane 1=benchmark molecular mass markers; Lane 2=total *E. coli* protein soluble fraction; Lane 3=purified material following initial capture on $Ni^{2+}$-charged Sepharose; Lane 4=purified final material post activation with enterokinase (5 µl); Lane 5=purified final material post activation with enterokinase (10 µl); Lane 6=purified final material post activation with enterokinase (20 µl); Lane 7=purified final material post activation with enterokinase+DTT (5 µl); Lane 8=purified final material post activation with enterokinase+DTT (10 µl); Lane 9=purified final material post activation with enterokinase+DTT (20 µl).

FIG. 19—Cleavage of SNAP-25 by CPNv(Ek)-A

Primary cultures of dorsal root ganglia (DRG) were exposed to varying concentrations of CPNv(Ek)-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. CPNv-A as prepared in Example 26 was used for comparison purposes. The percentage cleavage of SNAP-25 by CPNv(Ek)-A (labelled as En activated) and CPNv-A (labelled as Xa activated) are illustrated.

FIG. 20—Expressed/Purified CPNv-C Product

Proteins were subjected to SDS-PAGE prior to staining with Coomassie Blue. The electrophoresis profile indicates purification of a disulphide-bonded di-chain species of the expected molecular mass of CPNv-C. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified material following second capture on $Ni^{2+}$-charged Sepharose; Lane 6=final purified material; Lane 7=final purified material+DTT; Lane 8=benchmark molecular mass markers.

FIG. 21—Cleavage of Syntaxin by CPNv-C

Primary cultures of dorsal root ganglia (DRG) were exposed to varying concentrations of CPNv-C for 24 hours. Cellular proteins were separated by SDS-PAGE, Western blotted, and probed with anti-syntaxin to facilitate an assessment of syntaxin cleavage. The percentage of cleaved syntaxin was calculated by densitometric analysis. The fusion concentration required to achieve 50% maximal syntaxin cleavage is estimated to be 3.13±1.96 nM.

FIG. 22—CPN-A Efficacy in the Acute Capsaicin-Induced Mechanical Allodynia Model The ability of an LC/A-nociceptin-$H_N$/A fusion (CPN/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPN/A but before capsaicin (Pre-CAP); and following capsaicin challenge post-injection of CPN/A (average of responses at 15' and 30'; CAP). Capsaicin challenge was achieved by injection of 10 µL of a 0.3% solution. Sample dilutions were prepared in 0.5% BSA/saline.

FIG. 23—CPN-A Efficacy in the Streptozotocin (STZ)-Induced Peripheral Diabetic Neuropathy (Neuropathic Pain) Model Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 µl) are injected subcutaneously as a single injection (except gabapentin) and the PWT is measured at 1 day post-treatment and periodically thereafter over a 2 week period. Gabapentin (30 mg/kg i.p. @ 3 ml/kg injection volume) is injected daily, 2 hours prior to the start of PWT testing.

FIG. 24—CPNv-A Efficacy in the Acute Capsaicin-Induced Mechanical Allodynia Model The ability of an LC/A-nociceptin variant-$H_N$/A fusion (CPNv/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat), after subcutaneous intraplantar treatment with CPNv/A but before capsaicin (Pre-CAP), and following capsaicin challenge post-injection of CPNv/A (average of responses at 15' and 30'; CAP). Capsaicin challenge was achieved by injection of 10 µL of a 0.3% solution. Sample dilutions were prepared in 0.5% BSA/saline. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more potent than CPN/A since a lower dose of CPNv/A is required to achieve similar analgesic effect to that seen with CPN/A.

FIG. 25—Expressed/Purified LC/A-CPLE-H$_N$/A Product

Proteins were subjected to SDS-PAGE prior to staining with Coomassie Blue. The electrophoresis profile indicates purification of a disulphide-bonded di-chain species of the expected molecular mass of CPLE-A. Lane 1=benchmark molecular mass markers; Lane 2=total E. coli protein soluble fraction; Lane 3=purified material following initial capture on Ni$^{2+}$-charged Sepharose; Lane 4=Factor Xa treated material prior to final capture on Ni$^{2+}$-charged Sepharose; Lane 5=purified material following second capture on Ni$^{2+}$-charged Sepharose; Lane 6=final purified material; Lane 7=final purified material+DTT.

FIG. 26—Expressed/Purified LC/A-CPBE-H$_N$/A Product

Proteins were subjected to SDS-PAGE prior to staining with Coomassie Blue. The electrophoresis profile indicates purification of a disulphide-bonded di-chain species of the expected molecular mass of CPBE-A. Lane 1=total E. coli protein soluble fraction; Lane 2=purified material following initial capture on Ni$^{2+}$-charged Sepharose; Lane 3=Factor Xa treated material prior to final capture on Ni$^{2+}$-charged Sepharose; Lane 4=purified final material post activation with Factor Xa (5 µl); Lane 5=purified final material post activation with Factor Xa (10 µl); Lane 6=purified final material post activation with Factor Xa (20 µl); Lane 7=purified final material post activation with Factor Xa+DTT (5 µl); Lane 8=purified final material post activation with Factor Xa+DTT (10 µl); Lane 9=purified final material post activation with Factor Xa+DTT (20 µl); Lane 10=benchmark molecular mass markers.

FIG. 27—Expressed/Purified CPOP-A Product

Proteins were subjected to SDS-PAGE prior to staining with Coomassie Blue. The electrophoresis profile indicates purification of a disulphide-bonded di-chain species of the expected molecular mass of CPOP-A. Lane 1=benchmark molecular mass markers; Lane 2=purified material following initial capture on Ni$^{2+}$-charged Sepharose; Lane 3=Factor Xa treated material prior to final capture on Ni$^{2+}$-charged Sepharose; Lane 4=purified material following second capture on Ni$^{2+}$-charged Sepharose; Lane 5=purified final material post activation with Factor Xa (5 µl); Lane 6=purified final material post activation with Factor Xa (10 µl); Lane 7=purified final-material post-activation with Factor Xa (20 µl); Lane 8=purified final material post activation with Factor Xa+DTT (5 µl); Lane 9=purified final material post activation with Factor Xa+DTT (10 µl); Lane 10=purified final material post activation with Factor Xa+DTT (20 µl).

FIG. 28—Expressed/Purified CPOPv-A Product

Proteins were subjected to SDS-PAGE prior to staining with Coomassie Blue. The electrophoresis profile indicates purification of a disulphide-bonded di-chain species of the expected molecular mass of CPOPv-A. Lane 1=benchmark molecular mass markers; Lane 2=total E. coli protein soluble fraction; Lane 3=purified material following initial capture on Ni$^{2+}$-charged Sepharose; Lane 4=Factor Xa treated material prior to final capture on Ni$^{2+}$-charged Sepharose; Lane 5=purified final material post activation with Factor Xa (5 µl); Lane 6=purified final material post activation with Factor Xa (10 µl); Lane 7=purified final material post activation with Factor Xa (20 µl); Lane 8=purified final material post activation with Factor Xa+DTT (5 µl); Lane 9=purified final material post activation with Factor Xa+DTT (10 µl); Lane 10=purified final material post activation with Factor Xa+DTT (20 µl).

FIG. 29—In Vitro SNAP-25 Cleavage in a DRG Cell Model

Primary cultures of dorsal root ganglia (DRG) were exposed to varying concentrations of CPOPv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

FIG. 30—Expressed/Purified CPNv-A-FXa-HT (Removable his-tag)

Proteins were subjected to SDS-PAGE prior to staining with Coomassie Blue. The electrophoresis profile indicates purification of a disulphide-bonded di-chain species of the expected molecular mass of CPNv-A-FXa-HT. Lane 1-=benchmark molecular mass markers; Lane 2=total E. coli protein soluble fraction; Lane 3=Factor Xa treated material prior to final capture on Ni$^{2+}$-charged Sepharose; Lane 4=purified final material post activation with Factor Xa; Lane 5=purified final material post activation with Factor Xa+DTT.

FIG. 31—In Vitro Efficacy of LC/A-Nociceptin-H$_N$/A Fusion Proteins with Variable Spacer Length, as Assessed by Ligand Competition Assay The ability of LC/A-nociceptin-H$_N$/A fusions of variable spacer length to bind to the ORL$_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). The upper panel illustrates the displacement characteristics of the GS0, GS20, GS30 and Hx27 spacers, whilst the lower panel illustrates the displacement achieved by the GS10, GS15 and GS25 spaced fusion proteins. It is concluded that the GS0 and GS30 spacers are ineffective, and the GS10 is poorly effective, at displacing nociceptin from the ORL1 receptor.

FIG. 32—In Vitro Efficacy of LC/A-Nociceptin-H$_N$/A Fusion Proteins with Variable Spacer Length, as Assessed by In Vitro SNAP-25 Cleavage Primary cultures of dorsal root ganglia (DRG) were exposed to varying concentrations of CPN-A (of variable spacer length) for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The poorly effective binding characteristics of the GS10 spaced fusion protein (see FIG. 28) are reflected in the higher concentrations of fusion required to achieve cleavage of intracellular SNAP-25. GS0 and GS30 spaced fusion proteins. were completely ineffective (date not shown). GS15, 20 and 25-spaced fusion proteins were similarly effective.

| | SEQ ID Nos |
|---|---|
| SEQ ID1 | DNA sequence of N[1-17] |
| SEQ ID2 | Protein Sequence of N[1-17] |
| SEQ ID3 | DNA sequence of N[1-11] |
| SEQ ID4 | Protein sequence of N[1-11] |
| SEQ ID5 | DNA sequence of N[[Y10]1-11] |
| SEQ ID6 | Protein sequence of N[[Y10]1-11] |
| SEQ ID7 | DNA sequence of N[[Y11]1-11] |
| SEQ ID8 | Protein sequence of N[[Y11]1-11] |
| SEQ ID9 | DNA sequence of N[[Y14]1-17] |
| SEQ ID10 | Protein sequence of N[[Y14]1-17] |
| SEQ ID11 | DNA sequence of N[1-13] |

-continued

| | SEQ ID Nos |
|---|---|
| SEQ ID12 | Protein sequence of N[1-13] |
| SEQ ID13 | DNA sequence of Nv (also known as N[[R14K15]1-17]) |
| SEQ ID14 | Protein sequence of Nv (also known as N[[R14K15]1-17]) |
| SEQ ID15 | DNA sequence of N[1-17]-LH$_N$/A fusion protein |
| SEQ ID16 | Protein sequence of N[1-17]-LH$_N$/A fusion protein |
| SEQ ID17 | DNA sequence of N[[Y11]1-11]-LHN/A fusion protein |
| SEQ ID18 | Protein sequence of N[[Y11]1-11]-LHN/A fusion protein |
| SEQ ID19 | DNA sequence of N[1-13]-LHN/A fusion protein |
| SEQ ID20 | Protein sequence of N[1-13]-LHN/A fusion protein |
| SEQ ID21 | DNA sequence of LHN/A-N[1-17] fusion protein |
| SEQ ID22 | Protein sequence of LHN/A-N[1-17] fusion protein |
| SEQ ID23 | DNA sequence of LHN/C-N[1-11] fusion protein |
| SEQ ID24 | Protein sequence of LHN/C-N[1-11] fusion protein |
| SEQ ID25 | DNA sequence of N[[Y14]1-17]-LHN/C fusion protein |
| SEQ ID26 | Protein sequence of N[[Y14]1-17]-LHN/C fusion protein |
| SEQ ID27 | DNA sequence of the LC/A |
| SEQ ID28 | DNA sequence of the H$_N$/A |
| SEQ ID29 | DNA sequence of the LC/B |
| SEQ ID30 | DNA sequence of the H$_N$/B |
| SEQ ID31 | DNA sequence of the LC/C |
| SEQ ID32 | DNA sequence of the H$_N$/C |
| SEQ ID33 | DNA sequence of the CPN-A linker |
| SEQ ID34 | DNA sequence of the A linker |
| SEQ ID35 | DNA sequence of the N-terminal presentation nociceptin insert |
| SEQ ID36 | DNA sequence of the CPN-C linker |
| SEQ ID37 | DNA sequence of the CPBE-A linker |
| SEQ ID38 | DNA sequence of the CPNvar-A linker |
| SEQ ID39 | DNA sequence of the LC/A-CPN-H$_N$/A fusion |
| SEQ ID40 | Protein sequence of the LC/A-CPN-H$_N$/A fusion |
| SEQ ID41 | DNA sequence of the N-LC/A-H$_N$/A fusion |
| SEQ ID42 | Protein sequence of the N-LC/A-H$_N$/A fusion |
| SEQ ID43 | DNA sequence of the LC/C-CPN-H$_N$/C fusion |
| SEQ ID44 | Protein sequence of the LC/C-CPN-H$_N$/C fusion |
| SEQ ID45 | DNA sequence of the LC/C-CPN-H$_N$/C (A-linker) fusion |
| SEQ ID46 | Protein sequence of the LC/C-CPN-H$_N$/C (A-linker) fusion |
| SEQ ID47 | DNA sequence of the LC/A-CPME-H$_N$/A fusion |
| SEQ ID48 | Protein sequence of the LC/A-CPME-H$_N$/A fusion |
| SEQ ID49 | DNA sequence of the LC/A-CPBE-H$_N$/A fusion |
| SEQ ID50 | Protein sequence of the LC/A-CPBE-H$_N$/A fusion |
| SEQ ID51 | DNA sequence of the LC/A-CPNv-H$_N$/A fusion |
| SEQ ID52 | Protein sequence of the LC/A-CPNv-H$_N$/A fusion |
| SEQ ID53 | DNA sequence of the LC/A-CPN[1-11]-HN/A fusion |
| SEQ ID54 | Protein sequence of the LC/A-CPN[1-11]-HN/A fusion |
| SEQ ID55 | DNA sequence of the LC/A-CPN[[Y10]1-11]-HN/A fusion |
| SEQ ID56 | Protein sequence of the LC/A-CPN[[Y10]1-11]-HN/A fusion |
| SEQ ID57 | DNA sequence of the LC/A-CPN[[Y11]1-11]-HN/A fusion |
| SEQ ID58 | Protein sequence of the LC/A-CPN[[Y11]1-11]-HN/A fusion |
| SEQ ID59 | DNA sequence of the LC/A-CPN[[Y14]1-17]-HN/A fusion |
| SEQ ID60 | Protein sequence of the LC/A-CPN[[Y14]1-17]-HN/A fusion |
| SEQ ID61 | DNA sequence of the LC/A-CPN[1-13]-HN/A fusion |
| SEQ ID62 | Protein sequence of the LC/A- CPN[1-13]-HN/A fusion |
| SEQ ID63 | DNA sequence of the nociceptin-spacer-LC/A-H$_N$/A fusion |
| SEQ ID64 | Protein sequence of the nociceptin-spacer-LC/A-H$_N$/A fusion |
| SEQ ID65 | DNA sequence of the CPN-A GS10 linker |
| SEQ ID66 | DNA sequence of the CPN-A GS15 linker |
| SEQ ID67 | DNA sequence of the CPN-A GS25 linker |
| SEQ ID68 | DNA sequence of the CPN-A GS30 linker |
| SEQ ID69 | DNA sequence of the CPN-A HX27 linker |
| SEQ ID70 | DNA sequence of the LC/A-CPN(GS15)-H$_N$/A fusion |
| SEQ ID71 | Protein sequence of the LC/A-CPN(GS15)-H$_N$/A fusion |
| SEQ ID72 | DNA sequence of the LC/A-CPN(GS25)-H$_N$/A fusion |
| SEQ ID73 | Protein sequence of the LC/A-CPN(GS25)-H$_N$/A fusion |
| SEQ ID74 | DNA sequence of the CPNvar-A Enterokinase activatable linker |
| SEQ ID75 | DNA sequence of the LC/A-CPNv(Ek)-H$_N$/A fusion |
| SEQ ID76 | Protein sequence of the LC/A-CPNv(Ek)-H$_N$/A fusion |
| SEQ ID77 | DNA sequence of the CPNvar-A linker |
| SEQ ID78 | DNA sequence of the LC/C-CPNv-H$_N$/C fusion (act. A) |
| SEQ ID79 | Protein sequence of the LC/C-CPNv-H$_N$/C fusion (act. A) |
| SEQ ID80 | DNA sequence of the LC/A-CPLE-H$_N$/A fusion |
| SEQ ID81 | Protein sequence of the LC/A-CPLE-H$_N$/A fusion |
| SEQ ID82 | DNA sequence of the LC/A-CPOP-H$_N$/A fusion |
| SEQ ID83 | Protein sequence of the LC/A-CPOP-H$_N$/A fusion |
| SEQ ID84 | DNA sequence of the LC/A-CPOPv-H$_N$/A fusion |
| SEQ ID85 | Protein sequence of the LC/A-CPOPv-H$_N$/A fusion |
| SEQ ID86 | DNA sequence of the IgA protease |
| SEQ ID87 | DNA sequence of the IgA-CPNv-H$_N$/A fusion |
| SEQ ID88 | Protein sequence of the IgA-CPNv-H$_N$/A fusion |
| SEQ ID89 | DNA sequence of the FXa-HT |
| SEQ ID90 | DNA sequence of the CPNv-A-FXa-HT |
| SEQ ID91 | Protein sequence of the CPNv-A-FXa-HT fusion |
| SEQ ID92 | DNA sequence of the DT translocation domain |
| SEQ ID93 | DNA sequence of the CPLE-DT-A |
| SEQ ID94 | Protein sequence of the CPLE-DT-A fusion |
| SEQ ID95 | DNA sequence of the TeNT LC |
| SEQ ID96 | DNA sequence of the CPNv-TENT LC |
| SEQ ID97 | Protein sequence of the CPNV-TeNT LC fusion |
| SEQ ID98 | DNA sequence of the CPNvar-C linker |
| SEQ ID99 | DNA sequence of the LC/C-CPNv-H$_N$/C fusion (act. C) |
| SEQ ID100 | Protein sequence of the LC/C-CPNv-H$_N$/C fusion (act. C) |

EXAMPLES

Example 1

Confirmation of TM Agonist Activity by Measuring Release of Substance P from Neuronal Cell Cultures Materials
Substance P EIA is obtained from R&D Systems, UK.

Methods
Primary neuronal cultures of eDRG are established as described previously (Duggan et al., 2002). Substance P release from the cultures is assessed by EIA, essentially as described previously (Duggan et al., 2002); The TM of interest is added to the neuronal cultures (established for at least 2 weeks prior to treatment); control cultures are performed in parallel by addition of vehicle in place of TM. Stimulated (100 mM KCl) and basal release, together with total cell lysate content, of substance P are obtained for both control and TM treated cultures. Substance P immunoreactivity is measured using Substance P Enzyme Immunoassay Kits (Cayman Chemical Company, USA or R&D Systems, UK) according to manufacturers' instructions.

The amount of Substance P released by the neuronal cells in the presence of the TM of interest is compared to the release obtained in the presence and absence of 100 mM KCl. Stimulation of Substance P release by the TM of interest above the basal release, establishes that the TM of interest is an "agonist ligand" as defined in this specification. If desired the stimulation of Substance P release by the TM of interest can be compared to a standard Substance P release-curve produced using the natural ORL-1 receptor ligand, nociceptin (Tocris).

Example 2

Expression and Purification of Catalytically Active LH$_N$/A

Materials
Synthetic DNA obtained from Sigma Genosys.
Restriction enzymes obtained from New England Biolabs.

Methods
The expression and purification of catalytically active LH$_N$/A was carried out essentially as described in Sutton et al., (2005), Prot. Express. Purif., 40, pp 31-41.

Briefly, DNA encoding the light chain plus 423 amino acids from the N-terminal of the heavy chain of BoNT/A was synthesised by Sigma-Genosys to produce a synthetic $LH_N$/A gene with an *E. coli* codon bias. The linker region between the light chain and $H_N$ domain was engineered to contain a Factor Xa cleavage site by splice-overlap extension PCR. Two PCR products were generated using primer pairs consisting of a long, mutagenic primer and a shorter, non-mutagenic primer:

```
(5'-tccaaaactaaatctctgATAGAAGGTAGAaacaaagcgctgaacg
ac; SEQ ID NO:107) with (5'-CTTGATGTACTCTGTGAACGTGCTC; SEQ ID NO:108)
and (5'-gtcgttcagcgctttgttTCTACCTTCTATcagagatttagttttg
ga; SEQ ID NO:109) with (5'-ATGGAGTTCGTTAACAAACAGTTC; SEQ ID NO:110).
```

The products from these two reactions were used as templates for the splice-overlap extension PCR. A further PCR reaction was set up to add BamHI and SalI sites at either end of the activatable rec$LH_N$/A gene and these sites were used for insertion into an Invitrogen gateway entry vector. The entry vector was then used, along with a gateway recombination site adapted pMAL c2x, in a LR clonase reaction to form PMAL c2x rec$LH_N$/A. The pMAL c2x rec$LH_N$/A was modified to incorporate a 6'HIS tag at the N-terminus of the MBP. This was achieved by the insertion of annealed oligonucleotides encoding the HIS tag into the NdeI site of pMAL.

The expression vector expressing $LH_N$/A was transformed into *E. coli* HMS174 or AD494(DE3) (Novagen). Cultures were grown in Terrific broth complex medium supplemented with $ZnCl_2$ (1 μM), ampicillin (100 μg/ml), 0.2% (w/v) glucose. Parameters for expression of all the constructs were initially determined in shake flask cultures before transferring into 8 L fermentor systems. Starter cultures were grown for 16 hours at 37° C., 220 rpm and used to inoculate 1 L in which growth was continued at 37° C., 250 rpm. At an OD600 nm of 0.6 the temperature was reduced to 25° C. for 30 minutes before induction with 1 mM IPTG. Induction was continued for 4 hours before the cells were harvested and stored at −70° C.

Typically 16 g of cell paste was suspended in 160 ml PBS and lysed by sonication (MSE Soniprep 150). The resulting lysate was clarified by centrifugation prior loading onto a 25 ml amylose column and eluted with 10 mM maltose in PBS. The eluant contained approx. 50% pure fusion protein and was treated with Factor Xa (1 unit Factor Xa/100 μg fusion protein; 20 hours; 26° C.) to remove the HISMBP and cleave the LC-$H_N$ junction to activate the protein. After incubation the sample was filtered (0.45 mm) and diluted two fold with water to give a 0.5×PBS buffer composition. The cleaved, filtered and diluted rec$LH_N$/A was processed through a Q Sepharose FF column (10 ml) and eluted with a step gradient of 80 mM NaCl containing HISMBP and 120 mM NaCl containing approx. 75% pure rec$LH_N$/A. The addition of His tag to MBP overcame previous co-elution problems with $LH_N$/A and MBP. As a final polishing step to ensure complete removal of the HISMBP, the 120 mM NaCl elution from the Q Sepharose column was passed through a Nickel charged 5 ml HisTrap column (Amersham). The flow through from the HisTrap column contained approx. 95% pure rec$LH_N$/A (see the Figures in Sutton et al., (2005), Prot. Express. Purif., 40, pp 31-41 for an illustration of the purification scheme for $LH_N$/A).

Example 3

Expression and Purification of Catalytically Active Recombinant $LH_N$/B

The methodology described below will purify catalytically active $LH_N$/B protease from *E. coli* transformed with the appropriate plasmid encoding the $LH_N$/B polypeptide. It should be noted that various sequences of suitable $LH_N$/B polypeptides have been described in PCT/GB97/02273, granted US 6 461617 and U.S. patent application Ser. No. 10/241,596, incorporated herein by reference.

Methods

The coding region for $LH_N$/B is inserted in-frame to the 3' of the gene encoding maltose binding protein (MBP) in the expression vector pMAL (New England Biolabs) to create pMAL-c2x-$LH_N$/B. In this construct, the expressed MBP and $LH_N$/B polypeptides are separated by a Factor Xa cleavage site, and the LC and $H_N$ domains are separated by a peptide that is susceptible to cleavage with enterokinase. The expression clone is termed pMAL-c2X-syn$LH_N$/B.

pMAL-c2X-syn$LH_N$/B is transformed into *E. coli* HMS174 and cultured in Terrific broth complex medium in 8 L fermentor systems. Pre-induction bacterial growth is maintained at 37° C. to an D600 nm of 5.0, at which stage expression of recMBP-$LH_N$/B is induced by addition of IPTG to 0.5 mM and a reduction in temperature to 30° C. After four hours at 30° C. the bacteria are harvested by centrifugation and the resulting paste stored at −70° C.

The cell paste is resuspended in 20 mM Hepes pH 7.2, 125 mM NaCl, 1 μM $ZnCl_2$ and cell disruption achieved using an APV-Gaulin lab model 1000 homogeniser or a MSE Soniprep 150 sonicator. The resulting suspension is clarified by centrifugation prior to purification.

Following cell disruption, the MBP-fusion protein is captured either on an amylose affinity-resin in 20 mM Hepes pH 7.2, 125 mM NaCl, 1 μM $ZnCl_2$, or on a Q-Sepharose FF anion-exchange resin in 50 mM Hepes pH 7.2, 1 μM $ZnCl_2$ with no salt. A single peak is eluted from the amylose resin in the same buffer plus 10 mM maltose and from the Q-Sepharose in 150-200 mM salt. Cleavage of the MBP-$LH_N$/B junction is completed in an 18 hours incubation step at 22° C. with Factor Xa (NEB) at 1 U/50 μg fusion protein. A substrate (MBP-$LH_N$/B) concentration of at least 4 mg/ml is desirable for efficient cleavage to take place.

The cleaved protein is diluted with 20 mM Hepes to a buffer composition of 20 mM Hepes, 25 mM NaCl, 1 μM $ZnCl_2$, pH 7.2 and processed through a Q Sepharose column to separate the MBP from $LH_N$/B. The $LH_N$/B is eluted from the Q-Sepharose column with 120-170 mM salt. The linker between the light chain and $H_N$ domain is then nicked by incubation with enterokinase at 1 U/100 μg of $LH_N$/B at 22° C. for 16 hours. Finally, the enterokinase is separated from the nicked $LH_N$/B and other contaminating proteins on a Benzamidine Sepharose column, the enzyme preferentially binding to the resin over an incubation of 30 minutes at 4° C. Purified $LH_N$/B is stored at −20° C. until required. See FIG. 1 for an illustration of the purification scheme for rec$LH_N$/B.

Example 4

Expression and Purification of Catalytically Active Recombinant $LH_N$/C

The coding region for $LH_N$/C is inserted in-frame to the 3' of the gene encoding maltose binding protein (MBP) in the expression vector pMAL (New England Biolabs) to create PMAL-c2x-LH$_N$/C. In this construct the expressed MBP and LH$_N$/C polypeptides are separated by a Factor Xa cleavage site.

pMAL-c2x-LH$_N$/C is transformed into *E. coli* AD494 (DE3, IRL) and cultured in Terrific broth complex medium in 8 L fermentor systems. Pre-induction bacterial growth are maintained at 30° C. to an OD600 nm of 8.0, at which stage expression of recMBP-c2x-LH$_N$/C is induced by addition of IPTG to 0.5 mM and a reduction in temperature of culture to 25° C. After 4 hours at 25° C. the bacteria are harvested by centrifugation and the resulting paste stored at −70° C.

The cell paste is resuspended in 50 mM Hepes pH 7.2, 1 µM ZnCl$_2$ at 1:6 (w/v) and cell disruption is achieved using an APV-Gaulin lab model 1000 homogeniser or a MSE Soniprep 150 sonicator. The resulting suspension is clarified by centrifugation prior to purification.

Following cell disruption and clarification, the MBP-fusion protein is separated on a Q-Sepharose Fast Flow anion-exchange resin in 50 mM Hepes pH 7.2, 1 µM ZnCl$_2$ and eluted with the same buffer plus 100 mM NaCl. A double point cleavage is performed at the MBP-LH$_N$/C junction and the H$_N$-LC linker in a single incubation step with Factor Xa. The reaction is completed in a 16-hour incubation step at 22° C. with Factor Xa (NEB) at 1 U/100 µg fusion protein. The cleaved protein is diluted with 20 mM Hepes to a buffer composition of 20 mM Hepes, 25 mM NaCl, pH 7.2 and processed through a second Q-Sepharose column to separate the MBP from LH$_N$/C. Activated (disulphide-bonded cleaved linker) LH$_N$/C is eluted from the Q-Sepharose column by a salt gradient (20 mM Hepes, 500 mM NaCl, 1 µM ZnCl$_2$, pH 7.2) in 120-170 mM salt. See FIG. 2 for an illustration of the purification of LH$_N$/C.

Example 5

Production of a Chemical Conjugate of Nociceptin and LH$_N$/A

Materials

C-terminally extended nociceptin peptide obtained from Sigma Genosys.

Conjugation chemicals obtained from Pierce.

Methods

In order to couple the nociceptin peptide via a C-terminal Cys, the peptide was first synthesised (by standard procedures, commercially obtainable) to include a Cys as the final C-terminal amino acid.

This peptide was then used as the second component in a sulphydryl based coupling reaction as described below (see also previous publications WO 99/17806 and WO 96/33273 and Duggan et al., (2002), J. Biol. Chem. 277, 24846-34852 and Chaddock et al., (2000), Infect Immun., 68, 2587-2593).

Sulphydryl Based Coupling Reaction

Briefly, approximately two reactive leaving groups were introduced into LH$_N$/A (5 mg/ml in phosphate-buffered saline) by reaction with N-succinimidyl-3-(2-pyridyldithio) propionate (SPDP).

Derivatised material was isolated from excess SPDP by size exclusion chromatography. Reconstituted cysteine-tagged nociceptin ligand was mixed with the derivatised LH$_N$/A in a 4:1 molar ratio, and incubated at room temperature for 1 hour with gentle agitation in order to create a chemical conjugate through a reducible covalent disulphide bond. Initial fractionation of the conjugate mixture to remove unconjugated peptide was performed by size exclusion chromatography (Superose-12, or Superdex G-200 depending on scale of conjugation).

Example 6

Production of a Chemical Conjugate of Nociceptin and LH$_N$/B

Materials

C-terminally extended nociceptin peptide obtained from Sigma Genosys.

Conjugation chemicals obtained from Pierce.

Methods

Lyophilised nociceptin was dissolved by the addition of water and dialysed into MES buffer (0.1 M MES, 0.1 M NaCl, pH 5.0). To this solution (at a concentration of about 0.3 mg/ml) was added PDPH (100 mg/ml in DMF) to a final concentration of 1 mg/ml. After mixing, solid EDAC was added to produce a final concentration of about 0.2 mg/ml. The reaction was allowed to proceed for at least 30 minutes at room temperature. Excess PDPH was then removed by desalting over a PD-10 column (Pharmacia) previously equilibrated with MES buffer.

An amount of LH$_N$/B equivalent to half the weight of nociceptin used dissolved in triethanolamine buffer (0.02 M triethanolamine/HCl, 0.1 M sodium chloride, pH 7.8) at a concentration of about 1 mg/ml, was reacted with Traut's reagent (100 mM stock solution in 1 M triethanolamine/HCl, pH 8.0) at a final concentration of 2 mM. After 1 hour, the LH$_N$/B was desalted into PBSE (phosphate buffered saline with 1 mM EDTA) using a PD-10 column (Pharmacia). The protein peak from the column eluate was concentrated using a Microcon 50 (Amicon) to a concentration of about 2 mg/ml.

The derivatised nociceptin was subjected to a final concentration step resulting in a reduction in volume to less than 10% of the starting volume and then mixed with the derivatised LH$_N$/B overnight at room temperature. The products of the reaction were analysed by polyacrylamide gel electrophoresis in the presence of sodium dodecyl-sulphate (SDS-PAGE).

The conjugate resulting from the above reaction was partially purified by size exclusion chromatography over Bio-Gel P-100 (BioRad). The elution profile was followed by measuring the optical density at 280 nm and SDS-PAGE analysis of the fractions. This allowed the separation of conjugate from free nociceptin and by-products of the reaction.

Example 7

Production of a Chemical Conjugate of Nociceptin 1-11 and LH$_N$/B

Materials

C-terminally extended nociceptin 1-11 peptide obtained from Sigma Genosys.

Conjugation chemicals obtained from Pierce.

Methods

In order to couple the nociceptin 1-11 peptide via a C-terminal Cys, the peptide was first synthesised (by standard procedures, commercially obtainable) to include a Cys as the final C-terminal amino acid.

This peptide was then used as the second component in a sulphydryl based coupling reaction as described in Example 5.

Example 8

Production of a Chemical Conjugate of Nociceptin N[[Y14]1-17] and LH$_N$/C

Materials

C-terminally extended nociceptin N[[Y14]1-17] peptide obtained from Sigma Genosys.

Conjugation chemicals obtained from Pierce.

Methods

In order to couple the peptide via a C-terminal Cys, the peptide was first synthesised (by standard procedures, commercially obtainable) to include a Cys as the final C-terminal amino acid.

This peptide was then used as the second component in a sulphydryl based coupling reaction as described in Example 5.

Example 9

Recombinant Production of a Single Polypeptide Fusion of Nociceptin-LH$_N$/A (SEQ ID15 and SEQ ID16)

The DNA sequence for the nociceptin-LH$_N$/A was designed by back translation of the LC/A, H$_N$/A, and nociceptin amino acid sequences. The complete ORF containing the nociceptin-LC/A-activation loop-H$_N$/A sequence was assembled within standard DNA sequence manipulation software (EditSeq). The activation loop between the LC/A cysteine and the H$_N$/A cysteine (CVRGIITSKTKSLDKGY-NKALNDLC) was modified to incorporate a Factor Xa protease recognition site.

Restriction sites appropriate to facilitate cloning into the required expression vector (for example BamHI/SalI) were incorporated at the 5' and 3' ends respectively of the sequence maintaining the correct reading frame. The DNA sequence was screened (using software such as MapDraw, DNASTAR Inc.) for restriction enzyme cleavage sequences incorporated during the back translation. Any cleavage sequences that were found to be common to those required by the cloning system were removed manually from the proposed coding sequence ensuring common *E. coli* codon usage was maintained. *E. coli* codon usage was assessed by reference to software programs such as Graphical Codon Usage Analyser (Geneart), and the % GC content and codon usage ratio assessed by reference to published codon usage tables (for example GenBank Release 143, 13 Sep. 2004).

This optimised DNA sequence containing the nociceptin-LC/A-activation loop-H$_N$/A open reading frame (ORF) was then commercially synthesized and provided in the pCR 4 vector.

The DNA encoding the nociceptin-LH$_N$/A fusion was isolated from pCR 4 and transferred into pMAL vector backbone to facilitate protein expression. The resultant pMAL NO-LH$_N$/A vector was transformed into competent *E. coli* BL21 and correct transformants selected. A single colony of PMAL NO-LH$_N$/A was grown in Terrific broth complex medium supplemented with ZnCl$_2$ (1 mM), ampicillin (100 µg/ml), 0.2% (w/v) glucose. Expression of the insert was induced by the addition of IPTG (0.1 mM) and the culture maintained at 16° C. for 16 hours. After this period of expression the bacteria were isolated by centrifugation and the cell pellet stored at −20° C. until use.

10 g of *E. coli* BL21 cell paste was defrosted in a falcon tube containing 25 ml 50 mM HEPES, pH 7.2, 200 mM NaCl.

The thawed cell paste was made up to 80 ml 10 with 50 mM HEPES, pH 7.2, 200 mM NaCl and sonicated on ice 30 seconds on, 30 seconds off for 10 cycles at a power of 22 microns ensuring the sample remained cool. The lysed cells were centrifuged at 18 000 rpm, 4° C. for 30 minutes. The supernatant was loaded onto a 0.1 M NiSO$_4$ charged chelating column (20-30 ml column is sufficient) and equilibrated with 50 mM HEPES, pH 7.2, 200 mM NaCl.

Using a step gradient of 10 and 40 mM imidazol, the non-specific bound protein was washed away and the fusion protein eluted with 100 mM imidazol. The eluted fusion protein was dialysed against 5 L of 50 mM HEPES, pH 7.2, 200 mM NaCl at 4° C. overnight and the OD of the dialysed fusion protein measured. 1 unit of Factor Xa was added per 100 µg fusion protein and incubated at 25° C. static overnight. The cleavage mixture was loaded onto a 0.1 M NiSO$_4$ charged Chelating column (20-30 ml column is sufficient) and equilibrated with 50 mM HEPES, pH 7.2, 200 mM NaCl.

Using a step gradient of 10 and 40 mM imidazol, the non-specific bound protein was washed away and the fusion protein eluted with 100 mM imidazol. The eluted fusion protein was dialysed against 5 L of 50 mM HEPES, pH 7.2, 200 mM NaCl at 4° C. overnight and the fusion concentrated to about 2 mg/ml, aliquoted and stored at −20° C.

FIG. 3 shows the SDS-PAGE analysis of expression and purification of N[1-17]-LH$_N$/A.

Example 10

Recombinant Production of a Single Polypeptide Fusion of (Nociceptin 1-11)-LH$_N$/B The DNA sequence for the (nociceptin 1-11)-LH$_N$/B was designed by back translation of the LC/B, H$_N$/B, and nociceptin 1-11 amino acid sequences. The complete ORF containing the (nociceptin 1-11)-LC/B-activation loop-H$_N$/B sequence was assembled within standard DNA sequence manipulation software (EditSeq). The activation loop between the LC/B cysteine and the H$_N$/B cysteine was modified to incorporate a Factor Xa protease recognition site.

The recombinant fusion protein was then produced essentially as described in Example 9.

Example 11

Recombinant Production of a Single Polypeptide Fusion of (Nociceptin N[[Y14]1-17])-LH$_N$/C (SEQ ID25 and SEQ ID26)

The DNA sequence for the nociceptin N[[Y14]1-17] was designed by back translation of the LC/C, H$_N$/C, and nociceptin N[[Y14]1-17] amino acid sequences. The complete ORF containing the (nociceptin N[[Y14]1-17])-LC/C-activation loop-H$_N$/C sequence was assembled within standard DNA sequence manipulation software (EditSeq). The activation loop between the LC/C cysteine and the H$_N$/C cysteine was modified to incorporate a Factor Xa protease recognition site.

The recombinant fusion protein was then produced essentially as described in Example 9.

Example 12

Recombinant Production of a Single Polypeptide Fusion of LH$_N$/C-(nociceptin 1-11) (SEQ ID23 and SEQ ID24)

The DNA sequence for the LH$_N$/C-(nociceptin 1-11) was designed by back translation of the LC/C, H$_N$/C and nociceptin 1-11 amino acid sequences. The complete ORF (SEQ ID23) containing the LC/C-activation loop-$H_N$/C-flexible spacer-(nociceptin 1-11) was assembled within standard DNA sequence manipulation software (EditSeq).

The recombinant fusion protein (SEQ ID24) was then produced essentially as described in Example 9.

Example 13

Production of a Conjugate for Delivery of DNA Encoding LC/C into a Cell

The construction of a nociceptin-$H_N$[LC/C] conjugate is described below, where [LC/C] represents the polylysine condensed DNA encoding the light chain of botulinum neurotoxin type C.

Materials

SPDP is from Pierce Chemical Co.

Additional reagents are obtained from Sigma Ltd.

Methods

Using a plasmid containing the gene encoding LC/C under the control of a CMV (immediate early) promoter, condensation of DNA was achieved using SPDP-derivatised polylysine to a ratio of 2 DNA to 1 polylysine. Conjugates were then prepared by mixing condensed DNA (0.4 mg/ml) with $H_N$-nociceptin (100 µg/ml) for 16 h at 25° C. The SPDP-derivatised polylysine and the free —SH group present on the $H_N$ domain combine to facilitate covalent attachment of the DNA and protein.

Example 14

Production of a Conjugate for Delivery of DNA Encoding LC/B into a Cell

The construction of a (nociceptin 1-11)-$H_N$-[LC/B] conjugate is described below, where [LC/B] represents the polylysine condensed DNA encoding the light chain of botulinum neurotoxin type B.

Materials

SPDP is from Pierce Chemical Co.

Additional reagents are obtained from Sigma Ltd.

Methods

Using a plasmid containing the gene encoding LC/B under the control of a CMV (immediate early) promoter, condensation of DNA was achieved using SPDP-derivatised polylysine to a ratio of 2 DNA to 1 polylysine. Conjugates were then prepared by mixing condensed DNA (0.4 mg/ml) with $H_N$-(nociceptin 1-11) (100 µg/ml) for 16 h at 25° C. The SPDP-derivatised polylysine and the free —SH group present on the $H_N$ domain combine to facilitate covalent attachment of the DNA and protein.

Example 15

Assessment of the Activity of Nociceptin-$LH_N$/A in Substance P Releasing Neuronal Cells Using methodology described in Duggan et al., (2002, J. Biol. Chem., 277, 34846-34852), the activity of nociceptin-$LH_N$/A in substance P releasing neuronal cells was assessed.

Nociceptin-$LH_N$/A fusion protein was applied to 2-week old dorsal root ganglia neuronal cultures, and incubated at 37° C. for 16 hours. Following the incubation, the media was removed and the ability of the cells to undergo stimulated release of substance P(SP) was assessed.

The release of SP from the neuronal cells incubated with the nociceptin-$LH_N$/A fusion protein was assayed in comparison to (i) $LH_N$/A-only treated cells and (ii) cells treated with media alone. This allowed the % inhibition of substance P from the eDRG to be calculated. The ability of the nociceptin-$LH_N$/A fusion protein to inhibit SP release (relative to cells treated with media alone) was reported in Table 1. The data represent the mean of 3 determinations:

TABLE 1

| Test Material (µM) | nociceptin-$LH_N$/A fusion protein % Inhibition | $LH_N$/A-only % Inhibition |
|---|---|---|
| 1.0 | 47.3 | 25.6 |
| 0.1 | 13.8 | −11.5 |

Example 16

Confirmation of $ORL_1$ Receptor Activation by Measuring Forskolin-Stimulated cAMP Production Confirmation that a given TM is acting via the $ORL_1$ receptor is provided by the following test, in which the TMs ability to inhibit forskolin-stimulated cAMP production is assessed.

Materials

[$^3$H]adenine and [$^{14}$C]cAMP are Obtained from GE Healthcare

Methods

The test is conducted essentially as described previously by Meunier et al. [Isolation and structure of the endogenous agonist of opioid receptor-like $ORL_1$ receptor. Nature 377: 532-535,1995] in intact transfected-CHO cells plated on 24-well plastic plates.

To the cells is added [3H]adenine (1.0 µCi) in 0.4 ml of culture medium. The cells remain at 37° C. for 2 h to allow the adenine to incorporate into the intracellular ATP pool. After 2 h, the cells are washed once with incubation buffer containing: 130 mM NaCl, 4.8 mM KCl, 1.2 mM $KH_2PO_4$, 1.3 mM $CaCl_2$, 1.2 mM $MgSO_4$, 10 mM glucose, 1 mg/ml bovine serum albumin and 25 mM HEPES, pH 7.4, and replaced with buffer containing forskolin (10 µM) and isobutylmethylxanthine (50 µM) with or without the TM of interest. After 10 min., the medium is aspirated and replaced with 0.5 ml, 0.2 M HCl. Approximately 1000 cpm of [$^{14}$C]cAMP is added to each well and used as an internal standard. The contents of the wells are then transferred to columns of 0.65 g dry-alumina powder. The columns are eluted with 4 ml of 5 mM HCl, 0.5 ml of 0.1 M ammonium acetate, then two additional millilitres of ammonium acetate. The final eluate is collected into scintillation vials and counted for $^{14}$C and tritium. Amounts collected are corrected for recovery of [$^{14}$C]cAMP. TMs that are agonists at the $ORL_1$ receptor cause a reduction in the level of cAMP produced in response to forskolin.

Example 17

Confirmation of $ORL_1$ Receptor Activation Using a GTPγS Binding Functional Assay Confirmation that a given TM is acting via the $ORL_1$ receptor is also provided by the following test, a GTPγS binding functional assay.

Materials

[$^{35}$S]GTPγS is obtained from GE Healthcare

Wheatgerm agglutinin-coated (SPA) beads are obtained from GE Healthcare

Methods

This assay is carried out essentially as described by Traynor and Nahorski [Modulation by p-opioid agonists of guanosine-5-O-(3-[$^{35}$S]thio)triphosphate binding to membranes from human neuroblastoma SH-SY5Y cells. Mol. Pharmacol. 47:848-854, 1995].

Cells are scraped from tissue culture dishes into 20 mM HEPES, 1 mM ethylenediaminetetraacetic acid, then centrifuged at 500×g for 10 min. Cells are resuspended in this buffer and homogenized with a Polytron Homogenizer.

The homogenate is centrifuged at 27,000×g for 15 min., and the pellet resuspended in buffer A, containing: 20 mM HEPES, 10 mM MgCl$_2$, 100 mM NaCl, pH 7.4. The suspension is recentrifuged at 20,000×g and suspended once more in buffer A. For the binding assay, membranes (8-15 μg protein) are incubated with [$^{35}$S]GTP S (50 μM), GDP (10 μM), with and without the TM of interest, in a total volume of 1.0 ml, for 60 min. at −25° C. Samples are filtered over glass fibre filters and counted as described for the binding assays.

Example 18

Preparation of a LC/A and H$_N$/A Backbone Clones

The following procedure creates the LC and H$_N$ fragments for use as the component backbone for multidomain fusion expression. This example is based on preparation of a serotype A based clone (SEQ ID27 and SEQ ID28), though the procedures and methods are equally applicable to the other serotypes [illustrated by the sequence listing for serotype B (SEQ ID29 and SEQ ID30) and serotype C (SEQ ID31 and SEQ ID32)].

Preparation of Cloning and Expression Vectors pCR 4 (Invitrogen) is the chosen standard cloning vector, selected due to the lack of restriction sequences within the vector and adjacent sequencing primer sites for easy construct confirmation. The expression vector is based on the PMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (e.g. LC/A) Insert

The LC/A (SEQ ID27) is created by one of two ways:

The DNA sequence is designed by back translation of the LC/A amino acid sequence [obtained from freely available database sources such as GenBank (accession number P10845) or Swissprot (accession locus BXA1_CLOBO) using one of a variety of reverse translation software tools (for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence, maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the LC/A open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a supplier (for example MWG or Sigma-Genosys), so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for $Mg^{2+}$ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not-compatible with the cloning system are then removed using site directed mutagenesis [for example, using Quick-change (Stratagene Inc.)].

Preparation of Translocation (e.g. $H_N$) Insert

The $H_N$/A (SEQ ID28) is created by one of two ways:

The DNA sequence is designed by back translation of the $H_N$/A amino acid sequence [obtained from freely available database sources such as GenBank (accession number P10845) or Swissprot (accession locus BXA1_CLOBO)] using one of a variety of reverse translation software tools [for example EditSeq best *E. coli* reverse translation (DNASTAR Inc.), or Backtranslation tool v2.0 (Entelechon)]. A PstI restriction sequence added to the N-terminus and XbaI-stop codon-HindIII to the C-terminus ensuring the correct reading frame is maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis [for example using Quickchange (Stratagene Inc.)].

Example 19

Preparation of a LC/A-Nociceptin-$H_N$/A Fusion Protein (Nociceptin is N-Terminal of the $H_N$-Chain)

Preparation of Linker-Nociceptin-Spacer Insert

The LC-$H_N$ linker can be designed from first principle, using the existing sequence information for the linker as the template. For example, the serotype A linker (in this case defined as the inter-domain polypeptide region that exists between the cysteines of the disulphide bridge between LC and $H_N$) is 23 amino acids long and has the sequence VRGIITSKTKSLDKGYNKALNDL (amino acids 2-24 of SEQ ID NO: 111). Within this sequence, it is understood that proteolytic activation in nature leads to an $H_N$ domain that has an N-terminus of the sequence ALNDL. This sequence information is freely available from available database sources such as GenBank (accession number P10845) or Swissprot (accession locus BXA1_CLOBO). Into this linker a Factor Xa site, nociceptin and spacer are incorporated; and using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer-SpeI-PstI-XbaI-stop codon-Hind III (SEQ ID33). It is important to ensure the correct reading frame is maintained for the spacer, nociceptin and restriction sequences and that the XbaI sequence is not preceded by the bases, TC, which would result on DAM methylation. The DNA sequence is screened for restriction sequence incorporation, and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example, GenBank Release 143, 13 Sep. 2004). This optimised DNA sequence is then commercially synthesized (for example by Entelechon, Geneart or Sigma-Genosys) and is provided in the pCR 4 vector.

Preparation of the LC/A-Nociceptin-$H_N$/A Fusion

In order to create the LC-linker-nociceptin-spacer-$H_N$ construct (SEQ ID39), the pCR 4 vector encoding the linker (SEQ ID33) is cleaved with BamHI+SalI restriction enzymes. This cleaved vector then serves as the recipient vector for insertion and ligation of the LC/A DNA (SEQ ID27) cleaved with BamHI+SalI. The resulting plasmid DNA is then cleaved with PstI+XbaI restriction enzymes and serves as the recipient vector for the insertion and ligation of the $H_N$/A DNA (SEQ ID28) cleaved with PstI+XbaI. The final construct contains the LC-linker-nociceptin-spacer-$H_N$ ORF (SEQ ID39) for transfer into expression vectors for expression to result in a fusion protein of the sequence illustrated in SEQ ID40.

Example 20

Preparation of a Nociceptin-LC/A-$H_N$/A Fusion Protein (Nociceptin is N-terminal of the LC-Chain)

The LC/A-$H_N$/A backbone is constructed as described in Example 19 using the synthesised A serotype linker with the addition of a Factor Xa site for activation, arranged as BamHI-SalI-linker-protease site-linker-PstI-XbaI-stop codon-HindIII (SEQ ID34). The LC/A-$H_N$/A backbone and the synthesised N-terminal presentation nociceptin insert (SEQ ID35) are cleaved with BamHI+HindIII restriction enzymes, gel purified and ligated together to create a nociceptin-spacer-LC-linker-$H_N$. The ORF (SEQ ID41) is then cut out using restriction enzymes AvaI+XbaI for transfer into expression vectors for expression to result in a fusion protein of the sequence illustrated in SEQ ID42.

Example 21

Preparation of a LC/C-Nociceptin-$H_N$/C Fusion Protein

Following the methods used in Examples 1 and 2, the LC/C (SEQ ID31) and $H_N$/C (SEQ ID32) are created and inserted into the C serotype linker arranged as BamHI-SalI-linker-protease site-nociceptin-NheI-spacer-SpeI-PstI-XbaI-stop codon-HindIII (SEQ ID36). The final construct contains the LC-linker-nociceptin-spacer-$H_N$ ORF (SEQ ID43) for expression as a protein of the sequence illustrated in SEQ ID44.

Example 22

Preparation of a LC/C-Nociceptin-$H_N$/C Fusion Protein with a Serotype A Activation Sequence Following the methods used in Examples 1 and 2, the LC/C (SEQ ID31) and $H_N$/C (SEQ ID32) are created and inserted into the A serotype linker arranged as BamHI-SalI-linker-protease site-nociceptin-NheI-spacer-SpeI-PstI-XbaI-stop codon-HindIII (SEQ ID33). The final construct contains the LC-linker-nociceptin-spacer-$H_N$ ORF (SEQ ID45) for expression as a protein of the sequence illustrated in SEQ ID46.

Example 23

Preparation of a LC/A-met Enkephalin-$H_N$/A Fusion Protein

Due to the small, five-amino acid, size of the met-enkephalin ligand the LC/A-met enkephalin-$H_N$/A fusion is created by site directed mutagenesis [for example using Quickchange (Stratagene Inc.)] using the LC/A-nociceptin-$H_N$/A fusion (SEQ ID39) as a template. Oligonucleotides are designed encoding the YGGFM met-enkephalin peptide (SEQ ID NO:112), ensuring standard *E. coli* codon usage is maintained and no additional restriction sites are incorporated, flanked by sequences complimentary to the linker region of the LC/A-nociceptin-$H_N$/A fusion (SEQ ID39) either side on the nociceptin section. The SDM product is checked by sequencing and the final construct containing the LC-linkermet enkephalin-spacer-$H_N$ ORF (SEQ ID47) for expression as a protein of the sequence illustrated in SEQ ID48.

Example 24

Preparation of a LC/A-β Endorphin-$H_N$/A Fusion Protein

Following the methods used in Examples 1 and 2, the LC/A (SEQ ID27) and $H_N$/A (SEQ ID28) are created and inserted into the A serotype β endorphin linker arranged as BamHI-SalI-linker-protease site-β endorphin-NheI-spacer-SpeI-PstI-XbaI-stop codon-HindIII (SEQ ID37). The final construct contains the LC-linker-β endorphin-spacer-$H_N$ ORF (SEQ ID49) for expression as a protein of the sequence illustrated in SEQ ID50.

Example 25

Preparation of a LC/A-Nociceptin Variant-$H_N$/A Fusion Protein

Following the methods used in Examples 1 and 2, the LC/A (SEQ ID27) and $H_N$/A (SEQ ID28) are created and inserted into the A serotype nociceptin variant linker arranged as BamHI-SalI-linker-protease site-nociceptin variant-NheI-spacer-SpeI-PstI-XbaI-stop codon-HindIII (SEQ ID38). The final construct contains the LC-linker-nociceptin variant-spacer-$H_N$ ORF (SEQ ID51) for expression as a protein of the sequence illustrated in SEQ ID52.

Example 26

Purification Method for LC/A-Nociceptin-$H_N$/A Fusion Protein

Defrost falcon tube containing 25 ml 50 mM HEPES pH 7.2, 200-mM NaCl and approximately 10 g of *E. coli* BL21 cell paste. Make the thawed cell paste up to 80 ml with 50 mM HEPES pH 7.2, 200 mM NaCl and sonicate on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and measure the OD of the dialysed fusion protein. Add 1 unit of factor Xa per 100 µg fusion protein and Incubate at 25° C. static overnight. Load onto a 0.1 M $NiSO_4$ charged Chelating column (20-30 ml column is sufficient) equilibrated with 50 mM HEPES pH 7.2, 200 mM NaCl. Wash column to baseline with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and concentrate the fusion to about 2 mg/ml, aliquot sample and freeze at −20° C. Test purified protein using OD, BCA, purity analysis and SNAP-25 assessments.

Example 27

Preparation of a LC/A-nociceptin-$H_N$/A Fusion Protein (Nociceptin is N-Terminal of the $H_N$-Chain)

The linker-nociceptin-spacer insert is prepared as described in Example 19.

Preparation of the LC/A-Nociceptin-$H_N$/A Fusion

In order to create the LC-linker-nociceptin-spacer-$H_N$ construct (SEQ ID39), the pCR 4 vector encoding the linker (SEQ ID33) is cleaved with BamHI+SalI restriction enzymes. This cleaved vector then serves as the recipient for insertion and ligation of the LC/A DNA (SEQ ID27) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the PMAL vector (NEB). The $H_N$/A DNA (SEQ ID28) is then cleaved with PstI+HindIII restriction enzymes and inserted into the similarly cleaved pMAL-LC/A-linker construct. The final construct contains the LC-linker-nociceptin-spacer-$H_N$ ORF (SEQ ID39) for expression as a protein of the sequence illustrated in SEQ ID40.

Example 28

Preparation of a Nociceptin LC/A-$H_N$/A Fusion Protein (Nociceptin is N-Terminal of the $H_N$-Chain)

In order to create the nociceptin-spacer-LC/A-$H_N$/A construct, an A serotype linker with the addition of a Factor Xa site for activation, arranged as BamHI-SalI linker-protease site-linker-PstI-XbaI-stop codon-HindIII (SEQ ID34) is synthesised as described in Example 27. The pCR 4 vector encoding the linker is cleaved with BamHI+SalI restriction enzymes. This cleaved vector then serves as the recipient for insertion and ligation of the LC/A DNA (SEQ ID27) also cleaved with BamHI+SalI. The resulting plasmid DNA is then cleaved with BamHI+HindIII restriction enzymes and the LC/A-linker fragment inserted into a similarly cleaved vector containing the synthesised N-terminal presentation nociceptin insert (SEQ ID35). This construct is then cleaved with AvaI+HindIII and inserted into an expression vector such as the pMAL plasmid (NEB). The $H_N$/A DNA (SEQ ID28) is then cleaved with PstI+HindIII restriction enzymes and inserted into the similarly cleaved PMAL-nociceptin-LC/A-linker construct. The final construct contains the nociceptin-spacer-LC/A-$H_N$/A ORF (SEQ ID63) for expression as a protein of the sequence illustrated in SEQ ID64.

Example 29

Preparation and Purification of an LC/A-Nociceptin-$H_N$/A Fusion Protein Family with Variable Spacer Length Using the same strategy as employed in Example 19, a range of DNA linkers were prepared that encoded nociceptin and variable spacer content. Using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer- SpeI-PstI-XbaI-stop codon-HindIII (SEQ ID65 to SEQ ID69). It is important to ensure the correct reading frame is maintained for the spacer, nociceptin and restriction sequences and that the XbaI sequence is not preceded by the bases, TC which would result on DAM methylation. The DNA sequence is screened for restriction sequence incorporation and any additional sequences are removed manually from the remaining sequence ensuring common *E. Coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The spacers that were created included:

TABLE 2

| Code | Protein sequence of the linker | SEQ ID of the linker DNA |
|---|---|---|
| GS10 | ALAGGGGSALVLQ | 113 |
| GS15 | ALAGGGGSGGGGSALVLQ | 114 |
| GS25 | ALAGGGGSGGGGSGGGGSGGGGSALVLQ | 115 |
| GS30 | ALAGGGGSGGGGSGGGGSGGGGSGGGGSALVLQ | 116 |
| HX27 | ALAAEAAAKEAAAKEAAAKAGGGGSALVLQ | 117 |

By way of example, in order to create the LC/A-CPN (GS15)-$H_N$/A fusion construct (SEQ ID70), the pCR4 vector encoding the linker (SEQ ID66) is cleaved with BamHI+SalI restriction enzymes. This cleaved vector then serves as the recipient vector for insertion and ligation of the LC/A DNA (SEQ ID27) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the PMAL vector (NEB). The $H_N$/A DNA (SEQ ID28) is then cleaved with PstI+HindIII restriction enzymes and inserted into the similarly cleaved pMAL-LC/A-linker construct. The final construct contains the LC/A-CPN(GS15)-$H_N$/A ORF (SEQ ID70) for expression as a protein of the sequence illustrated in SEQ ID71.

As a further example, to create the LC/A-CPN(GS25)-$H_N$/A fusion construct (SEQ ID72), the pCR 4 vector encoding the linker (SEQ ID67) is cleaved with BamHI+SalI restriction enzymes. This cleaved vector then serves as the recipient vector for insertion and ligation of the LC/A DNA (SEQ ID27) cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The $H_N$/A DNA (SEQ ID28) is then cleaved with PstI+HindIII restriction enzymes and inserted into the similarly cleaved pMAL-LC/A-linker construct. The final construct contains the LC/A-CPN(GS25)-$H_N$/A ORF (SEQ ID72) for expression as a protein of the sequence illustrated in SEQ ID73.

Variants of the LG/A-CPN-$H_N$/A fusion consisting of GS10, GS30 and HX27 are similarly created. Using the purification methodology described in Example 26, fusion protein is purified from *E. coli* cell paste. FIG. 12 illustrates the purified product obtained in the case of LC/A-CPN(GS10)-$H_N$/A, LC/A-CPN(GS15)-$H_N$/A, LC/A-CPN(GS25)-$H_N$/A, LC/A-CPN(GS30)-$H_N$/A and LC/A-CPN(HX27)-$H_N$/A.

Example 30

Assessment of In Vitro Efficacy of an LC/A-Nociceptin-$H_N$/A Fusion

Fusion protein prepared according to Examples 2 and 9 was assessed in the eDRG neuronal cell model.

Assays for the inhibition of substance P release and cleavage of SNAP-25 have been previously reported (Duggan et al., 2002, *J. Biol. Chem.*, 277, 34846-34852). Briefly, dorsal root ganglia neurons are harvested from 15-day-old fetal Sprague-Dawley rats and dissociated cells plated onto 24-well plates coated with Matrigel at a density of 1×10$^6$ cells/well. One day post-plating the cells are treated with 10 µM cytosine β-D-arabinofuranoside for 48 h. Cells are maintained in Dulbecco's minimal essential medium supplemented with 5% heat-inactivated fetal bovine serum, 5 mM L-glutamine, 0.6% D-glucose, 2% B27 supplement, and 100 ng/ml 2.5 S mouse nerve growth factor. Cultures are maintained for 2 weeks at 37° C. in 95% air/5% $CO_2$ before addition of test materials.

Release of substance P from eDRG is assessed by enzyme-linked immunosorbent assay. Briefly, eDRG cells are washed twice with low potassium-balanced salt solution (BSS: 5 mM KCl, 137 mM NaCl, 1.2 mM $MgCl_2$, 5 mM glucose, 0.44 mM $KH_2PO_4$, 20 mM HEPES, pH 7.4, 2 mM $CaCl_2$). Basal samples are obtained by incubating each well for 5 min. with 1 ml of low potassium BSS. After removal of this buffer, the cells are stimulated to release by incubation with 1 ml of high potassium buffer (BSS as above with modification to include 100 mM KCl isotonically balanced with NaCl) for 5 min. All samples are removed to tubes on ice prior to assay of substance P. Total cell lysates are prepared by addition of 250 µl of 2 M acetic acid/0.1% trifluoroacetic acid to lyse the cells, centrifugal evaporation, and resuspension in 500 µl of assay buffer. Diluted samples are assessed for substance P content. Substance P immunoreactivity is measured using Substance P Enzyme Immunoassay Kits (Cayman Chemical Company or R&D Systems) according to manufacturers' instructions. Substance P is expressed in pg/ml relative to a standard substance P curve run in parallel.

SDS-PAGE and Western blot analysis were performed using standard protocols (Novex). SNAP-25 proteins were resolved on a 12% Tris/glycine polyacrylamide gel (Novex) and subsequently transferred to nitrocellulose membrane. The membranes were probed with a monoclonal antibody (SMI-81) that recognises cleaved and intact SNAP-25. Specific binding was visualised using peroxidase-conjugated secondary antibodies and a chemiluminescent detection system. Cleavage of SNAP-25 was quantified by scanning densitometry (Molecular Dynamics Personal SI, ImageQuant data analysis software). Percent SNAP-25 cleavage was calculated according to the formula: (Cleaved SNAP-25/ (Cleaved+Intact SNAP-25))'100.

Following exposure of eDRG neurons to an LC/A-nociceptin-$H_N$/A fusion (termed CPN-A), both inhibition of substance P release and cleavage of SNAP-25 are observed (FIG. 13). After 24 h exposure to the fusion, 50% of maximal SNAP-25 cleavage is achieved by a fusion concentration of 6.3±2.5 nM.

The effect of the fusion is also assessed at defined time points following a 16 h exposure of eDRG to CPN-A. FIG. 14 illustrates the prolonged duration of action of the CPN-A fusion protein, with measurable activity still being observed at 28 days post exposure.

Example 31

Assessment of In Vitro Efficacy of an LC/A-Nociceptin Variant-$H_N$/A Fusion

Fusion protein prepared according to Examples 8 and 9 was assessed in the eDRG neuronal cell mode using the method described in Example 30.

Following exposure of eDRG neurons to an LC/A-nociceptin variant-$H_N$/A fusion (termed CPNv-A), both inhibition of substance P release and cleavage of SNAP-25 are observed. After 24 h exposure to the fusion, 50% of maximal SNAP-25 cleavage is achieved by a fusion concentration of 1.4±0.4 nM (FIG. 15).

The effect of the fusion is also assessed at defined time points following a 16 h exposure of eDRG to CPN-A. FIG. 16 illustrates the prolonged duration of action of the CPN-A fusion protein, with measurable activity still being observed at 24 days post exposure.

The binding capability of the CPNv-A fusion protein is also assessed in comparison to the CPN-A fusion. FIG. 17 illustrates the results of a competition experiment to determine binding efficacy at the ORL-1 receptor. CPNv-A is demonstrated to displace [3H]-nociceptin, thereby confirming that access to the receptor is possible with the ligand in the central presentation format.

Example 32

Preparation of an LC/A-Nociceptin Variant-$H_N$/A Fusion Protein that is Activated by Treatment with Enterokinase Following the methods used in Examples 1 and 2, the LC/A (SEQ ID27) and $H_N$/A (SEQ ID28) are created and inserted into the A serotype nociceptin variant linker arranged as BamHI-SalI-linker-enterokinase protease site-nociceptin variant-NheI-spacer-SpeI-PstI-XbaI-stop codon-HindIII (SEQ ID74). The final construct contains the LC-linker-nociceptin variant-spacer-$H_N$ ORF sequences (SEQ ID75) for expression as a protein of the sequence illustrated in SEQ ID76. The fusion protein is termed CPNv(Ek)-A. FIG. 18 illustrates the purification of CPNv(Ek)-A from *E. coli* following the methods used in Example 26 but using Enterokinase for activation at 0.00064 µg per 100 µg of fusion protein.

Example 33

Assessment of In Vitro Efficacy of an LC/A-Nociceptin Variant-$H_N$/A Fusion that has Been Activated by Treatment with Enterokinase The CPNv(Ek)-A prepared in Example 32 is obtained in a purified form and applied to the eDRG cell model to assess cleavage of SNAP-25 (using methodology from Example 30). FIG. 19 illustrates the cleavage of SNAP-25 following 24 h exposure of eDRG to CPNv(Ek)-A. The efficiency of cleavage is observed to be similar to that achieved with the Factor Xa-cleaved material, as recorded in Example 31.

Example 34

Preparation of an LC/C-Nociceptin Variant-$H_N$/C Fusion Protein with a Factor Xa Activation Linker Derived from Serotype A Following the methods used in Example 21, the LC/C (SEQ ID31) and $H_N$/C (SEQ ID32) are created and inserted into the A serotype nociceptin variant linker arranged as BamHI-SalI-linker-nociceptin variant-NheI-spacer-SpeI-PstI-XbaI-stop codon-HindIII (SEQ ID77). The final construct contains the LC-linker-nociceptin variant-spacer-$H_N$ ORF sequences (SEQ ID78) for expression as a protein of the sequence illustrated in SEQ ID79. The fusion protein is termed CPNv-C (act. A). FIG. 20 illustrates the purification of CPNv-C (act. A) from *E. coli* following the methods used in Example 26.

Example 35

Assessment of In Vitro Efficacy of an LC/C-Nociceptin Variant-$H_N$/C Fusion Protein Following the methods used in Example 26, the CPNv-C (act. A) prepared in Example 34 is obtained in a purified form and applied to the eDRG cell model to assess cleavage of SNAP-25 (using methodology from Example 30). After 24 h exposure to the fusion, 50% of maximal syntaxin cleavage is achieved by a fusion concentration of 3.1±2.0 nM. FIG. 21 illustrates the cleavage of syntaxin following 24 h exposure of eDRG to CPNv-C (act. A).

Example 36

Assessment of In Vivo Efficacy of an LC/A-nociceptin-$H_N$/A Fusion

The ability of an LC/A-nociceptin-$H_N$/A fusion (CPN/A) to inhibit acute capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study, after subcutaneous treatment with CPN/A but before capsaicin, and following capsaicin challenge post-injection of CPN/A (average of responses at 15' and 30'). Capsaicin challenge is achieved by injection of 10 µL of a 0.3% solution. Sample dilutions are prepared in 0.5% BSA/saline. FIG. 22 illustrates the reversal of mechanical allodynia that is achieved by pre-treatment of the animals with a range of concentrations of LC/A-nociceptin-$H_N$/A fusion.

The ability of an LC/A-nociceptin-$H_N$/A fusion (CPN/A) to inhibit streptozotocin (STZ)-induced mechanical (tactile) allodynia in rats is evaluated. STZ-induced mechanical allodynia in rats is achieved by injection of streptozotocin (i.p. or i.v.) which yields destruction of pancreatic β-cells leading to loss of insulin production, with concomitant metabolic stress (hyperglycemia and hyperlipidemia). As such, STZ induces Type I diabetes. In addition, STZ treatment leads to progressive development of neuropathy, which serves as a model of chronic pain with hyperalgesia and allodynia that may reflect signs observed in diabetic humans (peripheral diabetic neuropathy).

Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 μl) are injected subcutaneously as a single injection (except gabapentin) and the PWT is measured at 1 day post treatment and periodically thereafter over a 2-week period. Gabapentin (30 mg/kg i.p. @ 3 ml/kg injection volume) is injected daily, 2 hours prior to the start of PWT testing. FIG. 23 illustrates the reversal of allodynia achieved by pre-treatment of the animals with 750 ng of CPN/A. Data were obtained over a 2-week period after a single injection of CPN/A

Example 37

Assessment of In Vivo Efficacy of an LC/A-Nociceptin Variant-$H_N$/A Fusion

The ability of an LC/A-nociceptin variant-$H_N$/A fusion (CPNv/A) to inhibit capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPNv/A but before capsaicin (Pre-CAP); and following capsaicin challenge post-injection of CPNv/A (average of responses at 15' and 30'; CAP). Capsaicin challenge is achieved by injection of 10 μL of a 0.3% solution. Sample dilutions are prepared in 0.5% BSA/saline.

FIG. 24 illustrates the reversal of allodynia that is achieved by pre-treatment of the animals with a range of concentrations of LC/A-nociceptin variant-$H_N$/A fusion in comparison to the reversal achieved with the addition of LC/A-nociceptin-$H_N$/A fusion. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more potent than CPN/A since a lower dose of CPNv/A is required to achieve similar analgesic effect to that seen with CPN/A.

Example 38

Preparation of an LC/A-Leu Enkephalin-$H_N$/A Fusion Protein

Due to the small, five-amino acid, size of the leu-enkephalin ligand the LC/A-leu enkephalin-$H_N$/A fusion is created by site directed mutagenesis [for example using Quickchange (Stratagene Inc.)] using the LC/A-nociceptin-$H_N$/A fusion (SEQ ID39) as a template. Oligonucleotides are designed encoding the YGGFL leu-enkephalin peptide, ensuring standard E. coli codon usage is maintained and no additional restriction sites are incorporated, flanked by sequences complimentary to the linker region of the LC/A-nociceptin-$H_N$/A fusion (SEQ ID39) either side on the nociceptin section. The SDM product is checked by sequencing and the final construct containing the LC-linker-leu enkephalin-spacer-$H_N$ ORF (SEQ ID80) for expression as a protein of the sequence illustrated in SEQ ID81. The fusion protein is termed CPLE-A. FIG. 25 illustrates the purification of CPLE-A from E. coli following the methods used in Example 26.

Example 39

Expression and Purification of an LC/A-beta-endorphin-$H_N$/A Fusion Protein

Following the methods used in Example 26, and with the LC/A-beta-endorphin-$H_N$/A fusion protein (termed CPBE-A) created in Example 24, the CPBE-A is purified from E. coli. FIG. 26 illustrates the purified protein as analysed by SDS-PAGE.

Example 40

Preparation of an LC/A-Nociceptin Mutant-$H_N$/A Fusion Protein

Due to the single amino acid modification necessary to mutate the nociceptin sequence at position 1 from a Phe to a Tyr, the LC/A-nociceptin mutant-$H_N$/A fusion is created by site directed mutagenesis [for example using Quickchange (Stratagene Inc.)] using the LC/A-nociceptin-$H_N$/A fusion (SEQ ID39) as a template. Oligonucleotides are designed encoding tyrosine at position 1 of the nociceptin sequence, ensuring standard E. Coli codon usage is maintained and no additional restriction sites are incorporated, flanked by sequences complimentary to the linker region of the LC/A-nociceptin-$H_N$/A fusion (SEQ ID39) either side on the nociceptin section. The SDM product is checked by sequencing and the final construct containing the LC/A-nociceptin mutant-spacer-$H_N$/A fusion ORF (SEQ ID82) for expression as a protein of the sequence illustrated in SEQ ID83. The fusion protein is termed GPOP-A. FIG. 27 illustrates the purification of GPOP-A from E. coli following the methods used in Example 26.

Example 41

Preparation and Assessment of an LC/A-Nociceptin Variant Mutant-$H_N$/A Fusion Protein Due to the single amino acid modification necessary to mutate the nociceptin sequence at position 1 from a Phe to a Tyr, the LC/A-nociceptin variant mutant-$H_N$/A fusion is created by site directed mutagenesis [for example using Quickchange (Stratagene Inc.)] using the LC/A-nociceptin variant-$H_N$/A fusion (SEQ ID51) as a template. Oligonucleotides are designed encoding tyrosine at position 1 of the nociceptin sequence, ensuring standard E. coli-codon usage is maintained and no additional restriction sites are incorporated, flanked by sequences complimentary to the linker region of the LC/A-nociceptin variant-$H_N$/A fusion (SEQ ID51) either side on the nociceptin section. The SDM product is checked by sequencing and the final construct containing the LC/A-nociceptin mutant-spacer-$H_N$/A fusion ORF (SEQ ID84) for expression as a protein of the sequence illustrated in SEQ ID85. The fusion protein is termed CPOPv-A. FIG. 28 illustrates the purification of CPOPv-A from E. coli following the methods used in Example 26.

Using methodology described in Example 30, CPOPv-A is assessed for its ability to cleave SNAP-25 in the eDRG cell model. FIG. 29 illustrates that CPOPv-A is able to cleave SNAP-25 in the eDRG model, achieving cleavage of 50% of the maximal SNAP-25 after exposure of the cells to approximately 5.9 nM fusion for 24 h.

Example 42

Preparation of an IgA Protease-Nociceptin Variant-$H_N$/A Fusion Protein

The IgA protease amino acid sequence was obtained from freely available database sources such as GenBank (accession number P09790). Information regarding the structure of the *N. Gonorrhoeae* IgA protease gene is available in the literature (Pohlner et al., Gene structure and extracellular secretion of *Neisseria gonorrhoeae* IgA protease, *Nature*, 1987, 325 (6103), 458-62). Using Backtranslation tool v2.0 (Entelechon), the DNA sequence encoding the IgA protease modified for *E. coli* expression was determined. A BamHI recognition sequence was incorporated at the 5' end and a codon encoding a cysteine amino acid and SalI recognition sequence were incorporated at the 3' end of the IgA DNA. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID86) containing the IgA open reading frame (ORF) is then commercially synthesized.

The IgA (SEQ ID86) is inserted into the LC-linker-nociceptin variant-spacer-$H_N$ ORF (SEQ ID51) using BamHI and SalI restriction enzymes to replace the LC with the IgA protease DNA. The final construct contains the IgA-linker-nociceptin variant-spacer-$H_N$ ORF (SEQ ID87) for expression as a protein of the sequence illustrated in SEQ ID88.

Example 43

Preparation and Assessment of a Nociceptin Targeted Endopeptidase Fusion Protein with a Removable Histidine Purification Tag DNA was prepared that encoded a Factor Xa removable his-tag (his6), although it is clear that alternative proteases site such as Enterokinase and alternative purification tags such as longer histidine tags are also possible. Using one of a variety of reverse translation software tools [for example EditSeq best *E. coli* reverse translation (DNASTAR Inc.), or Backtranslation tool v2.0 (Entelechon)], the DNA sequence encoding the Factor Xa removable his-tag region is determined. Restriction sites are then incorporated into the DNA sequence and can be arranged as NheI-linker-SpeI-PstI-$H_N$/A-XbaI-LEIEGRSGHHHHHHStop codon-HindIII (SEQ ID89). The DNA sequence is screened for restriction sequence incorporated and any additional sequences are-removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector. In order to create CPNv-A-FXa-HT (SEQ ID90, removable his-tag construct) the pCR 4 vector encoding the his-tag is cleaved with NheI and HindIII. The NheI-HindIII fragment is then inserted into the LC/A-CPNv-$H_N$/A vector (SEQ ID51) that has also been cleaved by NheI and HindIII. The final construct contains the LC/A-linker-nociceptin variant-spacer-$H_N$-FXa-Histag-HindIII ORF sequences (SEQ ID90) for expression as a protein of the sequence illustrated in SEQ ID91. FIG. 30 illustrates the purification of CPNv-A-FXa-HT from *E. coli* following the methods used in Example 26.

Example 44

Preparation of a Leu-Enkephalin Targeted Endopeptidase Fusion Protein Containing a Translocation Domain Derived from Diphtheria Toxin The DNA sequence is designed by back translation of the amino acid sequence of the translocation domain of the diphtheria toxin (obtained from freely available database sources such as GenBank (accession number 1XDTT) using one of a variety of reverse translation software tools [for example EditSeq best *E. coli* reverse translation (DNASTAR Inc.), or Backtranslation tool v2.0 (Entelechon)]. Restriction sites are then incorporated into the DNA sequence and can be arranged as NheI-Linker-SpeI-PstI-diphtheria translocation domain-XbaI-stop codon-HindIII (SEQ ID92). PstI/XbaI recognition sequences are incorporated at the 5' and 3' ends of the translocation domain respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the diphtheria translocation domain is then commercially synthesized as NheI-Linker-SpeI-PstI-diphtheria translocation domain-XbaI-stop codon-HindIII (for example by Entelechon, Geneart or Sigma-Genosys) and is provided in the pCR 4 vector (Invitrogen). The pCR 4 vector encoding the diphtheria translocation domain is cleaved with NheI and XbaI. The NheI-XbaI fragment is then inserted into the LC/A-CPLE-$H_N$/A vector (SEQ ID80) that has also been cleaved by NheI and XbaI. The final construct contains the LC/A-leu-enkephalin-spacer-diphtheria translocation domain ORF sequences (SEQ ID93) for expression as a protein of the sequence illustrated in SEQ ID94.

Example 45

Preparation of a Nociceptin Variant Targeted Endopeptidase Fusion Protein Containing a LC Domain Derived from Tetanus Toxin The DNA sequence is designed by back translation of the tetanus toxin LC amino acid sequence (obtained from freely available database sources such as GenBank (accession number X04436) using one of a variety of reverse translation software tools [for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence maintaining the correct reading frame (SEQ ID95). The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common E. coli codon usage is maintained. E. coli codon usage is assessed by reference to software programs such as Graphical Codon Usage Analyser (Geneart), and the % GC content and codon usage ratio assessed by reference to published codon usage tables (for example GenBank Release 143; 13 Sep. 2004). This optimised DNA sequence containing the tetanus toxin LC open reading frame (ORF) is then commercially synthesized (for example by Entelechon, Geneart or Sigma-Genosys) and is provided in the pCR 4 vector (invitrogen). The pCR 4 vector encoding the TeNT LC is cleaved with BamHI and SalI. The BamHI-SalI fragment is then inserted into the LC/A-CPNv-$H_N$/A vector (SEQ ID51) that has also been cleaved by BamHI and SalI. The final construct contains the TeNT LC-linker-nociceptin variant-spacer-$H_N$ ORF sequences (SEQ ID96) for expression as a protein of the sequence illustrated in SEQ ID97.

Example 46

Preparation of an LC/C-Nociceptin Variant-$H_N$/C Fusion Protein with a Native Serotype C Linker that is Susceptible to Factor Xa Cleavage Following the methods used in Example 21, the LC/C (SEQ ID31) and $H_N$/C (SEQ ID32) are created and inserted into the C serotype nociceptin variant linker arranged as BamHI-SalI-linker-nociceptin variant-NheI-spacer-SpeI-PstI-XbaI-stop codon-HindIII (SEQ ID98). The final construct contains the LC-linker-nociceptin variant-spacer-$H_N$ ORF sequences (SEQ ID99) for expression as a protein of the sequence illustrated in SEQ ID100. The fusion protein is termed CPNv-C (act. C).

What is claimed is:

1. A method of preparing an activated di-chain fusion protein, said di-chain fusion protein comprising a first domain comprising a botulinum neurotoxin light chain, a second domain comprising a botulinum neurotoxin heavy chain $H_N$ translocation domain, and a third domain comprising an amino acid sequence of SEQ ID NO:14, wherein the first domain and the second domain are linked by a disulfide bond, said method comprising:
   a) expressing a single-chain fusion protein from a nucleic acid sequence that encodes a single-chain fusion protein, wherein said single-chain fusion protein comprises:
      i) a first domain comprising a botulinum neurotoxin light chain,
      ii) a second domain comprising a botulinum neurotoxin heavy chain $H_N$ translocation domain,
      iii) an enterokinase cleavage site located between the first domain and the second domain, and
      iv) a third domain comprising the amino acid sequence set forth in SEQ ID NO:14, wherein the first domain and the second domain are linked by a disulfide bond;
   b) contacting the single-chain fusion protein of a) with an enterokinase protease under conditions permitting cleavage of the enterokinase cleavage site; and
   c) isolating activated di-chain fusion protein from b) having the enterokinase cleavage site cleaved, thereby preparing an activated di-chain fusion protein.

2. The method according to claim 1, wherein the enterokinase cleavage site has the amino acid sequence DDDDK (SEQ ID NO:102).

3. The method according to claim 1, wherein the nucleic acid sequence is encompassed within an expression vector.

4. An activated di-chain fusion protein produced by the method according to claim 1.

* * * * *

SEQUENCE LISTING

<160> NUMBER OF SEQ ID NOS: 117

<210> SEQ ID NO 1
<211> LENGTH: 51
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 1
tttggcggtt tcacgggcgc acgcaaatca gcgcgtaaat tagctaacca g         51

<210> SEQ ID NO 2
<211> LENGTH: 17
<212> TYPE: PRT
<213> ORGANISM: Artificial Sequence
<220> FEATURE:
<223> OTHER INFORMATION: chemically synthesized targeting moiety

<400> SEQUENCE: 2

Phe Gly Gly Phe Thr Gly Ala Arg Lys Ser Ala Arg Lys Leu Ala Asn
1               5                   10                  15

Gln

<210> SEQ ID NO 3
<211> LENGTH: 33
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 3
tttggcggtt tcacgggcgc acgcaaatca gcg                             33

<210> SEQ ID NO 4
<211> LENGTH: 11
<212> TYPE: PRT
<213> ORGANISM: Artificial Sequence
<220> FEATURE:
<223> OTHER INFORMATION: chemically synthesized targeting moiety

```
<400> SEQUENCE: 4

Phe Gly Gly Phe Thr Gly Ala Arg Lys Ser Ala
1               5                   10

<210> SEQ ID NO 5
<211> LENGTH: 33
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 5
tttggcggtt tcacgggcgc acgcaaatat gcg                                 33

<210> SEQ ID NO 6
<211> LENGTH: 11
<212> TYPE: PRT
<213> ORGANISM: Artificial Sequence
<220> FEATURE:
<223> OTHER INFORMATION: chemically synthesized targeting moiety

<400> SEQUENCE: 6

Phe Gly Gly Phe Thr Gly Ala Arg Lys Tyr Ala
1               5                   10

<210> SEQ ID NO 7
<211> LENGTH: 33
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 7
tttggcggtt tcacgggcgc acgcaaatca tat                                 33

<210> SEQ ID NO 8
<211> LENGTH: 11
<212> TYPE: PRT
<213> ORGANISM: Artificial Sequence
<220> FEATURE:
<223> OTHER INFORMATION: chemically synthesized targeting moiety

<400> SEQUENCE: 8

Phe Gly Gly Phe Thr Gly Ala Arg Lys Ser Tyr
1               5                   10

<210> SEQ ID NO 9
<211> LENGTH: 51
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 9
tttggcggtt tcacgggcgc acgcaaatca gcgcgtaaat atgctaacca g             51

<210> SEQ ID NO 10
<211> LENGTH: 17
<212> TYPE: PRT
<213> ORGANISM: Artificial Sequence
<220> FEATURE:
<223> OTHER INFORMATION: chemically synthesized targeting moiety

<400> SEQUENCE: 10
```

Phe Gly Gly Phe Thr Gly Ala Arg Lys Ser Ala Arg Lys Tyr Ala Asn
1               5                   10                  15

Gln

<210> SEQ ID NO 11
<211> LENGTH: 39
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 11
tttggcggtt tcacgggcgc acgcaaatca gcgcgtaaa                           39

<210> SEQ ID NO 12
<211> LENGTH: 13
<212> TYPE: PRT
<213> ORGANISM: Artificial Sequence
<220> FEATURE:
<223> OTHER INFORMATION: chemically synthesized targeting moiety

<400> SEQUENCE: 12

Phe Gly Gly Phe Thr Gly Ala Arg Lys Ser Ala Arg Lys
1               5                   10

<210> SEQ ID NO 13
<211> LENGTH: 51
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 13
tttggcggtt tcacgggcgc acgcaaatca gcgcgtaaac gcaaaaacca g             51

<210> SEQ ID NO 14
<211> LENGTH: 17
<212> TYPE: PRT
<213> ORGANISM: Artificial Sequence
<220> FEATURE:
<223> OTHER INFORMATION: chemically synthesized targeting moiety

<400> SEQUENCE: 14

Phe Gly Gly Phe Thr Gly Ala Arg Lys Ser Ala Arg Lys Arg Lys Asn
1               5                   10                  15

Gln

<210> SEQ ID NO 15
<211> LENGTH: 2736
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 15
ctcgggattg agggtcgttt tggcggtttc acgggcgcac gcaaatcagc gcgtaaatta    60
gctaaccaga ctagtggcgg tgggggtagt ggcggtggcg gttcgggcgg gggtgggagc   120
cctaggggat ccatggagtt cgttaacaaa cagttcaact ataaagaccc agttaacggt   180
gttgacattg cttacatcaa aatcccgaac gctggccaga tgcagccggt aaaggcattc   240

```
aaaatccaca acaaaatctg ggttatcccg gaacgtgata cctttactaa cccggaagaa    300
ggtgacctga acccgccacc ggaagcgaaa caggtgccgg tatcttacta tgactccacc    360
tacctgtcta ccgataacga aaggacaac tacctgaaag gtgttactaa actgttcgag     420
cgtatttact ccaccgacct gggccgtatg ctgctgacta gcatcgttcg cggtatcccg    480
ttctggggcg gttctaccat cgataccgaa ctgaaagtaa tcgacactaa ctgcatcaac    540
gttattcagc cggacggttc ctatcgttcc gaagaactga acctggtgat catcggcccg    600
tctgctgata tcatccagtt cgagtgtaag agctttggtc acgaagttct gaacctcacc    660
cgtaacggct acgttccac tcagtacatc cgtttctctc cggacttcac cttcggtttt     720
gaagaatccc tggaagtaga cacgaaccca ctgctgggcg ctggtaaatt cgcaactgat    780
cctgcggtta ccctggctca cgaactgatt catgcaggcc accgcctgta cggtatcgcc    840
atcaatccga accgtgtctt caaagttaac accaacgcgt attacgagat gtccggtctg    900
gaagttagct tcgaagaact gcgtactttt ggcggtcacg acgctaaatt catcgactct    960
ctgcaagaaa acgagttccg tctgtactac tataacaagt caaagatat cgcatccacc    1020 ctgaacaaag cgaaatccat cgtgggtacc actgcttctc tccagtacat gaagaacgtt    1080
tttaaagaaa ataccctgct cagcgaagac acctccggca aattctctgt agacaagttg    1140
aaattcgata aactttacaa aatgctgact gaaatttaca ccgaagacaa cttcgttaag    1200
ttctttaaag ttctgaaccg caaaacctat ctgaacttcg acaaggcagt attcaaaatc    1260
aacatcgtgc cgaaagttaa ctacactatc tacgatggtt tcaacctgcg taacaccaac    1320
ctggctgcta ttttaacgg ccagaacacg gaaatcaaca catgaactt cacaaaactg     1380 aaaaacttca ctggtctgtt cgagttttac aagctgctgt gcgtcgacgg catcattacc    1440
tccaaaacta aatctctgat agaaggtaga acaaagcgc tgaacgacct ctgtatcaag     1500
gttaacaact gggatttatt cttcagcccg agtgaagaca acttcaccaa cgacctgaac    1560
aaaggtgaag aaatcaccct cagatactaac atcgaagcag ccgaagaaaa catctcgctg    1620
gacctgatcc agcagtacta cctgaccttt aatttcgaca acgagccgga aaacatttct    1680
atcgaaaacc tgagctctga tatcatcggc cagctggaac tgatgccgaa catcgaacgt    1740
ttcccaaacg gtaaaaagta cgagctggac aaatatacca tgttccacta cctgcgcgcg    1800
caggaatttg aacacggcaa atcccgtatc gcactgacta actccgttaa cgaagctctg    1860
ctcaacccgt cccgtgtata caccttcttc tctagcgact acgtgaaaaa ggtcaacaaa    1920
gcgactgaag ctgcaatgtt cttgggttgg gttaacagc ttgtttatga ttttaccgac    1980
gagacgtccg aagtatctac taccgacaaa attgcggata tcactatcat catcccgtac    2040
atcggtccgg ctctgaacat tggcaacatg ctgtacaaag cgacttcgt tggcgcactg     2100 atcttctccg gtgcggtgat cctgctggag ttcatcccgg aaatcgccat cccggtactg    2160
ggcacctttg ctctggtttc ttacattgca acaaggttc tgactgtaca aaccatcgac     2220
aacgcgctga gcaaacgtaa cgaaaaatgg gatgaagttt acaaatatat cgtgaccaac    2280
tggctggcta aggttaatac tcagatcgac ctcatccgca aaaaatgaa agaagcactg    2340 gaaaaccagg cggaagctac caaggcaatc attaactacc agtacaacca gtacaccgag    2400
gaagaaaaaa acaacatcaa cttcaacatc gacgatctgt cctctaaaact gaacgaatcc    2460 atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgccctgc tgaaatacat ttacgacaac cgtggcactc tgatcggtca ggttgatcgt    2640
```

```
ctgaaggaca aagtgaacaa taccttatcg accgacatcc cttttcagct cagtaaatat    2700
gtcgataacc aacgccttt  gtccactcta gactag                              2736
```

<210> SEQ ID NO 16
<211> LENGTH: 911
<212> TYPE: PRT
<213> ORGANISM: Artificial Sequence
<220> FEATURE:
<223> OTHER INFORMATION: chemically synthesized fusion protein

<400> SEQUENCE: 16

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Ser Gly Gly
            20                  25                  30

Gly Gly Ser Gly Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Glu Ala Lys Gln Val
            100                 105                 110

Pro Val Ser Tyr Tyr Asp Ser Thr Tyr Leu Ser Thr Asp Asn Glu Lys
        115                 120                 125

Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
            180                 185                 190

Leu Asn Leu Val Ile Ile Gly Pro Ser Ala Asp Ile Ile Gln Phe Glu
        195                 200                 205

Cys Lys Ser Phe Gly His Glu Val Leu Asn Leu Thr Arg Asn Gly Tyr
    210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255

Phe Ala Thr Asp Pro Ala Val Thr Leu Ala His Glu Leu Ile His Ala
            260                 265                 270

Gly His Arg Leu Tyr Gly Ile Ala Ile Asn Pro Asn Arg Val Phe Lys
        275                 280                 285

Val Asn Thr Asn Ala Tyr Tyr Glu Met Ser Gly Leu Glu Val Ser Phe
    290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Tyr Asn Lys Phe Lys Asp
                325                 330                 335

Ile Ala Ser Thr Leu Asn Lys Ala Lys Ser Ile Val Gly Thr Thr Ala
```

-continued

```
                340                 345                 350
Ser Leu Gln Tyr Met Lys Asn Val Phe Lys Glu Lys Tyr Leu Leu Ser
        355                 360                 365
Glu Asp Thr Ser Gly Lys Phe Ser Val Asp Lys Leu Lys Phe Asp Lys
    370                 375                 380
Leu Tyr Lys Met Leu Thr Glu Ile Tyr Thr Glu Asp Asn Phe Val Lys
385                 390                 395                 400
Phe Phe Lys Val Leu Asn Arg Lys Thr Tyr Leu Asn Phe Asp Lys Ala
                405                 410                 415
Val Phe Lys Ile Asn Ile Val Pro Lys Val Asn Tyr Thr Ile Tyr Asp
            420                 425                 430
Gly Phe Asn Leu Arg Asn Thr Asn Leu Ala Ala Asn Phe Asn Gly Gln
        435                 440                 445
Asn Thr Glu Ile Asn Asn Met Asn Phe Thr Lys Leu Lys Asn Phe Thr
    450                 455                 460
Gly Leu Phe Glu Phe Tyr Lys Leu Leu Cys Val Asp Gly Ile Ile Thr
465                 470                 475                 480
Ser Lys Thr Lys Ser Leu Ile Glu Gly Arg Asn Lys Ala Leu Asn Asp
                485                 490                 495
Leu Cys Ile Lys Val Asn Asn Trp Asp Leu Phe Phe Ser Pro Ser Glu
            500                 505                 510
Asp Asn Phe Thr Asn Asp Leu Asn Lys Gly Glu Glu Ile Thr Ser Asp
        515                 520                 525
Thr Asn Ile Glu Ala Ala Glu Asn Ile Ser Leu Asp Leu Ile Gln
    530                 535                 540
Gln Tyr Tyr Leu Thr Phe Asn Phe Asp Asn Glu Pro Glu Asn Ile Ser
545                 550                 555                 560
Ile Glu Asn Leu Ser Ser Asp Ile Ile Gly Gln Leu Glu Leu Met Pro
                565                 570                 575
Asn Ile Glu Arg Phe Pro Asn Gly Lys Lys Tyr Glu Leu Asp Lys Tyr
            580                 585                 590
Thr Met Phe His Tyr Leu Arg Ala Gln Glu Phe Glu His Gly Lys Ser
        595                 600                 605
Arg Ile Ala Leu Thr Asn Ser Val Asn Glu Ala Leu Leu Asn Pro Ser
    610                 615                 620
Arg Val Tyr Thr Phe Phe Ser Ser Asp Tyr Val Lys Lys Val Asn Lys
625                 630                 635                 640
Ala Thr Glu Ala Ala Met Phe Leu Gly Trp Val Glu Gln Leu Val Tyr
                645                 650                 655
Asp Phe Thr Asp Glu Thr Ser Glu Val Ser Thr Thr Asp Lys Ile Ala
            660                 665                 670
Asp Ile Thr Ile Ile Ile Pro Tyr Ile Gly Pro Ala Leu Asn Ile Gly
        675                 680                 685
Asn Met Leu Tyr Lys Asp Asp Phe Val Gly Ala Leu Ile Phe Ser Gly
    690                 695                 700
Ala Val Ile Leu Leu Glu Phe Ile Pro Glu Ile Ala Ile Pro Val Leu
705                 710                 715                 720
Gly Thr Phe Ala Leu Val Ser Tyr Ile Ala Asn Lys Val Leu Thr Val
                725                 730                 735
Gln Thr Ile Asp Asn Ala Leu Ser Lys Arg Asn Glu Lys Trp Asp Glu
            740                 745                 750
Val Tyr Lys Tyr Ile Val Thr Asn Trp Leu Ala Lys Val Asn Thr Gln
        755                 760                 765
```

```
Ile Asp Leu Ile Arg Lys Lys Met Lys Glu Ala Leu Glu Asn Gln Ala
        770                 775                 780
Glu Ala Thr Lys Ala Ile Ile Asn Tyr Gln Tyr Asn Gln Tyr Thr Glu
785                 790                 795                 800
Glu Glu Lys Asn Asn Ile Asn Phe Asn Ile Asp Asp Leu Ser Ser Lys
                805                 810                 815
Leu Asn Glu Ser Ile Asn Lys Ala Met Ile Asn Ile Asn Lys Phe Leu
            820                 825                 830
Asn Gln Cys Ser Val Ser Tyr Leu Met Asn Ser Met Ile Pro Tyr Gly
        835                 840                 845
Val Lys Arg Leu Glu Asp Phe Asp Ala Ser Leu Lys Asp Ala Leu Leu
    850                 855                 860
Lys Tyr Ile Tyr Asp Asn Arg Gly Thr Leu Ile Gly Gln Val Asp Arg
865                 870                 875                 880
Leu Lys Asp Lys Val Asn Asn Thr Leu Ser Thr Asp Ile Pro Phe Gln
                885                 890                 895
Leu Ser Lys Tyr Val Asp Asn Gln Arg Leu Leu Ser Thr Leu Asp
            900                 905                 910

<210> SEQ ID NO 17
<211> LENGTH: 2700
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 17
tttggcggtt tcacgggcgc acgcaaatca tatactagtg gcggtggggg tagtggcggt      60
ggcggttcgg gcggggggtgg gagccctagg ggatccatgg agttcgttaa caaacagttc     120
aactataaag acccagttaa cggtgttgac attgcttaca tcaaaatccc gaacgctggc     180
cagatgcagc cggtaaaggc attcaaaatc cacaacaaaa tctgggttat cccggaacgt     240 gatacctta ctaaccccgga agaaggtgac ctgaacccgc caccggaagc gaaacaggtg     300
ccggtatctt actatgactc cacctacctg tctaccgata cgaaaaggaa caactacctg     360
aaaggtgtta ctaaactgtt cgagcgtatt tactccaccg acctgggccg tatgctgctg     420
actagcatcg ttcgcggtat cccgttctgg ggcggttcta ccatcgatac cgaactgaaa     480
gtaatcgaca ctaactgcat caacgttatt cagccggacg ttcctatcg ttccgaagaa      540 ctgaacctgg tgatcatcgg cccgtctgct gatatcatcc agttcgagtg taagagcttt     600
ggtcacgaag ttctgaacct cacccgtaac ggctacggtt ccactcagta catccgtttc     660
tctccggact tcaccttcgg ttttgaagaa tccctggaag tagacacgaa cccactgctg     720
ggcgctggta aattcgcaac tgatcctgcg gttaccctgg ctcacgaact gattcatgca     780
ggccaccgcc tgtacggtat cgccatcaat ccgaaccgtg tcttcaaagt taacaccaac     840
gcgtattacg agatgtccgg tctggaagtt agcttcgaag aactgcgtac ttttggcggt     900
cacgacgcta aattcatcga ctctctgcaa gaaaacgagt tccgtctgta ctactataac     960
aagttcaaag atatcgcatc caccctgaac aaagcgaaat ccatcgtggg taccactgct    1020
tctctccagt acatgaagaa cgttttttaaa gaaaaatacc tgctcagcga agacacctcc    1080
ggcaaattct ctgtagacaa gttgaaattc gataaacttt acaaaatgct gactgaaatt    1140
tacaccgaag acaacttcgt taagttcttt aaagttctga accgcaaaac ctatctgaac    1200
```

-continued

```
ttcgacaagg cagtattcaa atcaacatc gtgccgaaag ttaactacac tatctacgat    1260
ggtttcaacc tgcgtaacac caacctggct gctaatttta acggccagaa cacgaaatc    1320 aacaacatga acttcacaaa actgaaaaac ttcactggtc tgttcgagtt ttacaagctg   1380
ctgtgcgtcg acggcatcat tacctccaaa actaaatctc tgatagaagg tagaaacaaa   1440
gcgctgaacg acctctgtat caaggttaac aactgggatt tattcttcag cccgagtgaa   1500
gacaacttca ccaacgacct gaacaaaggt gaagaaatca cctcagatac taacatcgaa   1560
gcagccgaag aaaacatctc gctggacctg atccagcagt actacctgac ctttaatttc   1620
gacaacgagc cggaaaacat ttctatcgaa acctgagct ctgatatcat cggccagctg    1680
gaactgatgc cgaacatcga acgtttccca acggtaaaa agtacgagct ggacaaatat    1740
accatgttcc actacctgcg cgcgcaggaa tttgaacacg gcaaatcccg tatcgcactg   1800
actaactccg ttaacgaagc tctgctcaac ccgtcccgtg tatacacctt cttctctagc   1860
gactacgtga aaaaggtcaa caaagcgact gaagctgcaa tgttcttggg ttgggttgaa   1920
cagcttgttt atgattttac cgacgagacg tccgaagtat ctactaccga caaaattgcg   1980
gatatcacta tcatcatccc gtacatcggt ccggctctga acattggcaa catgctgtac   2040
aaagacgact tcgttggcgc actgatcttc tccggtgcgg tgatcctgct ggagttcatc   2100
ccggaaatcg ccatcccggt actgggcacc tttgctctgg tttcttacat tgcaaacaag   2160
gttctgactg tacaaaccat cgacaacgcg ctgagcaaac gtaacgaaaa atgggatgaa   2220
gtttacaaat atatcgtgac caactggctg gctaaggtta atactcagat cgacctcatc   2280
cgcaaaaaaa tgaaagaagc actggaaaac caggcggaag ctaccaaggc aatcattaac   2340
taccagtaca accagtacac cgaggaagaa aaaacaaca tcaacttcaa catcgacgat    2400
ctgtcctcta aactgaacga atccatcaac aaagctatga tcaacatcaa caagttcctg   2460
aaccagtgct ctgtaagcta tctgatgaac tccatgatcc cgtacggtgt aaacgtctg    2520 gaggacttcg atgcgtctct gaaagacgcc ctgctgaaat acatttacga caaccgtggc   2580
actctgatcg gtcaggttga tcgtctgaag gacaaagtga acaataccct tatcgaccgac  2640 atcccttttc agctcagtaa atatgtcgat aaccaacgcc ttttgtccac tctagactag   2700
```

<210> SEQ ID NO 18
<211> LENGTH: 899
<212> TYPE: PRT
<213> ORGANISM: Artificial Sequence
<220> FEATURE:
<223> OTHER INFORMATION: chemically synthesized fusion protein

<400> SEQUENCE: 18

```
Phe Gly Gly Phe Thr Gly Ala Arg Lys Ser Tyr Thr Ser Gly Gly Gly
1               5                   10                  15

Gly Ser Gly Gly Gly Gly Ser Gly Gly Gly Ser Pro Arg Gly Ser
            20                  25                  30

Met Glu Phe Val Asn Lys Gln Phe Asn Tyr Lys Asp Pro Val Asn Gly
        35                  40                  45

Val Asp Ile Ala Tyr Ile Lys Ile Pro Asn Ala Gly Gln Met Gln Pro
    50                  55                  60

Val Lys Ala Phe Lys Ile His Asn Lys Ile Trp Val Ile Pro Glu Arg
65                  70                  75                  80

Asp Thr Phe Thr Asn Pro Glu Glu Gly Asp Leu Asn Pro Pro Glu
            85                  90                  95

Ala Lys Gln Val Pro Val Ser Tyr Tyr Asp Ser Thr Tyr Leu Ser Thr
```

-continued

```
                100                 105                 110
Asp Asn Glu Lys Asp Asn Tyr Leu Lys Gly Val Thr Lys Leu Phe Glu
            115                 120                 125

Arg Ile Tyr Ser Thr Asp Leu Gly Arg Met Leu Leu Thr Ser Ile Val
130                 135                 140

Arg Gly Ile Pro Phe Trp Gly Gly Ser Thr Ile Asp Thr Glu Leu Lys
145                 150                 155                 160

Val Ile Asp Thr Asn Cys Ile Asn Val Ile Gln Pro Asp Gly Ser Tyr
                165                 170                 175

Arg Ser Glu Glu Leu Asn Leu Val Ile Ile Gly Pro Ser Ala Asp Ile
            180                 185                 190

Ile Gln Phe Glu Cys Lys Ser Phe Gly His Glu Val Leu Asn Leu Thr
        195                 200                 205

Arg Asn Gly Tyr Gly Ser Thr Gln Tyr Ile Arg Phe Ser Pro Asp Phe
    210                 215                 220

Thr Phe Gly Phe Glu Glu Ser Leu Glu Val Asp Thr Asn Pro Leu Leu
225                 230                 235                 240

Gly Ala Gly Lys Phe Ala Thr Asp Pro Ala Val Thr Leu Ala His Glu
                245                 250                 255

Leu Ile His Ala Gly His Arg Leu Tyr Gly Ile Ala Ile Asn Pro Asn
            260                 265                 270

Arg Val Phe Lys Val Asn Thr Asn Ala Tyr Tyr Glu Met Ser Gly Leu
        275                 280                 285

Glu Val Ser Phe Glu Glu Leu Arg Thr Phe Gly Gly His Asp Ala Lys
    290                 295                 300

Phe Ile Asp Ser Leu Gln Glu Asn Glu Phe Arg Leu Tyr Tyr Tyr Asn
305                 310                 315                 320

Lys Phe Lys Asp Ile Ala Ser Thr Leu Asn Lys Ala Lys Ser Ile Val
                325                 330                 335

Gly Thr Thr Ala Ser Leu Gln Tyr Met Lys Asn Val Phe Lys Glu Lys
            340                 345                 350

Tyr Leu Leu Ser Glu Asp Thr Ser Gly Lys Phe Ser Val Asp Lys Leu
        355                 360                 365

Lys Phe Asp Lys Leu Tyr Lys Met Leu Thr Glu Ile Tyr Thr Glu Asp
    370                 375                 380

Asn Phe Val Lys Phe Phe Lys Val Leu Asn Arg Lys Thr Tyr Leu Asn
385                 390                 395                 400

Phe Asp Lys Ala Val Phe Lys Ile Asn Ile Val Pro Lys Val Asn Tyr
                405                 410                 415

Thr Ile Tyr Asp Gly Phe Asn Leu Arg Asn Thr Asn Leu Ala Ala Asn
            420                 425                 430

Phe Asn Gly Gln Asn Thr Glu Ile Asn Asn Met Asn Phe Thr Lys Leu
        435                 440                 445

Lys Asn Phe Thr Gly Leu Phe Glu Phe Tyr Lys Leu Leu Cys Val Asp
    450                 455                 460

Gly Ile Ile Thr Ser Lys Thr Lys Ser Leu Ile Glu Gly Arg Asn Lys
465                 470                 475                 480

Ala Leu Asn Asp Leu Cys Ile Lys Val Asn Asn Trp Asp Leu Phe Phe
                485                 490                 495

Ser Pro Ser Glu Asp Asn Phe Thr Asn Asp Leu Asn Lys Gly Glu Glu
            500                 505                 510

Ile Thr Ser Asp Thr Asn Ile Glu Ala Ala Glu Glu Asn Ile Ser Leu
        515                 520                 525
```

```
Asp Leu Ile Gln Gln Tyr Tyr Leu Thr Phe Asn Phe Asp Asn Glu Pro
        530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                565                 570                 575

Leu Asp Lys Tyr Thr Met Phe His Tyr Leu Arg Ala Gln Glu Phe Glu
            580                 585                 590

His Gly Lys Ser Arg Ile Ala Leu Thr Asn Ser Val Asn Glu Ala Leu
        595                 600                 605

Leu Asn Pro Ser Arg Val Tyr Thr Phe Phe Ser Ser Asp Tyr Val Lys
    610                 615                 620

Lys Val Asn Lys Ala Thr Glu Ala Ala Met Phe Leu Gly Trp Val Glu
625                 630                 635                 640

Gln Leu Val Tyr Asp Phe Thr Asp Glu Thr Ser Glu Val Ser Thr Thr
                645                 650                 655

Asp Lys Ile Ala Asp Ile Thr Ile Ile Pro Tyr Ile Gly Pro Ala
            660                 665                 670

Leu Asn Ile Gly Asn Met Leu Tyr Lys Asp Asp Phe Val Gly Ala Leu
        675                 680                 685

Ile Phe Ser Gly Ala Val Ile Leu Leu Glu Phe Ile Pro Glu Ile Ala
    690                 695                 700

Ile Pro Val Leu Gly Thr Phe Ala Leu Val Ser Tyr Ile Ala Asn Lys
705                 710                 715                 720

Val Leu Thr Val Gln Thr Ile Asp Asn Ala Leu Ser Lys Arg Asn Glu
                725                 730                 735

Lys Trp Asp Glu Val Tyr Lys Tyr Ile Val Thr Asn Trp Leu Ala Lys
            740                 745                 750

Val Asn Thr Gln Ile Asp Leu Ile Arg Lys Lys Met Lys Glu Ala Leu
        755                 760                 765

Glu Asn Gln Ala Glu Ala Thr Lys Ala Ile Ile Asn Tyr Gln Tyr Asn
    770                 775                 780

Gln Tyr Thr Glu Glu Lys Asn Asn Ile Asn Phe Asn Ile Asp Asp
785                 790                 795                 800

Leu Ser Ser Lys Leu Asn Glu Ser Ile Asn Lys Ala Met Ile Asn Ile
                805                 810                 815

Asn Lys Phe Leu Asn Gln Cys Ser Val Ser Tyr Leu Met Asn Ser Met
            820                 825                 830

Ile Pro Tyr Gly Val Lys Arg Leu Glu Asp Phe Asp Ala Ser Leu Lys
        835                 840                 845

Asp Ala Leu Leu Lys Tyr Ile Tyr Asp Asn Arg Gly Thr Leu Ile Gly
    850                 855                 860

Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Asp

<210> SEQ ID NO 19
<211> LENGTH: 2706
<212> TYPE: DNA
<213> ORGANISM: Artificial Sequence
<220> FEATURE:
<223> OTHER INFORMATION: chemically synthesized polynucleotide encoding
``` a fusion protein

<400> SEQUENCE: 19

| | | | | |
|---|---|---|---|---|
| tttggcggtt | tcacgggcgc | acgcaaatca | gcgcgtaaaa | ctagtggcgg tgggggtagt | 60 |
| ggcggtggcg | gttcgggcgg | gggtgggagc | cctaggggat | ccatggagtt cgttaacaaa | 120 |
| cagttcaact | ataaagaccc | agttaacggt | gttgacattg | cttacatcaa atcccgaac | 180 |
| gctggccaga | tgcagccggt | aaaggcattc | aaaatccaca | acaaaatctg gttatcccg | 240 |
| gaacgtgata | cctttactaa | cccggaagaa | ggtgacctga | cccgccacc ggaagcgaaa | 300 |
| caggtgccgg | tatcttacta | tgactccacc | tacctgtcta | ccgataacga aaggacaac | 360 |
| tacctgaaag | gtgttactaa | actgttcgag | cgtatttact | ccaccgacct gggccgtatg | 420 |
| ctgctgacta | gcatcgttcg | cggtatcccg | ttctggggcg | gttctaccat cgataccgaa | 480 |
| ctgaaagtaa | tcgacactaa | ctgcatcaac | gttattcagc | cggacggttc ctatcgttcc | 540 |
| gaagaactga | acctggtgat | catcggcccg | tctgctgata | tcatccagtt cgagtgtaag | 600 |
| agctttggtc | acgaagttct | gaacctcacc | cgtaacggct | acggttccac tcagtacatc | 660 |
| cgtttctctc | cggacttcac | cttcggtttt | gaagaatccc | tggaagtaga cacgaaccca | 720 |
| ctgctgggcg | ctggtaaatt | cgcaactgat | cctgcggtta | ccctggctca cgaactgatt | 780 |
| catgcaggcc | accgcctgta | cggtatcgcc | atcaatccga | accgtgtctt caaagttaac | 840 |
| accaacgcgt | attacgagat | gtccggtctg | gaagttagct | tcgaagaact gcgtactttt | 900 |
| ggcggtcacg | acgctaaatt | catcgactct | ctgcaagaaa | acgagttccg tctgtactac | 960 |
| tataacaagt | tcaaagatat | cgcatccacc | ctgaacaaag | cgaaatccat cgtgggtacc | 1020 |
| actgcttctc | tccagtacat | gaagaacgtt | tttaaagaaa | ataccctgct cagcgaagac | 1080 |
| acctccggca | aattctctgt | agacaagttg | aaattcgata | aactttacaa aatgctgact | 1140 |
| gaaatttaca | ccgaagacaa | cttcgttaag | ttctttaaag | ttctgaaccg caaaaccctat | 1200 |
| ctgaacttcg | acaaggcagt | attcaaaatc | aacatcgtgc | cgaaagttaa ctacactatc | 1260 |
| tacgatggtt | tcaacctgcg | taacaccaac | ctggctgcta | ttttaacgg ccagaacacg | 1320 |
| gaaatcaaca | acatgaactt | cacaaaactg | aaaaacttca | ctggtctgtt cgagttttac | 1380 |
| aagctgctgt | gcgtcgacgg | catcattacc | tccaaaacta | atctctgat agaaggtaga | 1440 |
| aacaaagcgc | tgaacgacct | ctgtatcaag | gttaacaact | gggatttatt cttcagcccg | 1500 |
| agtgaagaca | acttcaccaa | cgacctgaac | aaaggtgaag | aaatcacctc agatactaac | 1560 |
| atcgaagcag | ccgaagaaaa | catctcgctg | gacctgatcc | agcagtacta cctgaccttt | 1620 |
| aatttcgaca | acgagccgga | aaacatttct | atcgaaaacc | tgagctctga tatcatcggc | 1680 |
| cagctggaac | tgatgccgaa | catcgaacgt | ttcccaaacg | gtaaaaagta cgagctggac | 1740 |
| aaatatacca | tgttccacta | cctgcgcgcg | caggaatttg | aacacggcaa atcccgtatc | 1800 |
| gcactgacta | actccgttaa | cgaagctctg | ctcaacccgt | cccgtgtata caccttcttc | 1860 |
| tctagcgact | acgtgaaaaa | ggtcaacaaa | gcgactgaag | ctgcaatgtt cttgggttgg | 1920 |
| gttgaacagc | ttgtttatga | ttttaccgac | gagacgtccg | aagtatctac taccgacaaa | 1980 |
| attgcggata | tcactatcat | catcccgtac | atcggtccgg | ctctgaacat ggcaacatg | 2040 |
| ctgtacaaag | acgacttcgt | tggcgcactg | atcttctccg | gtgcggtgat cctgctggag | 2100 |
| ttcatcccgg | aaatcgccat | cccggtactg | ggcacctttg | ctctggtttc ttacattgca | 2160 |
| aacaaggttc | tgactgtaca | aaccatcgac | aacgcgctga | gcaaacgtaa cgaaaaatgg | 2220 |
| gatgaagttt | acaaatatat | cgtgaccaac | tggctggcta | aggttaatac tcagatcgac | 2280 |

-continued

```
ctcatccgca aaaaaatgaa agaagcactg gaaaaccagg cggaagctac caaggcaatc    2340
attaactacc agtacaacca gtacaccgag gaagaaaaaa acaacatcaa cttcaacatc    2400
gacgatctgt cctctaaact gaacgaatcc atcaacaaag ctatgatcaa catcaacaag    2460
ttcctgaacc agtgctctgt aagctatctg atgaactcca tgatcccgta cggtgttaaa    2520
cgtctggagg acttcgatgc gtctctgaaa gacgccctgc tgaaatacat ttacgacaac    2580
cgtggcactc tgatcggtca ggttgatcgt ctgaaggaca aagtgaacaa taccttatcg    2640
accgacatcc cttttcagct cagtaaatat gtcgataacc aacgccttt gtccactcta    2700 gactag                                                               2706
```

<210> SEQ ID NO 20
<211> LENGTH: 901
<212> TYPE: PRT
<213> ORGANISM: Artificial Sequence
<220> FEATURE:
<223> OTHER INFORMATION: chemically synthesized fusion protein

<400> SEQUENCE: 20

```
Phe Gly Gly Phe Thr Gly Ala Arg Lys Ser Ala Arg Lys Thr Ser Gly
1               5                   10                  15

Gly Gly Gly Ser Gly Gly Gly Ser Gly Gly Gly Gly Ser Pro Arg
            20                  25                  30

Gly Ser Met Glu Phe Val Asn Lys Gln Phe Asn Tyr Lys Asp Pro Val
        35                  40                  45

Asn Gly Val Asp Ile Ala Tyr Ile Lys Ile Pro Asn Ala Gly Gln Met
    50                  55                  60

Gln Pro Val Lys Ala Phe Lys Ile His Asn Lys Ile Trp Val Ile Pro
65                  70                  75                  80

Glu Arg Asp Thr Phe Thr Asn Pro Glu Glu Gly Asp Leu Asn Pro Pro
                85                  90                  95

Pro Glu Ala Lys Gln Val Pro Val Ser Tyr Tyr Asp Ser Thr Tyr Leu
            100                 105                 110

Ser Thr Asp Asn Glu Lys Asp Asn Tyr Leu Lys Gly Val Thr Lys Leu
        115                 120                 125

Phe Glu Arg Ile Tyr Ser Thr Asp Leu Gly Arg Met Leu Leu Thr Ser
    130                 135                 140

Ile Val Arg Gly Ile Pro Phe Trp Gly Gly Ser Thr Ile Asp Thr Glu
145                 150                 155                 160

Leu Lys Val Ile Asp Thr Asn Cys Ile Asn Val Ile Gln Pro Asp Gly
                165                 170                 175

Ser Tyr Arg Ser Glu Glu Leu Asn Leu Val Ile Gly Pro Ser Ala
            180                 185                 190

Asp Ile Ile Gln Phe Glu Cys Lys Ser Phe Gly His Glu Val Leu Asn
        195                 200                 205

Leu Thr Arg Asn Gly Tyr Gly Ser Thr Gln Tyr Ile Arg Phe Ser Pro
    210                 215                 220

Asp Phe Thr Phe Gly Phe Glu Glu Ser Leu Glu Val Asp Thr Asn Pro
225                 230                 235                 240

Leu Leu Gly Ala Gly Lys Phe Ala Thr Asp Pro Ala Val Thr Leu Ala
                245                 250                 255

His Glu Leu Ile His Ala Gly His Arg Leu Tyr Gly Ile Ala Ile Asn
            260                 265                 270

Pro Asn Arg Val Phe Lys Val Asn Thr Asn Ala Tyr Tyr Glu Met Ser
```

-continued

```
                275                 280                 285
Gly Leu Glu Val Ser Phe Glu Leu Arg Thr Phe Gly Gly His Asp
            290                 295                 300
Ala Lys Phe Ile Asp Ser Leu Gln Glu Asn Glu Phe Arg Leu Tyr Tyr
305                 310                 315                 320
Tyr Asn Lys Phe Lys Asp Ile Ala Ser Thr Leu Asn Lys Ala Lys Ser
                325                 330                 335
Ile Val Gly Thr Thr Ala Ser Leu Gln Tyr Met Lys Asn Val Phe Lys
            340                 345                 350
Glu Lys Tyr Leu Leu Ser Glu Asp Thr Ser Gly Lys Phe Ser Val Asp
            355                 360                 365
Lys Leu Lys Phe Asp Lys Leu Tyr Lys Met Leu Thr Glu Ile Tyr Thr
            370                 375                 380
Glu Asp Asn Phe Val Lys Phe Phe Lys Val Leu Asn Arg Lys Thr Tyr
385                 390                 395                 400
Leu Asn Phe Asp Lys Ala Val Phe Lys Ile Asn Ile Val Pro Lys Val
                405                 410                 415
Asn Tyr Thr Ile Tyr Asp Gly Phe Asn Leu Arg Asn Thr Asn Leu Ala
            420                 425                 430
Ala Asn Phe Asn Gly Gln Asn Thr Glu Ile Asn Asn Met Asn Phe Thr
            435                 440                 445
Lys Leu Lys Asn Phe Thr Gly Leu Phe Glu Phe Tyr Lys Leu Leu Cys
            450                 455                 460
Val Asp Gly Ile Ile Thr Ser Lys Thr Lys Ser Leu Ile Glu Gly Arg
465                 470                 475                 480
Asn Lys Ala Leu Asn Asp Leu Cys Ile Lys Val Asn Asn Trp Asp Leu
                485                 490                 495
Phe Phe Ser Pro Ser Glu Asp Asn Phe Thr Asn Asp Leu Asn Lys Gly
                500                 505                 510
Glu Glu Ile Thr Ser Asp Thr Asn Ile Glu Ala Ala Glu Glu Asn Ile
            515                 520                 525
Ser Leu Asp Leu Ile Gln Gln Tyr Tyr Leu Thr Phe Asn Phe Asp Asn
530                 535                 540
Glu Pro Glu Asn Ile Ser Ile Glu Asn Leu Ser Ser Asp Ile Ile Gly
545                 550                 555                 560
Gln Leu Glu Leu Met Pro Asn Ile Glu Arg Phe Pro Asn Gly Lys Lys
                565                 570                 575
Tyr Glu Leu Asp Lys Tyr Thr Met Phe His Tyr Leu Arg Ala Gln Glu
            580                 585                 590
Phe Glu His Gly Lys Ser Arg Ile Ala Leu Thr Asn Ser Val Asn Glu
            595                 600                 605
Ala Leu Leu Asn Pro Ser Arg Val Tyr Thr Phe Phe Ser Ser Asp Tyr
            610                 615                 620
Val Lys Lys Val Asn Lys Ala Thr Glu Ala Ala Met Phe Leu Gly Trp
625                 630                 635                 640
Val Glu Gln Leu Val Tyr Asp Phe Thr Asp Glu Thr Ser Glu Val Ser
                645                 650                 655
Thr Thr Asp Lys Ile Ala Asp Ile Thr Ile Ile Pro Tyr Ile Gly
                660                 665                 670
Pro Ala Leu Asn Ile Gly Asn Met Leu Tyr Lys Asp Asp Phe Val Gly
            675                 680                 685
Ala Leu Ile Phe Ser Gly Ala Val Ile Leu Leu Glu Phe Ile Pro Glu
            690                 695                 700
```

```
Ile Ala Ile Pro Val Leu Gly Thr Phe Ala Leu Val Ser Tyr Ile Ala
705                 710                 715                 720

Asn Lys Val Leu Thr Val Gln Thr Ile Asp Asn Ala Leu Ser Lys Arg
            725                 730                 735

Asn Glu Lys Trp Asp Glu Val Tyr Lys Tyr Ile Val Thr Asn Trp Leu
        740                 745                 750

Ala Lys Val Asn Thr Gln Ile Asp Leu Ile Arg Lys Lys Met Lys Glu
    755                 760                 765

Ala Leu Glu Asn Gln Ala Glu Ala Thr Lys Ala Ile Ile Asn Tyr Gln
770                 775                 780

Tyr Asn Gln Tyr Thr Glu Glu Lys Asn Asn Ile Asn Phe Asn Ile
785                 790                 795                 800

Asp Asp Leu Ser Ser Lys Leu Asn Glu Ser Ile Asn Lys Ala Met Ile
            805                 810                 815

Asn Ile Asn Lys Phe Leu Asn Gln Cys Ser Val Ser Tyr Leu Met Asn
        820                 825                 830

Ser Met Ile Pro Tyr Gly Val Lys Arg Leu Glu Asp Phe Asp Ala Ser
    835                 840                 845

Leu Lys Asp Ala Leu Leu Lys Tyr Ile Tyr Asp Asn Arg Gly Thr Leu
850                 855                 860

Ile Gly Gln Val Asp Arg Leu Lys Asp Lys Val Asn Asn Thr Leu Ser
865                 870                 875                 880

Thr Asp Ile Pro Phe Gln Leu Ser Lys Tyr Val Asp Asn Gln Arg Leu
            885                 890                 895

Leu Ser Thr Leu Asp
            900

<210> SEQ ID NO 21
<211> LENGTH: 2691
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 21
atggagttcg ttaacaaaca gttcaactat aaagacccag ttaacggtgt tgacattgct      60
tacatcaaaa tcccgaacgc tggccagatg cagccggtaa aggcattcaa aatccacaac     120
aaaatctggg ttatcccgga acgtgatacc tttactaacc cggaagaagg tgacctgaac     180
ccgccaccgg aagcgaaaca ggtgccggta tcttactatg actccaccta cctgtctacc     240
gataacgaaa aggacaacta cctgaaaggt gttactaaac tgttcgagcg tatttactcc     300
accgacctgg ccgtatgct gctgactagc atcgttcgcg gtatcccgtt ctggggcggt     360
tctaccatcg ataccgaact gaaagtaatc gacactaact gcatcaacgt tattcagccg     420
gacggttcct atcgttccga agaactgaac ctggtgatca tcggcccgtc tgctgatatc     480
atccagttcg agtgtaagag ctttggtcac gaagttctga acctcacccg taacggctac     540
ggttccactc agtacatccg tttctctccg gacttcacct tcggttttga agaatccctg     600
gaagtagaca cgaacccact gctgggcgct ggtaaattcg caactgatcc tgcggttacc     660
ctggctcacg aactgattca tgcaggccac cgcctgtacg gtatcgccat caatccgaac     720
cgtgtcttca agttaacac caacgcgtat tacgagatgt ccggtctgga agttagcttc     780
gaagaactgc gtactttgg cggtcacgac gctaaattca tcgactctct gcaagaaaac     840
```

```
gagttccgtc tgtactacta taacaagttc aaagatatcg catccaccct gaacaaagcg    900
aaatccatcg tgggtaccac tgcttctctc cagtacatga agaacgtttt taaagaaaaa    960
tacctgctca gcgaagacac ctccggcaaa ttctctgtag acaagttgaa attcgataaa   1020
ctttacaaaa tgctgactga aatttacacc gaagacaact tcgttaagtt ctttaaagtt   1080
ctgaaccgca aaacctatct gaacttcgac aaggcagtat tcaaaatcaa catcgtgccg   1140
aaagttaact acactatcta cgatggtttc aacctgcgta acaccaacct ggctgctaat   1200
tttaacggcc agaacacgga aatcaacaac atgaacttca caaaactgaa aaacttcact   1260
ggtctgttcg agttttacaa gctgctgtgc gtcgacggca tcattacctc caaaactaaa   1320
tctctgatag aaggtagaaa caaagcgctg aacgacctct gtatcaaggt taacaactgg   1380
gatttattct tcagcccgag tgaagacaac ttcaccaacg acctgaacaa aggtgaagaa   1440
atcacctcag atactaacat cgaagcagcc gaagaaaaca tctcgctgga cctgatccag   1500
cagtactacc tgacctttaa tttcgacaac gagccggaaa acatttctat cgaaaacctg   1560
agctctgata tcatcggcca gctggaactg atgccgaaca tcgaacgttt cccaaacggt   1620
aaaaagtacg agctggacaa atataccatg ttccactacc tgcgcgcgca ggaatttgaa   1680
cacggcaaat cccgtatcgc actgactaac tccgttaacg aagctctgct caacccgtcc   1740
cgtgtataca ccttcttctc tagcgactac gtgaaaaagg tcaacaaagc gactgaagct   1800
gcaatgttct tgggttgggt tgaacagctt gtttatgatt ttaccgacga cgtccgaa    1860 gtatctacta ccgacaaaat tgcggatatc actatcatca tcccgtacat cggtccggct   1920
ctgaacattg caacatgct gtacaaagac gacttcgttg gcgcactgat cttctccggt   1980
gcggtgatcc tgctggagtt catcccggaa atcgccatcc cggtactggg caccttgct    2040 ctggtttctt acattgcaaa caaggttctg actgtacaaa ccatcgacaa cgcgctgagc   2100
aaacgtaacg aaaaatggga tgaagtttac aaatatatcg tgaccaactg gctggctaag   2160
gttaatactc agatcgacct catccgcaaa aaaatgaaag aagcactgga aaaccaggcg   2220
gaagctacca aggcaatcat taactaccag tacaaccagt acaccgagga agaaaaaaac   2280
aacatcaact tcaacatcga cgatctgtcc tctaaactga acgaatccat caacaaagct   2340
atgatcaaca tcaacaagtt cctgaaccag tgctctgtaa gctatctgat gaactccatg   2400
atcccgtacg gtgttaaacg tctggaggac ttcgatgcgt ctctgaaaga cgccctgctg   2460
aaatacattt acgacaaccg tggcactctg atcggtcagg ttgatcgtct gaaggacaaa   2520
gtgaacaata ccttatcgac cgacatccct tttcagctca gtaaatatgt cgataaccaa   2580
cgccttttgt ccactggcgg tggggtagt ggcggtggcg gttcgggcgg gggtgggagc    2640
tttggcggtt tcacgggcgc acgcaaatca gcgcgtaaat tagctaacca g            2691
```

<210> SEQ ID NO 22
<211> LENGTH: 897
<212> TYPE: PRT
<213> ORGANISM: Artificial Sequence
<220> FEATURE:
<223> OTHER INFORMATION: chemically synthesized fusion protein

<400> SEQUENCE: 22

Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg

-continued

```
             35                  40                  45
Asp Thr Phe Thr Asn Pro Glu Glu Gly Asp Leu Asn Pro Pro Glu
 50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Thr Lys Leu Phe Glu
                 85                  90                  95
Arg Ile Tyr Ser Thr Asp Leu Gly Arg Met Leu Leu Thr Ser Ile Val
                100                 105                 110
Arg Gly Ile Pro Phe Trp Gly Ser Thr Ile Asp Thr Glu Leu Lys
                115                 120                 125
Val Ile Asp Thr Asn Cys Ile Asn Val Ile Gln Pro Asp Gly Ser Tyr
130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
                180                 185                 190
Thr Phe Gly Phe Glu Glu Ser Leu Glu Val Asp Thr Asn Pro Leu Leu
                195                 200                 205
Gly Ala Gly Lys Phe Ala Thr Asp Pro Ala Val Thr Leu Ala His Glu
                210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
                370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Asp
                420                 425                 430
Gly Ile Ile Thr Ser Lys Thr Lys Ser Leu Ile Glu Gly Arg Asn Lys
                435                 440                 445
Ala Leu Asn Asp Leu Cys Ile Lys Val Asn Asn Trp Asp Leu Phe Phe
                450                 455                 460
```

```
Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
            595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Gly Gly Gly Gly Ser Gly Gly Gly Ser Gly Gly Gly Gly Ser
865                 870                 875                 880
```

Phe Gly Gly Phe Thr Gly Ala Arg Lys Ser Ala Arg Lys Leu Ala Asn
            885                 890                 895
Gln

<210> SEQ ID NO 23
<211> LENGTH: 2676
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 23

| | |
|---|---|
| atgccaataa caattaacaa ctttaattat tcagatcctg ttgataataa aaatattta | 60 |
| tatttagata ctcatttaaa tacactagct aatgagcctg aaaaagcctt tcgcattaca | 120 |
| ggaaatatat gggtaatacc tgatagattt tcaagaaatt ctaatccaaa tttaaataaa | 180 |
| cctcctcgag ttacaagccc taaaagtggt tattatgatc ctaattattt gagtactgat | 240 |
| tctgacaaag atacattttt aaaagaaatt ataaagttat taaaagaat taattctaga | 300 |
| gaaataggag aagaattaat atatagactt tcgacagata tacccttttcc tgggaataac | 360 |
| aatactccaa ttaataccct tgattttgat gtagatttta acagtgttga tgttaaaact | 420 |
| agacaaggta caactgggt taaaactggt agcataaatc ctagtgttat aataactgga | 480 |
| cctagagaaa acattataga tccagaaact tctacgttta aattaactaa caataccttt | 540 |
| gcggcacaag aaggatttgg tgctttatca ataatttcaa tatcacctag atttatgcta | 600 |
| acatatagta atgcaactaa tgatgtagga gagggtagat tttctaagtc tgaattttgc | 660 |
| atggatccaa tactaatttt aatgcatgaa cttaatcatg caatgcataa tttatatgga | 720 |
| atagctatac caaatgatca aacaatttca tctgtaacta gtaatatttt ttattctcaa | 780 |
| tataatgtga aattagagta tgcagaaata tatgcatttg gaggtccaac tatagacctt | 840 |
| attcctaaaa gtgcaaggaa atattttgag gaaaaggcat tggattatta tagatctata | 900 |
| gctaaaagac ttaatagtat aactactgca atccttcaa gctttaataa atatataggg | 960 |
| gaatataaac agaaacttat tagaaagtat agattcgtag tagaatcttc aggtgaagtt | 1020 |
| acagtaaatc gtaataagtt tgttgagtta tataatgaac ttacacaaat atttacagaa | 1080 |
| tttaactacg ctaaaatata taatgtacaa aataggaaaa tatatctttc aaatgtatat | 1140 |
| actccggtta cggcgaatat attagacgat aatgtttatg atatacaaaa tggatttaat | 1200 |
| atacctaaaa gtaatttaaa tgtactattt atgggtcaaa atttatctcg aaatccagca | 1260 |
| ttaagaaaag tcaatcctga aaatatgctt tatttattta caaaattttg tcataaagca | 1320 |
| atagatggta gatcattata taataaaaca ttagattgta gagagctttt agttaaaaat | 1380 |
| actgacttac cctttatagg tgatattagt gatgttaaaa ctgatatatt tttaagaaaa | 1440 |
| gatattaatg aagaaactga agttatatac atccggaca tgtttcagt agatcaagtt | 1500 |
| attctcagta agaataccctc agaacatgga caactagatt tattataccc tagtattgac | 1560 |
| agtgagagtg aaatattacc aggggagaat caagtctttt atgataatag aactcaaaat | 1620 |
| gttgattatt tgaattctta ttattaccta gaatctcaaa aactaagtga taatgttgaa | 1680 |
| gattttactt ttacgagatc aattgaggag gctttggata atagtgcaaa agtatataact | 1740 |
| tactttccta cactagctaa taagtaaat gcgggtgttc aaggtggttt atttttaatg | 1800 |
| tgggcaaatg atgtagttga agattttact acaaatattc taagaaaaga tacattgat | 1860 |
| aaaatatcag atgtatcagc tattattccc tatataggac ccgcattaaa tataagtaat | 1920 |

-continued

```
tctgtaagaa gaggaaattt tactgaagca tttgcagtta ctggtgtaac tattttatta     1980
gaagcatttc ctgaatttac aatacctgca cttggtgcat ttgtgattta tagtaaggtt     2040
caagaaagaa acgagattat taaaactata gataattgtt tagaacaaag gattaagaga     2100
tggaaagatt catatgaatg gatgatggga acgtggttat ccaggattat tactcaattt     2160
aataatataa gttatcaaat gtatgattct ttaaattatc aggcaggtgc aatcaaagct     2220
aaaatagatt tagaatataa aaatattca ggaagtgata agaaaatat aaaaagtcaa       2280 gttgaaaatt taaaaaatag tttagatgta aaaatttcgg aagcaatgaa taatataaat     2340
aaatttatac gagaatgttc cgtaacatat ttatttaaaa atatgttacc taaagtaatt     2400
gatgaattaa atgagtttga tcgaaatact aaagcaaaat taattaatct tatagatagt     2460
cataatatta ttctagttgg tgaagtagat aaattaaaag caaaagtaaa taatagcttt     2520
caaaatacaa tacccttta tattttttca tatactaata attctttatt aaaagatata     2580
attaatgaat atttcaatgg cggtgggggt agtggcggtg gcggttcggg cggggtggg      2640 agctttggcg gtttcacggg cgcacgcaaa tcagcg                               2676
```

<210> SEQ ID NO 24
<211> LENGTH: 892
<212> TYPE: PRT
<213> ORGANISM: Artificial Sequence
<220> FEATURE:
<223> OTHER INFORMATION: chemically synthesized fusion protein

<400> SEQUENCE: 24

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220
```

```
Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
            245                 250                 255

Phe Tyr Ser Gln Tyr Asn Val Lys Leu Glu Tyr Ala Glu Ile Tyr Ala
        260                 265                 270

Phe Gly Gly Pro Thr Ile Asp Leu Ile Pro Lys Ser Ala Arg Lys Tyr
    275                 280                 285

Phe Glu Glu Lys Ala Leu Asp Tyr Tyr Arg Ser Ile Ala Lys Arg Leu
290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
            325                 330                 335

Ser Gly Glu Val Thr Val Asn Arg Asn Lys Phe Val Glu Leu Tyr Asn
        340                 345                 350

Glu Leu Thr Gln Ile Phe Thr Glu Phe Asn Tyr Ala Lys Ile Tyr Asn
    355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
            405                 410                 415

Arg Asn Pro Ala Leu Arg Lys Val Asn Pro Glu Asn Met Leu Tyr Leu
        420                 425                 430

Phe Thr Lys Phe Cys His Lys Ala Ile Asp Gly Arg Ser Leu Tyr Asn
    435                 440                 445

Lys Thr Leu Asp Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
            485                 490                 495

Val Asp Gln Val Ile Leu Ser Lys Asn Thr Ser Glu His Gly Gln Leu
        500                 505                 510

Asp Leu Leu Tyr Pro Ser Ile Asp Ser Glu Ser Glu Ile Leu Pro Gly
    515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
            565                 570                 575

Lys Val Tyr Thr Tyr Phe Pro Thr Leu Ala Asn Lys Val Asn Ala Gly
        580                 585                 590

Val Gln Gly Gly Leu Phe Leu Met Trp Ala Asn Asp Val Val Glu Asp
    595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
```

-continued

```
                    645                 650                 655
Thr Ile Leu Leu Glu Ala Phe Pro Glu Phe Thr Ile Pro Ala Leu Gly
                660                 665                 670
Ala Phe Val Ile Tyr Ser Lys Val Gln Glu Arg Asn Glu Ile Ile Lys
            675                 680                 685
Thr Ile Asp Asn Cys Leu Glu Gln Arg Ile Lys Arg Trp Lys Asp Ser
        690                 695                 700
Tyr Glu Trp Met Met Gly Thr Trp Leu Ser Arg Ile Ile Thr Gln Phe
705                 710                 715                 720
Asn Asn Ile Ser Tyr Gln Met Tyr Asp Ser Leu Asn Tyr Gln Ala Gly
                725                 730                 735
Ala Ile Lys Ala Lys Ile Asp Leu Glu Tyr Lys Lys Tyr Ser Gly Ser
            740                 745                 750
Asp Lys Glu Asn Ile Lys Ser Gln Val Glu Asn Leu Lys Asn Ser Leu
        755                 760                 765
Asp Val Lys Ile Ser Glu Ala Met Asn Asn Ile Asn Lys Phe Ile Arg
    770                 775                 780
Glu Cys Ser Val Thr Tyr Leu Phe Lys Asn Met Leu Pro Lys Val Ile
785                 790                 795                 800
Asp Glu Leu Asn Glu Phe Asp Arg Asn Thr Lys Ala Lys Leu Ile Asn
                805                 810                 815
Leu Ile Asp Ser His Asn Ile Ile Leu Val Gly Glu Val Asp Lys Leu
            820                 825                 830
Lys Ala Lys Val Asn Asn Ser Phe Gln Asn Thr Ile Pro Phe Asn Ile
        835                 840                 845
Phe Ser Tyr Thr Asn Asn Ser Leu Leu Lys Asp Ile Ile Asn Glu Tyr
    850                 855                 860
Phe Asn Gly Gly Gly Ser Gly Gly Gly Ser Gly Gly Gly Gly
865                 870                 875                 880
Ser Phe Gly Gly Phe Thr Gly Ala Arg Lys Ser Ala
                885                 890
```

<210> SEQ ID NO 25
<211> LENGTH: 2712
<212> TYPE: DNA
<213> ORGANISM: Artificial Sequence
<220> FEATURE:
<223> OTHER INFORMATION: chemically synthesized polynucleotide encoding a fusion protein

<400> SEQUENCE: 25

| | | | | | |
|---|---|---|---|---|---|
| tttggcggtt | tcacgggcgc | acgcaaatca | gcgcgtaaat | atgctaacca gactagtggc | 60 |
| ggtgggggta | gtggcggtgg | cggttcgggc | ggggtgggga | gccctagggg atccatgcca | 120 |
| ataacaatta | caactttaa | ttattcagat | cctgttgata | taaaaatat tttatattta | 180 |
| gatactcatt | taaatacact | agctaatgag | cctgaaaaag | cctttcgcat acaggaaat | 240 |
| atatgggtaa | tacctgatag | attttcaaga | aattctaatc | caaatttaaa taaacctcct | 300 |
| cgagttacaa | gccctaaaag | tggttattat | gatcctaatt | atttgagtac tgattctgac | 360 |
| aaagatacat | ttttaaaaga | aattataaag | ttatttaaaa | gaattaattc tagagaaata | 420 |
| ggagaagaat | taatatatag | actttcgaca | gatataccct | tcctgggaa taacaatact | 480 |
| ccaattaata | cctttgattt | tgatgtagat | tttaacagtg | ttgatgttaa aactagacaa | 540 |
| ggtaacaact | gggttaaaac | tggtagcata | atcctagtg | ttataataac tggacctaga | 600 |
| gaaaacatta | tagatccaga | aacttctacg | tttaaattaa | ctaacaatac ctttgcggca | 660 |

```
caagaaggat tggtgctttt atcaataatt tcaatatcac ctagatttat gctaacatat      720
agtaatgcaa ctaatgatgt aggagagggt agattttcta agtctgaatt tgcatggat       780 ccaatactaa tttaatgca tgaacttaat catgcaatgc ataatttata tggaatagct       840
ataccaaatg atcaaacaat ttcatctgta actagtaata ttttttattc tcaatataat      900
gtgaaattag agtatgcaga aatatatgca tttggaggtc aactataga ccttattcct       960 aaaagtgcaa ggaaatattt tgaggaaaag gcattggatt attatagatc tatagctaaa    1020
agacttaata gtataactac tgcaaatcct tcaagcttta ataaatatat aggggaatat    1080
aaacagaaac ttattagaaa gtatagattc gtagtagaat cttcaggtga agttacagta    1140
aatcgtaata agtttgttga gttatataat gaacttacac aaatatttac agaatttaac    1200
tacgctaaaa tatataatgt acaaaatagg aaaatatatc tttcaaatgt atatactccg    1260
gttacggcga atatattaga cgataatgtt tatgatatac aaaatggatt taatataccc    1320
aaaagtaatt taaatgtact atttatgggt caaaatttat ctcgaaatcc agcattaaga    1380
aaagtcaatc ctgaaaatat gctttatttta tttacaaaat tttgtcataa agcaatagat    1440
ggtagatcat tatataataa aacattagat tgtagagagc ttttagttaa aaatactgac    1500
ttacccttta taggtgatat tagtgatgtt aaaactgata tattttaag aaaagatatt     1560 aatgaagaaa ctgaagttat atactatccg gacaatgttt cagtagatca agttattctc    1620
agtaagaata cctcagaaca tggacaacta gatttattat accctagtat tgacagtgag    1680
agtgaaatat taccagggga gaatcaagtc ttttatgata atagaactca aaatgttgat    1740
tatttgaatt cttattatta cctagaatct caaaaactaa gtgataatgt tgaagatttt    1800
acttttacga gatcaattga ggaggctttg gataatagtg caaaagtata tacttacttt    1860
cctacactag ctaataaagt aaatgcgggt gttcaaggtg gttttatttt aatgtgggca    1920
aatgatgtag ttgaagattt tactacaaat attctaagaa aagatacatt agataaaata    1980
tcagatgtat cagctattat tccctatata ggacccgcat taaatataag taattctgta    2040
agaagaggaa attttactga agcatttgca gttactggtg taactatttt attagaagca    2100
tttcctgaat ttacaatacc tgcacttggt gcatttgtga tttatagtaa ggttcaagaa    2160
agaaacgaga ttattaaaac tatagataat tgtttagaac aaaggattaa gagatggaaa    2220
gattcatatg aatggatgat gggaacgtgg ttatccagga ttattactca atttaataat    2280
ataagttatc aaatgtatga ttcttttaaat tatcaggcag gtgcaatcaa agctaaaata    2340
gatttagaat ataaaaaata ttcaggaagt gataaagaaa atataaaaag tcaagttgaa    2400
aatttaaaaa atagtttaga tgtaaaaatt tcggaagcaa tgaataatat aaataaattt    2460
atacgagaat gttccgtaac atatttattt aaaaatatgt tacctaaagt aattgatgaa    2520
ttaaatgagt tgatcgaaaa tactaaagca aaattaatta atcttataga tagtcataat    2580
attattctag ttggtgaagt agataaatta aaagcaaaag taataatag ctttcaaaat     2640 acaatacccc ttaatatttt ttcatatact aataattctt tattaaaaga tataattaat    2700
gaatatttca at                                                          2712
```

<210> SEQ ID NO 26
<211> LENGTH: 904
<212> TYPE: PRT
<213> ORGANISM: Artificial Sequence
<220> FEATURE:
<223> OTHER INFORMATION: chemically synthesized fusion protein -continued

```
<400> SEQUENCE: 26

Phe Gly Gly Phe Thr Gly Ala Arg Lys Ser Ala Arg Lys Tyr Ala Asn
1               5                   10                  15

Gln Thr Ser Gly Gly Gly Ser Gly Gly Gly Ser Gly Gly Gly
            20                  25                  30

Gly Ser Pro Arg Gly Ser Met Pro Ile Thr Ile Asn Asn Phe Asn Tyr
            35                  40                  45

Ser Asp Pro Val Asp Asn Lys Asn Ile Leu Tyr Leu Asp Thr His Leu
    50                  55                  60

Asn Thr Leu Ala Asn Glu Pro Glu Lys Ala Phe Arg Ile Thr Gly Asn
65                  70                  75                  80

Ile Trp Val Ile Pro Asp Arg Phe Ser Arg Asn Ser Asn Pro Asn Leu
                85                  90                  95

Asn Lys Pro Pro Arg Val Thr Ser Pro Lys Ser Gly Tyr Tyr Asp Pro
            100                 105                 110

Asn Tyr Leu Ser Thr Asp Ser Asp Lys Asp Thr Phe Leu Lys Glu Ile
            115                 120                 125

Ile Lys Leu Phe Lys Arg Ile Asn Ser Arg Glu Ile Gly Glu Glu Leu
130                 135                 140

Ile Tyr Arg Leu Ser Thr Asp Ile Pro Phe Pro Gly Asn Asn Asn Thr
145                 150                 155                 160

Pro Ile Asn Thr Phe Asp Phe Asp Val Asp Phe Asn Ser Val Asp Val
                165                 170                 175

Lys Thr Arg Gln Gly Asn Asn Trp Val Lys Thr Gly Ser Ile Asn Pro
            180                 185                 190

Ser Val Ile Ile Thr Gly Pro Arg Glu Asn Ile Ile Asp Pro Glu Thr
            195                 200                 205

Ser Thr Phe Lys Leu Thr Asn Asn Thr Phe Ala Ala Gln Glu Gly Phe
    210                 215                 220

Gly Ala Leu Ser Ile Ile Ser Ile Ser Pro Arg Phe Met Leu Thr Tyr
225                 230                 235                 240

Ser Asn Ala Thr Asn Asp Val Gly Glu Gly Arg Phe Ser Lys Ser Glu
                245                 250                 255

Phe Cys Met Asp Pro Ile Leu Ile Leu Met His Glu Leu Asn His Ala
            260                 265                 270

Met His Asn Leu Tyr Gly Ile Ala Ile Pro Asn Asp Gln Thr Ile Ser
            275                 280                 285

Ser Val Thr Ser Asn Ile Phe Tyr Ser Gln Tyr Asn Val Lys Leu Glu
    290                 295                 300

Tyr Ala Glu Ile Tyr Ala Phe Gly Gly Pro Thr Ile Asp Leu Ile Pro
305                 310                 315                 320

Lys Ser Ala Arg Lys Tyr Phe Glu Lys Ala Leu Asp Tyr Arg
                325                 330                 335

Ser Ile Ala Lys Arg Leu Asn Ser Ile Thr Thr Ala Asn Pro Ser Ser
            340                 345                 350

Phe Asn Lys Tyr Ile Gly Glu Tyr Lys Gln Lys Leu Ile Arg Lys Tyr
            355                 360                 365

Arg Phe Val Val Glu Ser Ser Gly Glu Val Thr Val Asn Arg Asn Lys
            370                 375                 380

Phe Val Glu Leu Tyr Asn Glu Leu Thr Gln Ile Phe Thr Glu Phe Asn
385                 390                 395                 400

Tyr Ala Lys Ile Tyr Asn Val Gln Asn Arg Lys Ile Tyr Leu Ser Asn
                405                 410                 415
```

```
Val Tyr Thr Pro Val Thr Ala Asn Ile Leu Asp Asp Asn Val Tyr Asp
            420                 425                 430

Ile Gln Asn Gly Phe Asn Ile Pro Lys Ser Asn Leu Asn Val Leu Phe
            435                 440                 445

Met Gly Gln Asn Leu Ser Arg Asn Pro Ala Leu Arg Lys Val Asn Pro
            450                 455                 460

Glu Asn Met Leu Tyr Leu Phe Thr Lys Phe Cys His Lys Ala Ile Asp
465                 470                 475                 480

Gly Arg Ser Leu Tyr Asn Lys Thr Leu Asp Cys Arg Glu Leu Leu Val
                485                 490                 495

Lys Asn Thr Asp Leu Pro Phe Ile Gly Asp Ile Ser Asp Val Lys Thr
            500                 505                 510

Asp Ile Phe Leu Arg Lys Asp Ile Asn Glu Glu Thr Glu Val Ile Tyr
            515                 520                 525

Tyr Pro Asp Asn Val Ser Val Asp Gln Val Ile Leu Ser Lys Asn Thr
            530                 535                 540

Ser Glu His Gly Gln Leu Asp Leu Leu Tyr Pro Ser Ile Asp Ser Glu
545                 550                 555                 560

Ser Glu Ile Leu Pro Gly Glu Asn Gln Val Phe Tyr Asp Asn Arg Thr
                565                 570                 575

Gln Asn Val Asp Tyr Leu Asn Ser Tyr Tyr Leu Glu Ser Gln Lys
            580                 585                 590

Leu Ser Asp Asn Val Glu Asp Phe Thr Phe Thr Arg Ser Ile Glu Glu
                595                 600                 605

Ala Leu Asp Asn Ser Ala Lys Val Tyr Thr Tyr Phe Pro Thr Leu Ala
            610                 615                 620

Asn Lys Val Asn Ala Gly Val Gln Gly Gly Leu Phe Leu Met Trp Ala
625                 630                 635                 640

Asn Asp Val Val Glu Asp Phe Thr Thr Asn Ile Leu Arg Lys Asp Thr
                645                 650                 655

Leu Asp Lys Ile Ser Asp Val Ser Ala Ile Ile Pro Tyr Ile Gly Pro
            660                 665                 670

Ala Leu Asn Ile Ser Asn Ser Val Arg Arg Gly Asn Phe Thr Glu Ala
            675                 680                 685

Phe Ala Val Thr Gly Val Thr Ile Leu Leu Glu Ala Phe Pro Glu Phe
            690                 695                 700

Thr Ile Pro Ala Leu Gly Ala Phe Val Ile Tyr Ser Lys Val Gln Glu
705                 710                 715                 720

Arg Asn Glu Ile Ile Lys Thr Ile Asp Asn Cys Leu Glu Gln Arg Ile
                725                 730                 735

Lys Arg Trp Lys Asp Ser Tyr Glu Trp Met Met Gly Thr Trp Leu Ser
            740                 745                 750

Arg Ile Ile Thr Gln Phe Asn Asn Ile Ser Tyr Gln Met Tyr Asp Ser
            755                 760                 765

Leu Asn Tyr Gln Ala Gly Ala Ile Lys Ala Lys Ile Asp Leu Glu Tyr
            770                 775                 780

Lys Lys Tyr Ser Gly Ser Asp Lys Glu Asn Ile Lys Ser Gln Val Glu
785                 790                 795                 800

Asn Leu Lys Asn Ser Leu Asp Val Lys Ile Ser Glu Ala Met Asn Asn
                805                 810                 815

Ile Asn Lys Phe Ile Arg Glu Cys Ser Val Thr Tyr Leu Phe Lys Asn
            820                 825                 830
```

```
Met Leu Pro Lys Val Ile Asp Glu Leu Asn Glu Phe Asp Arg Asn Thr
            835                 840                 845
Lys Ala Lys Leu Ile Asn Leu Ile Asp Ser His Asn Ile Ile Leu Val
        850                 855                 860
Gly Glu Val Asp Lys Leu Lys Ala Lys Val Asn Asn Ser Phe Gln Asn
865                 870                 875                 880
Thr Ile Pro Phe Asn Ile Phe Ser Tyr Thr Asn Asn Ser Leu Leu Lys
            885                 890                 895
Asp Ile Ile Asn Glu Tyr Phe Asn
            900
```

<210> SEQ ID NO 27
<211> LENGTH: 1302
<212> TYPE: DNA
<213> ORGANISM: Artificial Sequence
<220> FEATURE:
<223> OTHER INFORMATION: chemically synthesized polynucleotide encoding
      botulinum neurotoxin type A light chain

<400> SEQUENCE: 27

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct caccccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc acccctgaac     900
aaagcgaaat ccatcgtggg taccactgct tctctccagt acatgaagaa cgttttttaaa     960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg ac                       1302
```

<210> SEQ ID NO 28
<211> LENGTH: 1257
<212> TYPE: DNA
<213> ORGANISM: Artificial Sequence
<220> FEATURE:
<223> OTHER INFORMATION: chemically synthesized polynucleotide encoding
      botulinum neurotoxin type A heavy chain

<400> SEQUENCE: 28

```
ctgcagtgta tcaaggttaa caactgggat ttattcttca gcccgagtga agacaacttc    60
accaacgacc tgaacaaagg tgaagaaatc acctcagata ctaacatcga agcagccgaa   120
gaaaacatct cgctggacct gatccagcag tactacctga cctttaattt cgacaacgag   180
ccggaaaaca tttctatcga aaacctgagc tctgatatca tcggccagct ggaactgatg   240
ccgaacatcg aacgtttccc aaacggtaaa agtacgagc tggacaaata ccatgttc     300
cactacctgc gcgcgcagga atttgaacac ggcaaatccc gtatcgcact gactaactcc   360
gttaacgaag ctctgctcaa cccgtcccgt gtatacacct tcttctctag cgactacgtg   420
aaaaaggtca caaagcgac tgaagctgca atgttcttgg gttgggttga acagcttgtt    480
tatgatttta ccgacgagac gtccgaagta tctactaccg acaaaattgc ggatatcact   540
atcatcatcc cgtacatcgg tccggctctg aacattggca acatgctgta caaagacgac   600
ttcgttggcg cactgatctt ctccggtgcg gtgatcctgc tggagttcat cccggaaatc   660
gccatcccgg tactgggcac ctttgctctg gtttcttaca ttgcaaacaa ggttctgact   720
gtacaaacca tcgacaacgc gctgagcaaa cgtaacgaaa atgggatga agtttacaaa    780
tatatcgtga ccaactggct ggctaaggtt aatactcaga tcgacctcat ccgcaaaaaa   840
atgaaagaag cactggaaaa ccaggcgaaa gctaccaagg caatcattaa ctaccagtac   900
aaccagtaca ccgaggaaga aaaaaacaac atcaacttca acatcgacga tctgtcctct   960
aaactgaacg aatccatcaa caagctatg atcaacatca caagttcct gaaccagtgc    1020
tctgtaagct atctgatgaa ctccatgatc ccgtacggtg ttaaacgtct ggaggacttc   1080
gatgcgtctc tgaaagacgc cctgctgaaa tacatttacg caaccgtgg cactctgatc   1140
ggtcaggttg atcgtctgaa ggacaaagtg aacaatacct tatcgaccga catcccttt    1200
cagctcagta aatatgtcga taaccaacgc cttttgtcca ctctagacta gaagctt      1257
```

<210> SEQ ID NO 29
<211> LENGTH: 1323
<212> TYPE: DNA
<213> ORGANISM: Artificial Sequence
<220> FEATURE:
<223> OTHER INFORMATION: chemically synthesized polynucleotide encoding botulinum neurotoxin type B light chain

<400> SEQUENCE: 29

```
ggatccatgc cggttaccat caacaacttc aactacaacg acccgatcga caacaacaac    60
atcattatga tggaaccgcc gttcgcacgt ggtaccggac gttactacaa ggcttttaag   120
atcaccgacc gtatctggat catcccggaa cgttacacct tcggttacaa acctgaggac   180
ttcaacaaga gtagcgggat tttcaatcgt gacgtctgcg agtactatga tccagattat   240
ctgaatacca acgataagaa gaacatattc cttcagacta tgattaaact cttcaaccgt   300
atcaaaagca aaccgctcgg tgaaaaactc ctcgaaatga ttatcaacgg tatcccgtac   360
ctcggtgacc gtcgtgtccc gcttgaagag ttcaacacca acatcgcaag cgtcaccgtc   420
aacaaactca tcagcaaccc aggtgaagtc gaacgtaaaa aaggtatctt cgcaaacctc   480
atcatcttcg gtccgggtcc ggtcctcaac gaaaacgaaa ccatcgacat cggtatccag   540
aaccacttcg caagccgtga aggtttcggt ggtatcatgc agatgaaatt ctgcccggaa   600
tacgtcagtg tcttcaacaa cgtccaggaa aacaaaggtg caagcatctt caaccgtcgt   660
ggttacttca gcgacccggc actcatcctc atgcatgaac tcatccacgt cctccacggt   720
```

```
ctctacggta tcaaagttga cgacctcccg atcgtcccga acgagaagaa attcttcatg    780
cagagcaccg acgcaatcca ggctgaggaa ctctacacct tcggtggcca agacccaagt    840
atcataaccc cgtccaccga caaaagcatc tacgacaaag tcctccagaa cttcaggggt    900
atcgtggaca gactcaacaa agtcctcgtc tgcatcagcg acccgaacat caatatcaac    960
atatacaaga acaagttcaa agacaagtac aaattcgtcg aggacagcga aggcaaatac   1020
agcatcgacg tagaaagttt cgacaagctc tacaaaagcc tcatgttcgg tttcaccgaa   1080
accaacatcg ccgagaacta caagatcaag acaagggcaa gttacttcag cgacagcctc   1140
ccgcctgtca aaatcaagaa cctcttagac aacgagattt acacaattga gagggcttc    1200 aacatcagtg acaaagacat ggagaaggaa tacagaggtc agaacaaggc tatcaacaaa   1260
caggcatacg aggagatcag caaagaacac ctcgcagtct acaagatcca gatgtgcgtc   1320
gac                                                                1323

<210> SEQ ID NO 30
<211> LENGTH: 1260
<212> TYPE: DNA
<213> ORGANISM: Artificial Sequence
<220> FEATURE:
<223> OTHER INFORMATION: chemically synthesized polynucleotide encoding
      botulinum neurotoxin type B heavy chain

<400> SEQUENCE: 30
ctgcagtgca tcgacgttga caacgaagac ctgttcttca tcgctgacaa aaacagcttc    60
agtgacgacc tgagcaaaaa cgaacgtatc gaatacaaca cccagagcaa ctacatcgaa   120
aacgacttcc cgatcaacga actgatcctg acaccgacc tgataagtaa atcgaactg    180 ccgagcgaaa acaccgaaag tctgaccgac ttcaacgttg acgttccggt ttacgaaaaa   240
cagccggcta tcaagaaaat cttcaccgac gaaaacacca tcttccagta cctgtacagc   300
cagaccttcc cgctggacat ccgtgacatc agtctgacca gcagtttcga cgacgctctg   360
ctgttcagca acaaagtttta cagtttcttc agcatggact acatcaaaac cgctaacaaa   420
gttgttgaag cagggctgtt cgctggttgg gttaaacaga tcgttaacga cttcgttatc   480
gaagctaaca aaagcaacac tatggacaaa atcgctgaca tcagtctgat cgttccgtac   540
atcggtctgg ctctgaacgt tggtaacgaa accgctaaag gtaactttga aaacgctttc   600
gagatcgctg gtgcaagcat cctgctggag ttcatcccgg aactgctgat cccggttgtt   660
ggtgctttcc tgctggaaag ttacatcgac aacaaaaaca gatcatcaa accatcgac    720 aacgctctga ccaaacgtaa cgaaaaatgg agtgatatgt acggtctgat cgttgctcag   780
tggctgagca ccgtcaacac ccagttctac accatcaaag aaggtatgta caagctctg    840 aactaccagg ctcaggctct ggaagagatc atcaaatacc gttacaacat ctacagtgag   900
aaggaaaaga gtaacatcaa catcgacttc aacgacatca cagcaaact gaacgaaggt   960 atcaaccagg ctatcgacaa catcaacaac ttcatcaacg gttgcagtgt tagctacctg   1020
atgaagaaga tgatcccgct ggctgttgaa aaactgctgg acttcgacaa caccctgaaa   1080
aagaacctgc tgaactacat cgacgaaaac aagctgtacc tgatcggtag tgctgaatac   1140
gaaaaaagta agtgaacaa atacctgaag accatcatgc cgttcgacct gagtatctac   1200
accaacgaca ccatcctgat cgaaatgttc aacaaataca actctctaga ctagaagctt   1260

<210> SEQ ID NO 31
<211> LENGTH: 1329
<212> TYPE: DNA
```

<213> ORGANISM: Artificial Sequence
<220> FEATURE:
<223> OTHER INFORMATION: chemically synthesized polynucleotide encoding
    botulinum neurotoxin type C light chain

<400> SEQUENCE: 31

```
ggatccgaat tcatgccgat caccatcaac aacttcaact acagcgatcc ggtggataac      60
aaaaacatcc tgtacctgga tacccatctg aatccctgg cgaacgaacc ggaaaaagcg      120
tttcgtatca ccggcaacat ttgggttatt ccggatcgtt ttagccgtaa cagcaacccg      180
aatctgaata accgccgcg tgttaccagc ccgaaaagcg gttattacga tccgaactat      240
ctgagcaccg atagcgataa agatacctc ctgaaagaaa tcatcaaact gttcaaacgc      300
atcaacagcc gtgaaattgg cgaagaactg atctatcgcc tgagcaccga tattccgttt      360
ccgggcaaca caacaccccc gatcaacacc tttgatttcg atgtggattt caacagcgtt      420
gatgttaaaa cccgccaggg taacaattgg gtgaaaaccg gcagcattaa cccgagcgtg      480
attattaccg gtccgcgcga aaacattatt gatccggaaa ccagcacctt taaactgacc      540
aacaacacct ttgcggcgca ggaaggtttt ggcgcgctga gcattattag cattagcccg      600
cgctttatgc tgacctatag caacgcgacc aacgatgttg gtgaaggccg tttcagcaaa      660
agcgaatttt gcatggaccc gatcctgatc ctgatgcatg aactgaacca tgcgatgcat      720
aacctgtatg gcatcgcgat tccgaacgat cagaccatta gcagcgtgac cagcaacatc      780
ttttacagcc agtacaacgt gaaactggaa tatgcgaaaa tctatgcgtt ggcggtccg      840
accattgatc tgattccgaa aagcgcgcgc aaatacttcg aagaaaaagc gctggattac      900
tatcgcagca ttgcgaaacg tctgaacagc attaccaccg cgaatccgag cagcttcaac      960
aaatatatcg cgaatataa acagaaactg atccgcaaat atcgctttgt ggtggaaagc      1020
agcggcgaag ttaccgttaa ccgcaataaa ttcgtggaac tgtacaacga actgacccag      1080
atcttcaccg aatttaacta tgcgaaaatc tataacgtgc agaaccgtaa atctacctg      1140
agcaacgtgt ataccccggt gaccgcgaat attctggatg ataacgtgta cgatatccag      1200
aacggcttta acatcccgaa aagcaacctg aacgttctgt ttatgggcca gaacctgagc      1260
cgtaatccgg cgctgcgtaa agtgaacccg gaaaacatgc tgtacctgtt caccaaattt      1320
tgcgtcgac                                                              1329
```

<210> SEQ ID NO 32
<211> LENGTH: 1263
<212> TYPE: DNA
<213> ORGANISM: Artificial Sequence
<220> FEATURE:
<223> OTHER INFORMATION: chemically synthesized polynucleotide encoding
    botulinum neurotoxin type C heavy chain

<400> SEQUENCE: 32

```
ctgcagtgtc gtgaactgct ggtgaaaaac accgatctgc gtttattgg cgatatcagc      60
gatgtgaaaa ccgatatctt cctgcgcaaa gatatcaacg aagaaaccga agtgatctac      120
tacccggata acgtgagcgt tgatcaggtg atcctgagca aaaacaccag cgaacatggt      180
cagctggatc tgctgtatcc gagcattgat agcgaaagcg aaattctgcc gggcgaaaac      240
caggtgtttt acgataaccg tacccagaac gtggattacc tgaacagcta ttactacctg      300
gaaagccaga aactgagcga taacgtggaa gattttacct ttacccgcag cattgaagaa      360
gcgctggata cagcgcgaa agtttacacc tattttccga ccctggcgaa caaagttaat      420
gcgggtgttc agggcggtct gtttctgatg tgggcgaacg atgtggtgga agatttcacc      480
```

```
accaacatcc tgcgtaaaga taccctggat aaaatcagcg atgttagcgc gattattccg        540
tatattggtc cggcgctgaa cattagcaat agcgtgcgtc gtggcaattt taccgaagcg        600
tttgcggtta ccggtgtgac cattctgctg aaagcgtttc cggaatttac cattccggcg        660
ctgggtgcgt ttgtgatcta tagcaaagtg caggaacgca acgaaatcat caaaaccatc        720
gataactgcc tggaacagcg tattaaacgc tggaaagata gctatgaatg gatgatgggc        780
acctggctga ccgtattat cacccagttc aacaacatca gctaccagat gtacgatagc         840
ctgaactatc aggcgggtgc gattaaagcg aaaatcgatc tggaatacaa aaaatacagc        900
ggcagcgata agaaaaacat caaaagccag gttgaaaacc tgaaaaacag cctggatgtg        960
aaaattagcg aagcgatgaa taacatcaac aaattcatcc gcaatgcag cgtgacctac         1020 ctgttcaaaa acatgctgcc gaaagtgatc gatgaactga cgaatttga tcgcaacacc         1080 aaagcgaaac tgatcaacct gatcgatagc cacaacatta ttctggtggg cgaagtggat        1140
aaactgaaag cgaaagttaa caacagcttc cagaacacca tcccgtttaa catcttcagc        1200
tataccaaca acagcctgct gaaagatatc atcaacgaat acttcaatct agactagaag        1260
ctt                                                                     1263

<210> SEQ ID NO 33
<211> LENGTH: 207
<212> TYPE: DNA
<213> ORGANISM: Artificial Sequence
<220> FEATURE:
<223> OTHER INFORMATION: chemically synthesized polynucleotide encoding
      botulinum neurotoxin type C heavy chain

<400> SEQUENCE: 33
ggatccacgc acgtcgacgg catcattacc tccaaaacta aatctctgat cgaaggtcgt         60
tttggcggtt tcacgggcgc acgcaaatca gcgcgtaaat tagctaacca ggcgctagcg        120
ggcggtggcg gtagcggcgg tggcggtagc ggcggtggcg gtagcgcact agtgctgcag        180
acgcacggtc tagaatgata aaagctt                                            207

<210> SEQ ID NO 34
<211> LENGTH: 108
<212> TYPE: DNA
<213> ORGANISM: Artificial Sequence
<220> FEATURE:
<223> OTHER INFORMATION: chemically synthesized polynucleotide encoding
      linker

<400> SEQUENCE: 34
ggatccacgc acgtcgacgg catcattacc tccaaaacta aatctctgat agaaggtaga         60
aacaaagcgc tgaacctgca gacgcacggt ctagaatgat aaaagctt                     108

<210> SEQ ID NO 35
<211> LENGTH: 186
<212> TYPE: DNA
<213> ORGANISM: Artificial Sequence
<220> FEATURE:
<223> OTHER INFORMATION: chemically synthesized polynucleotide encoding
      N-terminal presentation nociceptin insert

<400> SEQUENCE: 35
catatgaata acctcgggat tgagggtcgt tttggcggtt tcacgggcgc acgcaaatca         60
gcgcgtaaat tagctaacca gactagtggc ggtggggta gtggcggtgg cggttcgggc        120
gggggtggga gccctagggg atccgtcgac ctgcagggtc tagaagcgct agcgtgataa       180
``` aagctt 186

<210> SEQ ID NO 36
<211> LENGTH: 180
<212> TYPE: DNA
<213> ORGANISM: Artificial Sequence
<220> FEATURE:
<223> OTHER INFORMATION: chemically synthesized polynucleotide encoding
      linker

<400> SEQUENCE: 36
ggatccacgc acgtcgacgc gattgatggt cgttttggcg gtttcacggg cgcacgcaaa       60
tcagcgcgta aattagctaa ccaggcgcta gcgggcggtg gcggtagcgg cggtggcggt      120
agcggcggtg gcggtagcgc actagtgctg cagacgcacg gtctagaatg ataaaagctt      180

<210> SEQ ID NO 37
<211> LENGTH: 249
<212> TYPE: DNA
<213> ORGANISM: Artificial Sequence
<220> FEATURE:
<223> OTHER INFORMATION: chemically synthesized polynucleotide encoding
      linker

<400> SEQUENCE: 37
ggatccacgc acgtcgacgg catcattacc tccaaaacta aatctctgat cgaaggtcgt       60
tacggtggtt tcatgacctc tgaaaaatct cagaccccgc tggttaccct gttcaaaaac      120
gctatcatca aaaacgctta caaaaaaggt gaagcgctag cgggtggtgg tggttctggt      180
ggtggtggtt ctggtggtgg tggttctgca ctagtgctgc agacgcacgg tctagaatga      240
taaaagctt                                                              249

<210> SEQ ID NO 38
<211> LENGTH: 207
<212> TYPE: DNA
<213> ORGANISM: Artificial Sequence
<220> FEATURE:
<223> OTHER INFORMATION: chemically synthesized polynucleotide encoding
      linker

<400> SEQUENCE: 38
ggatccacgc acgtcgacgg catcattacc tccaaaacta aatctctgat cgaaggtcgt       60
tttggcggtt tcacgggcgc acgcaaatca gcgcgtaaac gtaagaacca ggcgctagcg      120
ggcggtggcg gtagcggcgg tggcggtagc ggcggtggcg gtagcgcact agtgctgcag      180
acgcacggtc tagaatgata aaagctt                                          207

<210> SEQ ID NO 39
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 39
ggatccatgg agttcgttaa caaacagttc aactataaag acccagttaa cggtgttgac       60
attgcttaca tcaaaatccc gaacgctggc cagatgcagc cggtaaaggc attcaaaatc      120
cacaacaaaa tctgggttat cccggaacgt gataccttta ctaacccgga agaaggtgac      180 ctgaaccccgc caccggaagc gaaacaggtg ccggtatctt actatgactc cacctacctg      240

```
tctaccgata acgaaaagga caactacctg aaaggtgtta ctaaactgtt cgagcgtatt      300
tactccaccg acctgggccg tatgctgctg actagcatcg ttcgcggtat cccgttctgg      360
ggcggttcta ccatcgatac cgaactgaaa gtaatcgaca ctaactgcat caacgttatt      420
cagccggacg gttcctatcg ttccgaagaa ctgaacctgg tgatcatcgg cccgtctgct      480
gatatcatcc agttcgagtg taagagcttt ggtcacgaag ttctgaacct cacccgtaac      540
ggctacggtt ccactcagta catccgtttc tctccggact tcaccttcgg ttttgaagaa      600
tccctggaag tagacacgaa cccactgctg ggcgctggta aattcgcaac tgatcctgcg      660
gttaccctgg ctcacgaact gattcatgca ggccaccgcc tgtacggtat cgccatcaat      720
ccgaaccgtg tcttcaaagt taacaccaac gcgtattacg agatgtccgg tctggaagtt      780
agcttcgaag aactgcgtac ttttggcggt cacgacgcta aattcatcga ctctctgcaa      840
gaaaacgagt tccgtctgta ctactataac aagttcaaag atatcgcatc caccctgaac      900
aaagcgaaat ccatcgtggg taccactgct tctctccagt acatgaagaa cgtttttaaa      960
gaaaaatacc tgctcagcga agacacctcc ggcaaattct ctgtagacaa gttgaaattc     1020
gataaacttt acaaaatgct gactgaaatt tacaccgaag acaacttcgt taagttcttt     1080
aaagttctga ccgcaaaac ctatctgaac ttcgacaagg cagtattcaa aatcaacatc     1140
gtgccgaaag ttaactacac tatctacgat ggtttcaacc tgcgtaacac caacctggct     1200
gctaatttta acggccagaa cacggaaatc aacaacatga acttcacaaa actgaaaaac     1260
ttcactggtc tgttcgagtt ttacaagctg ctgtgcgtcg acggcatcat tacctccaaa     1320
actaaatctc tgatagaagg tagatttggc ggtttcacgg gcgcacgcaa atcagcgcgt     1380
aaattagcta accaggcgct agcgggcggt ggcggtagcg gcgtggcgg tagcggcggt      1440 ggcggtagcg cactagtgct gcagtgtatc aaggttaaca actgggattt attcttcagc     1500
ccgagtgaag acaacttcac caacgacctg aacaaaggtg aagaaatcac ctcagatact     1560
aacatcgaag cagccgaaga aaacatctcg ctggacctga tccagcagta ctacctgacc     1620 tttaattttcg acaacgagcc ggaaaacatt tctatcgaaa acctgagctc tgatatcatc     1680
ggccagctgg aactgatgcc gaacatcgaa cgtttcccaa acggtaaaaa gtacgagctg     1740
gacaaatata ccatgttcca ctacctgcgc gcgcaggaat ttgaacacgg caaatcccgt     1800
atcgcactga ctaactccgt taacgaagct ctgctcaacc cgtcccgtgt atacaccttc     1860
ttctctagcg actacgtgaa aaaggtcaac aaagcgactg aagctgcaat gttcttgggt     1920
tgggttgaac agcttgttta tgattttacc gacgagacgt ccgaagtatc tactaccgac     1980
aaaattgcgg atatcactat catcatcccg tacatcggtc cggctctgaa cattggcaac     2040
atgctgtaca aagacgactt cgttggcgca ctgatcttct ccggtgcggt gatcctgctg     2100
gagttcatcc cggaaatcgc catcccggta ctgggcacct tgctctggt ttcttacatt     2160 gcaaacaagg ttctgactgt acaaaccatc gacaacgcgc tgagcaaacg taacgaaaaa     2220
tgggatgaag tttacaaata tatcgtgacc aactggctgg ctaaggttaa tactcagatc     2280
gacctcatcc gcaaaaaaat gaagaagca ctggaaaaacc aggcggaagc taccaaggca     2340
atcattaact accagtacaa ccagtacacc gaggaagaaa aaacaacat caacttcaac      2400 atcgacgatc tgtcctctaa actgaacgaa tccatcaaca agctatgat caacatcaac      2460 aagttcctga ccagtgctc tgtaagctat ctgatgaact ccatgatccc gtacggtgtt     2520
aaacgtctgg aggacttcga tgcgtctctg aaagacgccc tgctgaaata catttacgac     2580
aaccgtggca ctctgatcgg tcaggttgat cgtctgaagg acaaagtgaa caatacctta     2640
```

```
tcgaccgaca tcccttttca gctcagtaaa tatgtcgata accaacgcct tttgtccact    2700
ctagactag                                                             2709
```

<210> SEQ ID NO 40
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 40

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
```

-continued

```
                340             345             350
Glu Asp Asn Phe Val Lys Phe Lys Val Leu Asn Arg Lys Thr Tyr
            355                 360                 365
Leu Asn Phe Asp Lys Ala Val Phe Lys Ile Asn Ile Val Pro Lys Val
370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Leu Ile Glu Gly Arg
            435                 440                 445
Phe Gly Gly Phe Thr Gly Ala Arg Lys Ser Ala Arg Lys Leu Ala Asn
            450                 455                 460
Gln Ala Leu Ala Gly Gly Gly Ser Gly Gly Gly Ser Gly Gly
465                 470                 475                 480
Gly Gly Ser Ala Leu Val Leu Gln Cys Ile Lys Val Asn Asn Trp Asp
                485                 490                 495
Leu Phe Phe Ser Pro Ser Glu Asp Asn Phe Thr Asn Asp Leu Asn Lys
            500                 505                 510
Gly Glu Glu Ile Thr Ser Asp Thr Asn Ile Glu Ala Ala Glu Glu Asn
            515                 520                 525
Ile Ser Leu Asp Leu Ile Gln Gln Tyr Tyr Leu Thr Phe Asn Phe Asp
530                 535                 540
Asn Glu Pro Glu Asn Ile Ser Ile Glu Asn Leu Ser Ser Asp Ile Ile
545                 550                 555                 560
Gly Gln Leu Glu Leu Met Pro Asn Ile Glu Arg Phe Pro Asn Gly Lys
                565                 570                 575
Lys Tyr Glu Leu Asp Lys Tyr Thr Met Phe His Tyr Leu Arg Ala Gln
            580                 585                 590
Glu Phe Glu His Gly Lys Ser Arg Ile Ala Leu Thr Asn Ser Val Asn
            595                 600                 605
Glu Ala Leu Leu Asn Pro Ser Arg Val Tyr Thr Phe Phe Ser Ser Asp
            610                 615                 620
Tyr Val Lys Lys Val Asn Lys Ala Thr Glu Ala Ala Met Phe Leu Gly
625                 630                 635                 640
Trp Val Glu Gln Leu Val Tyr Asp Phe Thr Asp Glu Thr Ser Glu Val
                645                 650                 655
Ser Thr Thr Asp Lys Ile Ala Asp Ile Thr Ile Ile Pro Tyr Ile
            660                 665                 670
Gly Pro Ala Leu Asn Ile Gly Asn Met Leu Tyr Lys Asp Asp Phe Val
            675                 680                 685
Gly Ala Leu Ile Phe Ser Gly Ala Val Ile Leu Leu Glu Phe Ile Pro
            690                 695                 700
Glu Ile Ala Ile Pro Val Leu Gly Thr Phe Ala Leu Val Ser Tyr Ile
705                 710                 715                 720
Ala Asn Lys Val Leu Thr Val Gln Thr Ile Asp Asn Ala Leu Ser Lys
                725                 730                 735
Arg Asn Glu Lys Trp Asp Glu Val Tyr Lys Tyr Ile Val Thr Asn Trp
            740                 745                 750
Leu Ala Lys Val Asn Thr Gln Ile Asp Leu Ile Arg Lys Lys Met Lys
            755                 760                 765
```

```
Glu Ala Leu Glu Asn Gln Ala Glu Ala Thr Lys Ala Ile Ile Asn Tyr
    770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
                820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900

<210> SEQ ID NO 41
<211> LENGTH: 2736
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 41
ctcgggattg agggtcgttt tggcggtttc acgggcgcac gcaaatcagc gcgtaaatta      60
gctaaccaga ctagtggcgg tggggtagt ggcggtggcg gttcgggcgg gggtgggagc     120
cctaggggat ccatggagtt cgttaacaaa cagttcaact ataaagaccc agttaacggt     180
gttgacattg cttacatcaa atcccgaac gctggccaga tgcagccggt aaaggcattc     240
aaaatccaca caaaaatctg ggttatcccg aacgtgata cctttactaa cccggaagaa     300
ggtgacctga cccgccacc ggaagcgaaa caggtgccgg tatcttacta tgactccacc     360
tacctgtcta ccgataacga aaaggacaac tacctgaaag tgttactaa actgttcgag     420 cgtatttact ccaccgacct gggccgtatg ctgctgacta gcatcgttcg cggtatcccg     480
ttctggggcg ttctaccat cgataccgaa ctgaaagtaa tcgacactaa ctgcatcaac     540
gttattcagc cggacggttc ctatcgttcc gaagaactga acctggtgat catcggcccg     600
tctgctgata tcatccagtt cgagtgtaag agctttggtc acgaagttct gaacctcacc     660
cgtaacggct acggttccac tcagtacatc cgtttctctc cggacttcac cttcggtttt     720
gaagaatccc tggaagtaga cacgaaccca ctgctgggcg ctggtaaatt cgcaactgat     780
cctgcggtta ccctggctca cgaactgatt catgcaggcc accgcctgta cggtatcgcc     840
atcaatccga accgtgtctt caaagttaac accaacgcgt attacgagat gtccggtctg     900
gaagttagct cgaagaact gcgtactttt ggcggtcacg acgctaaatt catcgactct     960
ctgcaagaaa acgagttccg tctgtactac tataacaagt tcaaagatat cgcatccacc    1020
ctgaacaaag cgaaatccat cgtgggtacc actgcttctc tccagtacat gaagaacgtt    1080 tttaagaaa ataccctgct cagcgaagac acctccggca aattctctgt agacaagttg    1140
aaattcgata actttacaa aatgctgact gaaatttaca ccgaagacaa cttcgttaag    1200
```

-continued

```
ttctttaaag ttctgaaccg caaaacctat ctgaacttcg acaaggcagt attcaaaatc      1260
aacatcgtgc cgaaagttaa ctacactatc tacgatggtt tcaacctgcg taacaccaac      1320
ctggctgcta attttaacgg ccagaacacg gaaatcaaca acatgaactt cacaaaactg      1380
aaaaacttca ctggtctgtt cgagttttac aagctgctgt gcgtcgacgg catcattacc      1440
tccaaaacta aatctctgat agaaggtaga aacaaagcgc tgaacgacct ctgtatcaag      1500
gttaacaact gggatttatt cttcagcccg agtgaagaca acttcaccaa cgacctgaac      1560
aaaggtgaag aaatcacctc agatactaac atcgaagcag ccgaagaaaa catctcgctg      1620
gacctgatcc agcagtacta cctgaccttt aatttcgaca acgagccgga aaacatttct      1680
atcgaaaacc tgagctctga tatcatcggc cagctggaac tgatgccgaa catcgaacgt      1740
ttcccaaacg gtaaaaagta cgagctggac aaatatacca tgttccacta cctgcgcgcg      1800
caggaatttg aacacggcaa atcccgtatc gcactgacta actccgttaa cgaagctctg      1860
ctcaacccgt cccgtgtata caccttcttc tctagcgact acgtgaaaaa ggtcaacaaa      1920
gcgactgaag ctgcaatgtt cttgggttgg gttgaacagc ttgtttatga ttttaccgac      1980
gagacgtccg aagtatctac taccgacaaa attgcggata tcactatcat catcccgtac      2040
atcggtccgg ctctgaacat tggcaacatg ctgtacaaag acgacttcgt tggcgcactg      2100
atcttctccg gtgcggtgat cctgctggag ttcatcccgg aaatcgccat cccggtactg      2160
ggcacctttg ctctggtttc ttacattgca aacaaggttc tgactgtaca aaccatcgac      2220
aacgcgctga gcaaacgtaa cgaaaaatgg gatgaagttt acaaatatat cgtgaccaac      2280
tggctggcta aggttaatac tcagatcgac ctcatccgca aaaaaatgaa agaagcactg      2340
gaaaaccagg cggaagctac caaggcaatc attaactacc agtacaacca gtacaccgag      2400
gaagaaaaaa acaacatcaa cttcaacatc gacgatctgt cctctaaact gaacgaatcc      2460
atcaacaaag ctatgatcaa catcaacaag ttcctgaacc agtgctctgt aagctatctg      2520
atgaactcca tgatcccgta cggtgttaaa cgtctggagg acttcgatgc gtctctgaaa      2580
gacgccctgc tgaaatacat ttacgacaac cgtggcactc tgatcggtca ggttgatcgt      2640
ctgaaggaca aagtgaacaa taccttatcg accgacatcc cttttcagct cagtaaatat      2700
gtcgataacc aacgcctttt gtccactcta gactag                                2736
```

<210> SEQ ID NO 42
<211> LENGTH: 911
<212> TYPE: PRT
<213> ORGANISM: Artificial Sequence
<220> FEATURE:
<223> OTHER INFORMATION: chemically synthesized fusion protein

<400> SEQUENCE: 42

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Gly Ser Gly Gly
                20                  25                  30

Gly Gly Ser Gly Gly Gly Gly Ser Pro Arg Gly Ser Met Glu Phe Val
            35                  40                  45

Asn Lys Gln Phe Asn Tyr Lys Asp Pro Val Asn Gly Val Asp Ile Ala
        50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95
```

-continued

```
Asn Pro Glu Glu Gly Asp Leu Asn Pro Pro Glu Ala Lys Gln Val
            100                 105                 110
Pro Val Ser Tyr Tyr Asp Ser Thr Tyr Leu Ser Thr Asp Asn Glu Lys
        115                 120                 125
Asp Asn Tyr Leu Lys Gly Val Thr Lys Leu Phe Glu Arg Ile Tyr Ser
    130                 135                 140
Thr Asp Leu Gly Arg Met Leu Leu Thr Ser Ile Val Arg Gly Ile Pro
145                 150                 155                 160
Phe Trp Gly Gly Ser Thr Ile Asp Thr Glu Leu Lys Val Ile Asp Thr
                165                 170                 175
Asn Cys Ile Asn Val Ile Gln Pro Asp Gly Ser Tyr Arg Ser Glu Glu
            180                 185                 190
Leu Asn Leu Val Ile Ile Gly Pro Ser Ala Asp Ile Ile Gln Phe Glu
        195                 200                 205
Cys Lys Ser Phe Gly His Glu Val Leu Asn Leu Thr Arg Asn Gly Tyr
    210                 215                 220
Gly Ser Thr Gln Tyr Ile Arg Phe Ser Pro Asp Phe Thr Phe Gly Phe
225                 230                 235                 240
Glu Glu Ser Leu Glu Val Asp Thr Asn Pro Leu Leu Gly Ala Gly Lys
                245                 250                 255
Phe Ala Thr Asp Pro Ala Val Thr Leu Ala His Glu Leu Ile His Ala
            260                 265                 270
Gly His Arg Leu Tyr Gly Ile Ala Ile Asn Pro Asn Arg Val Phe Lys
        275                 280                 285
Val Asn Thr Asn Ala Tyr Tyr Glu Met Ser Gly Leu Glu Val Ser Phe
    290                 295                 300
Glu Glu Leu Arg Thr Phe Gly Gly His Asp Ala Lys Phe Ile Asp Ser
305                 310                 315                 320
Leu Gln Glu Asn Glu Phe Arg Leu Tyr Tyr Tyr Asn Lys Phe Lys Asp
                325                 330                 335
Ile Ala Ser Thr Leu Asn Lys Ala Lys Ser Ile Val Gly Thr Thr Ala
            340                 345                 350
Ser Leu Gln Tyr Met Lys Asn Val Phe Lys Glu Lys Tyr Leu Leu Ser
        355                 360                 365
Glu Asp Thr Ser Gly Lys Phe Ser Val Asp Lys Leu Lys Phe Asp Lys
    370                 375                 380
Leu Tyr Lys Met Leu Thr Glu Ile Tyr Thr Glu Asp Asn Phe Val Lys
385                 390                 395                 400
Phe Phe Lys Val Leu Asn Arg Lys Thr Tyr Leu Asn Phe Asp Lys Ala
                405                 410                 415
Val Phe Lys Ile Asn Ile Val Pro Lys Val Asn Tyr Thr Ile Tyr Asp
            420                 425                 430
Gly Phe Asn Leu Arg Asn Thr Asn Leu Ala Ala Asn Phe Asn Gly Gln
        435                 440                 445
Asn Thr Glu Ile Asn Asn Met Asn Phe Thr Lys Leu Lys Asn Phe Thr
    450                 455                 460
Gly Leu Phe Glu Phe Tyr Lys Leu Leu Cys Val Asp Gly Ile Ile Thr
465                 470                 475                 480
Ser Lys Thr Lys Ser Leu Ile Glu Gly Arg Asn Lys Ala Leu Asn Asp
                485                 490                 495
Leu Cys Ile Lys Val Asn Asn Trp Asp Leu Phe Phe Ser Pro Ser Glu
            500                 505                 510
```

```
Asp Asn Phe Thr Asn Asp Leu Asn Lys Gly Glu Glu Ile Thr Ser Asp
            515                 520                 525
Thr Asn Ile Glu Ala Ala Glu Glu Asn Ile Ser Leu Asp Leu Ile Gln
        530                 535                 540
Gln Tyr Tyr Leu Thr Phe Asn Phe Asp Asn Glu Pro Glu Asn Ile Ser
545                 550                 555                 560
Ile Glu Asn Leu Ser Ser Asp Ile Ile Gly Gln Leu Glu Leu Met Pro
                565                 570                 575
Asn Ile Glu Arg Phe Pro Asn Gly Lys Lys Tyr Glu Leu Asp Lys Tyr
            580                 585                 590
Thr Met Phe His Tyr Leu Arg Ala Gln Glu Phe Glu His Gly Lys Ser
        595                 600                 605
Arg Ile Ala Leu Thr Asn Ser Val Asn Glu Ala Leu Leu Asn Pro Ser
    610                 615                 620
Arg Val Tyr Thr Phe Phe Ser Ser Asp Tyr Val Lys Val Asn Lys
625                 630                 635                 640
Ala Thr Glu Ala Ala Met Phe Leu Gly Trp Val Gln Leu Val Tyr
                645                 650                 655
Asp Phe Thr Asp Glu Thr Ser Glu Val Ser Thr Thr Asp Lys Ile Ala
            660                 665                 670
Asp Ile Thr Ile Ile Ile Pro Tyr Ile Gly Pro Ala Leu Asn Ile Gly
        675                 680                 685
Asn Met Leu Tyr Lys Asp Asp Phe Val Gly Ala Leu Ile Phe Ser Gly
    690                 695                 700
Ala Val Ile Leu Leu Glu Phe Ile Pro Glu Ile Ala Ile Pro Val Leu
705                 710                 715                 720
Gly Thr Phe Ala Leu Val Ser Tyr Ile Ala Asn Lys Val Leu Thr Val
                725                 730                 735
Gln Thr Ile Asp Asn Ala Leu Ser Lys Arg Asn Glu Lys Trp Asp Glu
            740                 745                 750
Val Tyr Lys Tyr Ile Val Thr Asn Trp Leu Ala Lys Val Asn Thr Gln
        755                 760                 765
Ile Asp Leu Ile Arg Lys Lys Met Lys Glu Ala Leu Glu Asn Gln Ala
    770                 775                 780
Glu Ala Thr Lys Ala Ile Ile Asn Tyr Gln Tyr Asn Gln Tyr Thr Glu
785                 790                 795                 800
Glu Glu Lys Asn Asn Ile Asn Phe Asn Ile Asp Asp Leu Ser Ser Lys
                805                 810                 815
Leu Asn Glu Ser Ile Asn Lys Ala Met Ile Asn Ile Asn Lys Phe Leu
            820                 825                 830
Asn Gln Cys Ser Val Ser Tyr Leu Met Asn Ser Met Ile Pro Tyr Gly
        835                 840                 845
Val Lys Arg Leu Glu Asp Phe Asp Ala Ser Leu Lys Asp Ala Leu Leu
    850                 855                 860
Lys Tyr Ile Tyr Asp Asn Arg Gly Thr Leu Ile Gly Gln Val Asp Arg
865                 870                 875                 880
Leu Lys Asp Lys Val Asn Asn Thr Leu Ser Thr Asp Ile Pro Phe Gln
                885                 890                 895
Leu Ser Lys Tyr Val Asp Asn Gln Arg Leu Leu Ser Thr Leu Asp
            900                 905                 910

<210> SEQ ID NO 43
<211> LENGTH: 2715
<212> TYPE: DNA
```

<213> ORGANISM: Artificial Sequence
<220> FEATURE:
<223> OTHER INFORMATION: chemically synthesized polynucleotide encoding fusion protein

<400> SEQUENCE: 43

```
ggatccgaat tcatgccgat caccatcaac aacttcaact acagcgatcc ggtggataac      60
aaaaacatcc tgtacctgga tacccatctg aatccctgg cgaacgaacc ggaaaaagcg     120
tttcgtatca ccggcaacat ttgggttatt ccggatcgtt ttagccgtaa cagcaacccg     180
aatctgaata accgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacaccccc gatcaacacc tttgatttcg atgtggattt caacagcgtt     420
gatgttaaaa cccgccaggg taacaattgg gtgaaaaccg gcagcattaa cccgagcgtg     480
attattaccg gtccgcgcga aacattatt gatccggaaa ccagcaccctt taaactgacc     540
aacaacacct tgcggcgca ggaaggtttt ggcgcgctga gcattattag cattagcccg     600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcgaaa tctatgcgtt tggcggtccg     840
accattgatc tgattccgaa aagcgcgcgc aaatacttcg aagaaaaagc gctggattac     900
tatcgcagca ttgcgaaacg tctgaacagc attaccaccg cgaatccgag cagcttcaac     960
aaatatatcg gcgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt atacccggt gaccgcgaat attctggatg ataacgtgta cgatatccag    1200
aacggcttta catcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg cgatagatgg tagatttggc ggtttcacgg cgcacgcaa atcagcgcgt    1380
aaattagcta accaggcgct agcgggcggt ggcggtagcg gcggtggcgg tagcggcggt    1440
ggcggtagcg cactagtgct gcagtgtcgt gaactgctgg tgaaaaacac cgatctgccg    1500
tttattggcg atatcagcga tgtgaaaacc gatatcttcc tgcgcaaaga tatcaacgaa    1560
gaaaccgaag tgatctacta cccggataac gtgagcgttg atcaggtgat cctgagcaaa    1620
aacaccagcg aacatggtca gctggatctg ctgtatccga gcattgatag cgaaagcgaa    1680
attctgccgg gcgaaaacca ggtgttttac gataaccgta cccagaacgt ggattacctg    1740
aacagctatt actacctgga aagccagaaa ctgagcgata acgtggaaga tttttacctttt    1800
acccgcagca ttgaagaagc gctggataac agcgcgaaag tttacaccta ttttccgacc    1860
ctggcgaaca aagttaatgc gggtgttcag ggcggtctgt ttctgatgtg ggcgaacgat    1920
gtggtggaag atttcaccac caacatcctg cgtaaagata ccctggataa atcagcgat    1980
gttagcgcga ttattccgta tattggtccg gcgctgaaca ttagcaatag cgtgcgtcgt    2040
ggcaatttta ccgaagcgtt tgcggttacc ggtgtgacca ttctgctgga agcgtttccg    2100
gaatttacca ttccggcgct gggtgcgttt gtgatctata gcaaagtgca ggaacgcaac    2160
```

-continued

```
gaaatcatca aaaccatcga taactgcctg gaacagcgta ttaaacgctg gaaagatagc    2220
tatgaatgga tgatgggcac ctggctgagc cgtattatca cccagttcaa caacatcagc    2280
taccagatgt acgatagcct gaactatcag gcgggtgcga ttaaagcgaa aatcgatctg    2340
gaatacaaaa aatacagcgg cagcgataaa gaaaacatca aaagccaggt tgaaaacctg    2400
aaaaacagcc tggatgtgaa aattagcgaa gcgatgaata acatcaacaa attcatccgc    2460
gaatgcagcg tgacctacct gttcaaaaac atgctgccga aagtgatcga tgaactgaac    2520
gaatttgatc gcaacaccaa agcgaaactg atcaacctga tcgatagcca caacattatt    2580
ctggtgggcg aagtggataa actgaaagcg aaagttaaca cagcttcca gaacaccatc     2640 ccgtttaaca tcttcagcta taccaacaac agcctgctga agatatcat caacgaatac     2700 ttcaatctag actag                                                     2715
```

<210> SEQ ID NO 44
<211> LENGTH: 904
<212> TYPE: PRT
<213> ORGANISM: Artificial Sequence
<220> FEATURE:
<223> OTHER INFORMATION: chemically synthesized fusion protein

<400> SEQUENCE: 44

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
```

```
              260                 265                 270
Glu Ile Tyr Ala Phe Gly Gly Pro Thr Ile Asp Leu Ile Pro Lys Ser
            275                 280                 285
Ala Arg Lys Tyr Phe Glu Glu Lys Ala Leu Asp Tyr Tyr Arg Ser Ile
            290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                325                 330                 335
Val Val Glu Ser Ser Gly Glu Val Thr Val Asn Arg Asn Lys Phe Val
            340                 345                 350
Glu Leu Tyr Asn Glu Leu Thr Gln Ile Phe Thr Glu Phe Asn Tyr Ala
            355                 360                 365
Lys Ile Tyr Asn Val Gln Asn Arg Lys Ile Tyr Leu Ser Asn Val Tyr
        370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                405                 410                 415
Gln Asn Leu Ser Arg Asn Pro Ala Leu Arg Lys Val Asn Pro Glu Asn
            420                 425                 430
Met Leu Tyr Leu Phe Thr Lys Phe Cys Val Asp Ala Ile Asp Gly Arg
            435                 440                 445
Phe Gly Gly Phe Thr Gly Ala Arg Lys Ser Ala Arg Lys Leu Ala Asn
450                 455                 460
Gln Ala Leu Ala Gly Gly Gly Ser Gly Gly Gly Ser Gly Gly
465                 470                 475                 480
Gly Gly Ser Ala Leu Val Leu Gln Cys Arg Glu Leu Leu Val Lys Asn
                485                 490                 495
Thr Asp Leu Pro Phe Ile Gly Asp Ile Ser Asp Val Lys Thr Asp Ile
            500                 505                 510
Phe Leu Arg Lys Asp Ile Asn Glu Glu Thr Glu Val Ile Tyr Tyr Pro
        515                 520                 525
Asp Asn Val Ser Val Asp Gln Val Ile Leu Ser Lys Asn Thr Ser Glu
530                 535                 540
His Gly Gln Leu Asp Leu Leu Tyr Pro Ser Ile Asp Ser Glu Ser Glu
545                 550                 555                 560
Ile Leu Pro Gly Glu Asn Gln Val Phe Tyr Asp Asn Arg Thr Gln Asn
                565                 570                 575
Val Asp Tyr Leu Asn Ser Tyr Tyr Tyr Leu Glu Ser Gln Lys Leu Ser
            580                 585                 590
Asp Asn Val Glu Asp Phe Thr Phe Thr Arg Ser Ile Glu Glu Ala Leu
            595                 600                 605
Asp Asn Ser Ala Lys Val Tyr Thr Tyr Phe Pro Thr Leu Ala Asn Lys
        610                 615                 620
Val Asn Ala Gly Val Gln Gly Gly Leu Phe Leu Met Trp Ala Asn Asp
625                 630                 635                 640
Val Val Glu Asp Phe Thr Thr Asn Ile Leu Arg Lys Asp Thr Leu Asp
                645                 650                 655
Lys Ile Ser Asp Val Ser Ala Ile Ile Pro Tyr Ile Gly Pro Ala Leu
            660                 665                 670
Asn Ile Ser Asn Ser Val Arg Arg Gly Asn Phe Thr Glu Ala Phe Ala
            675                 680                 685
```

```
Val Thr Gly Val Thr Ile Leu Leu Glu Ala Phe Pro Glu Phe Thr Ile
    690                 695                 700
Pro Ala Leu Gly Ala Phe Val Ile Tyr Ser Lys Val Gln Glu Arg Asn
705                 710                 715                 720
Glu Ile Ile Lys Thr Ile Asp Asn Cys Leu Glu Gln Arg Ile Lys Arg
                725                 730                 735
Trp Lys Asp Ser Tyr Glu Trp Met Met Gly Thr Trp Leu Ser Arg Ile
            740                 745                 750
Ile Thr Gln Phe Asn Asn Ile Ser Tyr Gln Met Tyr Asp Ser Leu Asn
        755                 760                 765
Tyr Gln Ala Gly Ala Ile Lys Ala Lys Ile Asp Leu Glu Tyr Lys Lys
    770                 775                 780
Tyr Ser Gly Ser Asp Lys Glu Asn Ile Lys Ser Gln Val Glu Asn Leu
785                 790                 795                 800
Lys Asn Ser Leu Asp Val Lys Ile Ser Glu Ala Met Asn Asn Ile Asn
                805                 810                 815
Lys Phe Ile Arg Glu Cys Ser Val Thr Tyr Leu Phe Lys Asn Met Leu
            820                 825                 830
Pro Lys Val Ile Asp Glu Leu Asn Glu Phe Asp Arg Asn Thr Lys Ala
        835                 840                 845
Lys Leu Ile Asn Leu Ile Asp Ser His Asn Ile Ile Leu Val Gly Glu
    850                 855                 860
Val Asp Lys Leu Lys Ala Lys Val Asn Asn Ser Phe Gln Asn Thr Ile
865                 870                 875                 880
Pro Phe Asn Ile Phe Ser Tyr Thr Asn Asn Ser Leu Leu Lys Asp Ile
                885                 890                 895
Ile Asn Glu Tyr Phe Asn Leu Asp
            900
```

<210> SEQ ID NO 45
<211> LENGTH: 2742
<212> TYPE: DNA
<213> ORGANISM: Artificial Sequence
<220> FEATURE:
<223> OTHER INFORMATION: chemically synthesized polynucleotide encoding fusion protein

<400> SEQUENCE: 45

```
ggatccgaat tcatgccgat caccatcaac aacttcaact acagcgatcc ggtggataac      60
aaaaacatcc tgtacctgga tacccatctg aatccctggc gaacgaaccc ggaaaaagcg     120
tttcgtatca ccggcaacat tgggttattc cggatcgttt tagccgtaac agcaacccg      180
aatctgaata aaccgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacaccccc gatcaacacc tttgatttcg atgtggattt caacagcgtt     420
gatgttaaaa cccgccaggg taacaattgg gtgaaaccgg cagcattaa cccgagcgtg     480
attattaccg gtccgcgcga aaacattatt gatccggaaa ccagcacctt taaactgacc     540
aacaacacct tgcggcgca ggaaggtttt ggcgcgctga gcattattag cattagcccg     600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
```

```
ttttacagcc agtacaacgt gaaactggaa tatgcggaaa tctatgcgtt tggcggtccg    840
accattgatc tgattccgaa agcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt ataccccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccg gaaacatgc tgtacctgtt caccaaattt   1320
tgcgtcgacg gcatcattac ctccaaaact aaatctctga tagaaggtag atttggcggt   1380
ttcacgggcg cacgcaaatc agcgcgtaaa ttagctaacc aggcgctagc gggcggtggc   1440
ggtagcggcg gtggcggtag cggcggtggc ggtagcgcac tagtgctgca gtgtcgtgaa   1500
ctgctggtga aaaacaccga tctgccgttt attggcgata tcagcgatgt gaaaaccgat   1560
atcttcctgc gcaaagatat caacgaagaa accgaagtga tctactaccc ggataacgtg   1620
agcgttgatc aggtgatcct gagcaaaaac accagcgaac atggtcagct ggatctgctg   1680
tatccgagca ttgatagcga aagcgaaatt ctgccgggcg aaaaccaggt gttttacgat   1740
aaccgtaccc agaacgtgga ttacctgaac agctattact acctggaaag ccagaaactg   1800
agcgataacg tggaagattt tacctttacc cgcagcattg aagaagcgct ggataacagc   1860
gcgaaagttt acacctattt tccgacccctg gcgaacaaag ttaatgcggg tgttcagggc   1920
ggtctgtttc tgatgtgggc gaacgatgtg gtggaagatt tcaccaccaa catcctgcgt   1980
aaagatacc tggataaaat cagcgatgtt agcgcgatta ttccgtatat tggtccggcg   2040
ctgaacatta gcaatagcgt gcgtcgtggc aatttaccg aagcgtttgc ggttaccggt   2100
gtgaccattc tgctggaagc gtttccggaa tttaccattc cggcgctggg tgcgtttgtg   2160
atctatagca aagtgcagga acgcaacgaa atcatcaaaa ccatcgataa ctgcctggaa   2220
cagcgtatta aacgctggaa agatagctat gaatggatga tgggcacctg gctgagccgt   2280
attatcaccc cagttcaaca catcagctac cagatgtacg atagcctgaa ctatcaggcg   2340
ggtgcgatta aagcgaaaat cgatctggaa tacaaaaaat acagcggcag cgataaagaa   2400
aacatcaaaa gccaggttga aaacctgaaa aacagcctgg atgtgaaaat tagcgaagcg   2460
atgaataaca tcaacaaatt catccgcgaa tgcagcgtga cctacctgtt caaaaacatg   2520
ctgccgaaag tgatcgatga actgaacgaa tttgatcgca acaccaaagc gaaactgatc   2580
aacctgatcg atagccacaa cattattctg gtgggcgaag tggataaact gaaagcgaaa   2640
gttaacaaca gcttccagaa caccatcccg tttaacatct tcagctatac caacaacagc   2700
ctgctgaaag atatcatcaa cgaatacttc aatctagact ag                     2742
```

<210> SEQ ID NO 46
<211> LENGTH: 913
<212> TYPE: PRT
<213> ORGANISM: Artificial Sequence
<220> FEATURE:
<223> OTHER INFORMATION: chemically synthesized fusion protein

<400> SEQUENCE: 46

```
Gly Ser Glu Phe Met Pro Ile Thr Ile Asn Asn Phe Asn Tyr Ser Asp
1               5                   10                  15
```

-continued

```
Pro Val Asp Asn Lys Asn Ile Leu Tyr Leu Asp Thr His Leu Asn Thr
             20                  25                  30
Leu Ala Asn Glu Pro Glu Lys Ala Phe Arg Ile Thr Gly Asn Ile Trp
         35                  40                  45
Val Ile Pro Asp Arg Phe Ser Arg Asn Ser Asn Pro Asn Leu Asn Lys
     50                  55                  60
Pro Pro Arg Val Thr Ser Pro Lys Ser Gly Tyr Tyr Asp Pro Asn Tyr
 65                  70                  75                  80
Leu Ser Thr Asp Ser Asp Lys Asp Thr Phe Leu Lys Glu Ile Ile Lys
                 85                  90                  95
Leu Phe Lys Arg Ile Asn Ser Arg Glu Ile Gly Glu Leu Ile Tyr
             100                 105                 110
Arg Leu Ser Thr Asp Ile Pro Phe Pro Gly Asn Asn Thr Pro Ile
             115                 120                 125
Asn Thr Phe Asp Phe Asp Val Asp Phe Asn Ser Val Asp Val Lys Thr
         130                 135                 140
Arg Gln Gly Asn Asn Trp Val Lys Thr Gly Ser Ile Asn Pro Ser Val
145                 150                 155                 160
Ile Ile Thr Gly Pro Arg Glu Asn Ile Ile Asp Pro Glu Thr Ser Thr
                 165                 170                 175
Phe Lys Leu Thr Asn Asn Thr Phe Ala Ala Gln Glu Gly Phe Gly Ala
             180                 185                 190
Leu Ser Ile Ile Ser Ile Ser Pro Arg Phe Met Leu Thr Tyr Ser Asn
         195                 200                 205
Ala Thr Asn Asp Val Gly Glu Gly Arg Phe Ser Lys Ser Glu Phe Cys
     210                 215                 220
Met Asp Pro Ile Leu Ile Leu Met His Glu Leu Asn His Ala Met His
225                 230                 235                 240
Asn Leu Tyr Gly Ile Ala Ile Pro Asn Asp Gln Thr Ile Ser Ser Val
                 245                 250                 255
Thr Ser Asn Ile Phe Tyr Ser Gln Tyr Asn Val Lys Leu Glu Tyr Ala
             260                 265                 270
Glu Ile Tyr Ala Phe Gly Gly Pro Thr Ile Asp Leu Ile Pro Lys Ser
         275                 280                 285
Ala Arg Lys Tyr Phe Glu Glu Lys Ala Leu Asp Tyr Tyr Arg Ser Ile
     290                 295                 300
Ala Lys Arg Leu Asn Ser Ile Thr Thr Ala Asn Pro Ser Ser Phe Asn
305                 310                 315                 320
Lys Tyr Ile Gly Glu Tyr Lys Gln Lys Leu Ile Arg Lys Tyr Arg Phe
                 325                 330                 335
Val Val Glu Ser Ser Gly Glu Val Thr Val Asn Arg Asn Lys Phe Val
             340                 345                 350
Glu Leu Tyr Asn Glu Leu Thr Gln Ile Phe Thr Glu Phe Asn Tyr Ala
         355                 360                 365
Lys Ile Tyr Asn Val Gln Asn Arg Lys Ile Tyr Leu Ser Asn Val Tyr
     370                 375                 380
Thr Pro Val Thr Ala Asn Ile Leu Asp Asp Asn Val Tyr Asp Ile Gln
385                 390                 395                 400
Asn Gly Phe Asn Ile Pro Lys Ser Asn Leu Asn Val Leu Phe Met Gly
                 405                 410                 415
Gln Asn Leu Ser Arg Asn Pro Ala Leu Arg Lys Val Asn Pro Glu Asn
             420                 425                 430
```

-continued

Met Leu Tyr Leu Phe Thr Lys Phe Cys Val Asp Gly Ile Ile Thr Ser
        435                 440                 445

Lys Thr Lys Ser Leu Ile Glu Gly Arg Phe Gly Phe Thr Gly Ala
    450                 455                 460

Arg Lys Ser Ala Arg Lys Leu Ala Asn Gln Ala Leu Ala Gly Gly Gly
465                 470                 475                 480

Gly Ser Gly Gly Gly Ser Gly Gly Gly Ser Ala Leu Val Leu
            485                 490                 495

Gln Cys Arg Glu Leu Leu Val Lys Asn Thr Asp Leu Pro Phe Ile Gly
            500                 505                 510

Asp Ile Ser Asp Val Lys Thr Asp Ile Phe Leu Arg Lys Asp Ile Asn
        515                 520                 525

Glu Glu Thr Glu Val Ile Tyr Tyr Pro Asp Asn Val Ser Val Asp Gln
    530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
            565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
        595                 600                 605

Phe Thr Arg Ser Ile Glu Glu Ala Leu Asp Asn Ser Ala Lys Val Tyr
        610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
            645                 650                 655

Asn Ile Leu Arg Lys Asp Thr Leu Asp Lys Ile Ser Asp Val Ser Ala
            660                 665                 670

Ile Ile Pro Tyr Ile Gly Pro Ala Leu Asn Ile Ser Asn Ser Val Arg
        675                 680                 685

Arg Gly Asn Phe Thr Glu Ala Phe Ala Val Thr Gly Val Thr Ile Leu
    690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Ile Lys Thr Ile Asp
            725                 730                 735

Asn Cys Leu Glu Gln Arg Ile Lys Arg Trp Lys Asp Ser Tyr Glu Trp
            740                 745                 750

Met Met Gly Thr Trp Leu Ser Arg Ile Ile Thr Gln Phe Asn Asn Ile
        755                 760                 765

Ser Tyr Gln Met Tyr Asp Ser Leu Asn Tyr Gln Ala Gly Ala Ile Lys
    770                 775                 780

Ala Lys Ile Asp Leu Glu Tyr Lys Lys Tyr Ser Gly Ser Asp Lys Glu
785                 790                 795                 800

Asn Ile Lys Ser Gln Val Glu Asn Leu Lys Asn Ser Leu Asp Val Lys
            805                 810                 815

Ile Ser Glu Ala Met Asn Asn Ile Asn Lys Phe Ile Arg Glu Cys Ser
            820                 825                 830

Val Thr Tyr Leu Phe Lys Asn Met Leu Pro Lys Val Ile Asp Glu Leu
        835                 840                 845

Asn Glu Phe Asp Arg Asn Thr Lys Ala Lys Leu Ile Asn Leu Ile Asp

|   |   |   |   |   |   |   |   |   |   |   |   |
|---|---|---|---|---|---|---|---|---|---|---|---|
|   | 850 |   |   |   | 855 |   |   |   | 860 |   |   |
| Ser | His | Asn | Ile | Ile | Leu | Val | Gly | Glu | Val | Asp | Lys | Leu | Lys | Ala | Lys |
| 865 |   |   |   |   | 870 |   |   |   | 875 |   |   |   |   | 880 |   |

Ser His Asn Ile Ile Leu Val Gly Glu Val Asp Lys Leu Lys Ala Lys
865                 870                 875                 880

Val Asn Asn Ser Phe Gln Asn Thr Ile Pro Phe Asn Ile Phe Ser Tyr
                885                 890                 895

Thr Asn Asn Ser Leu Leu Lys Asp Ile Ile Asn Glu Tyr Phe Asn Leu
            900                 905                 910

Asp

<210> SEQ ID NO 47
<211> LENGTH: 2673
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 47

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg ttcctatcg ttccgaagaa ctgaacctgg tgatcatcgg cccgtctgct     480
gatatcatcc agttcgagtg taagagcttt ggtcacgaag ttctgaacct caccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc caccctgaac     900
aaagcgaaat ccatcgtggg taccactgct ctctctccagt acatgaagaa cgttttttaa     960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc     1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagataccggt ggtttcatgg cgctagcggg cggtggcggt    1380
agcggcggtg gcggtagcgg cggtggcggt agcgcactag tgctgcagtg tatcaaggtt    1440
aacaactggg atttattctt cagcccgagt gaagacaact tcaccaacga cctgaacaaa    1500
ggtgaagaaa tcacctcaga tactaacatc gaagcagccg aagaaaacat ctcgctggac    1560
ctgatccagc agtactacct gaccctttaat ttcgacaacg agccggaaaa catttctatc    1620
gaaaacctga gctctgatat catcggccag ctggaactga tgccgaacat cgaacgtttc    1680
```

-continued

```
ccaaacggta aaaagtacga gctggacaaa tataccatgt ccactacct gcgcgcgcag   1740
gaatttgaac acggcaaatc ccgtatcgca ctgactaact ccgttaacga agctctgctc   1800
aacccgtccc gtgtatacac cttcttctct agcgactacg tgaaaaaggt caacaaagcg   1860
actgaagctg caatgttctt gggttggggtt gaacagcttg tttatgattt taccgacgag   1920
acgtccgaag tatctactac cgacaaaatt gcggatatca ctatcatcat cccgtacatc   1980
ggtccggctc tgaacattgg caacatgctg tacaaagacg acttcgttgg cgcactgatc   2040
ttctccggtg cggtgatcct gctggagttc atcccggaaa tcgccatccc ggtactgggc   2100
accttttgctc tggttttctta cattgcaaac aaggttctga ctgtacaaac catcgacaac   2160
gcgctgagca acgtaacga aaatgggat gaagtttaca atatatcgt gaccaactgg   2220
ctggctaagg ttaatactca gatcgacctc atccgcaaaa aaatgaaaga agcactggaa   2280
aaccaggcgg aagctaccaa ggcaatcatt aactaccagt acaaccagta caccgaggaa   2340
gaaaaaaaca acatcaactt caacatcgac gatctgtcct ctaaactgaa cgaatccatc   2400
aacaaagcta tgatcaacat caacaagttc ctgaaccagt gctctgtaag ctatctgatg   2460
aactccatga tcccgtacgg tgttaaacgt ctggaggact tcgatgcgtc tctgaaagac   2520
gccctgctga aatacattta cgacaaccgt ggcactctga tcggtcaggt tgatcgtctg   2580
aaggacaaag tgaacaatac cttatcgacc gacatcccct ttcagctcag taaatatgtc   2640
gataaccaac gccttttgtc cactctagac tag                              2673
```

<210> SEQ ID NO 48
<211> LENGTH: 890
<212> TYPE: PRT
<213> ORGANISM: Artificial Sequence
<220> FEATURE:
<223> OTHER INFORMATION: chemically synthesized fusion protein

<400> SEQUENCE: 48

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
```

-continued

```
                180             185             190
Asp Phe Thr Phe Gly Phe Glu Glu Ser Leu Glu Val Asp Thr Asn Pro
            195                 200                 205
Leu Leu Gly Ala Gly Lys Phe Ala Thr Asp Pro Ala Val Thr Leu Ala
        210                 215                 220
His Glu Leu Ile His Ala Gly His Arg Leu Tyr Gly Ile Ala Ile Asn
225                 230                 235                 240
Pro Asn Arg Val Phe Lys Val Asn Thr Asn Ala Tyr Tyr Glu Met Ser
                245                 250                 255
Gly Leu Glu Val Ser Phe Glu Glu Leu Arg Thr Phe Gly Gly His Asp
            260                 265                 270
Ala Lys Phe Ile Asp Ser Leu Gln Glu Asn Glu Phe Arg Leu Tyr Tyr
        275                 280                 285
Tyr Asn Lys Phe Lys Asp Ile Ala Ser Thr Leu Asn Lys Ala Lys Ser
290                 295                 300
Ile Val Gly Thr Thr Ala Ser Leu Gln Tyr Met Lys Asn Val Phe Lys
305                 310                 315                 320
Glu Lys Tyr Leu Leu Ser Glu Asp Thr Ser Gly Lys Phe Ser Val Asp
                325                 330                 335
Lys Leu Lys Phe Asp Lys Leu Tyr Lys Met Leu Thr Glu Ile Tyr Thr
            340                 345                 350
Glu Asp Asn Phe Val Lys Phe Phe Lys Val Leu Asn Arg Lys Thr Tyr
        355                 360                 365
Leu Asn Phe Asp Lys Ala Val Phe Lys Ile Asn Ile Val Pro Lys Val
    370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Leu Ile Glu Gly Arg
        435                 440                 445
Tyr Gly Gly Phe Met Ala Leu Ala Gly Gly Gly Ser Gly Gly Gly
    450                 455                 460
Gly Ser Gly Gly Gly Ser Ala Leu Val Leu Gln Cys Ile Lys Val
465                 470                 475                 480
Asn Asn Trp Asp Leu Phe Phe Ser Pro Ser Glu Asp Asn Phe Thr Asn
                485                 490                 495
Asp Leu Asn Lys Gly Glu Glu Ile Thr Ser Asp Thr Asn Ile Glu Ala
            500                 505                 510
Ala Glu Glu Asn Ile Ser Leu Asp Leu Ile Gln Gln Tyr Tyr Leu Thr
        515                 520                 525
Phe Asn Phe Asp Asn Glu Pro Glu Asn Ile Ser Ile Glu Asn Leu Ser
    530                 535                 540
Ser Asp Ile Ile Gly Gln Leu Glu Leu Met Pro Asn Ile Glu Arg Phe
545                 550                 555                 560
Pro Asn Gly Lys Lys Tyr Glu Leu Asp Lys Tyr Thr Met Phe His Tyr
                565                 570                 575
Leu Arg Ala Gln Glu Phe Glu His Gly Lys Ser Arg Ile Ala Leu Thr
            580                 585                 590
Asn Ser Val Asn Glu Ala Leu Leu Asn Pro Ser Arg Val Tyr Thr Phe
        595                 600                 605
```

```
Phe Ser Ser Asp Tyr Val Lys Lys Val Asn Lys Ala Thr Glu Ala Ala
        610                 615                 620

Met Phe Leu Gly Trp Val Glu Gln Leu Val Tyr Asp Phe Thr Asp Glu
625                 630                 635                 640

Thr Ser Glu Val Ser Thr Thr Asp Lys Ile Ala Asp Ile Thr Ile Ile
                645                 650                 655

Ile Pro Tyr Ile Gly Pro Ala Leu Asn Ile Gly Asn Met Leu Tyr Lys
            660                 665                 670

Asp Asp Phe Val Gly Ala Leu Ile Phe Ser Gly Ala Val Ile Leu Leu
        675                 680                 685

Glu Phe Ile Pro Glu Ile Ala Ile Pro Val Leu Gly Thr Phe Ala Leu
690                 695                 700

Val Ser Tyr Ile Ala Asn Lys Val Leu Thr Val Gln Thr Ile Asp Asn
705                 710                 715                 720

Ala Leu Ser Lys Arg Asn Glu Lys Trp Asp Glu Val Tyr Lys Tyr Ile
                725                 730                 735

Val Thr Asn Trp Leu Ala Lys Val Asn Thr Gln Ile Asp Leu Ile Arg
            740                 745                 750

Lys Lys Met Lys Glu Ala Leu Glu Asn Gln Ala Glu Ala Thr Lys Ala
        755                 760                 765

Ile Ile Asn Tyr Gln Tyr Asn Gln Tyr Thr Glu Glu Lys Asn Asn
770                 775                 780

Ile Asn Phe Asn Ile Asp Asp Leu Ser Ser Lys Leu Asn Glu Ser Ile
785                 790                 795                 800

Asn Lys Ala Met Ile Asn Ile Asn Lys Phe Leu Asn Gln Cys Ser Val
                805                 810                 815

Ser Tyr Leu Met Asn Ser Met Ile Pro Tyr Gly Val Lys Arg Leu Glu
            820                 825                 830

Asp Phe Asp Ala Ser Leu Lys Asp Ala Leu Leu Lys Tyr Ile Tyr Asp
        835                 840                 845

Asn Arg Gly Thr Leu Ile Gly Gln Val Asp Arg Leu Lys Asp Lys Val
850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
                885                 890

<210> SEQ ID NO 49
<211> LENGTH: 2751
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 49
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gatacccttta ctaacccgga agaaggtgac   180
ctgaacccgc accggaaagc gaaacaggtg ccggtatctt actatgactc cacctacctg   240
tctaccgata cgaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
```

-continued

```
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatcgaagg tcgttacggt ggtttcatga cctctgaaaa atctcagacc   1380
ccgctggtta ccctgttcaa aaacgctatc atcaaaaacg cttacaaaaa aggtgaagcg   1440
ctagcgggtg gtggtggttc tggtggtggt ggttctggtg gtggtggttc tgcactagtg   1500
ctgcagtgta tcaaggttaa caactgggat ttattcttca gcccgagtga agacaacttc   1560
accaacgacc tgaacaaagg tgaagaaatc acctcagata ctaacatcga agcagccgaa   1620
gaaaacatct cgctggacct gatccagcag tactacctga cctttaattt cgacaacgag   1680
ccggaaaaca tttctatcga aaacctgagc tctgatatca tcggccagct ggaactgatg   1740
ccgaacatcg aacgtttccc aaacggtaaa agtacgagc tggacaaata ccatgttc    1800
cactacctgc gcgcgcagga atttgaacac ggcaaatccc gtatcgcact gactaactcc   1860
gttaacgaag ctctgctcaa cccgtcccgt gtatacacct tcttctctag cgactacgtg   1920
aaaaaggtca caaagcgac tgaagctgca atgttcttgg gttgggttga acagcttgtt   1980
tatgatttta ccgacgagac gtccgaagta tctactaccg acaaaattgc ggatatcact   2040
atcatcatcc cgtacatcgg tccggctctg aacattggca acatgctgta caaagacgac   2100
ttcgttggcg cactgatctt ctccggtgcg gtgatcctgc tggagttcat cccggaaatc   2160
gccatcccgg tactgggcac ctttgctctg gtttcttaca ttgcaaacaa ggttctgact   2220
gtacaaacca tcgacaacgc gctgagcaaa cgtaacgaaa aatgggatga agtttacaaa   2280
tatatcgtga ccaactggct ggctaaggtt aatactcaga tcgacctcat ccgcaaaaaa   2340
atgaaagaag cactggaaaa ccaggcggaa gctaccaagg caatcattaa ctaccagtac   2400
aaccagtaca ccgaggaaga aaaaaacaac atcaacttca catcgacga tctgtcctct   2460
aaactgaacg aatccatcaa caagctatg atcaacatca acaagttcct gaaccagtgc   2520
tctgtaagct atctgatgaa ctccatgatc ccgtacggtg ttaaacgtct ggaggacttc   2580
gatgcgtctc tgaaagacgc cctgctgaaa tacatttacg acaaccgtgg cactctgatc   2640
ggtcaggttg atcgtctgaa ggacaaagtg aacaatacct atcgaccga catcccttt    2700
cagctcagta aatatgtcga taaccaacgc cttttgtcca ctctagacta g            2751
```

```
<210> SEQ ID NO 50
<211> LENGTH: 916
<212> TYPE: PRT
<213> ORGANISM: Artificial Sequence
<220> FEATURE:
<223> OTHER INFORMATION: chemically synthesized fusion protein

<400> SEQUENCE: 50

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365
```

```
Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Met Thr Ser Glu Lys Ser Gln Thr Pro Leu Val Thr
    450                 455                 460

Leu Phe Lys Asn Ala Ile Ile Lys Asn Ala Tyr Lys Lys Gly Glu Ala
465                 470                 475                 480

Leu Ala Gly Gly Gly Ser Gly Gly Gly Ser Gly Gly Gly
                485                 490                 495

Ser Ala Leu Val Leu Gln Cys Ile Lys Val Asn Asn Trp Asp Leu Phe
            500                 505                 510

Phe Ser Pro Ser Glu Asp Asn Phe Thr Asn Asp Leu Asn Lys Gly Glu
        515                 520                 525

Glu Ile Thr Ser Asp Thr Asn Ile Glu Ala Ala Glu Glu Asn Ile Ser
    530                 535                 540

Leu Asp Leu Ile Gln Gln Tyr Tyr Leu Thr Phe Asn Phe Asp Asn Glu
545                 550                 555                 560

Pro Glu Asn Ile Ser Ile Glu Asn Leu Ser Ser Asp Ile Ile Gly Gln
                565                 570                 575

Leu Glu Leu Met Pro Asn Ile Glu Arg Phe Pro Asn Gly Lys Lys Tyr
            580                 585                 590

Glu Leu Asp Lys Tyr Thr Met Phe His Tyr Leu Arg Ala Gln Glu Phe
        595                 600                 605

Glu His Gly Lys Ser Arg Ile Ala Leu Thr Asn Ser Val Asn Glu Ala
    610                 615                 620

Leu Leu Asn Pro Ser Arg Val Tyr Thr Phe Phe Ser Ser Asp Tyr Val
625                 630                 635                 640

Lys Lys Val Asn Lys Ala Thr Glu Ala Ala Met Phe Leu Gly Trp Val
                645                 650                 655

Glu Gln Leu Val Tyr Asp Phe Thr Asp Glu Thr Ser Glu Val Ser Thr
            660                 665                 670

Thr Asp Lys Ile Ala Asp Ile Thr Ile Ile Pro Tyr Ile Gly Pro
        675                 680                 685

Ala Leu Asn Ile Gly Asn Met Leu Tyr Lys Asp Asp Phe Val Gly Ala
    690                 695                 700

Leu Ile Phe Ser Gly Ala Val Ile Leu Leu Glu Phe Ile Pro Glu Ile
705                 710                 715                 720

Ala Ile Pro Val Leu Gly Thr Phe Ala Leu Val Ser Tyr Ile Ala Asn
                725                 730                 735

Lys Val Leu Thr Val Gln Thr Ile Asp Asn Ala Leu Ser Lys Arg Asn
            740                 745                 750

Glu Lys Trp Asp Glu Val Tyr Lys Tyr Ile Val Thr Asn Trp Leu Ala
        755                 760                 765

Lys Val Asn Thr Gln Ile Asp Leu Ile Arg Lys Met Lys Glu Ala
    770                 775                 780

Leu Glu Asn Gln Ala Glu Ala Thr Lys Ala Ile Ile Asn Tyr Gln Tyr
```

|  |  | 785 |  |  | 790 |  |  | 795 |  |  | 800 |  |
|---|---|---|---|---|---|---|---|---|---|---|---|---|

Asn Gln Tyr Thr Glu Glu Glu Lys Asn Asn Ile Asn Phe Asn Ile Asp
                        805                 810                 815

Asp Leu Ser Ser Lys Leu Asn Glu Ser Ile Asn Lys Ala Met Ile Asn
            820                 825                 830

Ile Asn Lys Phe Leu Asn Gln Cys Ser Val Ser Tyr Leu Met Asn Ser
        835                 840                 845

Met Ile Pro Tyr Gly Val Lys Arg Leu Glu Asp Phe Asp Ala Ser Leu
    850                 855                 860

Lys Asp Ala Leu Leu Lys Tyr Ile Tyr Asp Asn Arg Gly Thr Leu Ile
865                 870                 875                 880

Gly Gln Val Asp Arg Leu Lys Asp Lys Val Asn Asn Thr Leu Ser Thr
                885                 890                 895

Asp Ile Pro Phe Gln Leu Ser Lys Tyr Val Asp Asn Gln Arg Leu Leu
            900                 905                 910

Ser Thr Leu Asp
        915

<210> SEQ ID NO 51
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 51

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg ttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc cacctgaac      900
aaagcgaaat ccatcgtggg taccactgct tctctccagt acatgaagaa cgttttaaa      960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc     1140
gtgccgaaag ttaactacac tatctacgat ggtttcaacc tgcgtaacac caacctggct    1200
gctaattta acggccagaa cacggaaatc aacaacatga acttcacaaa actgaaaaac    1260
```

-continued

```
ttcactggtc tgttcgagtt ttacaagctg ctgtgcgtcg acggcatcat tacctccaaa    1320
actaaatctc tgatagaagg tagatttggc ggtttcacgg gcgcacgcaa atcagcgcgt    1380
aaacgtaaga accaggcgct agcgggcggt ggcggtagcg gcggtggcgg tagcggcggt    1440
ggcggtagcg cactagtgct gcagtgtatc aaggttaaca actgggattt attcttcagc    1500
ccgagtgaag acaacttcac caacgacctg aacaaaggtg aagaaatcac ctcagatact    1560
aacatcgaag cagccgaaga aaacatctcg ctggacctga tccagcagta ctacctgacc    1620
tttaatttcg acaacgagcc ggaaaacatt tctatcgaaa acctgagctc tgatatcatc    1680
ggccagctgg aactgatgcc gaacatcgaa cgtttcccaa acggtaaaaa gtacgagctg    1740
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgacttt cgttggcgca ctgatcttct ccggtgcggt gatcctgctg    2100
gagttcatcc cggaaatcgc catcccggta ctgggcacct ttgctctggt ttcttacatt    2160
gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaagaagca ctggaaaacc aggcggaagc taccaaggca    2340
atcattaact accagtacaa ccagtacacc gaggaagaaa aaaacaacat caacttcaac    2400
atcgacgatc tgtcctctaa actgaacgaa tccatcaaca agctatgat caacatcaac    2460 aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccta    2640 tcgaccgaca tcccttttca gctcagtaaa tatgtcgata ccaacgcct ttgtccact    2700 ctagactag                                                           2709
```

<210> SEQ ID NO 52
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 52

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
```

-continued

```
              100                 105                 110
Ile Val Arg Gly Ile Pro Phe Trp Gly Gly Ser Thr Ile Asp Thr Glu
            115                 120                 125
Leu Lys Val Ile Asp Thr Asn Cys Ile Asn Val Ile Gln Pro Asp Gly
130                 135                 140
Ser Tyr Arg Ser Glu Glu Leu Asn Leu Val Ile Ile Gly Pro Ser Ala
145                 150                 155                 160
Asp Ile Ile Gln Phe Glu Cys Lys Ser Phe Gly His Glu Val Leu Asn
                165                 170                 175
Leu Thr Arg Asn Gly Tyr Gly Ser Thr Gln Tyr Ile Arg Phe Ser Pro
            180                 185                 190
Asp Phe Thr Phe Gly Phe Glu Glu Ser Leu Glu Val Asp Thr Asn Pro
        195                 200                 205
Leu Leu Gly Ala Gly Lys Phe Ala Thr Asp Pro Ala Val Thr Leu Ala
    210                 215                 220
His Glu Leu Ile His Ala Gly His Arg Leu Tyr Gly Ile Ala Ile Asn
225                 230                 235                 240
Pro Asn Arg Val Phe Lys Val Asn Thr Asn Ala Tyr Tyr Glu Met Ser
                245                 250                 255
Gly Leu Glu Val Ser Phe Glu Glu Leu Arg Thr Phe Gly Gly His Asp
            260                 265                 270
Ala Lys Phe Ile Asp Ser Leu Gln Glu Asn Glu Phe Arg Leu Tyr Tyr
        275                 280                 285
Tyr Asn Lys Phe Lys Asp Ile Ala Ser Thr Leu Asn Lys Ala Lys Ser
    290                 295                 300
Ile Val Gly Thr Thr Ala Ser Leu Gln Tyr Met Lys Asn Val Phe Lys
305                 310                 315                 320
Glu Lys Tyr Leu Leu Ser Glu Asp Thr Ser Gly Lys Phe Ser Val Asp
                325                 330                 335
Lys Leu Lys Phe Asp Lys Leu Tyr Lys Met Leu Thr Glu Ile Tyr Thr
            340                 345                 350
Glu Asp Asn Phe Val Lys Phe Phe Lys Val Leu Asn Arg Lys Thr Tyr
        355                 360                 365
Leu Asn Phe Asp Lys Ala Val Phe Lys Ile Asn Ile Val Pro Lys Val
    370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Leu Ile Glu Gly Arg
        435                 440                 445
Phe Gly Gly Phe Thr Gly Ala Arg Lys Ser Ala Arg Lys Arg Lys Asn
    450                 455                 460
Gln Ala Leu Ala Gly Gly Gly Ser Gly Gly Gly Ser Gly Gly
465                 470                 475                 480
Gly Gly Ser Ala Leu Val Leu Gln Cys Ile Lys Val Asn Asn Trp Asp
                485                 490                 495
Leu Phe Phe Ser Pro Ser Glu Asp Asn Phe Thr Asn Asp Leu Asn Lys
            500                 505                 510
Gly Glu Glu Ile Thr Ser Asp Thr Asn Ile Glu Ala Ala Glu Glu Asn
        515                 520                 525
```

```
Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
                580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
                660                 665                 670

Gly Pro Ala Leu Asn Ile Gly Asn Met Leu Tyr Lys Asp Asp Phe Val
            675                 680                 685

Gly Ala Leu Ile Phe Ser Gly Ala Val Ile Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
                740                 745                 750

Leu Ala Lys Val Asn Thr Gln Ile Asp Leu Ile Arg Lys Lys Met Lys
            755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
    835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
                900

<210> SEQ ID NO 53
<211> LENGTH: 2691
<212> TYPE: DNA
<213> ORGANISM: Artificial Sequence
<220> FEATURE:
```

<223> OTHER INFORMATION: chemically synthesized polynucleotide encoding fusion protein

<400> SEQUENCE: 53

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata cgaaaaggaa caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc caccctgaac     900
aaagcgaaat ccatcgtggg taccactgct tctctccagt acatgaagaa cgttttaaa      960
gaaaaatacc tgctcagcga agacacctcc ggcaaattct ctgtagacaa gttgaaattc    1020
gataaacttt acaaaatgct gactgaaatt tacaccgaag acaacttcgt taagttctttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atcagcggcg    1380
ctagcgggcg gtggcggtag cggcggtggc ggtagcggcg gtggcggtag cgcactagtg    1440
ctgcagtgta tcaaggttaa caactgggat ttattcttca gcccgagtga agacaacttc    1500
accaacgacc tgaacaaagg tgaagaaatc acctcagata ctaacatcga agcagccgaa    1560
gaaaacatct cgctggacct gatccagcag tactacctga ccctttaattt cgacaacgag    1620
ccggaaaaca tttctatcga aaacctgagc tctgatatca tcggccagct ggaactgatg    1680
ccgaacatcg aacgtttccc aaacggtaaa aagtacgagc tggacaaata ccatgttc      1740
cactacctgc gcgcgcagga atttgaacac ggcaaatccc gtatcgcact gactaactcc    1800
gttaacgaag ctctgctcaa cccgtcccgt gtatacacct tcttctctag cgactacgtg    1860
aaaaaggtca caaagcgac tgaagctgca atgttcttgg gttgggttga acagcttgtt    1920
tatgatttta ccgacgagac gtccgaagta tctactaccg acaaaattgc ggatatcact    1980
atcatcatcc cgtacatcgg tccggctctg aacattggca acatgctgta caaagacgac    2040
ttcgttggcg cactgatctt ctccggtgcg gtgatcctgc tggagttcat cccggaaatc    2100
gccatcccgg tactgggcac cttgctctg gttcttaca ttgcaaacaa ggttctgact    2160
gtacaaacca tcgacaacgc gctgagcaaa cgtaacgaaa atgggatga agtttacaaa    2220
```

```
tatatcgtga ccaactggct ggctaaggtt aatactcaga tcgacctcat ccgcaaaaaa    2280
atgaaagaag cactggaaaa ccaggcggaa gctaccaagg caatcattaa ctaccagtac    2340
aaccagtaca ccgaggaaga aaaaaacaac atcaacttca acatcgacga tctgtcctct    2400
aaactgaacg aatccatcaa caaagctatg atcaacatca acaagttcct gaaccagtgc    2460
tctgtaagct atctgatgaa ctccatgatc ccgtacggtg ttaaacgtct ggaggacttc    2520
gatgcgtctc tgaaagacgc cctgctgaaa tacatttacg acaaccgtgg cactctgatc    2580
ggtcaggttg atcgtctgaa ggacaaagtg aacaatacct tatcgaccga catccctttt    2640
cagctcagta aatatgtcga taaccaacgc cttttgtcca ctctagacta g             2691
```

<210> SEQ ID NO 54
<211> LENGTH: 896
<212> TYPE: PRT
<213> ORGANISM: Artificial Sequence
<220> FEATURE:
<223> OTHER INFORMATION: chemically synthesized fusion protein

<400> SEQUENCE: 54

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285
```

-continued

```
Tyr Asn Lys Phe Lys Asp Ile Ala Ser Thr Leu Asn Lys Ala Lys Ser
    290                 295                 300
Ile Val Gly Thr Thr Ala Ser Leu Gln Tyr Met Lys Asn Val Phe Lys
305                 310                 315                 320
Glu Lys Tyr Leu Leu Ser Glu Asp Thr Ser Gly Lys Phe Ser Val Asp
                325                 330                 335
Lys Leu Lys Phe Asp Lys Leu Tyr Lys Met Leu Thr Glu Ile Tyr Thr
            340                 345                 350
Glu Asp Asn Phe Val Lys Phe Phe Lys Val Leu Asn Arg Lys Thr Tyr
        355                 360                 365
Leu Asn Phe Asp Lys Ala Val Phe Lys Ile Asn Ile Val Pro Lys Val
    370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Leu Ile Glu Gly Arg
        435                 440                 445
Phe Gly Gly Phe Thr Gly Ala Arg Lys Ser Ala Ala Leu Ala Gly Gly
    450                 455                 460
Gly Gly Ser Gly Gly Gly Gly Ser Gly Gly Gly Gly Ser Ala Leu Val
465                 470                 475                 480
Leu Gln Cys Ile Lys Val Asn Asn Trp Asp Leu Phe Phe Ser Pro Ser
                485                 490                 495
Glu Asp Asn Phe Thr Asn Asp Leu Asn Lys Gly Glu Glu Ile Thr Ser
            500                 505                 510
Asp Thr Asn Ile Glu Ala Ala Glu Glu Asn Ile Ser Leu Asp Leu Ile
        515                 520                 525
Gln Gln Tyr Tyr Leu Thr Phe Asn Phe Asp Asn Glu Pro Glu Asn Ile
    530                 535                 540
Ser Ile Glu Asn Leu Ser Ser Asp Ile Ile Gly Gln Leu Glu Leu Met
545                 550                 555                 560
Pro Asn Ile Glu Arg Phe Pro Asn Gly Lys Lys Tyr Glu Leu Asp Lys
                565                 570                 575
Tyr Thr Met Phe His Tyr Leu Arg Ala Gln Glu Phe Glu His Gly Lys
            580                 585                 590
Ser Arg Ile Ala Leu Thr Asn Ser Val Asn Glu Ala Leu Leu Asn Pro
        595                 600                 605
Ser Arg Val Tyr Thr Phe Phe Ser Ser Asp Tyr Val Lys Lys Val Asn
    610                 615                 620
Lys Ala Thr Glu Ala Ala Met Phe Leu Gly Trp Val Glu Gln Leu Val
625                 630                 635                 640
Tyr Asp Phe Thr Asp Glu Thr Ser Glu Val Ser Thr Thr Asp Lys Ile
                645                 650                 655
Ala Asp Ile Thr Ile Ile Ile Pro Tyr Ile Gly Pro Ala Leu Asn Ile
            660                 665                 670
Gly Asn Met Leu Tyr Lys Asp Asp Phe Val Gly Ala Leu Ile Phe Ser
        675                 680                 685
Gly Ala Val Ile Leu Leu Glu Phe Ile Pro Glu Ile Ala Ile Pro Val
    690                 695                 700
```

```
Leu Gly Thr Phe Ala Leu Val Ser Tyr Ile Ala Asn Lys Val Leu Thr
705                 710                 715                 720
Val Gln Thr Ile Asp Asn Ala Leu Ser Lys Arg Asn Glu Lys Trp Asp
            725                 730                 735
Glu Val Tyr Lys Tyr Ile Val Thr Asn Trp Leu Ala Lys Val Asn Thr
        740                 745                 750
Gln Ile Asp Leu Ile Arg Lys Lys Met Lys Glu Ala Leu Glu Asn Gln
    755                 760                 765
Ala Glu Ala Thr Lys Ala Ile Ile Asn Tyr Gln Tyr Asn Gln Tyr Thr
770                 775                 780
Glu Glu Lys Asn Asn Ile Asn Phe Asn Ile Asp Asp Leu Ser Ser
785                 790                 795                 800
Lys Leu Asn Glu Ser Ile Asn Lys Ala Met Ile Asn Ile Asn Lys Phe
                805                 810                 815
Leu Asn Gln Cys Ser Val Ser Tyr Leu Met Asn Ser Met Ile Pro Tyr
            820                 825                 830
Gly Val Lys Arg Leu Glu Asp Phe Asp Ala Ser Leu Lys Asp Ala Leu
        835                 840                 845
Leu Lys Tyr Ile Tyr Asp Asn Arg Gly Thr Leu Ile Gly Gln Val Asp
    850                 855                 860
Arg Leu Lys Asp Lys Val Asn Asn Thr Leu Ser Thr Asp Ile Pro Phe
865                 870                 875                 880
Gln Leu Ser Lys Tyr Val Asp Asn Gln Arg Leu Leu Ser Thr Leu Asp
                885                 890                 895

<210> SEQ ID NO 55
<211> LENGTH: 2691
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 55
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gataccttta ctaacccgga agaaggtgac   180
ctgaacccgc caccggaagc gaaacaggtg ccggtatctt actatgactc cacctacctg   240
tctaccgata cgaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg gttcctatcg ttccgaagaa ctgaacctgg tgatcatcgg cccgtctgct   480
gatatcatcc agttcgagtg taagagcttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta aattcgcaac tgatcctgcg   660
gttaccctgg ctcacgaact gattcatgca ggccaccgcc tgtacggtat cgccatcaat   720
ccgaaccgtg tcttcaaagt taacaccaac gcgtattacg agatgtccgg tctggaagtt   780
agcttcgaag aactgcgtac ttttggcggt cacgacgcta aattcatcga ctctctgcaa   840
gaaaacgagt ccgtctgta ctactataac aagttcaaag atatcgcatc caccctgaac   900
aaagcgaaat ccatcgtggg ctaccactgc ttctctccagt acatgaagaa cgttttaaa   960
```

-continued

```
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc     1140 gtgccgaaag ttaactacac tatctacgat ggtttcaacc tgcgtaacac caacctggct    1200
gctaatttta acggccagaa cacgaaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atatgcggcg    1380
ctagcgggcg gtggcggtag cggcggtggc ggtagcggcg gtggcggtag cgcactagtg    1440
ctgcagtgta tcaaggttaa caactgggat ttattcttca gcccgagtga agacaacttc    1500
accaacgacc tgaacaaagg tgaagaaatc acctcagata ctaacatcga agcagccgaa    1560 gaaacatct cgctggacct gatccagcag tactacctga cctttaattt cgacaacgag     1620
ccggaaaaca tttctatcga aacctgagc tctgatatca tcggccagct ggaactgatg     1680
ccgaacatcg aacgtttccc aaacggtaaa aagtacgagc tggacaaata ccatgttc     1740 cactacctgc gcgcgcagga atttgaacac ggcaaatccc gtatcgcact gactaactcc    1800
gttaacgaag ctctgctcaa cccgtcccgt gtatacacct tcttctctag cgactacgtg    1860
aaaaaggtca caaagcgac tgaagctgca atgttcttgg gttgggttga acagcttgtt     1920
tatgatttta ccgacgagac gtccgaagta tctactaccg acaaaattgc ggatatcact    1980
atcatcatcc cgtacatcgg tccggctctg aacattggca acatgctgta caaagacgac    2040
ttcgttggcg cactgatctt ctccggtgcg gtgatcctgc tggagttcat cccggaaatc    2100
gccatcccgg tactgggcac cttttgctctg gtttcttaca ttgcaaacaa ggttctgact    2160
gtacaaacca tcgacaacgc gctgagcaaa cgtaacgaaa aatgggatga agtttacaaa    2220
tatatcgtga ccaactggct ggctaaggtt aatactcaga tcgacctcat ccgcaaaaaa    2280
atgaaagaag cactggaaaa ccaggcggaa gctaccaagg caatcattaa ctaccagtac    2340
aaccagtaca ccgaggaaga aaaaaacaac atcaacttca acatcgacga tctgtcctct    2400
aaactgaacg aatccatcaa caagctatg atcaacatca acaagttcct gaaccagtgc    2460
tctgtaagct atctgatgaa ctccatgatc ccgtacggtg ttaaacgtct ggaggacttc    2520
gatgcgtctc tgaaagacgc cctgctgaaa tacatttacg acaaccgtgg cactctgatc    2580
ggtcaggttg atcgtctgaa ggacaaagtg aacaatacct tatcgaccga catcccttt      2640 cagctcagta aatatgtcga taaccaacgc cttttgtcca ctctagacta g             2691
```

<210> SEQ ID NO 56
<211> LENGTH: 896
<212> TYPE: PRT
<213> ORGANISM: Artificial Sequence
<220> FEATURE:
<223> OTHER INFORMATION: chemically synthesized fusion protein

<400> SEQUENCE: 56

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60
```

```
Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Tyr Ala Ala Leu Ala Gly Gly
    450                 455                 460

Gly Gly Ser Gly Gly Gly Ser Gly Gly Gly Ser Ala Leu Val
465                 470                 475                 480
```

```
Leu Gln Cys Ile Lys Val Asn Trp Asp Leu Phe Ser Pro Ser
            485             490             495

Glu Asp Asn Phe Thr Asn Asp Leu Asn Lys Gly Glu Glu Ile Thr Ser
            500             505             510

Asp Thr Asn Ile Glu Ala Ala Glu Glu Asn Ile Ser Leu Asp Leu Ile
            515             520             525

Gln Gln Tyr Tyr Leu Thr Phe Asn Phe Asp Asn Glu Pro Glu Asn Ile
            530             535             540

Ser Ile Glu Asn Leu Ser Ser Asp Ile Ile Gly Gln Leu Glu Leu Met
545             550             555             560

Pro Asn Ile Glu Arg Phe Pro Asn Gly Lys Lys Tyr Glu Leu Asp Lys
                565             570             575

Tyr Thr Met Phe His Tyr Leu Arg Ala Gln Glu Phe Glu His Gly Lys
            580             585             590

Ser Arg Ile Ala Leu Thr Asn Ser Val Asn Glu Ala Leu Leu Asn Pro
            595             600             605

Ser Arg Val Tyr Thr Phe Phe Ser Ser Asp Tyr Val Lys Lys Val Asn
            610             615             620

Lys Ala Thr Glu Ala Ala Met Phe Leu Gly Trp Val Glu Gln Leu Val
625             630             635             640

Tyr Asp Phe Thr Asp Glu Thr Ser Glu Val Ser Thr Thr Asp Lys Ile
                645             650             655

Ala Asp Ile Thr Ile Ile Ile Pro Tyr Ile Gly Pro Ala Leu Asn Ile
            660             665             670

Gly Asn Met Leu Tyr Lys Asp Asp Phe Val Gly Ala Leu Ile Phe Ser
            675             680             685

Gly Ala Val Ile Leu Leu Glu Phe Ile Pro Glu Ile Ala Ile Pro Val
690             695             700

Leu Gly Thr Phe Ala Leu Val Ser Tyr Ile Ala Asn Lys Val Leu Thr
705             710             715             720

Val Gln Thr Ile Asp Asn Ala Leu Ser Lys Arg Asn Glu Lys Trp Asp
                725             730             735

Glu Val Tyr Lys Tyr Ile Val Thr Asn Trp Leu Ala Lys Val Asn Thr
            740             745             750

Gln Ile Asp Leu Ile Arg Lys Lys Met Lys Glu Ala Leu Glu Asn Gln
            755             760             765

Ala Glu Ala Thr Lys Ala Ile Ile Asn Tyr Gln Tyr Asn Gln Tyr Thr
770             775             780

Glu Glu Glu Lys Asn Asn Ile Asn Phe Asn Ile Asp Asp Leu Ser Ser
785             790             795             800

Lys Leu Asn Glu Ser Ile Asn Lys Ala Met Ile Asn Ile Asn Lys Phe
                805             810             815

Leu Asn Gln Cys Ser Val Ser Tyr Leu Met Asn Ser Met Ile Pro Tyr
            820             825             830

Gly Val Lys Arg Leu Glu Asp Phe Asp Ala Ser Leu Lys Asp Ala Leu
            835             840             845

Leu Lys Tyr Ile Tyr Asp Asn Arg Gly Thr Leu Ile Gly Gln Val Asp
            850             855             860

Arg Leu Lys Asp Lys Val Asn Asn Thr Leu Ser Thr Asp Ile Pro Phe
865             870             875             880

Gln Leu Ser Lys Tyr Val Asp Asn Gln Arg Leu Leu Ser Thr Leu Asp
                885             890             895
```

<210> SEQ ID NO 57
<211> LENGTH: 2691
<212> TYPE: DNA
<213> ORGANISM: Artificial Sequence
<220> FEATURE:
<223> OTHER INFORMATION: chemically synthesized polynucleotide encoding fusion protein

<400> SEQUENCE: 57

| | | | | | |
|---|---|---|---|---|---|
| ggatccatgg | agttcgttaa | caaacagttc | aactataaag | acccagttaa | cggtgttgac | 60 |
| attgcttaca | tcaaaatccc | gaacgctggc | cagatgcagc | cggtaaaggc | attcaaaatc | 120 |
| cacaacaaaa | tctgggttat | cccgaacgt | gataccttta | ctaacccgga | agaaggtgac | 180 |
| ctgaacccgc | caccggaagc | gaaacaggtg | ccggtatctt | actatgactc | cacctacctg | 240 |
| tctaccgata | cgaaaagga | caactacctg | aaggtgtta | ctaaactgtt | cgagcgtatt | 300 |
| tactccaccg | acctgggccg | tatgctgctg | actagcatcg | ttcgcggtat | cccgttctgg | 360 |
| ggcggttcta | ccatcgatac | cgaactgaaa | gtaatcgaca | ctaactgcat | caacgttatt | 420 |
| cagccggacg | gttcctatcg | ttccgaagaa | ctgaacctgg | tgatcatcgg | cccgtctgct | 480 |
| gatatcatcc | agttcgagtg | taagagcttt | ggtcacgaag | ttctgaacct | cacccgtaac | 540 |
| ggctacggtt | ccactcagta | catccgtttc | tctccggact | tcaccttcgg | ttttgaagaa | 600 |
| tccctggaag | tagacacgaa | cccactgctg | ggcgctggta | aattcgcaac | tgatcctgcg | 660 |
| gttaccctgg | ctcacgaact | gattcatgca | ggccaccgcc | tgtacggtat | cgccatcaat | 720 |
| ccgaaccgtg | tcttcaaagt | taacaccaac | gcgtattacg | agatgtccgg | tctggaagtt | 780 |
| agcttcgaag | aactgcgtac | ttttggcggt | cacgacgcta | aattcatcga | ctctctgcaa | 840 |
| gaaaacgagt | tccgtctgta | ctactataac | aagttcaaag | atatcgcatc | caccctgaac | 900 |
| aaagcgaaat | ccatcgtggg | taccactgct | tctctccagt | acatgaagaa | cgtttttaaa | 960 |
| gaaaaatacc | tgctcagcga | agacacctcc | ggcaaattct | ctgtagacaa | gttgaaattc | 1020 |
| gataaacttt | acaaaatgct | gactgaaatt | tacaccgaag | acaacttcgt | taagttcttt | 1080 |
| aaagttctga | accgcaaaac | ctatctgaac | ttcgacaagg | cagtattcaa | atcaacatc | 1140 |
| gtgccgaaag | ttaactacac | tatctacgat | ggtttcaacc | tgcgtaacac | caacctggct | 1200 |
| gctaatttta | acggcagaa | cacgaaatc | aacaacatga | acttcacaaa | actgaaaaac | 1260 |
| ttcactggtc | tgttcgagtt | ttacaagctg | ctgtgcgtcg | acggcatcat | tacctccaaa | 1320 |
| actaaatctc | tgatagaagg | tagatttggc | ggtttcacgg | gcgcacgcaa | atcatatgcg | 1380 |
| ctagcgggcg | gtggcggtag | cggcggtggc | ggtagcggcg | gtggcggtag | cgcactagtg | 1440 |
| ctgcagtgta | tcaaggttaa | caactgggat | ttattcttca | gcccgagtga | agacaacttc | 1500 |
| accaacgacc | tgaacaaagg | tgaagaaatc | acctcagata | ctaacatcga | agcagccgaa | 1560 |
| gaaacatctc | cgctggacct | gatccagcag | tactacctga | cctttaattt | cgacaacgag | 1620 |
| ccggaaaaca | tttctatcga | aaacctgagc | tctgatatca | tcggccagct | ggaactgatg | 1680 |
| ccgaacatcg | aacgtttccc | aaacggtaaa | aagtacgagc | tggacaaata | ccatgttc | 1740 |
| cactacctgc | gcgcgcagga | atttgaacac | ggcaaatccc | gtatcgcact | gactaactcc | 1800 |
| gttaacgaag | ctctgctcaa | cccgtcccgt | gtatacacct | tcttctctag | cgactacgtg | 1860 |
| aaaaaggtca | acaaagcgac | tgaagctgca | atgttcttgg | gttgggttga | acagcttgtt | 1920 |
| tatgatttta | ccgacgagac | gtccgaagta | tctactaccg | acaaaattgc | ggatatcact | 1980 |
| atcatcatcc | cgtacatcgg | tccggctctg | aacattggca | acatgctgta | caaagacgac | 2040 |
| ttcgttggcg | cactgatctt | ctccggtgcg | gtgatcctgc | tggagttcat | cccggaaatc | 2100 |

-continued

```
gccatcccgg tactgggcac ctttgctctg gtttcttaca ttgcaaacaa ggttctgact    2160
gtacaaacca tcgacaacgc gctgagcaaa cgtaacgaaa aatgggatga agtttacaaa    2220
tatatcgtga ccaactggct ggctaaggtt aatactcaga tcgacctcat ccgcaaaaaa    2280
atgaaagaag cactggaaaa ccaggcggaa gctaccaagg caatcattaa ctaccagtac    2340
aaccagtaca ccgaggaaga aaaaaacaac atcaacttca acatcgacga tctgtcctct    2400
aaactgaacg aatccatcaa caaagctatg atcaacatca acaagttcct gaaccagtgc    2460
tctgtaagct atctgatgaa ctccatgatc ccgtacggtg ttaaacgtct ggaggacttc    2520
gatgcgtctc tgaaagacgc cctgctgaaa tacatttacg acaaccgtgg cactctgatc    2580
ggtcaggttg atcgtctgaa ggacaaagtg aacaatacct tatcgaccga catcccttt    2640 cagctcagta aatatgtcga taaccaacgc cttttgtcca ctctagacta g    2691
```

<210> SEQ ID NO 58
<211> LENGTH: 896
<212> TYPE: PRT
<213> ORGANISM: Artificial Sequence
<220> FEATURE:
<223> OTHER INFORMATION: chemically synthesized fusion protein

<400> SEQUENCE: 58

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255
```

-continued

```
Gly Leu Glu Val Ser Phe Glu Leu Arg Thr Phe Gly His Asp
            260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
            290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Lys Val Leu Asn Arg Lys Thr Tyr
            355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Ser Tyr Ala Leu Ala Gly Gly
    450                 455                 460

Gly Gly Ser Gly Gly Gly Ser Gly Gly Gly Ser Ala Leu Val
465                 470                 475                 480

Leu Gln Cys Ile Lys Val Asn Asn Trp Asp Leu Phe Phe Ser Pro Ser
            485                 490                 495

Glu Asp Asn Phe Thr Asn Asp Leu Asn Lys Gly Glu Glu Ile Thr Ser
            500                 505                 510

Asp Thr Asn Ile Glu Ala Ala Glu Glu Asn Ile Ser Leu Asp Leu Ile
            515                 520                 525

Gln Gln Tyr Tyr Leu Thr Phe Asn Phe Asp Asn Glu Pro Glu Asn Ile
            530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
            595                 600                 605

Ser Arg Val Tyr Thr Phe Phe Ser Ser Asp Tyr Val Lys Lys Val Asn
            610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
            645                 650                 655

Ala Asp Ile Thr Ile Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
```

```
                        675                 680                 685
Gly Ala Val Ile Leu Glu Phe Ile Pro Glu Ile Ala Ile Pro Val
    690                 695                 700
Leu Gly Thr Phe Ala Leu Val Ser Tyr Ile Ala Asn Lys Val Leu Thr
705                 710                 715                 720
Val Gln Thr Ile Asp Asn Ala Leu Ser Lys Arg Asn Glu Lys Trp Asp
                725                 730                 735
Glu Val Tyr Lys Tyr Ile Val Thr Asn Trp Leu Ala Lys Val Asn Thr
            740                 745                 750
Gln Ile Asp Leu Ile Arg Lys Lys Met Lys Glu Ala Leu Glu Asn Gln
        755                 760                 765
Ala Glu Ala Thr Lys Ala Ile Ile Asn Tyr Gln Tyr Asn Gln Tyr Thr
    770                 775                 780
Glu Glu Glu Lys Asn Asn Ile Asn Phe Asn Ile Asp Asp Leu Ser Ser
785                 790                 795                 800
Lys Leu Asn Glu Ser Ile Asn Lys Ala Met Ile Asn Ile Asn Lys Phe
                805                 810                 815
Leu Asn Gln Cys Ser Val Ser Tyr Leu Met Asn Ser Met Ile Pro Tyr
            820                 825                 830
Gly Val Lys Arg Leu Glu Asp Phe Asp Ala Ser Leu Lys Asp Ala Leu
        835                 840                 845
Leu Lys Tyr Ile Tyr Asp Asn Arg Gly Thr Leu Ile Gly Gln Val Asp
    850                 855                 860
Arg Leu Lys Asp Lys Val Asn Asn Thr Leu Ser Thr Asp Ile Pro Phe
865                 870                 875                 880
Gln Leu Ser Lys Tyr Val Asp Asn Gln Arg Leu Leu Ser Thr Leu Asp
                885                 890                 895

<210> SEQ ID NO 59
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 59
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg ttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
```

```
gaaaacgagt tccgtctgta ctactataac aagttcaaag atatcgcatc caccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa atcaacatc    1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat acctccaaa    1320
actaaatctc tgatagaagg tagatttggc ggtttcacgg cgcacgcaa atcagcgcgt    1380
aaatatgcta accaggcgct agcgggcggt ggcggtagcg gcggtggcgg tagcggcggt    1440
ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acggtaaaaa gtacgagctg   1740
gacaaatata ccatgttcca ctacctgcgc gcgcaggaat ttgaacacgg caaatcccgt   1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca agacgactt cgttggcgca ctgatcttct ccggtgcggt gatcctgctg   2100
gagttcatcc cggaaatcgc catcccggta ctgggcaccct ttgctctggt ttcttacatt   2160
gcaaacaagg ttctgactgt acaaaccatc gacaacgcgc tgagcaaacg taacgaaaaa   2220
tgggatgaag tttacaaata tcgtgacc aactggctgg ctaaggttaa tactcagatc   2280
gacctcatcc gcaaaaaaat gaagaagca ctggaaaacc aggcggaagc taccaaggca   2340
atcattaact accagtacaa ccagtacacc gaggaagaaa aaaacaacat caacttcaac   2400
atcgacgatc tgtcctctaa actgaacgaa tccatcaaca agctatgat caacatcaac   2460
aagttcctga accagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caatacctta   2640
tcgaccgaca tcccttttca gctcagtaaa tatgtcgata ccaacgcct tttgtccact   2700
ctagactag                                                          2709
```

<210> SEQ ID NO 60
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 60

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met

```
                  20                  25                  30
Gln Pro Val Lys Ala Phe Lys Ile His Asn Lys Ile Trp Val Ile Pro
                 35                  40                  45
Glu Arg Asp Thr Phe Thr Asn Pro Glu Glu Gly Asp Leu Asn Pro Pro
             50                  55                  60
Pro Glu Ala Lys Gln Val Pro Val Ser Tyr Tyr Asp Ser Thr Tyr Leu
 65                  70                  75                  80
Ser Thr Asp Asn Glu Lys Asp Asn Tyr Leu Lys Gly Val Thr Lys Leu
                 85                  90                  95
Phe Glu Arg Ile Tyr Ser Thr Asp Leu Gly Arg Met Leu Leu Thr Ser
                100                 105                 110
Ile Val Arg Gly Ile Pro Phe Trp Gly Gly Ser Thr Ile Asp Thr Glu
            115                 120                 125
Leu Lys Val Ile Asp Thr Asn Cys Ile Asn Val Ile Gln Pro Asp Gly
            130                 135                 140
Ser Tyr Arg Ser Glu Glu Leu Asn Leu Val Ile Ile Gly Pro Ser Ala
145                 150                 155                 160
Asp Ile Ile Gln Phe Glu Cys Lys Ser Phe Gly His Glu Val Leu Asn
                165                 170                 175
Leu Thr Arg Asn Gly Tyr Gly Ser Thr Gln Tyr Ile Arg Phe Ser Pro
            180                 185                 190
Asp Phe Thr Phe Gly Phe Glu Glu Ser Leu Glu Val Asp Thr Asn Pro
            195                 200                 205
Leu Leu Gly Ala Gly Lys Phe Ala Thr Asp Pro Ala Val Thr Leu Ala
    210                 215                 220
His Glu Leu Ile His Ala Gly His Arg Leu Tyr Gly Ile Ala Ile Asn
225                 230                 235                 240
Pro Asn Arg Val Phe Lys Val Asn Thr Asn Ala Tyr Tyr Glu Met Ser
                245                 250                 255
Gly Leu Glu Val Ser Phe Glu Glu Leu Arg Thr Phe Gly Gly His Asp
            260                 265                 270
Ala Lys Phe Ile Asp Ser Leu Gln Glu Asn Glu Phe Arg Leu Tyr Tyr
    275                 280                 285
Tyr Asn Lys Phe Lys Asp Ile Ala Ser Thr Leu Asn Lys Ala Lys Ser
290                 295                 300
Ile Val Gly Thr Thr Ala Ser Leu Gln Tyr Met Lys Asn Val Phe Lys
305                 310                 315                 320
Glu Lys Tyr Leu Leu Ser Glu Asp Thr Ser Gly Lys Phe Ser Val Asp
                325                 330                 335
Lys Leu Lys Phe Asp Lys Leu Tyr Lys Met Leu Thr Glu Ile Tyr Thr
            340                 345                 350
Glu Asp Asn Phe Val Lys Phe Phe Lys Val Leu Asn Arg Lys Thr Tyr
            355                 360                 365
Leu Asn Phe Asp Lys Ala Val Phe Lys Ile Asn Ile Val Pro Lys Val
        370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Leu Ile Glu Gly Arg
        435                 440                 445
```

```
Phe Gly Gly Phe Thr Gly Ala Arg Lys Ser Ala Arg Lys Tyr Ala Asn
    450                 455                 460
Gln Ala Leu Ala Gly Gly Gly Ser Gly Gly Gly Gly Ser Gly Gly
465             470                 475                 480
Gly Gly Ser Ala Leu Val Leu Gln Cys Ile Lys Val Asn Asn Trp Asp
                485                 490                 495
Leu Phe Phe Ser Pro Ser Glu Asp Asn Phe Thr Asn Asp Leu Asn Lys
                500                 505                 510
Gly Glu Glu Ile Thr Ser Asp Thr Asn Ile Glu Ala Ala Glu Glu Asn
                515                 520                 525
Ile Ser Leu Asp Leu Ile Gln Gln Tyr Tyr Leu Thr Phe Asn Phe Asp
    530                 535                 540
Asn Glu Pro Glu Asn Ile Ser Ile Glu Asn Leu Ser Ser Asp Ile Ile
545                 550                 555                 560
Gly Gln Leu Glu Leu Met Pro Asn Ile Glu Arg Phe Pro Asn Gly Lys
                565                 570                 575
Lys Tyr Glu Leu Asp Lys Tyr Thr Met Phe His Tyr Leu Arg Ala Gln
                580                 585                 590
Glu Phe Glu His Gly Lys Ser Arg Ile Ala Leu Thr Asn Ser Val Asn
                595                 600                 605
Glu Ala Leu Leu Asn Pro Ser Arg Val Tyr Thr Phe Phe Ser Ser Asp
    610                 615                 620
Tyr Val Lys Lys Val Asn Lys Ala Thr Glu Ala Ala Met Phe Leu Gly
625                 630                 635                 640
Trp Val Glu Gln Leu Val Tyr Asp Phe Thr Asp Glu Thr Ser Glu Val
                645                 650                 655
Ser Thr Thr Asp Lys Ile Ala Asp Ile Thr Ile Ile Ile Pro Tyr Ile
                660                 665                 670
Gly Pro Ala Leu Asn Ile Gly Asn Met Leu Tyr Lys Asp Asp Phe Val
                675                 680                 685
Gly Ala Leu Ile Phe Ser Gly Ala Val Ile Leu Leu Glu Phe Ile Pro
    690                 695                 700
Glu Ile Ala Ile Pro Val Leu Gly Thr Phe Ala Leu Val Ser Tyr Ile
705                 710                 715                 720
Ala Asn Lys Val Leu Thr Val Gln Thr Ile Asp Asn Ala Leu Ser Lys
                725                 730                 735
Arg Asn Glu Lys Trp Asp Glu Val Tyr Lys Tyr Ile Val Thr Asn Trp
                740                 745                 750
Leu Ala Lys Val Asn Thr Gln Ile Asp Leu Ile Arg Lys Lys Met Lys
                755                 760                 765
Glu Ala Leu Glu Asn Gln Ala Glu Ala Thr Lys Ala Ile Ile Asn Tyr
                770                 775                 780
Gln Tyr Asn Gln Tyr Thr Glu Glu Lys Asn Asn Ile Asn Phe Asn
785                 790                 795                 800
Ile Asp Asp Leu Ser Ser Lys Leu Asn Glu Ser Ile Asn Lys Ala Met
                805                 810                 815
Ile Asn Ile Asn Lys Phe Leu Asn Gln Cys Ser Val Ser Tyr Leu Met
                820                 825                 830
Asn Ser Met Ile Pro Tyr Gly Val Lys Arg Leu Glu Asp Phe Asp Ala
                835                 840                 845
Ser Leu Lys Asp Ala Leu Leu Lys Tyr Ile Tyr Asp Asn Arg Gly Thr
850                 855                 860
```

```
Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
            885                 890                 895

Leu Leu Ser Thr Leu Asp
            900

<210> SEQ ID NO 61
<211> LENGTH: 2697
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 61
```

| | | | | | |
|---|---|---|---|---|---|
| ggatccatgg | agttcgttaa | caaacagttc | aactataaag | acccagttaa | cggtgttgac | 60 |
| attgcttaca | tcaaaatccc | gaacgctggc | cagatgcagc | cggtaaaggc | attcaaaatc | 120 |
| cacaacaaaa | tctgggttat | cccggaacgt | gatacctta | ctaacccgga | agaaggtgac | 180 |
| ctgaacccgc | caccggaagc | gaaacaggtg | ccggtatctt | actatgactc | cacctacctg | 240 |
| tctaccgata | acgaaaagga | caactacctg | aaaggtgtta | ctaaactgtt | cgagcgtatt | 300 |
| tactccaccg | acctgggccg | tatgctgctg | actagcatcg | ttcgcggtat | cccgttctgg | 360 |
| ggcggttcta | ccatcgatac | cgaactgaaa | gtaatcgaca | ctaactgcat | caacgttatt | 420 |
| cagccggacg | ttcctatcg | ttccgaagaa | ctgaacctgg | tgatcatcgg | cccgtctgct | 480 |
| gatatcatcc | agttcgagtg | taagagcttt | ggtcacgaag | ttctgaacct | cacccgtaac | 540 |
| ggctacggtt | ccactcagta | catccgtttc | tctccggact | tcaccttcgg | ttttgaagaa | 600 |
| tccctggaag | tagacacgaa | cccactgctg | ggcgctggta | aattcgcaac | tgatcctgcg | 660 |
| gttaccctgg | ctcacgaact | gattcatgca | ggccaccgcc | tgtacggtat | cgccatcaat | 720 |
| ccgaaccgtg | tcttcaaagt | taacaccaac | gcgtattacg | agatgtccgg | tctggaagtt | 780 |
| agcttcgaag | aactgcgtac | ttttggcggt | cacgacgcta | aattcatcga | ctctctgcaa | 840 |
| gaaaacgagt | ccgtctgta | ctactataac | aagttcaaag | atatcgcatc | cacccctgaac | 900 |
| aaagcgaaat | ccatcgtggg | taccactgct | ctctccagt | acatgaagaa | cgttttaaa | 960 |
| gaaaatacc | tgctcagcga | agacacctcc | ggcaaattct | ctgtagacaa | gttgaaattc | 1020 |
| gataaacttt | acaaaatgct | gactgaaatt | tacaccgaag | acaacttcgt | taagttcttt | 1080 |
| aaagttctga | accgcaaaac | ctatctgaac | ttcgacaagg | cagtattcaa | atcaacatc | 1140 |
| gtgccgaaag | ttaactacac | tatctacgat | ggtttcaacc | tgcgtaacac | caacctggct | 1200 |
| gctaatttta | acgccagaa | cacggaaatc | aacaacatga | acttcacaaa | actgaaaaac | 1260 |
| ttcactggtc | tgttcgagtt | ttacaagctg | ctgtgcgtcg | acggcatcat | tacctccaaa | 1320 |
| actaaatctc | tgatagaagg | tagatttggc | ggtttcacgg | gcgcacgcaa | atcagcgcgt | 1380 |
| aaagcgctag | cgggcggtgg | cggtagcggc | ggtggcggta | gcggcggtgg | cggtagcgca | 1440 |
| ctagtgctgc | agtgtatcaa | ggttaacaac | tgggatttat | tcttcagccc | gagtgaagac | 1500 |
| aacttcacca | acgacctgaa | caaaggtgaa | gaaatcacct | cagatactaa | catcgaagca | 1560 |
| gccgaagaaa | acatctcgct | ggacctgatc | cagcagtact | acctgacctt | taatttcgac | 1620 |
| aacgagccgg | aaaacattc | tatcgaaaac | ctgagctctg | atatcatcgg | ccagctggaa | 1680 |
| ctgatgccga | acatcgaacg | tttccccaaac | ggtaaaaagt | acgagctgga | caaatatacc | 1740 |
| atgttccact | acctgcgcgc | gcaggaattt | gaacacggca | atcccgtat | cgcactgact | 1800 |

```
aactccgtta acgaagctct gctcaacccg tcccgtgtat acaccttctt ctctagcgac   1860
tacgtgaaaa aggtcaacaa agcgactgaa gctgcaatgt tcttgggttg ggttgaacag   1920
cttgtttatg attttaccga cgagacgtcc gaagtatcta ctaccgacaa aattgcggat   1980
atcactatca tcatcccgta catcggtccg gctctgaaca ttggcaacat gctgtacaaa   2040
gacgacttcg ttggcgcact gatcttctcc ggtgcggtga tcctgctgga gttcatcccg   2100
gaaatcgcca tcccggtact gggcaccttt gctctggttt cttacattgc aaacaaggtt   2160
ctgactgtac aaaccatcga caacgcgctg agcaaacgta acgaaaaatg ggatgaagtt   2220
tacaaatata tcgtgaccaa ctggctggct aaggttaata ctcagatcga cctcatccgc   2280
aaaaaaatga agaagcact ggaaaaccag gcggaagcta ccaaggcaat cattaactac   2340
cagtacaacc agtacaccga ggaagaaaaa aacaacatca acttcaacat cgacgatctg   2400
tcctctaaac tgaacgaatc catcaacaaa gctatgatca acatcaacaa gttcctgaac   2460
cagtgctctg taagctatct gatgaactcc atgatcccgt acggtgttaa acgtctggag   2520
gacttcgatg cgtctctgaa agacgccctg ctgaaataca tttacgacaa ccgtggcact   2580
ctgatcggtc aggttgatcg tctgaaggac aaagtgaaca ataccttatc gaccgacatc   2640
ccttttcagc tcagtaaata tgtcgataac caacgccttt tgtccactct agactag     2697
```

<210> SEQ ID NO 62
<211> LENGTH: 898
<212> TYPE: PRT
<213> ORGANISM: Artificial Sequence
<220> FEATURE:
<223> OTHER INFORMATION: chemically synthesized fusion protein

<400> SEQUENCE: 62

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205
```

```
Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
                260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Ser Ala Arg Lys Ala Leu Ala
    450                 455                 460

Gly Gly Gly Gly Ser Gly Gly Gly Ser Gly Gly Gly Ser Ala
465                 470                 475                 480

Leu Val Leu Gln Cys Ile Lys Val Asn Asn Trp Asp Leu Phe Phe Ser
                485                 490                 495

Pro Ser Glu Asp Asn Phe Thr Asn Asp Leu Asn Lys Gly Glu Glu Ile
            500                 505                 510

Thr Ser Asp Thr Asn Ile Glu Ala Ala Glu Asn Ile Ser Leu Asp
            515                 520                 525

Leu Ile Gln Gln Tyr Tyr Leu Thr Phe Asn Phe Asp Asn Glu Pro Glu
    530                 535                 540

Asn Ile Ser Ile Glu Asn Leu Ser Ser Asp Ile Ile Gly Gln Leu Glu
545                 550                 555                 560

Leu Met Pro Asn Ile Glu Arg Phe Pro Asn Gly Lys Lys Tyr Glu Leu
                565                 570                 575

Asp Lys Tyr Thr Met Phe His Tyr Leu Arg Ala Gln Glu Phe Glu His
            580                 585                 590

Gly Lys Ser Arg Ile Ala Leu Thr Asn Ser Val Asn Glu Ala Leu Leu
            595                 600                 605

Asn Pro Ser Arg Val Tyr Thr Phe Phe Ser Ser Asp Tyr Val Lys Lys
    610                 615                 620
```

```
Val Asn Lys Ala Thr Glu Ala Ala Met Phe Leu Gly Trp Val Glu Gln
625                 630                 635                 640

Leu Val Tyr Asp Phe Thr Asp Glu Thr Ser Glu Val Ser Thr Thr Asp
            645                 650                 655

Lys Ile Ala Asp Ile Thr Ile Ile Ile Pro Tyr Ile Gly Pro Ala Leu
        660                 665                 670

Asn Ile Gly Asn Met Leu Tyr Lys Asp Asp Phe Val Gly Ala Leu Ile
    675                 680                 685

Phe Ser Gly Ala Val Ile Leu Leu Glu Phe Ile Pro Glu Ile Ala Ile
690                 695                 700

Pro Val Leu Gly Thr Phe Ala Leu Val Ser Tyr Ile Ala Asn Lys Val
705                 710                 715                 720

Leu Thr Val Gln Thr Ile Asp Asn Ala Leu Ser Lys Arg Asn Glu Lys
            725                 730                 735

Trp Asp Glu Val Tyr Lys Tyr Ile Val Thr Asn Trp Leu Ala Lys Val
        740                 745                 750

Asn Thr Gln Ile Asp Leu Ile Arg Lys Lys Met Lys Glu Ala Leu Glu
    755                 760                 765

Asn Gln Ala Glu Ala Thr Lys Ala Ile Ile Asn Tyr Gln Tyr Asn Gln
770                 775                 780

Tyr Thr Glu Glu Glu Lys Asn Asn Ile Asn Phe Asn Ile Asp Asp Leu
785                 790                 795                 800

Ser Ser Lys Leu Asn Glu Ser Ile Asn Lys Ala Met Ile Asn Ile Asn
            805                 810                 815

Lys Phe Leu Asn Gln Cys Ser Val Ser Tyr Leu Met Asn Ser Met Ile
        820                 825                 830

Pro Tyr Gly Val Lys Arg Leu Glu Asp Phe Asp Ala Ser Leu Lys Asp
    835                 840                 845

Ala Leu Leu Lys Tyr Ile Tyr Asp Asn Arg Gly Thr Leu Ile Gly Gln
850                 855                 860

Val Asp Arg Leu Lys Asp Lys Val Asn Asn Thr Leu Ser Thr Asp Ile
865                 870                 875                 880

Pro Phe Gln Leu Ser Lys Tyr Val Asp Asn Gln Arg Leu Leu Ser Thr
            885                 890                 895

Leu Asp
```

<210> SEQ ID NO 63
<211> LENGTH: 2736
<212> TYPE: DNA
<213> ORGANISM: Artificial Sequence
<220> FEATURE:
<223> OTHER INFORMATION: chemically synthesized polynucleotide encoding fusion protein

<400> SEQUENCE: 63

```
ctcgggattg agggtcgttt tggcggtttc acgggcgcac gcaaatcagc gcgtaaatta      60
gctaaccaga ctagtggcgg tgggggtagt ggcggtggcg gttcgggcgg gggtgggagc     120
cctaggggat ccatggagtt cgttaacaaa cagttcaact ataaagaccc agttaacggt     180
gttgacattg cttacatcaa atcccgaac gctggccaga tgcagccggt aaaggcattc     240
aaaatccaca caaaatctg ggttatcccg gaacgtgata cctttactaa cccggaagaa     300
ggtgacctga acccgccacc ggaagcgaaa caggtgccgg tatcttacta tgactccacc     360
tacctgtcta ccgataacga aaaggacaac tacctgaaag tgttactaa actgttcgag     420 cgtatttact ccaccgacct gggccgtatg ctgctgacta gcatcgttcg cggtatcccg     480
```

```
ttctggggcg gttctaccat cgataccgaa ctgaaagtaa tcgacactaa ctgcatcaac    540
gttattcagc cggacggttc ctatcgttcc gaagaactga acctggtgat catcggcccg    600
tctgctgata tcatccagtt cgagtgtaag agctttggtc acgaagttct gaacctcacc    660
cgtaacggct acggttccac tcagtacatc cgtttctctc cggacttcac cttcggtttt    720
gaagaatccc tggaagtaga cacgaaccca ctgctgggcg ctggtaaatt cgcaactgat    780
cctgcggtta ccctggctca cgaactgatt catgcaggcc accgcctgta cggtatcgcc    840
atcaatccga accgtgtctt caaagttaac accaacgcgt attacgagat gtccggtctg    900
gaagttagct tcgaagaact gcgtactttt ggcggtcacg acgctaaatt catcgactct    960
ctgcaagaaa acgagttccg tctgtactac tataacaagt caaagatat cgcatccacc    1020
ctgaacaaag cgaaatccat cgtgggtacc actgcttctc tccagtacat gaagaacgtt    1080
tttaaagaaa ataccctgct cagcgaagac acctccggca aattctctgt agacaagttg    1140
aaattcgata aactttacaa aatgctgact gaaatttaca ccgaagacaa cttcgttaag    1200
ttctttaaag ttctgaaccg caaaacctat ctgaacttcg acaaggcagt attcaaaatc    1260
aacatcgtgc cgaaagttaa ctacactatc tacgatggtt caacctgcg taacaccaac    1320
ctggctgcta ttttaacgg ccagaacacg gaaatcaaca acatgaactt cacaaaactg    1380
aaaaacttca ctggtctgtt cgagttttac aagctgctgt gcgtcgacgg catcattacc    1440
tccaaaacta aatctctgat agaaggtaga acaaagcgc tgaacctgca gtgtatcaag    1500
gttaacaact gggatttatt cttcagcccg agtgaagaca acttcaccaa cgacctgaac    1560
aaaggtgaag aaatcacctc agatactaac atcgaagcag ccgaagaaaa catctcgctg    1620
gacctgatcc agcagtacta cctgaccttt aatttcgaca acgagccgga aaacatttct    1680
atcgaaaacc tgagctctga tatcatcggc cagctggaac tgatgccgaa catcgaacgt    1740
ttcccaaacg gtaaaaagta cgagctggac aaatataccagtgttccacta cctgcgcgcg   1800
caggaatttg aacacggcaa atcccgtatc gcactgacta actccgttaa cgaagctctg    1860
ctcaacccgt cccgtgtata caccttcttc tctagcgact acgtgaaaaa ggtcaacaaa    1920
gcgactgaag ctgcaatgtt cttgggttgg gttgaacagc ttgtttatga ttttaccgac    1980
gagacgtccg aagtatctac taccgacaaa attgcggata tcactatcat catcccgtac    2040
atcggtccgg ctctgaacat tggcaacatg ctgtacaaag acgacttcgt tggcgcactg    2100
atcttctccg gtgcggtgat cctgctggag ttcatcccgg aaatcgccat cccggtactg    2160
ggcacctttg ctctggtttc ttacattgca acaaggttc tgactgtaca aaccatcgac    2220
aacgcgctga gcaaacgtaa cgaaaaatgg gatgaagttt acaaatatat cgtgaccaac    2280
tggctggcta aggttaatac tcagatcgac ctcatccgca aaaaaatgaa agaagcactg    2340
gaaaaccagg cggaagctac caaggcaatc attaactacc agtacaacca gtacaccgag    2400
gaagaaaaaa acaacatcaa cttcaacatc gacgatctgt cctctaaact gaacgaatcc    2460
atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgcccctgc tgaaatacat ttacgacaac cgtggcactc tgatcggtca ggttgatcgt    2640
ctgaaggaca aagtgaacaa taccttatcg accgacatcc ctttttcagct cagtaaatat    2700
gtcgataacc aacgccttt gtccactcta gactag                                2736
```

<210> SEQ ID NO 64

-continued

```
<211> LENGTH: 911
<212> TYPE: PRT
<213> ORGANISM: Artificial Sequence
<220> FEATURE:
<223> OTHER INFORMATION: chemically synthesized fusion protein

<400> SEQUENCE: 64
```

| | | | | | | | | | | | | | | |
|---|---|---|---|---|---|---|---|---|---|---|---|---|---|---|
| Leu | Gly | Ile | Glu | Gly | Arg | Phe | Gly | Phe | Thr | Gly | Ala | Arg | Lys | Ser |
| 1 | | | | 5 | | | | | 10 | | | | | 15 |
| Ala | Arg | Lys | Leu | Ala | Asn | Gln | Thr | Ser | Gly | Gly | Gly | Ser | Gly | Gly |
| | | | 20 | | | | | 25 | | | | | 30 | |
| Gly | Gly | Ser | Gly | Gly | Gly | Ser | Pro | Arg | Gly | Ser | Met | Glu | Phe | Val |
| | | 35 | | | | | 40 | | | | | 45 | | |
| Asn | Lys | Gln | Phe | Asn | Tyr | Lys | Asp | Pro | Val | Asn | Gly | Val | Asp | Ile | Ala |
| | 50 | | | | | 55 | | | | | 60 | | | | |
| Tyr | Ile | Lys | Ile | Pro | Asn | Ala | Gly | Gln | Met | Gln | Pro | Val | Lys | Ala | Phe |
| 65 | | | | | 70 | | | | 75 | | | | | 80 | |
| Lys | Ile | His | Asn | Lys | Ile | Trp | Val | Ile | Pro | Glu | Arg | Asp | Thr | Phe | Thr |
| | | | 85 | | | | | 90 | | | | | 95 | | |
| Asn | Pro | Glu | Glu | Gly | Asp | Leu | Asn | Pro | Pro | Glu | Ala | Lys | Gln | Val |
| | | | 100 | | | | | 105 | | | | | 110 | |
| Pro | Val | Ser | Tyr | Tyr | Asp | Ser | Thr | Tyr | Leu | Ser | Thr | Asp | Asn | Glu | Lys |
| | | 115 | | | | | 120 | | | | | 125 | | | |
| Asp | Asn | Tyr | Leu | Lys | Gly | Val | Thr | Lys | Leu | Phe | Glu | Arg | Ile | Tyr | Ser |
| | 130 | | | | | 135 | | | | | 140 | | | | |
| Thr | Asp | Leu | Gly | Arg | Met | Leu | Leu | Thr | Ser | Ile | Val | Arg | Gly | Ile | Pro |
| 145 | | | | | 150 | | | | | 155 | | | | | 160 |
| Phe | Trp | Gly | Gly | Ser | Thr | Ile | Asp | Thr | Glu | Leu | Lys | Val | Ile | Asp | Thr |
| | | | | 165 | | | | | 170 | | | | | 175 | |
| Asn | Cys | Ile | Asn | Val | Ile | Gln | Pro | Asp | Gly | Ser | Tyr | Arg | Ser | Glu | Glu |
| | | | 180 | | | | | 185 | | | | | 190 | | |
| Leu | Asn | Leu | Val | Ile | Ile | Gly | Pro | Ser | Ala | Asp | Ile | Ile | Gln | Phe | Glu |
| | | | 195 | | | | | 200 | | | | | 205 | | |
| Cys | Lys | Ser | Phe | Gly | His | Glu | Val | Leu | Asn | Leu | Thr | Arg | Asn | Gly | Tyr |
| | 210 | | | | | 215 | | | | | 220 | | | | |
| Gly | Ser | Thr | Gln | Tyr | Ile | Arg | Phe | Ser | Pro | Asp | Phe | Thr | Phe | Gly | Phe |
| 225 | | | | | 230 | | | | | 235 | | | | | 240 |
| Glu | Glu | Ser | Leu | Glu | Val | Asp | Thr | Asn | Pro | Leu | Leu | Gly | Ala | Gly | Lys |
| | | | | 245 | | | | | 250 | | | | | 255 | |
| Phe | Ala | Thr | Asp | Pro | Ala | Val | Thr | Leu | Ala | His | Glu | Leu | Ile | His | Ala |
| | | | | 260 | | | | | 265 | | | | | 270 | |
| Gly | His | Arg | Leu | Tyr | Gly | Ile | Ala | Ile | Asn | Pro | Asn | Arg | Val | Phe | Lys |
| | | | 275 | | | | | 280 | | | | | 285 | | |
| Val | Asn | Thr | Asn | Ala | Tyr | Tyr | Glu | Met | Ser | Gly | Leu | Glu | Val | Ser | Phe |
| | 290 | | | | | 295 | | | | | 300 | | | | |
| Glu | Glu | Leu | Arg | Thr | Phe | Gly | Gly | His | Asp | Ala | Lys | Phe | Ile | Asp | Ser |
| 305 | | | | | 310 | | | | | 315 | | | | | 320 |
| Leu | Gln | Glu | Asn | Glu | Phe | Arg | Leu | Tyr | Tyr | Tyr | Asn | Lys | Phe | Lys | Asp |
| | | | | 325 | | | | | 330 | | | | | 335 | |
| Ile | Ala | Ser | Thr | Leu | Asn | Lys | Ala | Lys | Ser | Ile | Val | Gly | Thr | Thr | Ala |
| | | | 340 | | | | | 345 | | | | | 350 | | |
| Ser | Leu | Gln | Tyr | Met | Lys | Asn | Val | Phe | Lys | Glu | Lys | Tyr | Leu | Leu | Ser |
| | | 355 | | | | | 360 | | | | | 365 | | | |
| Glu | Asp | Thr | Ser | Gly | Lys | Phe | Ser | Val | Asp | Lys | Leu | Lys | Phe | Asp | Lys |
| | 370 | | | | | 375 | | | | | 380 | | | | |

```
Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
                405                 410                 415

Val Phe Lys Ile Asn Ile Val Pro Lys Val Asn Tyr Thr Ile Tyr Asp
                420                 425                 430

Gly Phe Asn Leu Arg Asn Thr Asn Leu Ala Ala Asn Phe Asn Gly Gln
                435                 440                 445

Asn Thr Glu Ile Asn Asn Met Asn Phe Thr Lys Leu Lys Asn Phe Thr
                450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Leu
                485                 490                 495

Gln Cys Ile Lys Val Asn Asn Trp Asp Leu Phe Phe Ser Pro Ser Glu
                500                 505                 510

Asp Asn Phe Thr Asn Asp Leu Asn Lys Gly Glu Glu Ile Thr Ser Asp
                515                 520                 525

Thr Asn Ile Glu Ala Ala Glu Glu Asn Ile Ser Leu Asp Leu Ile Gln
530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
                580                 585                 590

Thr Met Phe His Tyr Leu Arg Ala Gln Glu Phe Glu His Gly Lys Ser
                595                 600                 605

Arg Ile Ala Leu Thr Asn Ser Val Asn Glu Ala Leu Leu Asn Pro Ser
                610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
                660                 665                 670

Asp Ile Thr Ile Ile Ile Pro Tyr Ile Gly Pro Ala Leu Asn Ile Gly
                675                 680                 685

Asn Met Leu Tyr Lys Asp Asp Phe Val Gly Ala Leu Ile Phe Ser Gly
                690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
                740                 745                 750

Val Tyr Lys Tyr Ile Val Thr Asn Trp Leu Ala Lys Val Asn Thr Gln
                755                 760                 765

Ile Asp Leu Ile Arg Lys Lys Met Lys Glu Ala Leu Glu Asn Gln Ala
                770                 775                 780

Glu Ala Thr Lys Ala Ile Ile Asn Tyr Gln Tyr Asn Gln Tyr Thr Glu
785                 790                 795                 800
```

```
Glu Lys Asn Asn Ile Asn Phe Asn Ile Asp Asp Leu Ser Ser Lys
            805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
            835                 840                 845

Val Lys Arg Leu Glu Asp Phe Asp Ala Ser Leu Lys Asp Ala Leu Leu
        850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
                900                 905                 910
```

<210> SEQ ID NO 65
<211> LENGTH: 177
<212> TYPE: DNA
<213> ORGANISM: Artificial Sequence
<220> FEATURE:
<223> OTHER INFORMATION: chemically synthesized polynucleotide encoding
      linker

<400> SEQUENCE: 65

```
ggatccacgc acgtcgacgg catcattacc tccaaaacta atctctgat agaaggtaga      60 tttggcggtt tcacgggcgc acgcaaatca gcgcgtaaat tagctaacca ggcgctagcg    120
ggtggtggtg gttctgcact agtgctgcag acgcacggtc tagaatgata aaagctt      177
```

<210> SEQ ID NO 66
<211> LENGTH: 192
<212> TYPE: DNA
<213> ORGANISM: Artificial Sequence
<220> FEATURE:
<223> OTHER INFORMATION: chemically synthesized polynucleotide encoding
      linker

<400> SEQUENCE: 66

```
ggatccacgc acgtcgacgg catcattacc tccaaaacta atctctgat agaaggtaga      60 tttggcggtt tcacgggcgc acgcaaatca gcgcgtaaat tagctaacca ggcgctagcg    120
ggtggtggtg gttctggtgg tggtggttct gcactagtgc tgcagacgca cggtctagaa   180
tgataaaagc tt                                                        192
```

<210> SEQ ID NO 67
<211> LENGTH: 222
<212> TYPE: DNA
<213> ORGANISM: Artificial Sequence
<220> FEATURE:
<223> OTHER INFORMATION: chemically synthesized polynucleotide encoding
      linker

<400> SEQUENCE: 67

```
ggatccacgc acgtcgacgg catcattacc tccaaaacta atctctgat agaaggtaga      60 tttggcggtt tcacgggcgc acgcaaatca gcgcgtaaat tagctaacca ggcgctagcg    120
ggtggtggtg gttctggtgg tggtggttct ggtggtggtg gttctggtgg tggtggttct   180
gcactagtgc tgcagacgca cggtctagaa tgataaaagc tt                       222
```

<210> SEQ ID NO 68
<211> LENGTH: 237

```
<212> TYPE: DNA
<213> ORGANISM: Artificial Sequence
<220> FEATURE:
<223> OTHER INFORMATION: chemically synthesized polynucleotide encoding
      linker

<400> SEQUENCE: 68
ggatccacgc acgtcgacgg catcattacc tccaaaacta atctctgat agaaggtaga      60 tttggcggtt tcacgggcgc acgcaaatca gcgcgtaaat tagctaacca ggcgctagcg    120
ggtggtggtg gttctggtgg tggtggttct ggtggtggtg gttctggtgg tggtggttct   180
ggtggtggtg gttctgcact agtgctgcag acgcacggtc tagaatgata aaagctt       237

<210> SEQ ID NO 69
<211> LENGTH: 228
<212> TYPE: DNA
<213> ORGANISM: Artificial Sequence
<220> FEATURE:
<223> OTHER INFORMATION: chemically synthesized polynucleotide encoding
      linker

<400> SEQUENCE: 69
ggatccacgc acgtcgacgg catcattacc tccaaaacta atctctgat agaaggtaga      60 tttggcggtt tcacgggcgc acgcaaatca gcgcgtaaat tagctaacca ggcgctagcg    120
gctgaagctg ctgctaaaga agctgctgct aaagaagctg ctgctaaagc tggtggcggt   180
ggttccgcac tagtgctgca gacgcacggt ctagaatgat aaaagctt                228

<210> SEQ ID NO 70
<211> LENGTH: 2694
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 70
ggatccatgg agttcgttaa caaacagttc aactataaag acccagttaa cggtgttgac      60
attgcttaca tcaaaatccc gaacgctggc cagatgcagc cggtaaaggc attcaaaatc    120
cacaacaaaa tctgggttat cccggaacgt gatacccttta ctaacccgga agaaggtgac   180
ctgaacccgc caccggaagc gaaacaggtg ccggtatctt actatgactc cacctacctg   240
tctaccgata cgaaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg gttcctatcg ttccgaagaa ctgaacctgg tgatcatcgg cccgtctgct   480
gatatcatcc agttcgagtg taagagctttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta attcgcaac tgatcctgcg   660 gttaccctgg ctcacgaact gattcatgca ggccaccgcc tgtacggtat cgccatcaat   720
ccgaaccgtg tcttcaaagt taacaccaac gcgtattacg agatgtccgg tctggaagtt   780
agcttcgaag aactgcgtac ttttggcggt cacgacgcta aattcatcga ctctctgcaa   840
gaaaacgagt ccgtctgta ctactataac aagttcaaag atatcgcatc caccctgaac   900
aaagcgaaat ccatcgtggg taccactgct ctctctccagt acatgaagaa cgttttttaaa   960 gaaaaatacc tgctcagcga agacacctcc ggcaaattct ctgtagacaa gttgaaattc  1020
```

-continued

```
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atcagcgcgt    1380
aaattagcta accaggcgct agcgggtggt ggtggttctg gtggtggtgg ttctgcacta    1440
gtgctgcagt gtatcaaggt taacaactgg gatttattct tcagcccgag tgaagacaac    1500
ttcaccaacg acctgaacaa aggtgaagaa atcacctcag atactaacat cgaagcagcc    1560
gaagaaaaca tctcgctgga cctgatccag cagtactacc tgacctttaa tttcgacaac    1620
gagccggaaa acatttctat cgaaaacctg agctctgata tcatcggcca gctggaactg    1680
atgccgaaca tcgaacgttt cccaaacggt aaaaagtacg agctggacaa atataccatg    1740
ttccactacc tgcgcgcgca ggaatttgaa cacggcaaat cccgtatcgc actgactaac    1800
tccgttaacg aagctctgct caacccgtcc cgtgtataca ccttcttctc tagcgactac    1860
gtgaaaaagg tcaacaaagc gactgaagct gcaatgttct tgggttgggt tgaacagctt    1920
gtttatgatt ttaccgacga gacgtccgaa gtatctacta ccgacaaaat tgcggatatc    1980
actatcatca tcccgtacat cggtccggct ctgaacattg caacatgct gtacaaagac    2040 gacttcgttg gcgcactgat cttctccggt gcggtgatcc tgctggagtt catcccggaa    2100
atcgccatcc cggtactggg cacctttgct ctggtttctt acattgcaaa caaggttctg    2160
actgtacaaa ccatcgacaa cgcgctgagc aaacgtaacg aaaaatggga tgaagtttac    2220
aaatatatcg tgaccaactg gctggctaag gttaatactc agatcgacct catccgcaaa    2280
aaaatgaaag aagcactgga aaaccaggcg gaagctacca aggcaatcat taactaccag    2340
tacaaccagt acaccgagga agaaaaaaac aacatcaact tcaacatcga cgatctgtcc    2400
tctaaactga cgaatccat caacaaagct atgatcaaca tcaacaagtt cctgaaccag    2460
tgctctgtaa gctatctgat gaactccatg atcccgtacg gtgttaaacg tctggaggac    2520
ttcgatgcgt ctctgaaaga cgccctgctg aaatacattt acgacaaccg tggcactctg    2580
atcggtcagg ttgatcgtct gaaggacaaa gtgaacaata ccttatcgac cgacatccct    2640
tttcagctca gtaaatatgt cgataaccaa cgccttttgt ccactctaga ctag          2694
```

<210> SEQ ID NO 71
<211> LENGTH: 897
<212> TYPE: PRT
<213> ORGANISM: Artificial Sequence
<220> FEATURE:
<223> OTHER INFORMATION: chemically synthesized fusion protein

<400> SEQUENCE: 71

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60
```

-continued

```
Pro Glu Ala Lys Gln Val Pro Val Ser Tyr Tyr Asp Ser Thr Tyr Leu
 65                  70                  75                  80

Ser Thr Asp Asn Glu Lys Asp Asn Tyr Leu Lys Gly Val Thr Lys Leu
                 85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
            115                 120                 125

Leu Lys Val Ile Asp Thr Asn Cys Ile Asn Val Ile Gln Pro Asp Gly
        130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
            195                 200                 205

Leu Leu Gly Ala Gly Lys Phe Ala Thr Asp Pro Ala Val Thr Leu Ala
        210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
        290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
        370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Ser Ala Arg Lys Leu Ala Asn
        450                 455                 460

Gln Ala Leu Ala Gly Gly Gly Ser Gly Gly Gly Ser Ala Leu
465                 470                 475                 480

Val Leu Gln Cys Ile Lys Val Asn Asn Trp Asp Leu Phe Phe Ser Pro
```

-continued

```
                485                 490                 495
Ser Glu Asp Asn Phe Thr Asn Asp Leu Asn Lys Gly Glu Glu Ile Thr
                500                 505                 510

Ser Asp Thr Asn Ile Glu Ala Ala Glu Glu Asn Ile Ser Leu Asp Leu
                515                 520                 525

Ile Gln Gln Tyr Tyr Leu Thr Phe Asn Phe Asp Asn Glu Pro Glu Asn
                530                 535                 540

Ile Ser Ile Glu Asn Leu Ser Ser Asp Ile Ile Gly Gln Leu Glu Leu
545                 550                 555                 560

Met Pro Asn Ile Glu Arg Phe Pro Asn Gly Lys Lys Tyr Glu Leu Asp
                565                 570                 575

Lys Tyr Thr Met Phe His Tyr Leu Arg Ala Gln Glu Phe Glu His Gly
                580                 585                 590

Lys Ser Arg Ile Ala Leu Thr Asn Ser Val Asn Glu Ala Leu Leu Asn
                595                 600                 605

Pro Ser Arg Val Tyr Thr Phe Phe Ser Ser Asp Tyr Val Lys Lys Val
                610                 615                 620

Asn Lys Ala Thr Glu Ala Ala Met Phe Leu Gly Trp Val Glu Gln Leu
625                 630                 635                 640

Val Tyr Asp Phe Thr Asp Glu Thr Ser Glu Val Ser Thr Thr Asp Lys
                645                 650                 655

Ile Ala Asp Ile Thr Ile Ile Ile Pro Tyr Ile Gly Pro Ala Leu Asn
                660                 665                 670

Ile Gly Asn Met Leu Tyr Lys Asp Asp Phe Val Gly Ala Leu Ile Phe
                675                 680                 685

Ser Gly Ala Val Ile Leu Leu Glu Phe Ile Pro Glu Ile Ala Ile Pro
                690                 695                 700

Val Leu Gly Thr Phe Ala Leu Val Ser Tyr Ile Ala Asn Lys Val Leu
705                 710                 715                 720

Thr Val Gln Thr Ile Asp Asn Ala Leu Ser Lys Arg Asn Glu Lys Trp
                725                 730                 735

Asp Glu Val Tyr Lys Tyr Ile Val Thr Asn Trp Leu Ala Lys Val Asn
                740                 745                 750

Thr Gln Ile Asp Leu Ile Arg Lys Lys Met Lys Glu Ala Leu Glu Asn
                755                 760                 765

Gln Ala Glu Ala Thr Lys Ala Ile Ile Asn Tyr Gln Tyr Asn Gln Tyr
                770                 775                 780

Thr Glu Glu Glu Lys Asn Asn Ile Asn Phe Asn Ile Asp Asp Leu Ser
785                 790                 795                 800

Ser Lys Leu Asn Glu Ser Ile Asn Lys Ala Met Ile Asn Ile Asn Lys
                805                 810                 815

Phe Leu Asn Gln Cys Ser Val Ser Tyr Leu Met Asn Ser Met Ile Pro
                820                 825                 830

Tyr Gly Val Lys Arg Leu Glu Asp Phe Asp Ala Ser Leu Lys Asp Ala
                835                 840                 845

Leu Leu Lys Tyr Ile Tyr Asp Asn Arg Gly Thr Leu Ile Gly Gln Val
850                 855                 860

Asp Arg Leu Lys Asp Lys Val Asn Asn Thr Leu Ser Thr Asp Ile Pro
865                 870                 875                 880

Phe Gln Leu Ser Lys Tyr Val Asp Asn Gln Arg Leu Leu Ser Thr Leu
                885                 890                 895

Asp
```

<210> SEQ ID NO 72
<211> LENGTH: 2724
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 72

| | | | | | |
|---|---|---|---|---|---|
| ggatccatgg | agttcgttaa | caaacagttc | aactataaag | acccagttaa | cggtgttgac | 60 |
| attgcttaca | tcaaaatccc | gaacgctggc | cagatgcagc | cggtaaaggc | attcaaaatc | 120 |
| cacaacaaaa | tctgggttat | cccggaacgt | gataccttta | ctaacccgga | agaaggtgac | 180 |
| ctgaacccgc | caccggaagc | gaaacaggtg | ccggtatctt | actatgactc | cacctacctg | 240 |
| tctaccgata | acgaaaagga | caactacctg | aaaggtgtta | ctaaactgtt | cgagcgtatt | 300 |
| tactccaccg | acctgggccg | tatgctgctg | actagcatcg | ttcgcggtat | cccgttctgg | 360 |
| ggcggttcta | ccatcgatac | cgaactgaaa | gtaatcgaca | ctaactgcat | caacgttatt | 420 |
| cagccggacg | gttcctatcg | ttccgaagaa | ctgaacctgg | tgatcatcgg | cccgtctgct | 480 |
| gatatcatcc | agttcgagtg | taagagcttt | ggtcacgaag | ttctgaacct | cacccgtaac | 540 |
| ggctacggtt | ccactcagta | catccgtttc | tctccggact | tcaccttcgg | tttttgaagaa | 600 |
| tccctggaag | tagacacgaa | cccactgctg | ggcgctggta | aattcgcaac | tgatcctgcg | 660 |
| gttaccctgg | ctcacgaact | gattcatgca | ggccaccgcc | tgtacggtat | cgccatcaat | 720 |
| ccgaaccgtg | tcttcaaagt | taacaccaac | gcgtattacg | agatgtccgg | tctggaagtt | 780 |
| agcttcgaag | aactgcgtac | ttttggcggt | cacgacgcta | aattcatcga | ctctctgcaa | 840 |
| gaaaacgagt | tccgtctgta | ctactataac | aagttcaaag | atatcgcatc | cacccctgaac | 900 |
| aaagcgaaat | ccatcgtggg | taccactgct | tctctccagt | acatgaagaa | cgttttttaaa | 960 |
| gaaaaatacc | tgctcagcga | agacacctcc | ggcaaattct | ctgtagacaa | gttgaaattc | 1020 |
| gataaacttt | acaaaatgct | gactgaaatt | tacaccgaag | acaacttcgt | taagttcttt | 1080 |
| aaagttctga | accgcaaaac | ctatctgaac | ttcgacaagg | cagtattcaa | atcaacatc | 1140 |
| gtgccgaaag | ttaactacac | tatctacgat | ggtttcaacc | tgcgtaacac | caacctggct | 1200 |
| gctaattttta | acgccagaa | cacggaaatc | aacaacatga | acttcacaaa | actgaaaaac | 1260 |
| ttcactggtc | tgttcgagtt | ttacaagctg | ctgtgcgtcg | acggcatcat | acctccaaa | 1320 |
| actaaatctc | tgatagaagg | tagatttggc | ggttcacgg | gcgcacgcaa | atcagcgcgt | 1380 |
| aaattagcta | accaggcgct | agcgggtggt | ggtggttctg | gtggtggtgg | ttctggtggt | 1440 |
| ggtggttctg | gtggtggtgg | ttctgcacta | gtgctgcagt | gtatcaaggt | taacaactgg | 1500 |
| gatttattct | tcagcccgag | tgaagacaac | ttcaccaacg | acctgaacaa | aggtgaagaa | 1560 |
| atcacctcag | atactaacat | cgaagcagcc | gaagaaaaca | tctcgctgga | cctgatccag | 1620 |
| cagtactacc | tgacctttaa | tttcgacaac | gagccggaaa | acatttctat | cgaaaacctg | 1680 |
| agctctgata | tcatcggcca | gctggaactg | atgccgaaca | tcgaacgttt | cccaaacggt | 1740 |
| aaaaagtacg | agctggacaa | atataccatg | ttccactacc | tgcgcgcgca | ggaatttgaa | 1800 |
| cacggcaaat | cccgtatcgc | actgactaac | tccgttaacg | aagctctgct | caacccgtcc | 1860 |
| cgtgtataca | ccttcttctc | tagcgactac | gtgaaaaagg | tcaacaaagc | gactgaagct | 1920 |
| gcaatgttct | tgggttgggt | tgaacagctt | gtttatgatt | ttaccgacga | gacgtccgaa | 1980 |
| gtatctacta | ccgacaaaat | tgcggatatc | actatcatca | tcccgtacat | cggtccggct | 2040 |

-continued

```
ctgaacattg gcaacatgct gtacaaagac gacttcgttg gcgcactgat cttctccggt      2100
gcggtgatcc tgctggagtt catcccggaa atcgccatcc cggtactggg cacctttgct      2160
ctggtttctt acattgcaaa caaggttctg actgtacaaa ccatcgacaa cgcgctgagc      2220
aaacgtaacg aaaaatggga tgaagtttac aaatatatcg tgaccaactg gctggctaag      2280
gttaatactc agatcgacct catccgcaaa aaaatgaaag aagcactgga aaaccaggcg      2340
gaagctacca aggcaatcat taactaccag tacaaccagt acaccgagga agaaaaaaac      2400
aacatcaact tcaacatcga cgatctgtcc tctaaactga cgaatccat  caacaaagct      2460 atgatcaaca tcaacaagtt cctgaaccag tgctctgtaa gctatctgat gaactccatg      2520
atcccgtacg gtgttaaacg tctggaggac ttcgatgcgt ctctgaaaga cgccctgctg      2580
aaatacattt acgacaaccg tggcactctg atcggtcagg ttgatcgtct gaaggacaaa      2640
gtgaacaata ccttatcgac cgacatccct tttcagctca gtaaatatgt cgataaccaa      2700
cgccttttgt ccactctaga ctag                                             2724
```

<210> SEQ ID NO 73
<211> LENGTH: 907
<212> TYPE: PRT
<213> ORGANISM: Artificial Sequence
<220> FEATURE:
<223> OTHER INFORMATION: chemically synthesized fusion protein

<400> SEQUENCE: 73

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240
```

-continued

```
Pro Asn Arg Val Phe Lys Val Asn Thr Asn Ala Tyr Tyr Glu Met Ser
            245                 250                 255

Gly Leu Glu Val Ser Phe Glu Glu Leu Arg Thr Phe Gly Gly His Asp
        260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Gly Gly
465                 470                 475                 480

Gly Gly Ser Gly Gly Gly Gly Ser Ala Leu Val Leu Gln Cys Ile Lys
                485                 490                 495

Val Asn Asn Trp Asp Leu Phe Phe Ser Pro Ser Glu Asp Asn Phe Thr
            500                 505                 510

Asn Asp Leu Asn Lys Gly Glu Glu Ile Thr Ser Asp Thr Asn Ile Glu
        515                 520                 525

Ala Ala Glu Glu Asn Ile Ser Leu Asp Leu Ile Gln Gln Tyr Tyr Leu
    530                 535                 540

Thr Phe Asn Phe Asp Asn Glu Pro Glu Asn Ile Ser Ile Glu Asn Leu
545                 550                 555                 560

Ser Ser Asp Ile Ile Gly Gln Leu Glu Leu Met Pro Asn Ile Glu Arg
                565                 570                 575

Phe Pro Asn Gly Lys Lys Tyr Glu Leu Asp Lys Tyr Thr Met Phe His
            580                 585                 590

Tyr Leu Arg Ala Gln Glu Phe Glu His Gly Lys Ser Arg Ile Ala Leu
        595                 600                 605

Thr Asn Ser Val Asn Glu Ala Leu Leu Asn Pro Ser Arg Val Tyr Thr
    610                 615                 620

Phe Phe Ser Ser Asp Tyr Val Lys Lys Val Asn Lys Ala Thr Glu Ala
625                 630                 635                 640

Ala Met Phe Leu Gly Trp Val Glu Gln Leu Val Tyr Asp Phe Thr Asp
                645                 650                 655

Glu Thr Ser Glu Val Ser Thr Thr Asp Lys Ile Ala Asp Ile Thr Ile
```

```
                  660                 665                 670
Ile Ile Pro Tyr Ile Gly Pro Ala Leu Asn Ile Gly Asn Met Leu Tyr
            675                 680                 685

Lys Asp Asp Phe Val Gly Ala Leu Ile Phe Ser Gly Ala Val Ile Leu
690                 695                 700

Leu Glu Phe Ile Pro Glu Ile Ala Ile Pro Val Leu Gly Thr Phe Ala
705                 710                 715                 720

Leu Val Ser Tyr Ile Ala Asn Lys Val Leu Thr Val Gln Thr Ile Asp
            725                 730                 735

Asn Ala Leu Ser Lys Arg Asn Glu Lys Trp Asp Glu Val Tyr Lys Tyr
            740                 745                 750

Ile Val Thr Asn Trp Leu Ala Lys Val Asn Thr Gln Ile Asp Leu Ile
            755                 760                 765

Arg Lys Lys Met Lys Glu Ala Leu Glu Asn Gln Ala Glu Ala Thr Lys
            770                 775                 780

Ala Ile Ile Asn Tyr Gln Tyr Asn Gln Tyr Thr Glu Glu Glu Lys Asn
785                 790                 795                 800

Asn Ile Asn Phe Asn Ile Asp Asp Leu Ser Ser Lys Leu Asn Glu Ser
            805                 810                 815

Ile Asn Lys Ala Met Ile Asn Ile Asn Lys Phe Leu Asn Gln Cys Ser
            820                 825                 830

Val Ser Tyr Leu Met Asn Ser Met Ile Pro Tyr Gly Val Lys Arg Leu
            835                 840                 845

Glu Asp Phe Asp Ala Ser Leu Lys Asp Ala Leu Leu Lys Tyr Ile Tyr
            850                 855                 860

Asp Asn Arg Gly Thr Leu Ile Gly Gln Val Asp Arg Leu Lys Asp Lys
865                 870                 875                 880

Val Asn Asn Thr Leu Ser Thr Asp Ile Pro Phe Gln Leu Ser Lys Tyr
            885                 890                 895

Val Asp Asn Gln Arg Leu Leu Ser Thr Leu Asp
            900                 905

<210> SEQ ID NO 74
<211> LENGTH: 207
<212> TYPE: DNA
<213> ORGANISM: Artificial Sequence
<220> FEATURE:
<223> OTHER INFORMATION: chemically synthesized polynucleotide encoding
      linker

<400> SEQUENCE: 74
ggatccacgc acgtcgacgg catcattacc tccaaaacta aatctgacga tgacgataaa      60
tttggcggtt tcacgggcgc acgcaaatca gcgcgtaaac gtaagaacca ggcgctagcg     120
ggcggtggcg gtagcggcgg tggcggtagc ggcggtggcg gtagcgcact agtgctgcag     180
acgcacggtc tagaatgata aaagctt                                         207

<210> SEQ ID NO 75
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 75
ggatccatgg agttcgttaa caacagttc aactataaag acccagttaa cggtgttgac      60
```

```
attgcttaca tcaaaatccc gaacgctggc cagatgcagc cggtaaaggc attcaaaatc    120
cacaacaaaa tctgggttat cccggaacgt gataccttta ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgttttaaa     960 gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200 gctaattta acggccagaa cacggaaatc aacaacatga acttcacaaa actgaaaaac    1260
ttcactggtc tgttcgagtt ttacaagctg ctgtgcgtcg acggcatcat acctccaaa    1320 actaaatctg acgatgacga taaatttggc ggtttcacgg cgcacgcaa atcagcgcgt    1380 aaacgtaaga accaggcgct agcgggcggt ggcggtagcg gcggtggcgg tagcggcggt   1440
ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa cggtaaaaaa gtacgagctg   1740
gacaaatata ccatgttcca ctacctgcgc gcgcaggaat ttgaacacgg caaatcccgt   1800
atcgcactga ctaactccgt taacgaagct ctgctcaacc cgtcccgtgt ataccttc    1860 ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca agacgactt cgttggcgca ctgatcttct ccggtgcggt gatcctgctg    2100
gagttcatcc cggaaatcgc catcccggta ctgggcacct ttgctctggt ttcttacatt   2160
gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaaat gaaagaagca ctggaaaacc aggcggaagc taccaaggca   2340
atcattaact accagtacaa ccagtacacc gaggaagaaa aaaacaacat caacttcaac   2400
atcgacgatc tgtcctctaa actgaacgaa tccatcaaca aagctatgat caacatcaac   2460
```

-continued

```
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccttα    2640 tcgaccgaca tcccttttca gctcagtaaa tatgtcgata ccaacgcct tttgtccact     2700 ctagactag                                                              2709
```

<210> SEQ ID NO 76
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 76

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
```

-continued

```
            305                 310                 315                 320
Glu Lys Tyr Leu Leu Ser Glu Asp Thr Ser Gly Lys Phe Ser Val Asp
                    325                 330                 335
Lys Leu Lys Phe Asp Lys Leu Tyr Lys Met Leu Thr Glu Ile Tyr Thr
                340                 345                 350
Glu Asp Asn Phe Val Lys Phe Phe Lys Val Leu Asn Arg Lys Thr Tyr
                355                 360                 365
Leu Asn Phe Asp Lys Ala Val Phe Lys Ile Asn Ile Val Pro Lys Val
            370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
                420                 425                 430
Val Asp Gly Ile Ile Thr Ser Lys Thr Lys Ser Asp Asp Asp Asp Lys
            435                 440                 445
Phe Gly Gly Phe Thr Gly Ala Arg Lys Ser Ala Arg Lys Arg Lys Asn
450                 455                 460
Gln Ala Leu Ala Gly Gly Gly Ser Gly Gly Gly Ser Gly Gly
465                 470                 475                 480
Gly Gly Ser Ala Leu Val Leu Gln Cys Ile Lys Val Asn Asn Trp Asp
                485                 490                 495
Leu Phe Phe Ser Pro Ser Glu Asp Asn Phe Thr Asn Asp Leu Asn Lys
                500                 505                 510
Gly Glu Glu Ile Thr Ser Asp Thr Asn Ile Glu Ala Ala Glu Glu Asn
            515                 520                 525
Ile Ser Leu Asp Leu Ile Gln Gln Tyr Tyr Leu Thr Phe Asn Phe Asp
            530                 535                 540
Asn Glu Pro Glu Asn Ile Ser Ile Glu Asn Leu Ser Ser Asp Ile Ile
545                 550                 555                 560
Gly Gln Leu Glu Leu Met Pro Asn Ile Glu Arg Phe Pro Asn Gly Lys
                565                 570                 575
Lys Tyr Glu Leu Asp Lys Tyr Thr Met Phe His Tyr Leu Arg Ala Gln
                580                 585                 590
Glu Phe Glu His Gly Lys Ser Arg Ile Ala Leu Thr Asn Ser Val Asn
            595                 600                 605
Glu Ala Leu Leu Asn Pro Ser Arg Val Tyr Thr Phe Phe Ser Ser Asp
            610                 615                 620
Tyr Val Lys Lys Val Asn Lys Ala Thr Glu Ala Ala Met Phe Leu Gly
625                 630                 635                 640
Trp Val Glu Gln Leu Val Tyr Asp Phe Thr Asp Glu Thr Ser Glu Val
                645                 650                 655
Ser Thr Thr Asp Lys Ile Ala Asp Ile Thr Ile Ile Pro Tyr Ile
                660                 665                 670
Gly Pro Ala Leu Asn Ile Gly Asn Met Leu Tyr Lys Asp Asp Phe Val
            675                 680                 685
Gly Ala Leu Ile Phe Ser Gly Ala Val Ile Leu Leu Glu Phe Ile Pro
            690                 695                 700
Glu Ile Ala Ile Pro Val Leu Gly Thr Phe Ala Leu Val Ser Tyr Ile
705                 710                 715                 720
Ala Asn Lys Val Leu Thr Val Gln Thr Ile Asp Asn Ala Leu Ser Lys
                725                 730                 735
```

| | | | | | | | | | | | |
|---|---|---|---|---|---|---|---|---|---|---|---|
|Arg|Asn|Glu|Lys|Trp|Asp|Glu|Val|Tyr|Lys|Tyr|Ile|Val|Thr|Asn|Trp|
| |  |740|   |   |   |745|   |   |   |   |750|

Arg Asn Glu Lys Trp Asp Glu Val Tyr Lys Tyr Ile Val Thr Asn Trp
              740                 745                 750

Leu Ala Lys Val Asn Thr Gln Ile Asp Leu Ile Arg Lys Lys Met Lys
                755                 760                 765

Glu Ala Leu Glu Asn Gln Ala Glu Ala Thr Lys Ala Ile Ile Asn Tyr
            770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
                820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900

<210> SEQ ID NO 77
<211> LENGTH: 207
<212> TYPE: DNA
<213> ORGANISM: Artificial Sequence
<220> FEATURE:
<223> OTHER INFORMATION: chemically synthesized polynucleotide encoding
      linker

<400> SEQUENCE: 77
ggatccacgc acgtcgacgg catcattacc tccaaaacta aatctctgat agaaggtaga      60
tttggcggtt tcacgggcgc acgcaaatca gcgcgtaaac gtaagaacca ggcgctagcg     120
ggcggtggcg gtagcggcgg tggcggtagc ggcggtggcg gtagcgcact agtgctgcag     180
acgcacggtc tagaatgata aagctt                                          207

<210> SEQ ID NO 78
<211> LENGTH: 2742
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 78
ggatccgaat tcatgccgat caccatcaac aacttcaact acagcgatcc ggtggataac      60
aaaaacatcc tgtacctgga tacccatctg aatccctggc gaacgaaccg gaaaaagcg     120 tttcgtatca ccggcaacat tgggttattc cggatcgttt tagccgtaac agcaacccg     180 aatctgaata accgccgcg tgttaccagc ccgaaaagcg gttattacga tccgaactat     240
ctgagcaccg atagcgataa agatacctcc tgaaagaaa tcatcaaact gttcaaacgc     300
atcaacagcc gtgaaattgg cgaagaactg atctatcgcc tgagcaccga tattccgttt     360
ccgggcaaca caacacccc gatcaacacc tttgatttcg atgtggattt caacagcgtt     420
gatgttaaaa cccgccaggg taacaattgg gtgaaaaccg gcagcattaa cccgagcgtg     480

```
attattaccg gtccgcgcga aaacattatt gatccggaaa ccagcacctt taaactgacc    540
aacaacacct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg cgatcgcgat tccgaacgat cagaccatta gcagcgtgac cagcaacatc    780
ttttacagcc agtacaacgt gaaactggaa tatgcggaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt atacccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccg gaaaacatgc tgtacctgtt caccaaattt   1320
tgcgtcgacg gcatcattac ctccaaaact aaatctctga tagaaggtag atttggcggt   1380
ttcacgggcg cacgcaaatc agcgcgtaaa cgtaagaacc aggcgctagc gggcggtggc   1440
ggtagcggcg gtggcggtag cggcggtggc ggtagcgcac tagtgctgca gtgtcgtgaa   1500
ctgctggtga aaaacaccga tctgccgttt attggcgata tcagcgatgt gaaaaccgat   1560
atcttcctgc gcaaagatat caacgaagaa accgaagtga tctactaccc ggataacgtg   1620
agcgttgatc aggtgatcct gagcaaaaac accagcgaac atggtcagct ggatctgctg   1680
tatccgagca ttgatagcga aagcgaaatt ctgccgggcg aaaaccaggt gttttacgat   1740
aaccgtaccc agaacgtgga ttacctgaac agctattact acctggaaag ccagaaactg   1800
agcgataacg tggaagattt tacctttacc cgcagcattg aagaagcgct ggataacagc   1860
gcgaaagttt acacctattt tccgacccctg gcgaacaaag ttaatgcggg tgttcagggc   1920
ggtctgtttc tgatgtgggc gaacgatgtg gtggaagatt tcaccaccaa catcctgcgt   1980
aaagataccc tggataaaat cagcgatgtt agcgcgatta ttccgtatat tggtccggcg   2040
ctgaacatta gcaatagcgt gcgtcgtggc aattttaccg aagcgtttgc ggttaccggt   2100
gtgaccattc tgctggaagc gttccggaa tttaccattc cggcgctggg tgcgtttgtg   2160
atctatagca aagtgcagga acgcaacgaa atcatcaaaa ccatcgataa ctgcctggaa   2220
cagcgtatta acgctggaaa agatagctat gaatggatga tgggcacctg gctgagccgt   2280
attatcacccc agttcaacaa catcagctac cagatgtacg atagcctgaa ctatcaggcg   2340
ggtgcgatta agcgaaaat cgatctggaa tacaaaaaat acagcggcag cgataaagaa   2400
aacatcaaaa gccaggttga aaacctgaaa aacagcctgg atgtgaaaat tagcgaagcg   2460
atgaataaca tcaacaaatt catccgcgaa tgcagcgtga cctacctgtt caaaaacatg   2520
ctgccgaaag tgatcgatga actgaacgaa tttgatcgca acaccaaagc gaaactgatc   2580
aacctgatcg atagccacaa cattattctg gtgggcgaag tggataaact gaaagcgaaa   2640
gttaacaaca gcttccagaa caccatcccg tttaacatct tcagctatac caacaacagc   2700
ctgctgaaag atatcatcaa cgaatacttc aatctagact ag                      2742
```

<210> SEQ ID NO 79

<211> LENGTH: 913
<212> TYPE: PRT
<213> ORGANISM: Artificial Sequence
<220> FEATURE:
<223> OTHER INFORMATION: chemically synthesized fusion protein

<400> SEQUENCE: 79

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

```
Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
            405                 410                 415

Gln Asn Leu Ser Arg Asn Pro Ala Leu Arg Lys Val Asn Pro Glu Asn
                420                 425                 430

Met Leu Tyr Leu Phe Thr Lys Phe Cys Val Asp Gly Ile Ile Thr Ser
            435                 440                 445

Lys Thr Lys Ser Leu Ile Glu Gly Arg Phe Gly Phe Thr Gly Ala
    450                 455                 460

Arg Lys Ser Ala Arg Lys Arg Lys Asn Gln Ala Leu Ala Gly Gly Gly
465                 470                 475                 480

Gly Ser Gly Gly Gly Ser Gly Gly Gly Ser Ala Leu Val Leu
                485                 490                 495

Gln Cys Arg Glu Leu Leu Val Lys Asn Thr Asp Leu Pro Phe Ile Gly
                500                 505                 510

Asp Ile Ser Asp Val Lys Thr Asp Ile Phe Leu Arg Lys Asp Ile Asn
            515                 520                 525

Glu Glu Thr Glu Val Ile Tyr Tyr Pro Asp Asn Val Ser Val Asp Gln
530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
                565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
            595                 600                 605

Phe Thr Arg Ser Ile Glu Glu Ala Leu Asp Asn Ser Ala Lys Val Tyr
            610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
                645                 650                 655

Asn Ile Leu Arg Lys Asp Thr Leu Asp Lys Ile Ser Asp Val Ser Ala
            660                 665                 670

Ile Ile Pro Tyr Ile Gly Pro Ala Leu Asn Ile Ser Asn Ser Val Arg
            675                 680                 685

Arg Gly Asn Phe Thr Glu Ala Phe Ala Val Thr Gly Val Thr Ile Leu
690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Lys Thr Ile Asp
            725                 730                 735

Asn Cys Leu Glu Gln Arg Ile Lys Arg Trp Lys Asp Ser Tyr Glu Trp
            740                 745                 750

Met Met Gly Thr Trp Leu Ser Arg Ile Ile Thr Gln Phe Asn Asn Ile
            755                 760                 765

Ser Tyr Gln Met Tyr Asp Ser Leu Asn Tyr Gln Ala Gly Ala Ile Lys
            770                 775                 780

Ala Lys Ile Asp Leu Glu Tyr Lys Lys Tyr Ser Gly Ser Asp Lys Glu
785                 790                 795                 800
```

```
Asn Ile Lys Ser Gln Val Glu Asn Leu Lys Asn Ser Leu Asp Val Lys
                805                 810                 815
Ile Ser Glu Ala Met Asn Asn Ile Asn Lys Phe Ile Arg Glu Cys Ser
            820                 825                 830
Val Thr Tyr Leu Phe Lys Asn Met Leu Pro Lys Val Ile Asp Glu Leu
        835                 840                 845
Asn Glu Phe Asp Arg Asn Thr Lys Ala Lys Leu Ile Asn Leu Ile Asp
    850                 855                 860
Ser His Asn Ile Ile Leu Val Gly Glu Val Asp Lys Leu Lys Ala Lys
865                 870                 875                 880
Val Asn Asn Ser Phe Gln Asn Thr Ile Pro Phe Asn Ile Phe Ser Tyr
                885                 890                 895
Thr Asn Asn Ser Leu Leu Lys Asp Ile Ile Asn Glu Tyr Phe Asn Leu
                900                 905                 910
Asp

<210> SEQ ID NO 80
<211> LENGTH: 2673
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 80
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg tttttgaagaa     600 tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc cacccctgaac     900 aaagcgaaat ccatcgtggg taccactgct ctctctccagt acatgaagaa cgtttttaaa     960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200 gctaattttta acggccagaa cacggaaatc aacaacatga cttcacaaa actgaaaaac    1260 ttcactggtc tgttcgagtt ttacaagctg ctgtgcgtcg acggcatcat acctccaaa     1320 actaaatctc tgatagaagg tagatacggt ggtttcctgg cgctagcggg cggtggcggt    1380
```

```
agcggcggtg gcggtagcgg cggtggcggt agcgcactag tgctgcagtg tatcaaggtt    1440
aacaactggg atttattctt cagcccgagt gaagacaact tcaccaacga cctgaacaaa    1500
ggtgaagaaa tcacctcaga tactaacatc gaagcagccg aagaaaacat ctcgctggac    1560
ctgatccagc agtactacct gacctttaat ttcgacaacg agccggaaaa catttctatc    1620
gaaaacctga gctctgatat catcggccag ctggaactga tgccgaacat cgaacgtttc    1680
ccaaacggta aaagtacga gctggacaaa tataccatgt tccactacct gcgcgcgcag    1740
gaatttgaac acggcaaatc ccgtatcgca ctgactaact ccgttaacga agctctgctc    1800
aacccgtccc gtgtatacac cttcttctct agcgactacg tgaaaaaggt caacaaagcg    1860
actgaagctg caatgttctt gggttgggtt gaacagcttg tttatgattt taccgacgag    1920
acgtccgaag tatctactac cgacaaaatt gcggatatca ctatcatcat cccgtacatc    1980
ggtccggctc tgaacattgg caacatgctg tacaaagacg acttcgttgg cgcactgatc    2040
ttctccggtg cggtgatcct gctggagttc atcccggaaa tcgccatccc ggtactgggc    2100
acctttgctc tggttttctta cattgcaaac aaggttctga ctgtacaaac catcgacaac    2160
gcgctgagca acgtaacga aaaatgggat gaagtttaca aatatatcgt gaccaactgg    2220
ctggctaagg ttaatactca gatcgacctc atccgcaaaa aaatgaaaga agcactggaa    2280
aaccaggcgg aagctaccaa ggcaatcatt aactaccagt acaaccagta caccgaggaa    2340
gaaaaaaaca acatcaactt caacatcgac gatctgtcct ctaaactgaa cgaatccatc    2400
aacaaagcta tgatcaacat caacaagttc ctgaaccagt gctctgtaag ctatctgatg    2460
aactccatga tcccgtacgg tgttaaacgt ctggaggact cgatgcgtc tctgaaagac    2520 gccctgctga aatacattta cgacaaccgt ggcactctga tcggtcaggt tgatcgtctg    2580
aaggacaaag tgaacaatac cttatcgacc gacatccctt ttcagctcag taaatatgtc    2640
gataaccaac gccttttgtc cactctagac tag                                 2673
```

<210> SEQ ID NO 81
<211> LENGTH: 890
<212> TYPE: PRT
<213> ORGANISM: Artificial Sequence
<220> FEATURE:
<223> OTHER INFORMATION: chemically synthesized fusion protein

<400> SEQUENCE: 81

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

-continued

```
Leu Lys Val Ile Asp Thr Asn Cys Ile Asn Val Ile Gln Pro Asp Gly
130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Leu Ala Leu Ala Gly Gly Gly Ser Gly Gly Gly
450                 455                 460

Gly Ser Gly Gly Gly Ser Ala Leu Val Leu Gln Cys Ile Lys Val
465                 470                 475                 480

Asn Asn Trp Asp Leu Phe Phe Ser Pro Ser Glu Asp Asn Phe Thr Asn
                485                 490                 495

Asp Leu Asn Lys Gly Glu Glu Ile Thr Ser Asp Thr Asn Ile Glu Ala
            500                 505                 510

Ala Glu Glu Asn Ile Ser Leu Asp Leu Ile Gln Gln Tyr Tyr Leu Thr
        515                 520                 525

Phe Asn Phe Asp Asn Glu Pro Glu Asn Ile Ser Ile Glu Asn Leu Ser
530                 535                 540

Ser Asp Ile Ile Gly Gln Leu Glu Leu Met Pro Asn Ile Glu Arg Phe
```

```
                545                 550                 555                 560
Pro Asn Gly Lys Lys Tyr Glu Leu Asp Lys Tyr Thr Met Phe His Tyr
                565                 570                 575

Leu Arg Ala Gln Glu Phe Glu His Gly Lys Ser Arg Ile Ala Leu Thr
                580                 585                 590

Asn Ser Val Asn Glu Ala Leu Leu Asn Pro Ser Arg Val Tyr Thr Phe
                595                 600                 605

Phe Ser Ser Asp Tyr Val Lys Lys Val Asn Lys Ala Thr Glu Ala Ala
                610                 615                 620

Met Phe Leu Gly Trp Val Glu Gln Leu Val Tyr Asp Phe Thr Asp Glu
625                 630                 635                 640

Thr Ser Glu Val Ser Thr Thr Asp Lys Ile Ala Asp Ile Thr Ile Ile
                645                 650                 655

Ile Pro Tyr Ile Gly Pro Ala Leu Asn Ile Gly Asn Met Leu Tyr Lys
                660                 665                 670

Asp Asp Phe Val Gly Ala Leu Ile Phe Ser Gly Ala Val Ile Leu Leu
                675                 680                 685

Glu Phe Ile Pro Glu Ile Ala Ile Pro Val Leu Gly Thr Phe Ala Leu
                690                 695                 700

Val Ser Tyr Ile Ala Asn Lys Val Leu Thr Val Gln Thr Ile Asp Asn
705                 710                 715                 720

Ala Leu Ser Lys Arg Asn Glu Lys Trp Asp Glu Val Tyr Lys Tyr Ile
                725                 730                 735

Val Thr Asn Trp Leu Ala Lys Val Asn Thr Gln Ile Asp Leu Ile Arg
                740                 745                 750

Lys Lys Met Lys Glu Ala Leu Glu Asn Gln Ala Glu Ala Thr Lys Ala
                755                 760                 765

Ile Ile Asn Tyr Gln Tyr Asn Gln Tyr Thr Glu Glu Lys Asn Asn
                770                 775                 780

Ile Asn Phe Asn Ile Asp Asp Leu Ser Ser Lys Leu Asn Glu Ser Ile
785                 790                 795                 800

Asn Lys Ala Met Ile Asn Ile Asn Lys Phe Leu Asn Gln Cys Ser Val
                805                 810                 815

Ser Tyr Leu Met Asn Ser Met Ile Pro Tyr Gly Val Lys Arg Leu Glu
                820                 825                 830

Asp Phe Asp Ala Ser Leu Lys Asp Ala Leu Leu Lys Tyr Ile Tyr Asp
                835                 840                 845

Asn Arg Gly Thr Leu Ile Gly Gln Val Asp Arg Leu Lys Asp Lys Val
                850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
                885                 890

<210> SEQ ID NO 82
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 82
ggatccatgg agttcgttaa caaacagttc aactataaag acccagttaa cggtgttgac        60
attgcttaca tcaaaatccc gaacgctggc cagatgcagc cggtaaaggc attcaaaatc       120
```

```
cacaacaaaa tctgggttat cccggaacgt gatacctttc ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct caccccgtaac    540 ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc cacccctgaac    900 aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatatggc ggtttcacgg gcgcacgcaa atcagcgcgt   1380
aaattagcta accaggcgct agcgggcggt ggcggtagcg gcgtggcgg tagcggcggt   1440 ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acggtaaaaa gtacgagctg   1740
gacaaatata ccatgttcca ctacctgcgc gcgcaggaat ttgaacacgg caaatcccgt   1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt   1920
tgggttgaac agcttgttta tgatttaacc gacgagacgt ccgaagtatc tactaccgac   1980
aaaattgcgg atatcactat catcatcccg tacatcggtc cggctctgaa cattggcaac   2040
atgctgtaca agacgacttt cgttggcgca ctgatcttct ccggtgcggt gatcctgctg   2100
gagttcatcc cggaaatcgc catcccggta ctgggcacct ttgctctggt ttcttacatt   2160
gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaaat gaaagaagca ctggaaaacc aggcggaagc taccaaggca   2340
atcattaact accagtacaa ccagtacacc gaggaagaaa aaaacaacat caacttcaac   2400
atcgacgatc tgtcctctaa actgaacgaa tccatcaaca aagctatgat caacatcaac   2460
```

-continued

```
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccttc    2640
tcgaccgaca tcccttttca gctcagtaaa tatgtcgata ccaacgcct tttgtccact     2700 ctagactag                                                             2709
```

<210> SEQ ID NO 83
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 83

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320
```

-continued

```
Glu Lys Tyr Leu Leu Ser Glu Asp Thr Ser Gly Lys Phe Ser Val Asp
                325                 330                 335
Lys Leu Lys Phe Asp Lys Leu Tyr Lys Met Leu Thr Glu Ile Tyr Thr
            340                 345                 350
Glu Asp Asn Phe Val Lys Phe Lys Val Leu Asn Arg Lys Thr Tyr
            355                 360                 365
Leu Asn Phe Asp Lys Ala Val Phe Lys Ile Asn Ile Val Pro Lys Val
        370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Leu Ile Glu Gly Arg
        435                 440                 445
Tyr Gly Gly Phe Thr Gly Ala Arg Lys Ser Ala Arg Lys Leu Ala Asn
    450                 455                 460
Gln Ala Leu Ala Gly Gly Gly Ser Gly Gly Gly Ser Gly Gly
465                 470                 475                 480
Gly Gly Ser Ala Leu Val Leu Gln Cys Ile Lys Val Asn Asn Trp Asp
                485                 490                 495
Leu Phe Phe Ser Pro Ser Glu Asp Asn Phe Thr Asn Asp Leu Asn Lys
            500                 505                 510
Gly Glu Glu Ile Thr Ser Asp Thr Asn Ile Glu Ala Ala Glu Glu Asn
        515                 520                 525
Ile Ser Leu Asp Leu Ile Gln Gln Tyr Tyr Leu Thr Phe Asn Phe Asp
530                 535                 540
Asn Glu Pro Glu Asn Ile Ser Ile Glu Asn Leu Ser Ser Asp Ile Ile
545                 550                 555                 560
Gly Gln Leu Glu Leu Met Pro Asn Ile Glu Arg Phe Pro Asn Gly Lys
            565                 570                 575
Lys Tyr Glu Leu Asp Lys Tyr Thr Met Phe His Tyr Leu Arg Ala Gln
        580                 585                 590
Glu Phe Glu His Gly Lys Ser Arg Ile Ala Leu Thr Asn Ser Val Asn
    595                 600                 605
Glu Ala Leu Leu Asn Pro Ser Arg Val Tyr Thr Phe Phe Ser Ser Asp
610                 615                 620
Tyr Val Lys Lys Val Asn Lys Ala Thr Glu Ala Ala Met Phe Leu Gly
625                 630                 635                 640
Trp Val Glu Gln Leu Val Tyr Asp Phe Thr Asp Glu Thr Ser Glu Val
            645                 650                 655
Ser Thr Thr Asp Lys Ile Ala Asp Ile Thr Ile Ile Pro Tyr Ile
        660                 665                 670
Gly Pro Ala Leu Asn Ile Gly Asn Met Leu Tyr Lys Asp Asp Phe Val
    675                 680                 685
Gly Ala Leu Ile Phe Ser Gly Ala Val Ile Leu Leu Glu Phe Ile Pro
    690                 695                 700
Glu Ile Ala Ile Pro Val Leu Gly Thr Phe Ala Leu Val Ser Tyr Ile
705                 710                 715                 720
Ala Asn Lys Val Leu Thr Val Gln Thr Ile Asp Asn Ala Leu Ser Lys
                725                 730                 735
```

```
Arg Asn Glu Lys Trp Asp Glu Val Tyr Lys Tyr Ile Val Thr Asn Trp
                740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
                820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900
```

<210> SEQ ID NO 84
<211> LENGTH: 2709
<212> TYPE: DNA
<213> ORGANISM: Artificial Sequence
<220> FEATURE:
<223> OTHER INFORMATION: chemically synthesized polynucleotide encoding fusion protein

<400> SEQUENCE: 84

```
ggatccatgg agttcgttaa caaacagttc aactataaag acccagttaa cggtgttgac        60
attgcttaca tcaaaatccc gaacgctggc cagatgcagc cggtaaaggc attcaaaatc       120
cacaacaaaa tctgggttat cccggaacgt gataccttta ctaacccgga agaaggtgac       180
ctgaacccgc caccggaagc gaaacaggtg ccggtatctt actatgactc cacctacctg       240
tctaccgata cgaaaagga caactacctg aaaggtgtta ctaaactgtt cgagcgtatt        300
tactccaccg acctgggccg tatgctgctg actagcatcg ttcgcggtat cccgttctgg       360
ggcggttcta ccatcgatac cgaactgaaa gtaatcgaca ctaactgcat caacgttatt       420
cagccggacg ttcctatcg ttccgaagaa ctgaacctgg tgatcatcgg cccgtctgct       480
gatatcatcc agttcgagtg taagagcttt ggtcacgaag ttctgaacct cacccgtaac       540
ggctacggtt ccactcagta catccgtttc tctccggact tcaccttcgg ttttgaagaa       600
tccctggaag tagacacgaa cccactgctg ggcgctggta aattcgcaac tgatcctgcg       660
gttaccctgg ctcacgaact gattcatgca ggccaccgcc tgtacggtat cgccatcaat       720
ccgaaccgtg tcttcaaagt taacaccaac gcgtattacg agatgtccgg tctggaagtt       780
agcttcgaag aactgcgtac ttttggcggt cacgacgcta attcatcga ctctctgcaa       840
gaaaacgagt ccgtctgta ctactataac aagttcaaag atatcgcatc caccctgaac       900
aaagcgaaat ccatcgtggg taccactgct tctctccagt acatgaagaa cgttttaaa       960
gaaaatacc tgctcagcga agacacctcc ggcaaattct ctgtagacaa gttgaaattc      1020
gataaacttt acaaaatgct gactgaaatt tacaccgaag acaacttcgt taagttcttt      1080
```

```
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200 gctaattttta acggcagaa cacggaaatc aacaacatga acttcacaaa actgaaaaac    1260
ttcactggtc tgttcgagtt ttacaagctg ctgtgcgtcg acggcatcat acctccaaa     1320 actaaatctc tgatagaagg tagatatggc ggtttcacgg cgcacgcaa atcagcgcgt     1380 aaacgtaaga accaggcgct agcgggcggt ggcggtagcg gcggtggcgg tagcggcggt    1440
ggcggtagcg cactagtgct gcagtgtatc aaggttaaca actgggattt attcttcagc    1500
ccgagtgaag acaacttcac caacgacctg aacaaggtg aagaaatcac ctcagatact     1560
aacatcgaag cagccgaaga aaacatctcg ctggacctga tccagcagta ctacctgacc    1620
tttaatttcg acaacgagcc ggaaaacatt tctatcgaaa acctgagctc tgatatcatc    1680
ggccagctgg aactgatgcc gaacatcgaa cgtttcccaa acggtaaaaa gtacgagctg    1740
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgactt cgttggcgca ctgatcttct ccggtgcggt gatcctgctg     2100
gagttcatcc cggaaatcgc catcccggta ctgggcacct ttgctctggt ttcttacatt    2160
gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaat gaaagaagca ctggaaaacc aggcggaagc taccaaggca    2340
atcattaact accagtacaa ccagtacacc gaggaagaaa aaacaacat caacttcaac     2400 atcgacgatc tgtcctctaa actgaacgaa tccatcaaca agctatgat caacatcaac     2460 aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccta    2640 tcgaccgaca tcccttttca gctcagtaaa tatgtcgata ccaacgcct tttgtccact     2700 ctagactag                                                            2709
```

<210> SEQ ID NO 85
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 85

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
                20                  25                  30

Gln Pro Val Lys Ala Phe Lys Ile His Asn Lys Ile Trp Val Ile Pro
            35                  40                  45

Glu Arg Asp Thr Phe Thr Asn Pro Glu Glu Gly Asp Leu Asn Pro Pro
        50                  55                  60
```

```
Pro Glu Ala Lys Gln Val Pro Val Ser Tyr Tyr Asp Ser Thr Tyr Leu
 65                  70                  75                  80

Ser Thr Asp Asn Glu Lys Asp Asn Tyr Leu Lys Gly Val Thr Lys Leu
                 85                  90                  95

Phe Glu Arg Ile Tyr Ser Thr Asp Leu Gly Arg Met Leu Leu Thr Ser
                100                 105                 110

Ile Val Arg Gly Ile Pro Phe Trp Gly Gly Ser Thr Ile Asp Thr Glu
            115                 120                 125

Leu Lys Val Ile Asp Thr Asn Cys Ile Asn Val Ile Gln Pro Asp Gly
        130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
                180                 185                 190

Asp Phe Thr Phe Gly Phe Glu Glu Ser Leu Glu Val Asp Thr Asn Pro
            195                 200                 205

Leu Leu Gly Ala Gly Lys Phe Ala Thr Asp Pro Ala Val Thr Leu Ala
        210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
                260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
        290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
                340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
        370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Leu Ile Glu Gly Arg
            435                 440                 445

Tyr Gly Gly Phe Thr Gly Ala Arg Lys Ser Ala Arg Lys Arg Lys Asn
        450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
```

```
                    485                 490                 495
Leu Phe Phe Ser Pro Ser Glu Asp Asn Phe Thr Asn Asp Leu Asn Lys
                500                 505                 510
Gly Glu Glu Ile Thr Ser Asp Thr Asn Ile Glu Ala Ala Glu Glu Asn
            515                 520                 525
Ile Ser Leu Asp Leu Ile Gln Gln Tyr Tyr Leu Thr Phe Asn Phe Asp
        530                 535                 540
Asn Glu Pro Glu Asn Ile Ser Ile Glu Asn Leu Ser Ser Asp Ile Ile
545                 550                 555                 560
Gly Gln Leu Glu Leu Met Pro Asn Ile Glu Arg Phe Pro Asn Gly Lys
                565                 570                 575
Lys Tyr Glu Leu Asp Lys Tyr Thr Met Phe His Tyr Leu Arg Ala Gln
            580                 585                 590
Glu Phe Glu His Gly Lys Ser Arg Ile Ala Leu Thr Asn Ser Val Asn
        595                 600                 605
Glu Ala Leu Leu Asn Pro Ser Arg Val Tyr Thr Phe Phe Ser Ser Asp
        610                 615                 620
Tyr Val Lys Lys Val Asn Lys Ala Thr Glu Ala Ala Met Phe Leu Gly
625                 630                 635                 640
Trp Val Glu Gln Leu Val Tyr Asp Phe Thr Asp Glu Thr Ser Glu Val
                645                 650                 655
Ser Thr Thr Asp Lys Ile Ala Asp Ile Thr Ile Ile Pro Tyr Ile
                660                 665                 670
Gly Pro Ala Leu Asn Ile Gly Asn Met Leu Tyr Lys Asp Asp Phe Val
            675                 680                 685
Gly Ala Leu Ile Phe Ser Gly Ala Val Ile Leu Leu Glu Phe Ile Pro
        690                 695                 700
Glu Ile Ala Ile Pro Val Leu Gly Thr Phe Ala Leu Val Ser Tyr Ile
705                 710                 715                 720
Ala Asn Lys Val Leu Thr Val Gln Thr Ile Asp Asn Ala Leu Ser Lys
                725                 730                 735
Arg Asn Glu Lys Trp Asp Glu Val Tyr Lys Tyr Ile Val Thr Asn Trp
            740                 745                 750
Leu Ala Lys Val Asn Thr Gln Ile Asp Leu Ile Arg Lys Lys Met Lys
        755                 760                 765
Glu Ala Leu Glu Asn Gln Ala Glu Ala Thr Lys Ala Ile Ile Asn Tyr
        770                 775                 780
Gln Tyr Asn Gln Tyr Thr Glu Glu Lys Asn Asn Ile Asn Phe Asn
785                 790                 795                 800
Ile Asp Asp Leu Ser Ser Lys Leu Asn Glu Ser Ile Asn Lys Ala Met
                805                 810                 815
Ile Asn Ile Asn Lys Phe Leu Asn Gln Cys Ser Val Ser Tyr Leu Met
            820                 825                 830
Asn Ser Met Ile Pro Tyr Gly Val Lys Arg Leu Glu Asp Phe Asp Ala
        835                 840                 845
Ser Leu Lys Asp Ala Leu Leu Lys Tyr Ile Tyr Asp Asn Arg Gly Thr
850                 855                 860
Leu Ile Gly Gln Val Asp Arg Leu Lys Asp Lys Val Asn Asn Thr Leu
865                 870                 875                 880
Ser Thr Asp Ile Pro Phe Gln Leu Ser Lys Tyr Val Asp Asn Gln Arg
                885                 890                 895
Leu Leu Ser Thr Leu Asp
            900
```

<210> SEQ ID NO 86
<211> LENGTH: 2889
<212> TYPE: DNA
<213> ORGANISM: Artificial Sequence
<220> FEATURE:
<223> OTHER INFORMATION: chemically synthesized polynucleotide encoding IgA protease

<400> SEQUENCE: 86

```
ggatccttgg tacgagatga cgttgactat caaattttcc gcgactttgc ggaaaataaa      60
ggtaagtttt tcgtcggcgc cacagacctg tccgtcaaaa ataagagagg ccagaacatc     120
ggtaacgcac tgagcaacgt ccctatgatt gattttagtg tagcggacgt taataaacgg     180
attgcaaccg tcgttgatcc gcagtatgct gtcagcgtca acatgctaa agcggaagtt     240
catacgttct attacgggca atataacggc cataacgatg tggctgataa agaaaatgaa     300
tatcgcgtgg tcgagcagaa caattacgaa ccgcacaaag cgtggggcgc gagtaattta     360
ggccgcctgg aggactataa catggcccgt ttcaataaat tcgtgaccga ggtagcaccg     420
atcgccccca cagatgctgg tgggggcctg ataccctaca agataaaaaa ccgcttctct     480
agcttcgtgc gcattggcgc cggtcgtcag ctcgtgtacg agaagggtgt ctatcaccag     540
gaaggtaatg aaaagggta cgacctccgt gatttgtccc aggcgtatcg ctacgctatt     600
gccggaaccc cgtataaaga tattaatatc gatcaaacca tgaataccga aggcctaatt     660
ggtttcggga atcataataa gcaatatagc gcagaagagc taaagcaggc cctcagccaa     720
gatgcgttaa ccaattacgg agtgttaggc gatagcggca gtccgctgtt tgccttcgat     780
aaacagaaaa atcaatgggt gtttctgggc acttatgatt attgggccgg atatggtaaa     840
aagagctggc aggaatggaa tatttataaa aaggaattcg cagacaaaat caagcagcat     900
gacaacgcag gtacggtgaa ggggaacggc gaacatcact ggaagacgac cggcacgaat     960
agtcatatcg gatcgacggc cgttcgcctg gcgaacaatg agggcgatgc aaacaatggg    1020
caaaacgtga cctttgagga caacggtacc ctggtcctta accagaacat aaatcagggc    1080
gcgggaggct tgttctttaa aggcgactat actgttaagg gagcaaacaa tgacatcacc    1140
tggttagggg ccgtattga cgttgcggat ggaaaaaagg tggtttggca ggttaaaaac    1200
cctaacgggg accggctggc aaaaatcggc aaagggacat tggaaattaa tggtaccggt    1260
gtgaatcagg tcagctgaa agtgggagat gggaccgtga ttctgaacca gaaagcagac    1320
gctgacaaaa aggtgcaagc ctttagccaa gtaggaattg ttagtggtcg tggcacactc    1380
gtcttgaact caagcaacca aataaatccg gataacctgt actttggatt tcgtggcgga    1440
cgcctggatg ctaacgggaa tgatctgacc tttgaacata tccgtaacgt tgacgagggt    1500
gcgcgcatag ttaatcataa tactgaccat gcatcaacta tccaccttgac cgggaaaagt    1560
ctgattacaa acccaaactc tctgtcagta cattccatcc agaatgatta tgatgaagac    1620
gattactcat actattaccg gccgcgtaga ccaattccac aaggtaaaga tctttattac    1680
aaaaattacc gttattacgc attaaaatcc ggagggcggc tgaatgcacc tatgccggaa    1740
aatggcgtgg ccgaaaacaa tgactggatt tttatgggtt atactcaaga agaggctcgc    1800
aaaaatgcaa tgaaccataa aaataaccga aggatcggtg atttcggcgg attttttcgat    1860
gaggaaaatg gtaaaggtca caatggtgcg ctgaatctaa attttaacgg caaaagtgcc    1920
cagaaacgtt tccttctgac tggtggcgct aatctgaatg gtaaaatcag tgtgacgcag    1980
ggtaacgtgc tgctttctgg ccggccaact ccgcatgcac gtgattttgt aaataaatcg    2040
```

```
agcgctcgta aagatgcgca ttttctaaa aataacgagg tcgtgtttga agatgactgg    2100
ataaatcgca cctttaaagc ggcagaaatc gcggttaatc agagtgcgag cttttcatcg    2160
ggtaggaatg tatctgatat tacagcaaac attacagcca ctgataatgc gaaggtcaac    2220
ctgggttata aaacggtga tgaagtttgt gttcgatcgg attacacggg ctatgttacc    2280
tgcaacactg gcaatctgtc tgataaagcg cttaactctt ttgacgccac gcgcattaac    2340
gggaatgtga acctgaacca aaacgctgcc ttggtacttg gtaaggccgc gttgtggggt    2400
aaaattcagg gccagggcaa ctcccgtgtg tctctgaacc agcactcgaa gtggcacctg    2460
acgggggact cgcaggtgca caacttgtcc ctggccgata gccatattca ccttaacaat    2520
gcgtccgatg cccagtcagc taataaatat catacgatca aaatcaatca cctctctggc    2580
aacggtcact ttcactactt aacggattta gcaaaaaact tagggggataa agtcctggta    2640 aaagaatcag cgagcggaca ttatcagtta catgtacaga acaaaacagg cgagccaaat    2700
caggaaggcc ttgacttatt tgatgcttca tcggtacaag atcgttccag actgttcgtt    2760
tcactcgcga atcactacgt tgatctgggt gcgctgcgct atactataaa gacggaaaat    2820
ggcataacac gcctctataa tccctatgcc ggtaacggcc gtccggtgaa acctgctccc    2880
tgcgtcgac                                                            2889

<210> SEQ ID NO 87
<211> LENGTH: 4296
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 87
ggatccttgg tacgagatga cgttgactat caaattttcc gcgactttgc ggaaaataaa      60
ggtaagtttt tcgtcggcgc cacagacctg tccgtcaaaa ataagagagg ccagaacatc    120
ggtaacgcac tgagcaacgt ccctatgatt gattttagtg tagcggacgt taataaacgg    180
attgcaaccg tcgttgatcc gcagtatgct gtcagcgtca acatgctaa agcggaagtt    240 catacgttct attacgggca atataacggc cataacgatg tggctgataa agaaaatgaa    300
tatcgcgtgg tcgagcagaa caattacgaa ccgcacaaag cgtggggcgc gagtaattta    360
ggccgcctgg aggactataa catggcccgt ttcaataaat tcgtgaccga ggtagcaccg    420
atcgccccca cagatgctgg tgggggcctg gatacctaca aagataaaaa ccgcttctct    480
agcttcgtgc gcattggcgc cggtcgtcag ctcgtgtacg agaagggtgt ctatcaccag    540
gaaggtaatg aaaaggggta cgacctccgt gatttgtccc aggcgtatcg ctacgctatt    600
gccggaaccc cgtataaaga tattaatatc gatcaaacca tgaataccga aggcctaatt    660
ggtttcggga atcataataa gcaatatagc gcagaagagc taaagcaggc cctcagccaa    720
gatgcgttaa ccaattacgg agtgttaggc gatagcggca gtccgctgtt tgccttcgat    780
aaacagaaaa atcaatgggt gtttctgggc acttatgatt attgggccgg atatggtaaa    840
aagagctggc aggaatggaa tatttataaa aaggaattcg cagacaaaat caagcagcat    900
gacaacgcag gtacggtgaa ggggaacggc gaacatcact ggaagacgac cggcacgaat    960
agtcatatcg gatcgacggc cgttcgcctg gcgaacaatg agggcgatgc aaacaatggg   1020
caaaacgtga cctttgagga caacggtacc ctggtcctta accagaacat aaatcagggc   1080
gcgggaggct tgttctttaa aggcgactat actgttaagg gagcaaacaa tgacatcacc   1140
```

```
tggttagggg ccggtattga cgttgcggat ggaaaaaagg tggtttggca ggttaaaaac    1200
cctaacgggg accggctggc aaaaatcggc aaagggacat tggaaattaa tggtaccggt    1260
gtgaatcagg gtcagctgaa agtgggagat gggaccgtga ttctgaacca gaaagcagac    1320
gctgacaaaa aggtgcaagc cttttagccaa gtaggaattg ttagtggtcg tggcacactc    1380
gtcttgaact caagcaacca aataaatccg gataacctgt actttggatt tcgtggcgga    1440
cgcctggatg ctaacgggaa tgatctgacc tttgaacata tccgtaacgt tgacgagggt    1500
gcgcgcatag ttaatcataa tactgaccat gcatcaacta tcaccttgac cgggaaaagt    1560
ctgattacaa acccaaactc tctgtcagta cattccatcc agaatgatta tgatgaagac    1620
gattactcat actattaccg gccgcgtaga ccaattccac aaggtaaaga tctttattac    1680
aaaaattacc gttattacgc attaaaatcc ggagggcggc tgaatgcacc tatgccggaa    1740
aatggcgtgg ccgaaaacaa tgactggatt tttatgggtt atactcaaga agaggctcgc    1800
aaaaatgcaa tgaaccataa aaataaccga aggatcggtg atttcggcgg atttttcgat    1860
gaggaaaatg gtaaaggtca caatggtgcg ctgaatctaa attttaacgg caaaagtgcc    1920
cagaaacgtt tccttctgac tggtggcgct aatctgaatg gtaaaatcag tgtgacgcag    1980
ggtaacgtgc tgcttttctgg ccggccaact ccgcatgcac gtgattttgt aaataaatcg    2040
agcgctcgta aagatgcgca tttttctaaa aataacgagg tcgtgtttga agatgactgg    2100
ataaatcgca cctttaaagc ggcagaaatc gcggttaatc agagtgcgag cttttcatcg    2160
ggtaggaatg tatctgatat tacagcaaac attacagcca ctgataatgc gaaggtcaac    2220
ctgggttata aaacggtga tgaagtttgt gttcgatcgg attacacggg ctatgttacc    2280
tgcaacactg gcaatctgtc tgataaagcg cttaactctt ttgacgccac gcgcattaac    2340
gggaatgtga acctgaacca aaacgctgcc ttggtacttg gtaaggccgc gttgtggggt    2400
aaaattcagg gccagggcaa ctcccgtgtg tctctgaacc agcactcgaa gtggcacctg    2460 acggggggact cgcaggtgca caacttgtcc ctggccgata gccatattca ccttaacaat    2520
gcgtccgatg cccagtcagc taataaatat catacgatca aaatcaatca cctctctggc    2580
aacggtcact ttcactactt aacggattta gcaaaaaact tagggggataa agtcctggta    2640 aaagaatcag cgagcggaca ttatcagtta catgtacaga acaaaacagg cgagccaaat    2700
caggaaggcc ttgacttatt tgatgcttca tcggtacaag atcgttccag actgttcgtt    2760
tcactcgcga atcactacgt tgatctgggt gcgctgcgct atactataaa gacggaaaat    2820
ggcataacac gcctctataa tccctatgcc ggtaacggcc gtccggtgaa acctgctccc    2880
tgcgtcgacg gcatcattac ctccaaaact aaatctctga tagaaggtag atttggcggt    2940
ttcacgggcg cacgcaaatc agcgcgtaaa cgtaagaacc aggcgctagc gggcggtggc    3000
ggtagcggcg gtgcggtag cggcggtggc ggtagcgcac tagtgctgca gtgtatcaag    3060
gttaacaact gggatttatt cttcagcccg agtgaagaca acttccaccaa cgacctgaac    3120 aaaggtgaag aaatcacctc agatactaac atcgaagcag ccgaagaaaa catctcgctg    3180
gacctgatcc agcagtacta cctgaccttt aatttcgaca acgagccgga aaacatttct    3240
atcgaaaacc tgagctctga tatcatcggc cagctggaac tgatgccgaa catcgaacgt    3300
ttcccaaacg gtaaaaagta cgagctggac aaatatacca tgttccacta cctgcgcgcg    3360
caggaatttg aacacggcaa atcccgtatc gcactgacta actccgttaa cgaagctctg    3420
ctcaacccgt cccgtgtata caccttcttc tctagcgact acgtgaaaaa ggtcaacaaa    3480
```

```
gcgactgaag ctgcaatgtt cttgggttgg gttgaacagc ttgtttatga ttttaccgac    3540
gagacgtccg aagtatctac taccgacaaa attgcggata tcactatcat catcccgtac    3600
atcggtccgg ctctgaacat tggcaacatg ctgtacaaag acgacttcgt tggcgcactg    3660
atcttctccg gtgcggtgat cctgctggag ttcatcccgg aaatcgccat cccggtactg    3720
ggcacctttg ctctggtttc ttacattgca acaaggttc tgactgtaca aaccatcgac     3780
aacgcgctga gcaaacgtaa cgaaaaatgg gatgaagttt acaaatatat cgtgaccaac    3840
tggctggcta aggttaatac tcagatcgac ctcatccgca aaaaaatgaa agaagcactg    3900
gaaaaccagg cggaagctac caaggcaatc attaactacc agtacaacca gtacaccgag    3960
gaagaaaaaa acaacatcaa cttcaacatc gacgatctgt cctctaaact gaacgaatcc    4020
atcaacaaag ctatgatcaa catcaacaag ttcctgaacc agtgctctgt aagctatctg    4080
atgaactcca tgatcccgta cggtgttaaa cgtctggagg acttcgatgc gtctctgaaa    4140
gacgccctgc tgaaatacat ttacgacaac cgtggcactc tgatcggtca ggttgatcgt    4200
ctgaaggaca aagtgaacaa taccttatcg accgacatcc ttttcagct cagtaaatat     4260
gtcgataacc aacgcctttt gtccactcta gactag                              4296
```

<210> SEQ ID NO 88
<211> LENGTH: 1431
<212> TYPE: PRT
<213> ORGANISM: Artificial Sequence
<220> FEATURE:
<223> OTHER INFORMATION: chemically synthesized fusion protein

<400> SEQUENCE: 88

```
Gly Ser Leu Val Arg Asp Asp Val Asp Tyr Gln Ile Phe Arg Asp Phe
1               5                   10                  15

Ala Glu Asn Lys Gly Lys Phe Phe Val Gly Ala Thr Asp Leu Ser Val
            20                  25                  30

Lys Asn Lys Arg Gly Gln Asn Ile Gly Asn Ala Leu Ser Asn Val Pro
        35                  40                  45

Met Ile Asp Phe Ser Val Ala Asp Val Asn Lys Arg Ile Ala Thr Val
    50                  55                  60

Val Asp Pro Gln Tyr Ala Val Ser Val Lys His Ala Lys Ala Glu Val
65                  70                  75                  80

His Thr Phe Tyr Tyr Gly Gln Tyr Asn Gly His Asn Asp Val Ala Asp
                85                  90                  95

Lys Glu Asn Glu Tyr Arg Val Val Glu Gln Asn Tyr Glu Pro His
            100                 105                 110

Lys Ala Trp Gly Ala Ser Asn Leu Gly Arg Leu Glu Asp Tyr Asn Met
        115                 120                 125

Ala Arg Phe Asn Lys Phe Val Thr Glu Val Ala Pro Ile Ala Pro Thr
    130                 135                 140

Asp Ala Gly Gly Gly Leu Asp Thr Tyr Lys Asp Lys Asn Arg Phe Ser
145                 150                 155                 160

Ser Phe Val Arg Ile Gly Ala Gly Arg Gln Leu Val Tyr Glu Lys Gly
                165                 170                 175

Val Tyr His Gln Glu Gly Asn Glu Lys Gly Tyr Asp Leu Arg Asp Leu
            180                 185                 190

Ser Gln Ala Tyr Arg Tyr Ala Ile Ala Gly Thr Pro Tyr Lys Asp Ile
        195                 200                 205

Asn Ile Asp Gln Thr Met Asn Thr Glu Gly Leu Ile Gly Phe Gly Asn
    210                 215                 220
```

-continued

```
His Asn Lys Gln Tyr Ser Ala Glu Glu Leu Lys Gln Ala Leu Ser Gln
225                 230                 235                 240

Asp Ala Leu Thr Asn Tyr Gly Val Leu Gly Asp Ser Gly Ser Pro Leu
            245                 250                 255

Phe Ala Phe Asp Lys Gln Lys Asn Gln Trp Val Phe Leu Gly Thr Tyr
        260                 265                 270

Asp Tyr Trp Ala Gly Tyr Gly Lys Lys Ser Trp Gln Glu Trp Asn Ile
    275                 280                 285

Tyr Lys Lys Glu Phe Ala Asp Lys Ile Lys Gln His Asp Asn Ala Gly
290                 295                 300

Thr Val Lys Gly Asn Gly Glu His His Trp Lys Thr Thr Gly Thr Asn
305                 310                 315                 320

Ser His Ile Gly Ser Thr Ala Val Arg Leu Ala Asn Asn Glu Gly Asp
                325                 330                 335

Ala Asn Asn Gly Gln Asn Val Thr Phe Glu Asp Asn Gly Thr Leu Val
            340                 345                 350

Leu Asn Gln Asn Ile Asn Gln Gly Ala Gly Gly Leu Phe Phe Lys Gly
        355                 360                 365

Asp Tyr Thr Val Lys Gly Ala Asn Asn Asp Ile Thr Trp Leu Gly Ala
    370                 375                 380

Gly Ile Asp Val Ala Asp Gly Lys Lys Val Val Trp Gln Val Lys Asn
385                 390                 395                 400

Pro Asn Gly Asp Arg Leu Ala Lys Ile Gly Lys Gly Thr Leu Glu Ile
                405                 410                 415

Asn Gly Thr Gly Val Asn Gln Gly Gln Leu Lys Val Gly Asp Gly Thr
            420                 425                 430

Val Ile Leu Asn Gln Lys Ala Asp Ala Asp Lys Lys Val Gln Ala Phe
        435                 440                 445

Ser Gln Val Gly Ile Val Ser Gly Arg Gly Thr Leu Val Leu Asn Ser
    450                 455                 460

Ser Asn Gln Ile Asn Pro Asp Asn Leu Tyr Phe Gly Phe Arg Gly Gly
465                 470                 475                 480

Arg Leu Asp Ala Asn Gly Asn Asp Leu Thr Phe Glu His Ile Arg Asn
                485                 490                 495

Val Asp Glu Gly Ala Arg Ile Val Asn His Asn Thr Asp His Ala Ser
            500                 505                 510

Thr Ile Thr Leu Thr Gly Lys Ser Leu Ile Thr Asn Pro Asn Ser Leu
        515                 520                 525

Ser Val His Ser Ile Gln Asn Asp Tyr Asp Glu Asp Tyr Ser Tyr
    530                 535                 540

Tyr Tyr Arg Pro Arg Pro Ile Pro Gln Gly Lys Asp Leu Tyr Tyr
545                 550                 555                 560

Lys Asn Tyr Arg Tyr Tyr Ala Leu Lys Ser Gly Gly Arg Leu Asn Ala
                565                 570                 575

Pro Met Pro Glu Asn Gly Val Ala Glu Asn Asn Asp Trp Ile Phe Met
            580                 585                 590

Gly Tyr Thr Gln Glu Glu Ala Arg Lys Asn Ala Met Asn His Lys Asn
        595                 600                 605

Asn Arg Arg Ile Gly Asp Phe Gly Gly Phe Phe Asp Glu Glu Asn Gly
    610                 615                 620

Lys Gly His Asn Gly Ala Leu Asn Leu Asn Phe Asn Gly Lys Ser Ala
625                 630                 635                 640
```

-continued

Gln Lys Arg Phe Leu Leu Thr Gly Gly Ala Asn Leu Asn Gly Lys Ile
                645                 650                 655

Ser Val Thr Gln Gly Asn Val Leu Leu Ser Gly Arg Pro Thr Pro His
            660                 665                 670

Ala Arg Asp Phe Val Asn Lys Ser Ser Ala Arg Lys Asp Ala His Phe
            675                 680                 685

Ser Lys Asn Asn Glu Val Val Phe Glu Asp Asp Trp Ile Asn Arg Thr
    690                 695                 700

Phe Lys Ala Ala Glu Ile Ala Val Asn Gln Ser Ala Ser Phe Ser Ser
705                 710                 715                 720

Gly Arg Asn Val Ser Asp Ile Thr Ala Asn Ile Thr Ala Thr Asp Asn
                725                 730                 735

Ala Lys Val Asn Leu Gly Tyr Lys Asn Gly Asp Glu Val Cys Val Arg
            740                 745                 750

Ser Asp Tyr Thr Gly Tyr Val Thr Cys Asn Thr Gly Asn Leu Ser Asp
            755                 760                 765

Lys Ala Leu Asn Ser Phe Asp Ala Thr Arg Ile Asn Gly Asn Val Asn
    770                 775                 780

Leu Asn Gln Asn Ala Ala Leu Val Leu Gly Lys Ala Ala Leu Trp Gly
785                 790                 795                 800

Lys Ile Gln Gly Gln Gly Asn Ser Arg Val Ser Leu Asn Gln His Ser
                805                 810                 815

Lys Trp His Leu Thr Gly Asp Ser Gln Val His Asn Leu Ser Leu Ala
            820                 825                 830

Asp Ser His Ile His Leu Asn Asn Ala Ser Asp Ala Gln Ser Ala Asn
            835                 840                 845

Lys Tyr His Thr Ile Lys Ile Asn His Leu Ser Gly Asn Gly His Phe
    850                 855                 860

His Tyr Leu Thr Asp Leu Ala Lys Asn Leu Gly Asp Lys Val Leu Val
865                 870                 875                 880

Lys Glu Ser Ala Ser Gly His Tyr Gln Leu His Val Gln Asn Lys Thr
                885                 890                 895

Gly Glu Pro Asn Gln Glu Gly Leu Asp Leu Phe Asp Ala Ser Ser Val
            900                 905                 910

Gln Asp Arg Ser Arg Leu Phe Val Ser Leu Ala Asn His Tyr Val Asp
            915                 920                 925

Leu Gly Ala Leu Arg Tyr Thr Ile Lys Thr Glu Asn Gly Ile Thr Arg
    930                 935                 940

Leu Tyr Asn Pro Tyr Ala Gly Asn Gly Arg Pro Val Lys Pro Ala Pro
945                 950                 955                 960

Cys Val Asp Gly Ile Ile Thr Ser Lys Thr Lys Ser Leu Ile Glu Gly
                965                 970                 975

Arg Phe Gly Gly Phe Thr Gly Ala Arg Lys Ser Ala Arg Lys Arg Lys
            980                 985                 990

Asn Gln Ala Leu Ala Gly Gly Gly Ser Gly Gly Gly Gly Ser Gly
        995                 1000                1005

Gly Gly Gly Ser Ala Leu Val Leu Gln Cys Ile Lys Val Asn Asn
        1010                1015                1020

Trp Asp Leu Phe Phe Ser Pro Ser Glu Asp Asn Phe Thr Asn Asp
        1025                1030                1035

Leu Asn Lys Gly Glu Glu Ile Thr Ser Asp Thr Asn Ile Glu Ala
        1040                1045                1050

Ala Glu Glu Asn Ile Ser Leu Asp Leu Ile Gln Gln Tyr Tyr Leu

```
                1055                1060                1065
Thr Phe Asn Phe Asp Asn Glu Pro Glu Asn Ile Ser Ile Glu Asn
    1070                1075                1080

Leu Ser Ser Asp Ile Ile Gly Gln Leu Glu Leu Met Pro Asn Ile
    1085                1090                1095

Glu Arg Phe Pro Asn Gly Lys Lys Tyr Glu Leu Asp Lys Tyr Thr
    1100                1105                1110

Met Phe His Tyr Leu Arg Ala Gln Glu Phe Glu His Gly Lys Ser
    1115                1120                1125

Arg Ile Ala Leu Thr Asn Ser Val Asn Glu Ala Leu Leu Asn Pro
    1130                1135                1140

Ser Arg Val Tyr Thr Phe Phe Ser Ser Asp Tyr Val Lys Lys Val
    1145                1150                1155

Asn Lys Ala Thr Glu Ala Ala Met Phe Leu Gly Trp Val Glu Gln
    1160                1165                1170

Leu Val Tyr Asp Phe Thr Asp Glu Thr Ser Glu Val Ser Thr Thr
    1175                1180                1185

Asp Lys Ile Ala Asp Ile Thr Ile Ile Pro Tyr Ile Gly Pro
    1190                1195                1200

Ala Leu Asn Ile Gly Asn Met Leu Tyr Lys Asp Asp Phe Val Gly
    1205                1210                1215

Ala Leu Ile Phe Ser Gly Ala Val Ile Leu Leu Glu Phe Ile Pro
    1220                1225                1230

Glu Ile Ala Ile Pro Val Leu Gly Thr Phe Ala Leu Val Ser Tyr
    1235                1240                1245

Ile Ala Asn Lys Val Leu Thr Val Gln Thr Ile Asp Asn Ala Leu
    1250                1255                1260

Ser Lys Arg Asn Glu Lys Trp Asp Glu Val Tyr Lys Tyr Ile Val
    1265                1270                1275

Thr Asn Trp Leu Ala Lys Val Asn Thr Gln Ile Asp Leu Ile Arg
    1280                1285                1290

Lys Lys Met Lys Glu Ala Leu Glu Asn Gln Ala Glu Ala Thr Lys
    1295                1300                1305

Ala Ile Ile Asn Tyr Gln Tyr Asn Gln Tyr Thr Glu Glu Glu Lys
    1310                1315                1320

Asn Asn Ile Asn Phe Asn Ile Asp Asp Leu Ser Ser Lys Leu Asn
    1325                1330                1335

Glu Ser Ile Asn Lys Ala Met Ile Asn Ile Asn Lys Phe Leu Asn
    1340                1345                1350

Gln Cys Ser Val Ser Tyr Leu Met Asn Ser Met Ile Pro Tyr Gly
    1355                1360                1365

Val Lys Arg Leu Glu Asp Phe Asp Ala Ser Leu Lys Asp Ala Leu
    1370                1375                1380

Leu Lys Tyr Ile Tyr Asp Asn Arg Gly Thr Leu Ile Gly Gln Val
    1385                1390                1395

Asp Arg Leu Lys Asp Lys Val Asn Asn Thr Leu Ser Thr Asp Ile
    1400                1405                1410

Pro Phe Gln Leu Ser Lys Tyr Val Asp Asn Gln Arg Leu Leu Ser
    1415                1420                1425

Thr Leu Asp
    1430

<210> SEQ ID NO 89
```

<211> LENGTH: 1357
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 89

| | | | | | |
|---|---|---|---|---|---|
| gctagcgggc | ggtggcggta | gcggcggtgg | cggtagcggc | ggtggcggta | gcgcactagt | 60 |
| gctgcagtgt | atcaaggtta | caactggga | tttattcttc | agcccgagtg | aagacaactt | 120 |
| caccaacgac | ctgaacaaag | gtgaagaaat | cacctcagat | actaacatcg | aagcagccga | 180 |
| agaaaacatc | tcgctggacc | tgatccagca | gtactacctg | acctttaatt | cgacaacga | 240 |
| gccggaaaac | atttctatcg | aaaacctgag | ctctgatatc | atcggccagc | tggaactgat | 300 |
| gccgaacatc | gaacgtttcc | caaacggtaa | aaagtacgag | ctggacaaat | ataccatgtt | 360 |
| ccactacctg | cgcgcgcagg | aatttgaaca | cggcaaatcc | cgtatcgcac | tgactaactc | 420 |
| cgttaacgaa | gctctgctca | acccgtcccg | tgtatacacc | ttcttctcta | gcgactacgt | 480 |
| gaaaaaggtc | aacaaagcga | ctgaagctgc | aatgttcttg | ggttgggttg | aacagcttgt | 540 |
| ttatgatttt | accgacgaga | cgtccgaagt | atctactacc | gacaaaattg | cggatatcac | 600 |
| tatcatcatc | ccgtacatcg | gtccggctct | gaacattggc | aacatgctgt | acaaagacga | 660 |
| cttcgttggc | gcactgatct | ctccggtgc | ggtgatcctg | ctggagttca | tcccggaaat | 720 |
| cgccatcccg | gtactgggca | cctttgctct | ggtttcttac | attgcaaaca | aggttctgac | 780 |
| tgtacaaacc | atcgacaacg | cgctgagcaa | acgtaacgaa | aaatgggatg | aagtttacaa | 840 |
| atatatcgtg | accaactggc | tggctaaggt | taatactcag | atcgacctca | tccgcaaaaa | 900 |
| aatgaaagaa | gcactggaaa | accaggcgga | agctaccaag | gcaatcatta | actaccagta | 960 |
| caaccagtac | accgaggaag | aaaaaaacaa | catcaacttc | aacatcgacg | atctgtcctc | 1020 |
| taaactgaac | gaatccatca | acaaagctat | gatcaacatc | aacaagttcc | tgaaccagtg | 1080 |
| ctctgtaagc | tatctgatga | actccatgat | cccgtacggt | gttaaacgtc | tggaggactt | 1140 |
| cgatgcgtct | ctgaaagacg | ccctgctgaa | atacatttac | gacaaccgtg | gcactctgat | 1200 |
| cggtcaggtt | gatcgtctga | aggacaaagt | gaacaatacc | ttatcgaccg | acatcccttt | 1260 |
| tcagctcagt | aaatatgtcg | ataaccaacg | ccttttgtcc | actctagaaa | tagaaggtag | 1320 |
| aagtgggcac | catcaccatc | accattaatg | aaagctt | | | 1357 |

<210> SEQ ID NO 90
<211> LENGTH: 2745
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 90

| | | | | | |
|---|---|---|---|---|---|
| ggatccatgg | agttcgttaa | caacagttc | aactataaag | acccagttaa | cggtgttgac | 60 |
| attgcttaca | tcaaaatccc | gaacgctggc | cagatgcagc | cggtaaaggc | attcaaaatc | 120 |
| cacaacaaaa | tctgggttat | cccggaacgt | gataccttta | ctaacccgga | agaaggtgac | 180 |
| ctgaacccgc | caccggaagc | gaaacaggtg | ccggtatctt | actatgactc | cacctacctg | 240 |
| tctaccgata | acgaaaagga | caactacctg | aaaggtgtta | ctaaactgtt | cgagcgtatt | 300 |
| tactccaccg | acctgggccg | tatgctgctg | actagcatgc | ttcgcggtat | cccgttctgg | 360 |
| ggcggttcta | ccatcgatac | cgaactgaaa | gtaatcgaca | ctaactgcat | caacgttatt | 420 |

-continued

```
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgttttttaaa   960 gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatttggc ggtttcacgg gcgcacgcaa atcagcgcgt   1380
aaacgtaaga accaggcgct agcgggcggt ggcggtagcg gcggtggcgg tagcggcggt   1440
ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acgtaaaaaa gtacgagctg   1740
gacaaatata ccatgttcca ctacctgcgc gcgcaggaat ttgaacacgg caaatcccgt   1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca agacgactt cgttggcgca ctgatcttct ccggtgcggt gatcctgctg   2100
gagttcatcc cggaaatcgc catcccggta ctgggcacct ttgctctggt ttcttacatt   2160
gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaaat gaagaagca ctggaaaaacc aggcggaagc taccaaggca    2340
atcattaact accagtacaa ccagtacacc gaggaagaaa aaacaacat caacttcaac   2400 atcgacgatc tgtcctctaa actgaacgaa tccatcaaca agctatgat caacatcaac   2460 aagttcctga ccagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caatacctta   2640
tcgaccgaca tcccttttca gctcagtaaa tatgtcgata accaacgcct tttgtccact   2700
ctagaaatag aaggtagaag tgggcaccat caccatcacc attaa               2745
```

<210> SEQ ID NO 91
<211> LENGTH: 914
<212> TYPE: PRT
<213> ORGANISM: Artificial Sequence
<220> FEATURE:
<223> OTHER INFORMATION: chemically synthesized fusion protein

<400> SEQUENCE: 91

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365
```

```
Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Ser Ala Arg Lys Arg Lys Asn
    450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
            485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
            515                 520                 525

Ile Ser Leu Asp Leu Ile Gln Gln Tyr Tyr Leu Thr Phe Asn Phe Asp
530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
            565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
            595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
            645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
    675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
            725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
            755                 760                 765

Glu Ala Leu Glu Asn Gln Ala Glu Ala Thr Lys Ala Ile Ile Asn Tyr
            770                 775                 780

Gln Tyr Asn Gln Tyr Thr Glu Glu Glu Lys Asn Asn Ile Asn Phe Asn
```

```
                    785                 790                 795                 800
Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Glu Ile Glu Gly Arg Ser Gly His His His His
            900                 905                 910

His His

<210> SEQ ID NO 92
<211> LENGTH: 619
<212> TYPE: DNA
<213> ORGANISM: Artificial Sequence
<220> FEATURE:
<223> OTHER INFORMATION: chemically synthesized polynucleotide encoding
      translocation domain

<400> SEQUENCE: 92
gctagcgggc ggtggcggta gcggcggtgg cggtagcggc ggtggcggta gcgcactagt      60
gctgcagtgt atcaatctgg attgggacgt aatccgtgat aagaccaaaa caaaaatcga    120
gtctttgaaa gaacacggcc cgatcaaaaa taagatgtct gaatcaccca ataaaactgt    180
ttcggaggaa aaagcgaaac agtatttgga agagtttcat caaaccgcgc ttgaacatcc    240
ggagctcagt gaactgaaaa cagtgacggg aacgaatcct gttttttgcag gcgcaaacta    300 tgcggcttgg ccgtgaatg ttgcccaagt aattgatagt gagaccgcag acaacctgga    360
aaagacgacc gcagcgttaa gcattttacc ggggattggt tccgtgatgg gtatagcgga    420
tggagcggtc caccataaca ctgaggaaat tgtcgcccag tcaatcgctc tgagttccct    480
gatggttgca caggctatcc cactcgtggg ggaactggtt gacataggtt cgccgccta    540 caacttcgta gaaagcatta ttaatctttt tcaggtggtg cataacagct acaaccgccc    600
tctagaatga taaaagctt                                                  619

<210> SEQ ID NO 93
<211> LENGTH: 1971
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 93
ggatccatgg agttcgttaa caaacagttc aactataaag acccagttaa cggtgttgac    60
attgcttaca tcaaaatccc gaacgctggc cagatgcagc cggtaaaggc attcaaaatc    120
cacaacaaaa tctgggttat cccggaacgt gatacctta ctaaccccgga agaaggtgac    180 ctgaacccgc caccggaagc gaaacaggtg ccggtatctt actatgactc cacctacctg    240
tctaccgata cgaaaagga caactacctg aaaggtgtta ctaaactgtt cgagcgtatt    300
```

-continued

```
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct caccgtaac    540
ggctacggtt ccactcagta catccgtttc tctccggact tcaccttcgg ttttgaagaa    600
tccctggaag tagacacgaa cccactgctg ggcgctggta attcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgttttaaa    960
gaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa atcaacatc   1140
gtgccgaaag ttaactacac tatctacgat ggtttcaacc tgcgtaacac caacctggct   1200
gctaatttta cggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatacggt ggtttcctgg cgctagcggg cggtggcggt   1380
agcggcggtg gcggtagcgg cggtggcggt agcgcactag tgctgcagtg tatcaatctg   1440
gattgggacg taatccgtga taagaccaaa acaaaaatcg agtctttgaa agaacacggc   1500
ccgatcaaaa ataagatgtc tgaatcaccc aataaaactg tttcggagga aaaagcgaaa   1560
cagtatttgg aagagtttca tcaaaccgcg cttgaacatc cggagctcag tgaactgaaa   1620
acagtgacgg gaacgaatcc tgttttttgca ggcgcaaact atgcggcttg ggccgtgaat   1680
gttgcccaag taattgatag tgagaccgca gacaacctgg aaaagacgac cgcagcgtta   1740
agcattttac cggggattgg ttccgtgatg ggtatagcgg atggagcggt ccaccataac   1800
actgaggaaa ttgtcgccca gtcaatcgct ctgagttccc tgatggttgc acaggctatc   1860
ccactcgtgg gggaactggt tgacataggt ttcgccgcct acaacttcgt agaaagcatt   1920
attaatcttt ttcaggtggt gcataacagc tacaaccgcc tctagaatg a             1971
```

<210> SEQ ID NO 94
<211> LENGTH: 656
<212> TYPE: PRT
<213> ORGANISM: Artificial Sequence
<220> FEATURE:
<223> OTHER INFORMATION: chemically synthesized fusion protein

<400> SEQUENCE: 94

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
```

-continued

```
                65                  70                  75                  80
Ser Thr Asp Asn Glu Lys Asp Asn Tyr Leu Lys Gly Val Thr Lys Leu
                    85                  90                  95

Phe Glu Arg Ile Tyr Ser Thr Asp Leu Gly Arg Met Leu Leu Thr Ser
                100                 105                 110

Ile Val Arg Gly Ile Pro Phe Trp Gly Ser Thr Ile Asp Thr Glu
                115                 120                 125

Leu Lys Val Ile Asp Thr Asn Cys Ile Asn Val Ile Gln Pro Asp Gly
        130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
                180                 185                 190

Asp Phe Thr Phe Gly Phe Glu Glu Ser Leu Glu Val Asp Thr Asn Pro
                195                 200                 205

Leu Leu Gly Ala Gly Lys Phe Ala Thr Asp Pro Ala Val Thr Leu Ala
        210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
                260                 265                 270

Ala Lys Phe Ile Asp Ser Leu Gln Glu Asn Glu Phe Arg Leu Tyr Tyr
                275                 280                 285

Tyr Asn Lys Phe Lys Asp Ile Ala Ser Thr Leu Asn Lys Ala Lys Ser
                290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
                340                 345                 350

Glu Asp Asn Phe Val Lys Phe Phe Lys Val Leu Asn Arg Lys Thr Tyr
                355                 360                 365

Leu Asn Phe Asp Lys Ala Val Phe Lys Ile Asn Ile Val Pro Lys Val
        370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Leu Ile Glu Gly Arg
        435                 440                 445

Tyr Gly Gly Phe Leu Ala Leu Ala Gly Gly Gly Ser Gly Gly Gly
        450                 455                 460

Gly Ser Gly Gly Gly Ser Ala Leu Val Leu Gln Cys Ile Asn Leu
465                 470                 475                 480

Asp Trp Asp Val Ile Arg Asp Lys Thr Lys Thr Lys Ile Glu Ser Leu
                485                 490                 495
```

```
Lys Glu His Gly Pro Ile Lys Asn Lys Met Ser Glu Ser Pro Asn Lys
            500                 505                 510
Thr Val Ser Glu Glu Lys Ala Lys Gln Tyr Leu Glu Glu Phe His Gln
        515                 520                 525
Thr Ala Leu Glu His Pro Glu Leu Ser Glu Leu Lys Thr Val Thr Gly
    530                 535                 540
Thr Asn Pro Val Phe Ala Gly Ala Asn Tyr Ala Ala Trp Ala Val Asn
545                 550                 555                 560
Val Ala Gln Val Ile Asp Ser Glu Thr Ala Asp Asn Leu Glu Lys Thr
                565                 570                 575
Thr Ala Ala Leu Ser Ile Leu Pro Gly Ile Gly Ser Val Met Gly Ile
            580                 585                 590
Ala Asp Gly Ala Val His His Asn Thr Glu Glu Ile Val Ala Gln Ser
        595                 600                 605
Ile Ala Leu Ser Ser Leu Met Val Ala Gln Ala Ile Pro Leu Val Gly
    610                 615                 620
Glu Leu Val Asp Ile Gly Phe Ala Ala Tyr Asn Phe Val Glu Ser Ile
625                 630                 635                 640
Ile Asn Leu Phe Gln Val Val His Asn Ser Tyr Asn Arg Pro Leu Glu
                645                 650                 655

<210> SEQ ID NO 95
<211> LENGTH: 1329
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 95
ggatccatgc ctattactat taacaatttt cgttatagcg atcccgtcaa caatgacacc      60
attatcatga tggaaccgcc atattgcaaa ggactggaca tttactataa agccttcaag     120
attactgacc gcatttggat tgttccagag cgttacgagt tcgggacgaa accagaagat     180
tttaacccgc cttcatcgct gatcgaagga gcatcagagt attacgatcc gaactatctg     240
cgtacggaca gcgataaaga ccgcttctta cagaccatgg tcaaacttt taaccgtatt     300 aagaacaatg tggccggaga agcactcttg ataagatta tcaacgcgat tccatacctg     360
ggcaattctt acagcctgct ggataaattt gacacaaata gtaattcagt cagctttaac     420
ctgttagaac aagatccgag tggcgcaacc acgaagtctg ccatgctgac aaatctgatc     480 attttggtc caggtcctgt actgaataaa aatgaagtac gcggcatcgt tctccgcgtg     540
gacaataaga actacttccc atgccgtgac ggcttcggtt cgatcatgca gatggctttc     600
tgtccggagt acgttccgac gtttgataat gttattgaga atatcacgag tttaacaatc     660
ggtaagtcaa atatttttca agatccggcc cttctcctta tgcatgaact gattcacgtg     720
ctgcacggct tatatggtat gcaagtgtcc tcgcatgaaa tcattccgtc aaacaggaa     780 atttatatgc agcataccta cccgatttca gctgaagagt gtttacgtt tggtggccag     840 gacgcgaatt tgatctccat cgacatcaaa acgatctgt atgagaaaac attaaatgac     900
tataaagcga ttgcgaacaa actgtctcag gtgactagct gcaacgatcc taacattgat     960
attgattcct acaaacaaat ttatcaacag aaataccagt tcgataaaga cagcaatggt    1020
cagtatatcg taaacgaaga taaatttcag atcctgtata acagcattat gtatggcttt    1080
accgaaattg agttggggaa gaaatttaac attaaaaccc gtctgtctta ttttagtatg    1140
```

```
aaccatgatc cggtgaaaat ccccaatctg cttgatgata ccatttataa tgataccgaa    1200
gggttcaaca ttgaatctaa ggatctgaaa tccgaataca aaggccaaaa tatgcgtgtt    1260
aatactaacg ctttccgtaa tgttgatggt agtggactcg tctcgaaact gattgggttg    1320
tgtgtcgac                                                            1329
```

<210> SEQ ID NO 96
<211> LENGTH: 2736
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 96

```
ggatccatgc ctattactat taacaatttt cgttatagcg atcccgtcaa caatgacacc      60
attatcatga tggaaccgcc atattgcaaa ggactggaca tttactataa agccttcaag     120
attactgacc gcatttggat tgttccagag cgttacgagt tcgggacgaa accagaagat     180
tttaacccgc cttcatcgct gatcgaagga gcatcagagt tattacgatcc gaactatctg    240 cgtacggaca gcgataaaga ccgcttctta cagaccatgg tcaaactttt taaccgtatt    300
aagaacaatg tggccggaga agcactcttg ataagatta tcaacgcgat tccatacctg     360
ggcaattctt acagcctgct ggataaattt gacacaaata gtaattcagt cagctttaac    420
ctgttagaac aagatccgag tggcgcaacc acgaagtctg ccatgctgac aaatctgatc    480 attttggtc caggtcctgt actgaataaa aatgaagtac gcggcatcgt tctccgcgtg     540
gacaataaga actacttccc atgccgtgac ggcttcggtt cgatcatgca gatggctttc    600
tgtccggagt acgttccgac gtttgataat gttattgaga atatcacgag tttaacaatc    660
ggtaagtcaa aatatttca agatccggcc cttctcctta tgcatgaact gattcacgtg     720
ctgcacggct tatatggtat gcaagtgtcc tcgcatgaaa tcattccgtc caaacaggaa    780
atttatatgc agcataccta cccgatttca gctgaagagt tgtttacgtt tggtggccag    840
gacgcgaatt tgatctccat cgacatcaaa aacgatctgt atgagaaaac attaaatgac    900
tataaagcga ttgcgaacaa actgtctcag gtgactagct gcaacgatcc taacattgat    960
attgattcct acaaacaaat ttatcaacag aaataccagt tcgataaaga cagcaatggt   1020
cagtatatcg taaacgaaga taaatttcag atcctgtata acagcattat gtatggcttt   1080
accgaaattg agttggggaa gaaatttaac attaaaaccc gtctgtctta ttttagtatg   1140
aaccatgatc cggtgaaaat ccccaatctg cttgatgata ccatttataa tgataccgaa   1200
gggttcaaca ttgaatctaa ggatctgaaa tccgaataca aaggccaaaa tatgcgtgtt   1260
aatactaacg ctttccgtaa tgttgatggt agtggactcg tctcgaaact gattgggttg   1320
tgtgtcgacg gcatcattac ctccaaaact aaatctctga tagaaggtag atttggcggt   1380
ttcacgggcg cacgcaaatc agcgcgtaaa cgtaagaacc aggcgctagc gggcggtggc   1440
ggtagcggcg gtggcggtag cggcggtggc ggtagcgcac tagtgctgca gtgtatcaag   1500
gttaacaact gggatttatt cttcagcccg agtgaagaca acttcaccaa cgacctgaac   1560
aaaggtgaag aaatcacctc agatactaac atcgaagcag ccgaagaaaa catctcgctg   1620
gacctgatcc agcagtacta cctgaccttt aatttcgaca acgagccgga aacatttct    1680 atcgaaaacc tgagctctga tatcatcggc cagctggaac tgatgccgaa catcgaacgt   1740
ttcccaaacg gtaaaaagta cgagctggac aaatatacca tgttccacta cctgcgcgcg   1800
```

```
caggaatttg aacacggcaa atcccgtatc gcactgacta actccgttaa cgaagctctg   1860
ctcaacccgt cccgtgtata caccttcttc tctagcgact acgtgaaaaa ggtcaacaaa   1920
gcgactgaag ctgcaatgtt cttgggttgg gttgaacagc ttgtttatga ttttaccgac   1980
gagacgtccg aagtatctac taccgacaaa attgcggata tcactatcat catcccgtac   2040
atcggtccgg ctctgaacat tggcaacatg ctgtacaaag acgacttcgt tggcgcactg   2100
atcttctccg gtgcggtgat cctgctggag ttcatcccgg aaatcgccat cccggtactg   2160
ggcacctttg ctctggtttc ttacattgca aacaaggttc tgactgtaca aaccatcgac   2220
aacgcgctga gcaaacgtaa cgaaaaatgg gatgaagttt acaaatatat cgtgaccaac   2280
tggctggcta aggttaatac tcagatcgac ctcatccgca aaaaaatgaa agaagcactg   2340
gaaaaccagg cggaagctac caaggcaatc attaactacc agtacaacca gtacaccgag   2400
gaagaaaaaa acaacatcaa cttcaacatc gacgatctgt cctctaaact gaacgaatcc   2460
atcaacaaag ctatgatcaa catcaacaag ttcctgaacc agtgctctgt aagctatctg   2520
atgaactcca tgatcccgta cggtgttaaa cgtctggagg acttcgatgc gtctctgaaa   2580
gacgccctgc tgaaatacat ttacgacaac cgtggcactc tgatcggtca ggttgatcgt   2640
ctgaaggaca agtgaacaa taccttatcg accgacatcc cttttcagct cagtaaatat   2700
gtcgataacc aacgcctttt gtccactcta gactag                             2736
```

<210> SEQ ID NO 97
<211> LENGTH: 911
<212> TYPE: PRT
<213> ORGANISM: Artificial Sequence
<220> FEATURE:
<223> OTHER INFORMATION: chemically synthesized fusion protein

<400> SEQUENCE: 97

```
Gly Ser Met Pro Ile Thr Ile Asn Asn Phe Arg Tyr Ser Asp Pro Val
1               5                   10                  15

Asn Asn Asp Thr Ile Ile Met Met Glu Pro Pro Tyr Cys Lys Gly Leu
            20                  25                  30

Asp Ile Tyr Tyr Lys Ala Phe Lys Ile Thr Asp Arg Ile Trp Ile Val
        35                  40                  45

Pro Glu Arg Tyr Glu Phe Gly Thr Lys Pro Glu Asp Phe Asn Pro Pro
    50                  55                  60

Ser Ser Leu Ile Glu Gly Ala Ser Glu Tyr Tyr Asp Pro Asn Tyr Leu
65                  70                  75                  80

Arg Thr Asp Ser Asp Lys Asp Arg Phe Leu Gln Thr Met Val Lys Leu
                85                  90                  95

Phe Asn Arg Ile Lys Asn Asn Val Ala Gly Glu Ala Leu Leu Asp Lys
            100                 105                 110

Ile Ile Asn Ala Ile Pro Tyr Leu Gly Asn Ser Tyr Ser Leu Leu Asp
        115                 120                 125

Lys Phe Asp Thr Asn Ser Asn Ser Val Ser Phe Asn Leu Leu Glu Gln
    130                 135                 140

Asp Pro Ser Gly Ala Thr Thr Lys Ser Ala Met Leu Thr Asn Leu Ile
145                 150                 155                 160

Ile Phe Gly Pro Gly Pro Val Leu Asn Lys Asn Glu Val Arg Gly Ile
                165                 170                 175

Val Leu Arg Val Asp Asn Lys Asn Tyr Phe Pro Cys Arg Asp Gly Phe
            180                 185                 190
```

-continued

```
Gly Ser Ile Met Gln Met Ala Phe Cys Pro Glu Tyr Val Pro Thr Phe
    195                 200                 205

Asp Asn Val Ile Glu Asn Ile Thr Ser Leu Thr Ile Gly Lys Ser Lys
210                 215                 220

Tyr Phe Gln Asp Pro Ala Leu Leu Met His Glu Leu Ile His Val
225                 230                 235                 240

Leu His Gly Leu Tyr Gly Met Gln Val Ser Ser His Glu Ile Ile Pro
                245                 250                 255

Ser Lys Gln Glu Ile Tyr Met Gln His Thr Tyr Pro Ile Ser Ala Glu
                260                 265                 270

Glu Leu Phe Thr Phe Gly Gly Gln Asp Ala Asn Leu Ile Ser Ile Asp
            275                 280                 285

Ile Lys Asn Asp Leu Tyr Glu Lys Thr Leu Asn Asp Tyr Lys Ala Ile
290                 295                 300

Ala Asn Lys Leu Ser Gln Val Thr Ser Cys Asn Asp Pro Asn Ile Asp
305                 310                 315                 320

Ile Asp Ser Tyr Lys Gln Ile Tyr Gln Gln Lys Tyr Gln Phe Asp Lys
                325                 330                 335

Asp Ser Asn Gly Gln Tyr Ile Val Asn Glu Asp Lys Phe Gln Ile Leu
            340                 345                 350

Tyr Asn Ser Ile Met Tyr Gly Phe Thr Glu Ile Glu Leu Gly Lys Lys
            355                 360                 365

Phe Asn Ile Lys Thr Arg Leu Ser Tyr Phe Ser Met Asn His Asp Pro
370                 375                 380

Val Lys Ile Pro Asn Leu Leu Asp Asp Thr Ile Tyr Asn Asp Thr Glu
385                 390                 395                 400

Gly Phe Asn Ile Glu Ser Lys Asp Leu Lys Ser Glu Tyr Lys Gly Gln
                405                 410                 415

Asn Met Arg Val Asn Thr Asn Ala Phe Arg Asn Val Asp Gly Ser Gly
            420                 425                 430

Leu Val Ser Lys Leu Ile Gly Leu Cys Val Asp Gly Ile Ile Thr Ser
            435                 440                 445

Lys Thr Lys Ser Leu Ile Glu Gly Arg Phe Gly Phe Thr Gly Ala
    450                 455                 460

Arg Lys Ser Ala Arg Lys Arg Lys Asn Gln Ala Leu Ala Gly Gly Gly
465                 470                 475                 480

Gly Ser Gly Gly Gly Ser Gly Gly Gly Ser Ala Leu Val Leu
                485                 490                 495

Gln Cys Ile Lys Val Asn Asn Trp Asp Leu Phe Ser Pro Ser Glu
    500                 505                 510

Asp Asn Phe Thr Asn Asp Leu Asn Lys Gly Glu Glu Ile Thr Ser Asp
    515                 520                 525

Thr Asn Ile Glu Ala Ala Glu Glu Asn Ile Ser Leu Asp Leu Ile Gln
530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
            595                 600                 605

Arg Ile Ala Leu Thr Asn Ser Val Asn Glu Ala Leu Leu Asn Pro Ser
```

```
                610             615             620
Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
        675                 680                 685

Asn Met Leu Tyr Lys Asp Asp Phe Val Gly Ala Leu Ile Phe Ser Gly
690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
                740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
                820                 825                 830

Asn Gln Cys Ser Val Ser Tyr Leu Met Asn Ser Met Ile Pro Tyr Gly
                835                 840                 845

Val Lys Arg Leu Glu Asp Phe Asp Ala Ser Leu Lys Asp Ala Leu Leu
        850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
                900                 905                 910

<210> SEQ ID NO 98
<211> LENGTH: 180
<212> TYPE: DNA
<213> ORGANISM: Artificial Sequence
<220> FEATURE:
<223> OTHER INFORMATION: chemically synthesized polynucleotide encoding
      linker

<400> SEQUENCE: 98
ggatccacgc acgtcgacgc gattgatggt cgttttggcg gtttcacggg cgcacgcaaa       60
tcagcgcgta aacgtaagaa ccaggcgcta gcgggcggtg gcggtagcgg cggtggcggt      120
agcggcggtg gcggtagcgc actagtgctg cagacgcacg gtctagaatg ataaaagctt      180

<210> SEQ ID NO 99
<211> LENGTH: 2715
<212> TYPE: DNA
<213> ORGANISM: Artificial Sequence
<220> FEATURE:
```

<223> OTHER INFORMATION: chemically synthesized polynucleotide encoding fusion protein

<400> SEQUENCE: 99

```
ggatccgaat tcatgccgat caccatcaac aacttcaact acagcgatcc ggtggataac      60
aaaaacatcc tgtacctgga tacccatctg aataccctgg cgaacgaacc ggaaaaagcg     120
tttcgtatca ccggcaacat ttgggttatt ccggatcgtt ttagccgtaa cagcaacccg     180
aatctgaata accgccgcg tgttaccagc ccgaaaagcg gttattacga tccgaactat     240
ctgagcaccg atagcgataa agatacctc ctgaaagaaa tcatcaaact gttcaaacgc     300
atcaacagcc gtgaaattgg cgaagaactg atctatcgcc tgagcaccga tattccgttt     360
ccgggcaaca caacacccc gatcaacacc tttgatttcg atgtggattt caacagcgtt     420
gatgttaaaa cccgccaggg taacaattgg gtgaaaaccg gcagcattaa cccgagcgtg     480
attattaccg gtccgcgcga aacattatt gatccggaaa ccagcacctt taaactgacc     540
aacaacacct ttgcggcgca ggaaggtttt ggcgcgctga gcattattag cattagcccg     600
cgctttatgc tgacctatag caacgcgacc aacgatgttg tgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcggaaa tctatgcgtt tggcggtccg     840
accattgatc tgattccgaa aagcgcgcgc aaatacttcg aagaaaaagc gctggattac     900
tatcgcagca ttgcgaaacg tctgaacagc attaccaccg cgaatccgag cagcttcaac     960
aaatatatcg cgaatataaa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt atacccccggt gaccgcgaat attctggatg ataacgtgta cgatatccag    1200
aacggctta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg cgattgatgg tcgttttggc ggtttcacgg gcgcacgcaa atcagcgcgt    1380
aaacgtaaga accaggcgct agcgggcggt ggcggtagcg gcggtggcgg tagcggcggt    1440
ggcggtagcg cactagtgct gcagtgtcgt gaactgctgg tgaaaaacac cgatctgccg    1500
tttattggcg atatcagcga tgtgaaaacc gatatcttcc tgcgcaaaga tatcaacgaa    1560
gaaaccgaag tgatctacta cccggataac gtgagcgttg atcaggtgat cctgagcaaa    1620
aacaccagcg aacatggtca gctggatctg ctgtatccga gcattgatag cgaaagcgaa    1680
attctgccgg gcgaaaacca ggtgttttac gataaccgta cccagaacgt ggattacctg    1740
aacagctatt actacctgga aagccagaaa ctgagcgata cgtggaaga ttttacccttt    1800
acccgcagca ttgaagaagc gctggataac agcgcgaaag tttacaccta ttttccgacc    1860
ctggcgaaca agttaatgc gggtgttcag ggcggtctgt ttctgatgtg ggcgaacgat    1920
gtggtggaag atttcaccac caacatcctg cgtaaagata ccctggataa aatcagcgat    1980
gttagcgcga ttattccgta tattggtccg gcgctgaaca ttagcaatag cgtgcgtcgt    2040
ggcaatttta ccgaagcgtt tgcggttacc ggtgtgacca ttctgctgga agcgtttccg    2100
gaatttacca ttccggcgct gggtgcgttt gtgatctata gcaaagtgca ggaacgcaac    2160
gaaatcatca aaccatcga taactgcctg aacagcgta ttaaacgctg gaaagatagc    2220
```

```
tatgaatgga tgatgggcac ctggctgagc cgtattatca cccagttcaa caacatcagc    2280
taccagatgt acgatagcct gaactatcag gcgggtgcga ttaaagcgaa aatcgatctg    2340
gaatacaaaa aatacagcgg cagcgataaa gaaaacatca aaagccaggt tgaaaacctg    2400
aaaaacagcc tggatgtgaa aattagcgaa gcgatgaata acatcaacaa attcatccgc    2460
gaatgcagcg tgacctacct gttcaaaaac atgctgccga agtgatcga tgaactgaac    2520 gaatttgatc gcaacaccaa agcgaaactg atcaacctga tcgatagcca caacattatt    2580
ctggtgggcg aagtggataa actgaaagcg aaagttaaca acagcttcca gaacaccatc    2640
ccgtttaaca tcttcagcta taccaacaac agcctgctga agatatcat caacgaatac    2700 ttcaatctag actag                                                     2715
```

<210> SEQ ID NO 100
<211> LENGTH: 904
<212> TYPE: PRT
<213> ORGANISM: Artificial Sequence
<220> FEATURE:
<223> OTHER INFORMATION: chemically synthesized fusion protein

<400> SEQUENCE: 100

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270
```

-continued

```
Glu Ile Tyr Ala Phe Gly Gly Pro Thr Ile Asp Leu Ile Pro Lys Ser
            275                 280                 285

Ala Arg Lys Tyr Phe Glu Lys Ala Leu Asp Tyr Arg Ser Ile
        290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Phe Gly Gly Phe Thr Gly Ala Arg Lys Ser Ala Arg Lys Arg Lys Asn
    450                 455                 460

Gln Ala Leu Ala Gly Gly Gly Ser Gly Gly Gly Ser Gly Gly
465                 470                 475                 480

Gly Gly Ser Ala Leu Val Leu Gln Cys Arg Glu Leu Leu Val Lys Asn
                485                 490                 495

Thr Asp Leu Pro Phe Ile Gly Asp Ile Ser Asp Val Lys Thr Asp Ile
            500                 505                 510

Phe Leu Arg Lys Asp Ile Asn Glu Glu Thr Glu Val Ile Tyr Tyr Pro
        515                 520                 525

Asp Asn Val Ser Val Asp Gln Val Ile Leu Ser Lys Asn Thr Ser Glu
    530                 535                 540

His Gly Gln Leu Asp Leu Leu Tyr Pro Ser Ile Asp Ser Glu Ser Glu
545                 550                 555                 560

Ile Leu Pro Gly Glu Asn Gln Val Phe Tyr Asp Asn Arg Thr Gln Asn
                565                 570                 575

Val Asp Tyr Leu Asn Ser Tyr Tyr Leu Glu Ser Gln Lys Leu Ser
            580                 585                 590

Asp Asn Val Glu Asp Phe Thr Phe Thr Arg Ser Ile Glu Glu Ala Leu
        595                 600                 605

Asp Asn Ser Ala Lys Val Tyr Thr Tyr Phe Pro Thr Leu Ala Asn Lys
    610                 615                 620

Val Asn Ala Gly Val Gln Gly Gly Leu Phe Leu Met Trp Ala Asn Asp
625                 630                 635                 640

Val Val Glu Asp Phe Thr Thr Asn Ile Leu Arg Lys Asp Thr Leu Asp
                645                 650                 655

Lys Ile Ser Asp Val Ser Ala Ile Ile Pro Tyr Ile Gly Pro Ala Leu
            660                 665                 670

Asn Ile Ser Asn Ser Val Arg Arg Gly Asn Phe Thr Glu Ala Phe Ala
        675                 680                 685

Val Thr Gly Val Thr Ile Leu Leu Glu Ala Phe Pro Glu Phe Thr Ile
```

```
                690             695             700
Pro Ala Leu Gly Ala Phe Val Ile Tyr Ser Lys Val Gln Glu Arg Asn
705                 710                 715                 720

Glu Ile Ile Lys Thr Ile Asp Asn Cys Leu Glu Gln Arg Ile Lys Arg
                725                 730                 735

Trp Lys Asp Ser Tyr Glu Trp Met Met Gly Thr Trp Leu Ser Arg Ile
            740                 745                 750

Ile Thr Gln Phe Asn Asn Ile Ser Tyr Gln Met Tyr Asp Ser Leu Asn
                755                 760                 765

Tyr Gln Ala Gly Ala Ile Lys Ala Lys Ile Asp Leu Glu Tyr Lys Lys
770                 775                 780

Tyr Ser Gly Ser Asp Lys Glu Asn Ile Lys Ser Gln Val Glu Asn Leu
785                 790                 795                 800

Lys Asn Ser Leu Asp Val Lys Ile Ser Glu Ala Met Asn Asn Ile Asn
                805                 810                 815

Lys Phe Ile Arg Glu Cys Ser Val Thr Tyr Leu Phe Lys Asn Met Leu
                820                 825                 830

Pro Lys Val Ile Asp Glu Leu Asn Glu Phe Asp Arg Asn Thr Lys Ala
                835                 840                 845

Lys Leu Ile Asn Leu Ile Asp Ser His Asn Ile Ile Leu Val Gly Glu
850                 855                 860

Val Asp Lys Leu Lys Ala Lys Val Asn Asn Ser Phe Gln Asn Thr Ile
865                 870                 875                 880

Pro Phe Asn Ile Phe Ser Tyr Thr Asn Asn Ser Leu Leu Lys Asp Ile
                885                 890                 895

Ile Asn Glu Tyr Phe Asn Leu Asp
            900

<210> SEQ ID NO 101
<211> LENGTH: 23
<212> TYPE: PRT
<213> ORGANISM: Influenza virus

<400> SEQUENCE: 101

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 102
<211> LENGTH: 5
<212> TYPE: PRT
<213> ORGANISM: Artificial Sequence
<220> FEATURE:
<223> OTHER INFORMATION: chemically synthesized enterokinase cleavage
      site

<400> SEQUENCE: 102

Asp Asp Asp Asp Lys
1               5

<210> SEQ ID NO 103
<211> LENGTH: 8
<212> TYPE: PRT
<213> ORGANISM: Artificial Sequence
<220> FEATURE:
<223> OTHER INFORMATION: chemically synthesized Factor Xa cleavage site

<400> SEQUENCE: 103
```

Ile Glu Gly Arg Ile Asp Gly Arg
1               5

<210> SEQ ID NO 104
<211> LENGTH: 7
<212> TYPE: PRT
<213> ORGANISM: Artificial Sequence
<220> FEATURE:
<223> OTHER INFORMATION: chemically synthesized tobacco etch virus
      cleavage site

<400> SEQUENCE: 104

Glu Asn Leu Tyr Phe Gln Gly
1               5

<210> SEQ ID NO 105
<211> LENGTH: 6
<212> TYPE: PRT
<213> ORGANISM: Artificial Sequence
<220> FEATURE:
<223> OTHER INFORMATION: chemically synthesized thrombin cleavage site

<400> SEQUENCE: 105

Leu Val Pro Arg Gly Ser
1               5

<210> SEQ ID NO 106
<211> LENGTH: 8
<212> TYPE: PRT
<213> ORGANISM: Artificial Sequence
<220> FEATURE:
<223> OTHER INFORMATION: chemically synthesized PreScission cleavage
      site

<400> SEQUENCE: 106

Leu Glu Val Leu Phe Gln Gly Pro
1               5

<210> SEQ ID NO 107
<211> LENGTH: 48
<212> TYPE: DNA
<213> ORGANISM: Artificial Sequence
<220> FEATURE:
<223> OTHER INFORMATION: chemically synthesized PCR primer

<400> SEQUENCE: 107
tccaaaacta aatctctgat agaaggtaga aacaaagcgc tgaacgac                 48

<210> SEQ ID NO 108
<211> LENGTH: 25
<212> TYPE: DNA
<213> ORGANISM: Artificial Sequence
<220> FEATURE:
<223> OTHER INFORMATION: chemically synthesized PCR primer

<400> SEQUENCE: 108
cttgatgtac tctgtgaacg tgctc                                          25

<210> SEQ ID NO 109
<211> LENGTH: 48
<212> TYPE: DNA
<213> ORGANISM: Artificial Sequence
<220> FEATURE:
<223> OTHER INFORMATION: chemically synthesized PCR primer

<400> SEQUENCE: 109
gtcgttcagc gctttgtttc taccttctat cagagattta gttttgga                 48

<210> SEQ ID NO 110
<211> LENGTH: 24
<212> TYPE: DNA
<213> ORGANISM: Artificial Sequence
<220> FEATURE:
<223> OTHER INFORMATION: chemically synthesized PCR primer

<400> SEQUENCE: 110
atggagttcg ttaacaaaca gttc                                          24

<210> SEQ ID NO 111
<211> LENGTH: 25
<212> TYPE: PRT
<213> ORGANISM: Artificial Sequence
<220> FEATURE:
<223> OTHER INFORMATION: chemically synthesized activation loop

<400> SEQUENCE: 111

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 112
<211> LENGTH: 5
<212> TYPE: PRT
<213> ORGANISM: Artificial Sequence
<220> FEATURE:
<223> OTHER INFORMATION: chemically synthesized met-enkephalin peptide

<400> SEQUENCE: 112

Tyr Gly Gly Phe Met
1               5

<210> SEQ ID NO 113
<211> LENGTH: 13
<212> TYPE: PRT
<213> ORGANISM: Artificial Sequence
<220> FEATURE:
<223> OTHER INFORMATION: chemically synthesized peptide linker

<400> SEQUENCE: 113

Ala Leu Ala Gly Gly Gly Gly Ser Ala Leu Val Leu Gln
1               5                   10

<210> SEQ ID NO 114
<211> LENGTH: 18
<212> TYPE: PRT
<213> ORGANISM: Artificial Sequence
<220> FEATURE:
<223> OTHER INFORMATION: chemically synthesized peptide linker

<400> SEQUENCE: 114

Ala Leu Ala Gly Gly Gly Gly Ser Gly Gly Gly Gly Ser Ala Leu Val
1               5                   10                  15

Leu Gln

<210> SEQ ID NO 115
<211> LENGTH: 28
<212> TYPE: PRT
<213> ORGANISM: Artificial Sequence
<220> FEATURE:
<223> OTHER INFORMATION: chemically synthesized peptide linker

<400> SEQUENCE: 115

```
Ala Leu Ala Gly Gly Gly Gly Ser Gly Gly Gly Gly Ser Gly Gly Gly
1               5                   10                  15

Gly Ser Gly Gly Gly Gly Ser Ala Leu Val Leu Gln
            20                  25

<210> SEQ ID NO 116
<211> LENGTH: 33
<212> TYPE: PRT
<213> ORGANISM: Artificial Sequence
<220> FEATURE:
<223> OTHER INFORMATION: chemically synthesized peptide linker

<400> SEQUENCE: 116

Ala Leu Ala Gly Gly Gly Gly Ser Gly Gly Gly Gly Ser Gly Gly Gly
1               5                   10                  15

Gly Ser Gly Gly Gly Gly Ser Gly Gly Gly Gly Ser Ala Leu Val Leu
            20                  25                  30

Gln

<210> SEQ ID NO 117
<211> LENGTH: 30
<212> TYPE: PRT
<213> ORGANISM: Artificial Sequence
<220> FEATURE:
<223> OTHER INFORMATION: chemically synthesized peptide linker

<400> SEQUENCE: 117

Ala Leu Ala Ala Glu Ala Ala Ala Lys Glu Ala Ala Ala Lys Glu Ala
1               5                   10                  15

Ala Ala Lys Ala Gly Gly Gly Gly Ser Ala Leu Val Leu Gln
            20                  25                  30
```